United States Patent
Carroll et al.

(10) Patent No.: US 8,492,371 B2
(45) Date of Patent: *Jul. 23, 2013

(54) COMPOUNDS AS CANNABINOID RECEPTOR LIGANDS

(75) Inventors: William A. Carroll, Evanston, IL (US); Michael J. Dart, Highland Park, IL (US); Jennifer M. Frost, Gurnee, IL (US); Steven P. Latshaw, Round Lake Beach, IL (US); Tongmei Li, Lake Bluff, IL (US); Bo Liu, Waukegan, IL (US); Sridhar Peddi, Grayslake, IL (US); Xueqing Wang, Evanston, IL (US); Teodozyj Kolasa, Lake Villa, IL (US); Derek W. Nelson, Highland Park, IL (US); Arturo Perez-Medrano, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 102 days.

This patent is subject to a terminal disclaimer.

(21) Appl. No.: 12/732,421

(22) Filed: Mar. 26, 2010

(65) Prior Publication Data

US 2010/0249129 A1    Sep. 30, 2010

Related U.S. Application Data

(60) Provisional application No. 61/163,999, filed on Mar. 27, 2009.

(51) Int. Cl.
| | |
|---|---|
| A61K 31/397 | (2006.01) |
| A61K 31/433 | (2006.01) |
| A61K 31/42 | (2006.01) |
| A61K 31/416 | (2006.01) |
| A61K 31/4155 | (2006.01) |
| A61K 31/422 | (2006.01) |
| C07D 205/02 | (2006.01) |
| C07D 285/12 | (2006.01) |
| C07D 261/02 | (2006.01) |
| C07D 231/10 | (2006.01) |
| C07D 231/54 | (2006.01) |
| C07D 263/02 | (2006.01) |

(52) U.S. Cl.
USPC ...... 514/210.01; 514/363; 514/374; 514/378; 514/406; 548/136; 548/215; 548/240; 548/360.1; 548/364.1; 548/950

(58) Field of Classification Search
USPC ..... 514/210.01, 363, 374, 378, 406; 548/136, 548/215, 240, 360.1, 364.1, 950
See application file for complete search history.

(56) References Cited

U.S. PATENT DOCUMENTS

| | | | |
|---|---|---|---|
| 3,928,327 A | 12/1975 | Takamizawa et al. | |
| 5,250,498 A * | 10/1993 | Andree et al. | 504/105 |
| 5,468,722 A | 11/1995 | Shibata et al. | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2004/0259912 A1 | 12/2004 | Matsumoto et al. | |
| 2006/0199817 A1 | 9/2006 | Tasker et al. | |
| 2007/0155738 A1 | 7/2007 | Steeneck et al. | |
| 2008/0312435 A1 | 12/2008 | Saito et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |

FOREIGN PATENT DOCUMENTS

| | | |
|---|---|---|
| EP | 0639569 A1 | 2/1995 |
| EP | 1300401 A1 | 9/2003 |
| EP | 1640369 A1 | 3/2006 |
| EP | 1820504 A1 | 8/2007 |
| EP | 1820504 A1 | 8/2007 |
| FR | 2254339 A1 | 7/1975 |
| JP | 57171986 A1 | 10/1982 |
| WO | WO9507271 A1 | 3/1995 |
| WO | WO9710223 A1 | 3/1997 |
| WO | WO2005099353 A2 | 10/2005 |
| WO | WO2006008754 A1 | 1/2006 |
| WO | WO2009048936 A1 | 4/2009 |
| WO | WO2010019547 A1 | 2/2010 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Arevalo-Martin, et al., "Therapeutic Action of Cannabinoids in a Murine Model of Multiple Sclerosis," Journal of Neuroscience, 2003, vol. 23 (7), pp. 2511-2516.

(Continued)

*Primary Examiner* — Samantha Shterengarts
(74) *Attorney, Agent, or Firm* — Lisa V. Mueller; Michael Best & Friedrich LLP

(57) ABSTRACT

Disclosed herein are compounds of formula (I)

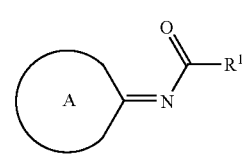

(I)

wherein Ring A and $R^1$ are as defined in the specification. Pharmaceutical compositions comprising such compounds, and methods for treating conditions and disorders using such compounds and pharmaceutical compositions are also disclosed.

17 Claims, No Drawings

OTHER PUBLICATIONS

Benito, et al., "Cannabinoid CB2 Receptors and Fatty Acid Amide Hydrolase are Selectively Overexpressed in Neurotic Plaque-Associated Glia in Alzheimer's Disease Brains," Journal of Neuroscience, 2003, vol. 23 (35), pp. 11136-11141.

Berge, et al., "Pharmaceutical Salts," Journal of Pharmaceutical Sciences, 1977, vol. 66 (1), pp. 1-19.

Beylot, et al., "In Vivo Studies of Intrahepatic Metabolic Pathways," Diabetes Metabolism, 1997, vol. 23 (3), pp. 251-257.

Blagojevic, et al., "Role of heavy water in Boron Neutron Capture Therapy," Topics in Dosimetry & Treatment Planning for Neutron Capture Therapy, 1994, pp. 125-134.

Blake, et al., "Studies With Deuterated Drugs," Journal of Pharmaceutical Sciences, 1975, vol. 64 (3), pp. 367-391.

Bouchard, et al., "Contribution of Endocannabinoids in the Endothelial Protection Afforded by Ischemic Preconditioning in the Isolated Rat Heart," Life Sciences, 2003, vol. 72 (16), pp. 1859-1870.

Boyle, et al., "Osteoclast Differentiation and Activation," Nature, 2003, vol. 423 (6937), pp. 337-342.

Brennan, et al., "Characterization of a Rat Model of Incisional Pain," Pain, 1996, vol. 64, pp. 493-450.

Brickner, et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

Buckley, et al., "Immunomodulation by Cannabinoids is Absent in Mice Deficient for the Cannabinoid CB2 Receptor," European Journal of Pharmacology, 2000, vol. 396, pp. 141-149.

Carlisle, et al., "Differential Expression of the CB2 Cannabinoid Receptor by Rodent Macrophages and Macrophage-like Cells in Relation to Cell Activation," International Immunopharmacology, 2002, vol. 2, pp. 69.

Carrier, et al., "Endocannabinoids in Neuroimmunology and Stress," Current Drug Targets—CNS and Neurological Disorders, 2005, vol. 4, pp. 657-665.

Casanova, et al., "Inhibition of Skin Tumor Growth and Angiogenesis in vivo by Activation of Cannabinoid Receptors," Journal of Clinical Investigation, 2003, vol. 111 (1), pp. 43-50.

Chaplan, et al., "Quantitative Assessment of Tactile Allodynia in the Rat Paw," Journal of Neuroscience Methods, 1994, vol. 53, pp. 55-63.

Cichewicz, "Synergistic Interactions Between Cannabinoid and Opioid Analgesics," Life Sciences, 2004, vol. 74 (11), pp. 1317-1324.

Clayton, et al., "CB1 and CB2 Cannabinoid Receptors are Implicated in Inflammatory Pain," Pain, 2002, vol. 96 (3), pp. 253-260.

Cotarca, et al., "Bis (trichloromethyl) Carbonate in Organic Synthesis," 1996, vol. 6, pp. 553-576.

Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.

Czajka, et al., "Effect of Deuterium Oxide on the Reproductive Potential of Mice," Annals of the New York Academy of Sciences, 1960, vol. 84, pp. 770-779.

Czajka, et al., "Physiological Effects of Deuterium on Dogs," American Journal of Physiology, 1961, vol. 201 (2), pp. 357-362.

Dixon, "Efficient Analysis of Experimental Observations," Annual Review of Pharmacology and Toxicology, 1980, vol. 20, pp. 441-462.

Ebata, et al., "Synthesis of Both Enantiomers of 4-Hexanolide and 4-Dodecanolide," Agriculture Biochemical, 1991, vol. 55 (6), pp. 1685-1686.

Eckert, et al., "Triphosgene, a Crystalline Phosgene Substitute," Angewandte Chemie International Edition in English, 1987, vol. 26 (9), pp. 894-895.

Filippo, et al., "Cannabinoid CB2 Receptor Activation Reduces Mouse Myocardial Ischemia-Reperfusion Injury: Involvement of Cytokine/Chemokines and PMN," Journal of Leukocyte Biology, 2004, vol. 75 (3), pp. 453-459.

Foster, et al., "Deuterium Isotope Effects in the Metabolism of Drugs and Xenobiotics: Implications for Drug Design," Advances in Drug Research, 1985, vol. 14, pp. 2-36.

Galiégue, et al., "Expression of Central and Peripheral Cannabinoid Receptors in Human Immune Tissues and Leukocyte Subpopulations," European Journal of Biochemistry, 1995, vol. 232 (1), pp. 54-61.

Greene, et al., "Protection for the Amino group," Protective Groups in Organic Synthesis, 1999, Third Edition, pp. 494-653.

Greene, et al., Protective Groups in Organic Synthesis, 3rd Edition, John Wiley and Sons, Inc., 1999, Table of Contents.

Grotenhermen, et al., "IACM 2nd Conference on Cannabinoids in Medicine," Expert Opinion in Pharmacotherapy, 1976, vol. 4 (12), pp. 2367-2371.

Hamuro, et al., "Solid-Phase Synthesis of Acyclic and Cyclic Amino Acid Derived Urea Peptidomimetics Using Phoxime Resin," The Journal of Combinatorial Chemistry, 1999, vol. 1, pp. 163-172.

Hanus, et al., "HU-308: A Specific Agonist for CB 2, a Peripheral Cannabinoid Receptor," Proceedings of the National Academy of Science, 1999, vol. 96, pp. 14228-14233.

Hohmann, et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.

Hutchins, et al., "A General Method for the Solid Phase Synthesis of Ureas," Tetrahedron Letters, 1994, vol. 35 (24), pp. 4055-4058.

Hutchins, et al., "A Strategy for Urea Linked Diamine Libraries," Tetrahedron Letters, 1995, vol. 36 (15), pp. 2583-2586.

Ibrahim, et al., "Activation of CB2 Cannabinoid Receptors by AM1241 Inhibits Experimental Neuropathic Pain: Pain Inhibition by Receptors not Present in the CNS," Proceedings of the National Academy of Science, 2003, vol. 100 (18), pp. 10529-10533.

Ibrahim, et al., "CB2 Cannabinoid Receptor Activation Produces Antinociception by Stimulating Peripheral Release of Endogenous Opioids," Proceedings of the National Academy of Science, 2005, vol. 102 (8), pp. 3093-3098.

Ihenetu, et al., "Inhibition of Interleukin-8 Release in the Human Colonic Epithelial Cell Line HT-29 by Cannabinoids," European Journal of Pharmacology, 2003, vol. 458 (1-2), pp. 207-215.

International Search Report for Application No. PCT/US08/079182, mailed on Dec. 15, 2008, 1 page.

International Search Report for Application No. PCT/US2010/028790, mailed Jul. 19, 2010, 3 pages.

Izdebski, et al., "A New Convenient Method for the Synthesis of Symmetrical and Unsymmetrical N,N'-Disubstituted Ureas," Synthesis, 1989, pp. 423-425.

Joshi, et al., "Comparison of Antinociceptive Actoins of Standard Analgesics in Attenuating Capsaicin and Nerve-Injury-Induced Mechanical Hypersensitivty," Neuroscience, 2006, vol. 143, pp. 587-596.

Julien, et al., "Antifibrogenic Role of the Cannabinoid Receptor CB2 in the Liver," Gastroenterology, 2005, vol. 128, pp. 742-755.

Karsak, et al., "Cannabinoid Receptor Type 2 Gene is Associated with Human Osteoporosis," Human Molecular Genetics, 2005, vol. 14 (22), pp. 3389-3396.

Kato, et al., "Synthesis of Deuterated Mosapride Citrate," Journal of Labelled Compounds and Radiopharmaceuticals, 1995, vol. 36 (10), pp. 927-932.

Katritzky, et al., "A General Synthesis of Unsymmetrical Tetrasubstituted Ureas," Journal of Organic Chemistry, 1997, vol. 62 (11), pp. 4155-4158.

Knolker, et al., "A Novel Method for the Synthesis of Isocyanates Under Mild Conditions," Angewandte Chemie International Edition in English, 1995, vol. 34 (22), pp. 2497-2500.

Knolker, et al., "Synthesis of Symmetrical and Unsymmetrical Ureas by DMAP-Catalyzed Reaction of Alkyl- and Arylamines with Di-tert-butyldicarbonate," Synlett, 1996, pp. 502-504.

Kruijtzer, et al., "Approaches to the Synthesis of Ureapeptoid Peptidomimetics," Tetrahedron Letters, 1997, vol. 38 (30), pp. 5335-5338.

Kushner, et al., "Pharmacological uses and perspectives of heavy water and deuterated compounds," Canadian Journal of Physiology and Pharmacology, 1999, vol. 77 (2), pp. 79-88.

Lamothe, et al., "A Simple One-Pot Preparation of N,N'-unsymmetrical ureas from N-Boc Protected Primary Anilines and Amines," Synlett, 1996, vol. 6, pp. 507-508.

Lemoucheux, et al., "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry," Journal of Organic Chemistry, 2003, vol. 68 (19), pp. 7289-7297.

Lepicier, et al., "Endocannabinoids Protect the RAt Isolated Heart Against Ischaemia," British Journal of Pharmacology, 2003, vol. 139, pp. 805-815.

Leung, et al., "S,S-Dimethyl Dithiocarbonate: A Convenient Reagent for the Synthesis of Symmetrical and Unsymmetrical Ureas," Journal of Organic Chemistry, 1996, vol. 61 (12), pp. 4175-4179.

Lizondo, et al., "Linezolid: Oxazolidinone antibacterial," Drugs of the Future, 1996, vol. 21 (11), pp. 1116-1123.

Lotersztajn, et al., "Hepatic Fibrosis: Molecular Mechanisms and Drug Targets," Annual Review of Pharmacology and Toxicology, 2005, vol. 45, pp. 605-628.

Majer, et al., "A Safe and Efficient Method for Preparation of N,"-Unsymmetrically Disubstituted Ureas Utilizing Triphosgene," Journal of Organic Chemistry, 1994, vol. 59, pp. 1937-1938.

Malan, et al., "CB2 Cannabinoid Receptor-Mediated Peripheral Antinociception," Pain, 2001, vol. 93, pp. 239-245.

Mallesham, et al., "Highly Efficient Cui-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Maresz, et al., "Modulation of the Cannabinoid CB2 Receptor in Microglial Cells in Response to Inflammatory Stimuli," Journal of Neurochemistry, 2005, vol. 95, pp. 437-445.

Mathison, et al., "Effects of Cannabinoid Receptor-2 Activation on Accelerated Gastrointestinal Transit in Lipopolysaccharide-Treated Rats," British Journal of Pharmacology, 2004, vol. 142, pp. 1247-1254.

McKallip, et al., "Targeting CB2 Cannabinoid Receptors as a Novel Therapy to Treat Malignant Lymphoblastic Disease," Blood, 2002, vol. 15 (2), pp. 627-634.

Miyaura, et al., ed., Topics in Current Chemistry: Cross-Coupling Reactions, Springer, 2002, Table of Contents.

Nackley, et al., "Selective Activation of Cannabinoid CB2 Receptors Suppresses Spinal for Protein Expression and Pain Behavior in a Rat Model of Inflammation," Neuroscience, 2003, vol. 119, pp. 747-757.

Negishi, et al., eds., Handbook of Organopalladium Chemistry for Organic Synthesis, vol. 1, John Wiley & Sons, 2002, Table of Contents.

Ni, et al., "Win 55212-2, a Cannabinoid Receptor Agonist, Attenuates Leukocyte/Endothelial Interactions in an Experimental Autoimmune Encephalomyelitis Model," Multiple Sclerosis, 2004, vol. 10, pp. 158-164.

Nieuwenhuijzen, et al., "Solid and Solution Phase Combinatorial Synthesis of Ureas," Tetrahedron Letters, 1998, vol. 39, pp. 7811-7814.

Ozaki, et al., "Recent Advances in Isocyanate Chemistry," Chemical Reviews, 1972, vol. 72 (5), pp. 457-496.

Patel, et al., "Inhibition of Guinea-Pig and Human Sensory Nerve Activity and the Cough Reflex in Guinea-Pigs by Cannabinoid (CB2) Receptor Activation," British Journal of Pharmacology, 2003, vol. 140 (2), pp. 261-268.

Pertwee, "Cannabinoids and Multiple Sclerosis," Pharmacology & Therapeutics, 2002, vol. 95, pp. 165-174.

Poste, et al., "Lipid Vesicles as Carriers for Introducing Biologically Active Materials into Cells," Methods in Cell Biology, 1976, vol. 14, pp. 33-71.

Quartilho, et al., "Inhibition of Inflammatory Hyperalgesia by Activation of Peripheral CB2 Cannabinoid Receptors," Anesthesiology, 2003, vol. 99, pp. 955-960.

Ralston, "Regulation of Bone Mass, Bone Loss and Osteoclast Activity by Cannabinoid Receptors," Nature Medicine, 2005, vol. 11 (7), pp. 774-779.

Ramirez, et al., "Prevention of Alzheimers Disease Pathology by Cannabinoids: Neuroprotection Mediated by Blockade of Microglial Activation," Journal of Neuroscience, 2005, vol. 25 (8), pp. 1904-1913.

Sanchez, et al., "Inhibition of Glioma Growth in Vivo by Selective Activation of the CB2 Cannabinoid Receptor1," Cancer Research, 2001, vol. 61, pp. 5784-5789.

Scialdone, et al., "Phosgenated p-nitrophenyl(polystyrene)ketoxime or phoxime resin. A new resin for the solid-phase synthesis of ureas via thermolytic cleavage of oxime-carbamates?," Journal of Organic Chemistry, 1998, vol. 63, pp. 4802-4807.

Steffens, et al., "Low Dose Oral Cannabinoid Therapy Reduces Progression of Atherosclerosis in Mice," Nature, 2005, vol. 434, pp. 782-786.

Takeda, et al., "Convenient Methods for Syntheses of Active Carbamates, Ureas and Nitrosoureas Using N,N-disuccinimido Carbonate (DSC)," Tetrahedron Letters, 1983, vol. 24, pp. 4569-4572.

Thomson, "Physiological Effects of D20 In Mammals," Annals of the New York Academy of Sciences, 1960, vol. 84, pp. 736-744.

Valenzano, et al., "Pharmacological and Pharmacokinetic Characterization of the Cannabinoid Receptor 2 Agonist, Gw405833, Utilizing Rodent Models of Acute and Chronic Pain,Anxiety, Ataxia and Catalepsy," Neuropharmacology, 2005, vol. 48, pp. 658-672.

Walter, et al., "Cannabinoids and Neuroinflammation," British Journal of Pharmacology, 2004, vol. 141 (5), pp. 775-785.

Warhurst, et al., "Interferon Gamma Induces Differential Upregulation of Alpha and Beta Chemokine Secretion in Colonic Epithelial Cell Lines," Gut, 1998, vol. 42 (2), pp. 208-213.

Wright, et al., "Differential Expression of Cannabinoid Receptors in the Human Colon: Cannabinoids Promote Epithelial Wound Healing," Gastroenterology, 2005, vol. 129 (2), pp. 437-453.

Yoshihara, et al., "Cannabinoid Receptor Agonists Inhibit Sensory Nerve Activation in Guinea Pig Airways," American Journal of Respiratory and Critical Care Medicine, 2004, vol. 170 (9), pp. 941-946.

Yoshihara, et al., "Endogenous Cannabinoid Receptor Agonists Inhibit Neurogenic Inflammations in Guinea Pig Airways," Allergy and Immunology, 2005, vol. 138, pp. 80-87.

Yoshihara, et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.

Supplementary European Search Report for Application No. EP08837396, mailed on Jan. 16, 2012, 2 pages.

Vasileva, et al., "Synthesis and properties of 2-imino-3-benzyl-5-phenyl-1,3,4-oxadiazoline," Accession No. 121444, 1970.

Ohta, et al., "N-Alkyidenearylcarboxamides as a new Potent and Selective CB2 Cannabinoid Receptor Agonist with an Analgesic Action," Bioorganic and Medicinal Chemical Letters, 2007, vol. 17(22), pp. 6299-6304.

Schuart, et al., "2-Aminooxazole and 2-iminooxazoline, 3. Chosen Examples of the Homologous Series of 3-substituted-2-imino-4-methyl-5-phenyloxazoline," Accession No. 403802, Pharmazie 29(3), 1974, pp. 170-172.

International Preliminary Report on Patentability and Written Opinion for Application No. PCT/US08/079182, mailed on Apr. 13, 2010, 5 pages.

International Preliminary Report on Patentability and Written Opinion for Application No. PCT/US2010/028790, mailed on Sep. 27, 2011, 5 pages.

* cited by examiner

COMPOUNDS AS CANNABINOID RECEPTOR LIGANDS

This application claims priority to U.S. Application Ser. No. 61/163,999 filed Mar. 27, 2009, and is incorporated herein by reference in its entirety.

TECHNICAL FIELD $CB_2$ receptor ligands, compositions comprising such compounds, and methods of treating conditions and disorders using such compounds and compositions are disclosed.

BACKGROUND (−)-$\Delta^9$-Tetrahydrocannabinol ($\Delta^9$-THC), the major psychoactive constituent of marijuana, exerts a broad range of biological effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there can be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, fibromyalgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

Accordingly, the need exists to further explore and develop $CB_2$ receptor ligands that exhibit immunomodulatory and anti-inflammatory properties. These $CB_2$ receptors ligands can offer a unique pharmacotherapy for the treatment of immune and inflammatory disorders.

SUMMARY

Provided generally herein are compounds that are $CB_2$ receptor ligands, pharmaceutical compositions comprising such compounds, and methods for the treatment of disorders using these compounds and pharmaceutical compositions.

One embodiment is related to compounds of formula (I), or pharmaceutically acceptable salts, solvates, prodrugs, salts of prodrugs, or combinations thereof

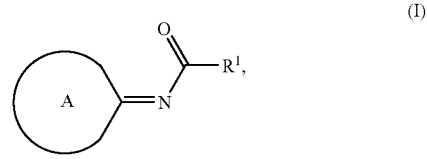

wherein $R^1$ is alkyl, haloalkyl, $G^1$, —$(CR^xR^y)_m$-$G^1$, or —$N(R^{1a})(R^z)$;

$R^z$ is alkyl, haloalkyl, $G^2$, —$(CR^xR^y)_m$-$G^2$, —$(CR^xR^y)_n$—$OR^{za}$, —$(CR^xR^y)_n$—$N(R^{za})(R^{zb})$, —$(CR^xR^y)_m$—$C(O)O(R^{za})$, —$(CR^xR^y)_m$—$C(O)R^{za}$, —$(CR^xR^y)_m$C(O)N(R^{za})(R^{zb})$, —$(CR^xR^y)_m$—$S(O)_2O(R^{za})$, —$(CR^xR^y)_m$—$S(O)_2R^{za}$, —$(CR^xR^y)_m$—$S(O)_2N(R^{za})(R^{zb})$, or —$(CR^xR^y)_m$—$CN$;

$G^1$ and $G^2$, at each occurrence, are each independently aryl, heteroaryl, heterocycle, cycloalkyl, or cycloalkenyl; wherein each ring is independently unsubstituted or substituted with 1, 2, 3, 4, 5, or 6 substituents independently selected from the group consisting of alkyl, alkenyl, alkynyl, —$NO_2$, —$CN$, halogen, oxo, —$OR^e$, —$O$—$(CR^jR^k)_n$—$N(R^w)_2$, —$OC(O)R^e$, —$SR^e$, —$SF_5$, —$S(O)R^f$, —$S(O)_2R^f$, —$S(O)_2N(R^e)(R^g)$, —$N(R^e)(R^g)$, —$N(R^g)C(O)R^e$, —$N(R^g)C(O)O(R^f)$, —$N(R^g)S(O)_2R^f$, —$N(R^g)C(O)N(R^e)(R^g)$, —$N(R^g)S(O)_2N(R^e)(R^g)$, —$C(O)R^e$, —$C(O)O(R^e)$, —$C(O)N(R^e)(R^g)$, alkoxyalkenyl, hydroxyalkenyl, haloalkyl, —$(CR^jR^k)_q$—CN, —$(CR^jR^k)_q$—$OR^e$, —$(CR^jR^k)_q$—$OC(O)R^e$, —$(CR^jR^k)_q$—$SR^e$, —$(CR^jR^k)_q$—$S(O)R^f$, —$(CR^jR^k)_q$—$S(O)_2R^f$, —$(CR^jR^k)_q$—$N(R^e)(R^g)$, —$(CR^jR^k)_q$—$N(R^g)C(O)R^e$, —$(CR^jR^k)_q$—$N(R^g)S(O)_2R^f$, —$(CR^jR^k)_q$—$N(R^g)C(O)N(R^e)(R^g)$, —$(CR^jR^k)_q$—$N(R^g)S(O)_2N(R^e)(R^g)$, —$(CR^jR^k)_q$ —C(O)R$^e$, —(CR$^j$R$^k$)$_q$—C(O)O(R$^e$), —(CR$^j$R$^k$)$_q$—C(O)N(R$^e$)(R$^g$), —C(R$^w$)=N—OR$^w$, and morpholinyl;

Ring A represents formula (a), (b), (c), or (d)

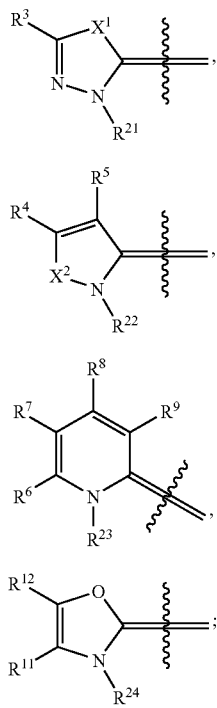

R$^{21}$, R$^{22}$, R$^{23}$, and R$^{24}$ are -alkylene-G$^3$ wherein G$^3$, at each occurrence, is independently furanyl, oxazolyl, isoxazolyl, oxadiazolyl, or a 4-, 5-, 6-, 7-, 8-, or 9-membered monocyclic heterocycle containing zero or one double bond, one or two oxygen, and zero or one nitrogen as ring atoms, wherein two non-adjacent atoms of said monocyclic heterocycle is optionally linked by an alkenylene bridge of 2, 3, or 4 carbon atoms, or optionally linked by an alkylene bridge of 1, 2, 3, or 4 carbon atoms; each G$^3$ ring is optionally fused with a monocyclic ring selected from the group consisting of benzo, cycloalkyl, cycloalkenyl, heterocycle, and heteroaryl; and each G$^3$ is independently unsubstituted or substituted with 1, 2, 3, 4, 5, or 6 substituents independently selected from the group consisting of oxo, alkyl, halogen, —OH, —O(alkyl), —O(haloalkyl), and haloalkyl;

R$^w$, at each occurrence, is independently hydrogen or alkyl;

R$^3$, R$^6$, R$^7$, R$^8$, R$^9$, R$^{11}$, and R$^{12}$ are each independently hydrogen, alkyl, alkenyl, alkynyl, —NO$_2$, —CN, halogen, —OR$^a$, —N(R$^a$)(R$^b$), —C(O)R$^a$, —C(O)O(R$^a$), haloalkyl, —(CR$^c$R$^d$)$_p$—OR$^a$, —(CR$^c$R$^d$)$_p$—N(R$^a$)(R$^b$), —(CR$^c$R$^d$)$_p$—C(O)R$^a$, —(CR$^c$R$^d$)$_p$—C(O)O(R$^a$), cycloalkyl, cycloalkenyl, or heterocycle;

R$^4$ and R$^5$, are each independently hydrogen, alkyl, alkenyl, alkynyl, —NO$_2$, —CN, halogen, —OR$^a$, —N(R$^a$)(R$^b$), —C(O)R$^a$, —C(O)O(R$^a$), haloalkyl, —(CR$^c$R$^d$)$_p$—OR$^a$, —(CR$^c$R$^d$)$_p$—N(R$^a$)(R$^b$), —(CR$^c$R$^d$)$_p$—C(O)R$^a$, —(CR$^c$R$^d$)$_p$—C(O)O(R$^a$), cycloalkyl, cycloalkenyl, or heterocycle; or R$^4$ and R$^5$, together with the carbon atoms to which they are attached, form a monocyclic cycloalkyl ring which is optionally further substituted with 1, 2, 3, or 4 substituents selected from the group consisting of halogen, alkyl, haloalkyl, and oxo;

R$^a$, R$^b$, R$^{1a}$, R$^{za}$, and R$^{zb}$, at each occurrence, are each independently hydrogen, alkyl, or haloalkyl;

R$^x$, at each occurrence, is independently hydrogen, halogen, alkyl, haloalkyl, or benzyl;

R$^y$, R$^c$, and R$^d$, at each occurrence, are each independently hydrogen, halogen, alkyl, or haloalkyl;

X$^1$ and X$^2$ are independently O, S, or N(R$^{10}$) wherein R$^{10}$ is alkyl, alkoxyalkyl, haloalkoxyalkyl, or haloalkyl;

the cycloalkyl, cycloalkenyl, and heterocycle, as represented by R$^3$, R$^4$, R$^5$, R$^6$, R$^7$, R$^8$, R$^9$, R$^{11}$, and R$^{12}$ are each independently unsubstituted or substituted with 1, 2, 3, 4, 5, or 6 substituents independently selected from the group consisting of alkyl, alkenyl, alkynyl, —NO$_2$, —CN, halogen, oxo, —OR$^e$, —OC(O)R$^e$, —SR$^e$, —S(O)R$^f$, —S(O)$_2$R$^f$, —S(O)$_2$N(R$^e$)(R$^g$), —N(R$^e$)(R$^g$), —N(R$^g$)C(O)R$^e$, —N(R$^g$)S(O)$_2$R$^f$, —N(R$^g$)C(O)N(R$^e$)(R$^g$), —N(R$^g$)S(O)$_2$N(R$^e$)(R$^g$), —C(O)R$^e$, —C(O)O(R$^e$), —C(O)N(R$^e$)(R$^g$), haloalkyl, —(CR$^j$R$^k$)$_q$—CN, —(CR$^j$R$^k$)$_q$—OR$^e$, —(CR$^j$R$^k$)$_q$—OC(O)R$^e$, —(CR$^j$R$^k$)$_q$—SR$^e$, —(CR$^j$R$^k$)$_q$—S(O)R$^f$, —(CR$^j$R$^k$)$_q$—S(O)$_2$R$^f$, —(CR$^j$R$^k$)$_q$—N(R$^e$)(R$^g$), —(CR$^j$R$^k$)$_q$—N(R$^g$)C(O)R$^e$, —(CR$^j$R$^k$)$_q$—N(R$^g$)S(O)$_2$R$^f$, —(CR$^j$R$^k$)$_q$—N(R$^g$)C(O)N(R$^e$)(R$^g$), —(CR$^j$R$^k$)$_q$—N(R$^g$)S(O)$_2$N(R$^e$)(R$^g$), —(CR$^j$R$^k$)$_q$—C(O)R$^e$, —(CR$^j$R$^k$)$_q$—C(O)O(R$^e$), and —(CR$^j$R$^k$)$_q$—C(O)N(R$^e$)(R$^g$);

R$^e$ and R$^g$, at each occurrence, are each independently hydrogen, alkyl, alkenyl, alkynyl, alkoxyalkyl, cycloalkyl, cycloalkylalkyl, heterocycle, aryl, heteroaryl, haloalkoxyalkyl, or haloalkyl; wherein the aryl, the heteroaryl, the cycloalkyl, and the heterocycle moieties, by itself or as part of the substituents of R$^e$ and R$^g$, are each independently unsubstituted or substituted with 1, 2, 3, 4, 5 or 6 substituents selected from the group consisting of alkyl, halogen, haloalkyl, hydroxy, oxo, =N—O(H), =N—O(alkyl), and alkoxy;

R$^f$, at each occurrence, is independently alkyl or haloalkyl;

R$^j$ and R$^k$, at each occurrence, are each independently hydrogen, halogen, alkyl, or haloalkyl;

m, p, and q, at each occurrence, are each independently 1, 2, 3, or 4; and n is 2, 3 or 4.

Another aspect relates to pharmaceutical compositions comprising therapeutically effective amount of a compound described herein or a pharmaceutically acceptable salt, solvate, salt of a solvate, or solvate of a salt thereof, in combination with a pharmaceutically acceptable carrier. Such compositions can be administered in accordance with a method of the invention, typically as part of a therapeutic regimen for treatment or prevention of conditions and disorders related to cannabinoid (CB) receptor subtype CB$_2$. More particularly, the method is useful for treating conditions related to neuropathic pain, nociceptive pain, post-operative pain, osteoarthritis pain, cancer pain, inflammatory pain, cancer pain, lower back pain, eye pain, inflammatory disorders, immune disorders, neurological disorders, cancers of the immune system, respiratory disorders, obesity, diabetes, cardiovascular disorders, or for providing neuroprotection.

Further provided herein are the use of present compounds or pharmaceutically acceptable salts, solvates, salts of solvates, or solvates of salts thereof, in the manufacture of a medicament for the treatment of the disease conditions described above, alone or in combination with one or more pharmaceutically acceptable carrier(s), particularly for the treatment of pain such as, but not limited to, neuropathic pain, nociceptive pain, osteoarthritis pain, inflammatory pain, cancer pain, lower back pain, eye pain, and post-operative pain, or combinations thereof.

The compounds, compositions comprising the compounds, and methods for treating or preventing conditions and disorders by administering the compounds are further described herein.

These and other objectives of the invention are described in the following paragraphs.

These objectives should not be deemed to narrow the scope of the invention.

DETAILED DESCRIPTION

Compounds of formula (I)

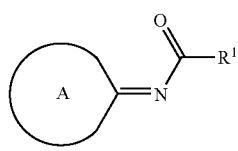

wherein $R^1$ and A are as defined above in the Summary and below in the Detailed Description are disclosed. Compositions comprising such compounds and methods for treating conditions and disorders using such compounds and compositions are also disclosed.

In various embodiments, there can be variables that occur more than one time in any substituent or in the compound or any other formulae herein. Definition of a variable on each occurrence is independent of its definition at another occurrence. Further, combinations of variables or substituents are permissible only if such combinations result in stable compounds. Stable compounds are compounds which can be isolated from a reaction mixture.

a. Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. Representative examples of alkenyl include, but are not limited to, ethenyl, 3-methylbut-2-enyl, prop-1-enyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched hydrocarbon chain of 2, 3, or 4 carbon atoms and contains at least one carbon-carbon double. Representative examples of alkenylene include, but are not limited to, —CH═CH— and —CH₂CH═CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkenyl" as used herein, means an alkoxy group, as defined herein, appended to the parent molecular moiety through an alkenylene group, as defined herein. Representative example of alkoxyalkenyl includes, but is not limited to, 3-methoxyprop-1-enyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-methoxyethyl, 3-methoxy-3-methylbutyl, 2-methoxypropyl, 3-methoxypropyl, 2-ethoxyethyl, 2-methoxyethyl, 3-ethoxypropyl, and methoxymethyl.

The term "alkyl" as used herein, means a saturated, straight or branched hydrocarbon chain containing from 1 to 10 carbon atoms. The terms "$C_1$-$C_4$ alkyl" and "$C_4$-$C_8$ alkyl" as used herein, means a saturated, straight or branched hydrocarbon chain containing from 1 to 4 and from 4 to 8 carbon atoms respectively. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" means a divalent group derived from a saturated, straight or branched hydrocarbon chain of from 1 to 10 carbon atoms. Representative examples of alkylene include, but are not limited to, —CH₂—, —CH(CH₃)—, —CH(C₂H₅), —CH(CH(CH₃)(C₂H₅))—, —C(H)(CH₃)CH₂CH₂—, —C(CH₃)₂—, —CH₂CH₂—, —CH₂CH₂CH₂—, —CH₂CH₂CH₂CH₂—, and —CH₂CH(CH₃)CH₂—.

The term "alkynyl" as used herein, means a straight or branched hydrocarbon chain containing from 2 to 10 carbon atoms and containing at least one carbon-carbon triple bond. Representative examples of alkynyl include, but are not limited, to acetylenyl, 1-propynyl, 2-propynyl, 1,1-dimethylprop-2-ynyl, 1-propyl-pent-3-ynyl, 3-butynyl, 2-pentynyl, and 1-butynyl.

The term "aryl" as used herein, means phenyl, a bicyclic aryl or a tricyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl (including 1,2,3,4-tetrahydronaphthalen-1-yl). The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryls include, but are not limited to, anthracene, phenanthrene, dihydroanthracenyl, fluorenyl, 1,2-dihydroacenaphthylenyl, and tetrahydrophenanthrenyl. The phenyl, bicyclic and tricyclic aryls are attached to the parent molecular moiety through any carbon atom contained within the phenyl, bicyclic and tricyclic aryls respectively, and are optionally substituted.

The term "cycloalkenyl" as used herein, means a monocyclic or bicyclic ring system containing zero heteroatoms in the ring. The monocyclic cycloalkenyl has three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. Bicyclic cycloalkenyls are exemplified by a monocyclic cycloalkenyl fused to a monocyclic cycloalkyl, or a monocyclic cycloalkenyl fused to a monocyclic cycloalkenyl. Representative examples of bicyclic ring systems include, but are not limited to 3a, 4, 5, 6, 7, 7a-hexahydro-1H-indenyl, 4,5,6,7-tetrahydro-3aH-indene, and octahydronaphthalenyl. The cycloalkenyl groups of are optionally substituted and are appended to the parent molecular moiety through any substitutable carbon atom within the groups, and can contain one or two alkylene bridges of 1, 2, 3, or 4 carbon atoms, wherein each bridge links two non-adjacent atoms within the groups.

The term "cycloalkyl" as used herein, means a monocyclic, or a bicyclic cycloalkyl, or a spirocyclic cycloalkyl, each of which is optionally substituted. The term "$C_3$-$C_6$ cycloalkyl" as used herein, means a monocyclic cycloalkyl having 3, 4, 5, or 6 carbon atoms in the ring. The monocyclic cycloalkyl is a carbocyclic ring system containing 3, 4, 5, 6, 7, or 8 carbon atoms and zero heteroatoms as ring atoms, and has zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Representative examples of bicyclic cycloalkyls include, but are not limited to, bicyclo[4.1.0]heptane, bicyclo[6.1.0]nonane, octahydroindene, and decahydronaphthalene. The monocyclic and the bicyclic cycloalkyl groups can contain one or two alkylene bridges of 1, 2, 3, or 4 carbon atoms, wherein each bridge links two non-adjacent atoms within the groups. Examples of such bridged cycloalkyls include, but are not limited to, bicyclo[3.1.1]heptyl (including bicyclo[3.1.1]hept-2-yl), bicyclo[2.2.1]heptyl, bicyclo[3.1.1]heptyl, bicyclo[2.2.2]octyl, bicyclo[3.3.1]nonyl, adamantyl (tricyclo[3.3.1.1$^{3,7}$]decane), and noradamantyl (octahydro-2,5-methanopentalene). Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The monocyclic, bicyclic, and spirocyclic cycloalkyl groups can be appended to the parent molecular moiety through any substitutable carbon atom of the groups.

The term "cycloalkylalkyl" means a cycloalkyl group, as defined herein, appended to the parent moiety through an alkylene group, as defined herein.

The term "halo" or "halogen" as used herein, means —Cl, —Br, —I or —F.

The term "haloalkoxy" as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkyl" as used herein, means a haloalkoxy group, as defined herein, appended to the parent molecular moiety through an alkyl group, as defined herein.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2-fluoropropyl, 2-fluoro-1-methylethyl, 2,2-difluoroethyl, trifluoromethyl, 2,2,2-trifluoroethyl, 2,2,2-trifluoro-1,1-dimethylethyl, difluoromethyl, 3-fluoro-3-methylbutyl, 3,3,3-trifluoropropyl, pentafluoroethyl, 2-chloro-3-fluoropentyl, and 2-iodoethyl.

The term "heteroaryl," as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, benzoxadiazolyl, 1,3-benzothiazolyl, benzimidazolyl, benzodioxolyl, benzothienyl, chromenyl, cinnolinyl, furopyridine, indolyl, indazolyl, isoindolyl, isoquinolinyl, naphthyridinyl, oxazolopyridine, quinolinyl, and thienopyridinyl. The monocyclic and the bicyclic heteroaryl groups are connected to the parent molecular moiety through any substitutable carbon atom or any substitutable nitrogen atom contained within the groups. The nitrogen and sulfur heteroatoms of the heteroaryl rings can optionally be oxidized, and are contemplated within the scope of the invention.

The term "heterocycle" or "heterocyclic" as used herein, means a monocyclic, bicyclic, or a spirocyclic ring system containing at least one heteroatom. The monocyclic heterocycle is a 3-, 4-5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S. Representative examples of monocyclic heterocycles include, but are not limited to, azetidinyl (including azetidin-3-yl), azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl (including 1,3-oxazolidin-4-yl), oxetanyl, piperazinyl, piperidinyl, pyranyl, pyrazolinyl, pyrazolidinyl, pyrrolinyl, pyrrolidinyl (including pyrrolidin-3-yl), tetrahydrofuranyl (including tetrahydrofuran-2-yl and tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Representative examples of bicyclic heterocycle include, but are not limited to, 1,3-benzodioxol-4-yl, 1,3-benzodithiolyl, 2,3-dihydro-1,4-benzodioxinyl, 2,3-dihydrobenzofuranyl (including 2,3-dihydro-1-benzofuran-7-yl), 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 4-, 5-, or 6-membered monocyclic cycloalkyl. One example of a spiroheterocycle is 5-oxaspiro[3,4]octane. The heterocycle groups are connected to the parent molecular moiety through any substitutable carbon atom or any substitutable nitrogen atom contained within the group. The monocyclic or bicyclic heterocycle groups can contain an alkenylene bridge of 2, 3, or 4 carbon atoms, or one or two alkylene bridges of 1, 2, 3, or 4 carbon atoms, wherein each bridge links two non-adjacent carbon atoms within the groups. Examples of such bridged heterocycles include, but are not limited to, oxaadamantane (2-oxatricyclo[3.3.1.1$^{3,7}$]decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane. The nitrogen and sulfur heteroatoms in the heterocycle rings can optionally be oxidized and the nitrogen atoms can optionally be quarternized.

The term "hydroxyalkenyl" means an hydroxy group, as defined herein, appended to the parent molecular moiety through an alkenylene group, as defined herein. An example of hydroxyalkenyl includes, but is not limited to, 3-hydroxy-3-methylbut-1-enyl.

The term "hydroxyl" or "hydroxy" means an OH group.

The term "oxo" means =O.

"Treatment" or "treating" pain includes acute or chronic pain and refers to: (1) preventing pain, i.e. causing pain not to develop or occur with less intensity in a subject that can be exposed or predisposed to pain but does not yet experience or display pain, (2) inhibiting pain, i.e., arresting the development or reversing pain, or (3) relieving pain, i.e., decreasing the amount of pain experienced by the subject.

The term "subject" includes animals such as mammals, including, but not limited to, primates (e.g., humans), cows, sheep, goats, horses, dogs, cats, rabbits, rats, mice and the like. In preferred embodiments, the subject is a human.

b. Compounds $CB_2$ ligands have formula (I) as described above.

Particular values of variable groups in compounds of formula (I) are as follows. Such values can be used where appropriate with any of the other values, definitions, claims or embodiments defined hereinbefore or hereinafter.

In compounds of formula (I), $R^1$ is alkyl, haloalkyl, $G^1$, —$(CR^xR^y)_m$-$G^1$, or —$N(R^{1a})(R^z)$, wherein $G^1$, $R^x$, $R^y$, $R^{1a}$, $R^z$, and m are as disclosed in the Summary and in embodiments herein below.

In certain embodiments, $R^1$ is $G^1$ or —$N(R^{1a})(R^z)$, wherein $G^1$, $R^{1a}$, $R^z$, and m are as disclosed in the Summary and in embodiments herein below.

In certain embodiments, $R^1$ is $G^1$ wherein $G^1$ is as disclosed in the Summary. For example, $G^1$ is phenyl or naphthyl, each of which is optionally substituted as described in the Summary and embodiments herein. In certain embodiments, $G^1$ is optionally substituted phenyl.

Other embodiments relate to compounds wherein $R^1$ is $G^1$, and $G^1$ is optionally substituted cycloalkyl (for example, adamantyl, bicyclo[2.2.1]heptyl, each of which is optionally substituted as described in the Summary and in embodiments herein).

Yet other embodiments relate to compounds wherein $R^1$ is $G^1$, and $G^1$ is optionally substituted heterocycle. Example of said heterocycle includes, but is not limited to, optionally substituted 2,3-dihydrobenzofuranyl (including but not limited thereto, optionally substituted 2,3-dihydro-1-benzofuran-7-yl).

Yet other embodiments relate to compounds wherein $R^1$ is $G^1$, and $G^1$ is heteroaryl, optionally substituted as described in the Summary. For example, $R^1$ is optionally substituted quinolinyl (including but not limited thereto, optionally substituted quinolin-8-yl).

Optional substituents of $G^1$ are as described in the Summary. Examples of the optional substituents of $G^1$ include, but are not limited to, alkenyl, alkyl, —$NO_2$, —CN, halogen, —$OR^e$, —O—$(CR^jR^k)_n$—$N(R^w)_2$, —$SF_5$, —$SR^e$, —$S(O)_2R^f$, —$N(R^e)(R^g)$, —$N(R^g)C(O)O(R^f)$, —$N(R^g)S(O)_2R^f$, —$N(R^g)S(O)_2N(R^e)(R^g)$, —$C(O)R^e$, —$C(O)O(R^e)$, alkoxyalkenyl, hydroxyalkenyl, haloalkyl, —$(CR^jR^k)_q$—$OR^e$, —$(CR^jR^k)_q$—$C(O)O(R^e)$, —$C(R^w)$=N—$OR^w$; and morpholinyl; wherein $R^e$, $R^j$, $R^k$, $R^f$, $R^w$, n, q, and $R^g$ are as disclosed in the Summary and in embodiments herein. For example, in certain embodiments, the optional substituents of $G^1$ are alkyl (e.g. $C_1$-$C_4$ alkyl such as, but not limited thereto, methyl, ethyl); alkenyl (e.g. vinyl, prop-1-enyl), —$NO_2$, —CN; halogen (e.g. Cl, Br, F), —$OR^e$ ($R^e$, for example, is hydrogen, alkyl such as methyl, ethyl, tert-butyl, and the like; alkoxyalkyl such as 3-methoxy3-methylbutyl, 2-methoxyethyl, 2-methoxypropyl, 3-ethoxypropyl, 3-methoxypropyl, 2-ethoxyethyl, and the like; alkenyl such as, but not limited to, 3-methylbut-2-enyl and the like; haloalkyl such as 2,2,2-trifluoroethyl, 2-fluoroethyl, 2,2-difluoroethyl, 2-fluoropropyl, 2-fluoro-1-methylethyl, 3-fluoro-3-methylbutyl, and the like; cycloalkylalkyl such as cyclopropylmethyl, cyclobutylmethyl, cyclopentylmethyl, cyclopentylethyl, and the like, wherein the cyclopropyl, cyclobutyl and the cyclopentyl moieties are each optionally substituted as described in the Summary; or optionally substituted heterocycle such as tetrahydrofuranyl, azetidinyl, pyrrolidinyl, and the like, each of which is optionally substituted; and optionally substituted phenyl); —O—$(CR^jR^k)_n$—$N(R^w)_2$ (e.g. $R^j$, $R^k$, and $R^w$, are each independently hydrogen or alkyl such as, but not limited to, methyl); —$SF_5$; —$SR^e$ (e.g. $R^e$ is heteroaryl such as oxidopyridinyl); —$S(O)_2R^f$ ($R^f$, for example, is $C_1$-$C_4$ alkyl such as, but not limited to, methyl); —$N(R^e)(R^g)$ (e.g., $R^e$ is hydrogen, alkyl (e.g. methyl), haloalkyl (e.g., 2-fluoroethyl), or alkoxyalkyl (e.g. 2-methyoxyethyl, 2-ethoxyethyl), and $R^g$, for example, is hydrogen, alkyl, or alkoxyalkyl such as, but not limited to, 2-methyoxyethyl, 2-ethoxyethyl); —$N(R^g)C(O)O(R^e)$($R^g$, for example, is hydrogen, $R^f$, for example, is $C_1$-$C_4$ alkyl such as, but not limited to, methyl, ethyl, tert-butyl); —$N(R^g)S(O)_2R^f$($R^g$, for example, is hydrogen, $R^f$, for example, is $C_1$-$C_4$ alkyl such as, but not limited to, methyl, ethyl, isobutyl); —$N(R^g)S(O)_2N(R^e)(R^g)$($R^e$ and $R^g$, for example, are each independently, hydrogen or $C_1$-$C_4$ alkyl such as, but not limited to, methyl, ethyl); —$C(O)R^e$ ($R^e$, for example, is $C_1$-$C_4$ alkyl such as, but not limited to, methyl, ethyl); —$C(O)O(R^e)$($R^e$, for example, is alkyl such as, but not limited to, methyl, ethyl, tert-butyl); alkoxyalkenyl (e.g. 3-methoxyprop-1-enyl and the like); hydroxyalkenyl (e.g. 3-hydroxyl-3-methylbut-1-enyl, and the like); haloalkyl (e.g., trifluoromethyl and the like); —$(CR^jR^k)_q$—$OR^e$ ($R^j$, $R^k$, and $R^e$ are, for example, each independently hydrogen or $C_1$-$C_4$ alkyl such as, but not limited to, methyl, ethyl); —$(CR^jR^k)_q$—$C(O)O(R^e)$($R^j$, $R^k$, and $R^e$ at each occurrence, are for example, hydrogen or $C_1$-$C_4$ alkyl such as, but not limited to, methyl, tert-butyl); —$C(R^w)$=N—$OR^w$ (each $R^w$, for example, is independently hydrogen or $C_1$-$C_4$ alkyl such as methyl, ethyl, tert-butyl); and morphilinyl.

Other embodiments are directed to compounds wherein $R^1$ is —$N(R^{1a})(R^z)$, and $R^{1a}$ and $R^z$ are as defined in the Summary and in embodiments herein. For example, $R^{1a}$ is hydrogen or alkyl (e.g. $C_1$-$C_4$ alkyl such as, but not limited to, methyl, ethyl). In certain embodiments, $R^{1a}$ is hydrogen.

Examples of $R^z$ include, but are not limited to, alkyl (e.g. $C_4$-$C_8$ alkyl such as, but not limited to, neopentyl, 2-ethylhexyl, tert-butyl, 1,2-dimethylpropyl, 1-ethylpropyl, and the like); $G^2$ such as optionally substituted cycloalkyl (e.g. cyclopentyl, cyclohexyl, cycloheptyl, each of which is optionally substituted), or optionally substituted aryl (e.g. optionally substituted 1,2,3,4-tetrahydronaphthalenyl); —$(CR^xR^y)_m$-$G^2$ ($G^2$, for example, is optionally substituted cycloalkyl such as, but not limited to, cyclopentyl, cyclohexyl, adamantyl or bicyclo[3.1.1]heptyl, each of which is optionally substituted; or optionally substituted aryl such as, but not limited to, optionally substituted phenyl; $R^x$ and $R^y$ are, for example, hydrogen or alkyl such as, but not limited to $C_1$-$C_4$ alkyl); —$(CR^xR^y)_m$—$C(O)N(R^{za})(R^{zb})$ (e.g. ($R^{za}$ and $R^{zb}$, are each independently hydrogen or $C_1$-$C_4$ alkyl such as, but not limited to, methyl, ethyl, $R^x$ is hydrogen, alkyl (e.g. $C_1$-$C_4$ alkyl such as, but not limited to, isopropyl, 1-methylpropyl, tert-butyl, isobutyl), or benzyl; $R^y$, for example, is hydrogen; m, for example, is 1 or 2); or —$(CR^xR^y)_n$—$OR^{za}$ (e.g., $R^{za}$ is hydrogen, $R^x$ is hydrogen or alkyl (e.g. $C_1$-$C_4$ alkyl such as, but not limited to, isopropyl, 1-methylpropyl, tert-butyl, isobutyl); $R^y$ is, for example, hydrogen, and n, for example, is 2).

Ring A of formula (I) is described generally in the Summary and in embodiments herein.

In certain embodiments, ring A is formula (a)

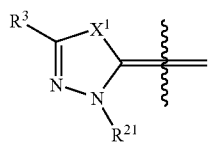

(a)

wherein $R^3$, $X^1$, and $R^{21}$ are as described in the Summary and in embodiments herein.

Examples of compounds include, but are not limited to, those wherein $X^1$ is S.

In conjunction with any of the embodiments herein above and below, examples of $R^3$ include, but are not limited to, alkyl (e.g. $C_1$-$C_4$ alkyl such as, but not limited to, methyl, isopropyl, tert-butyl), alkenyl, alkynyl (e.g. 1,1-dimethylprop-2-yny), haloalkyl (e.g. 2,2,2-trifluoro-1,1-dimethylethyl), or optionally substituted cycloalkyl (e.g. optionally substituted $C_3$-$C_6$ cycloalkyl). In certain embodiments, $R^3$ is alkyl (e.g. $C_1$-$C_4$ alkyl such as, but not limited to, methyl, isopropyl, tert-butyl, and the like) or optionally substituted cycloalkyl (e.g. optionally substituted $C_3$-$C_6$ cycloalkyl). In certain embodiments, $R^3$ is alky (e.g. $C_1$-$C_4$ alkyl such as, but not limited to, methyl, isopropyl, tert-butyl, and the like). In certain embodiments, $R^3$ is optionally substituted cycloalkyl (e.g. optionally substituted $C_3$-$C_6$ cycloalkyl). Particular examples of $R^3$ include, but are not limited to, methyl, isopropyl, tert-butyl, 1,1-dimethylprop-2-ynyl, 2,2,2-trifluoro-1,1-dimethylethyl, optionally substituted $C_3$-$C_6$ cycloalkyl (e.g. cyclopropyl, and cyclobutyl, wherein the cyclopropyl and cyclobutyl are independently unsubstituted or substituted as described in the Summary and herein below). Examples of the optional substituents of cycloalkyl include, but are not limited to, alkyl (e.g. $C_1$-$C_4$ alkyl such as, but not limited to, methyl, ethyl), haloalkyl (e.g. trifluoromethyl), and halogen (e.g. F, Cl, Br).

In other embodiments, ring A is formula (b)

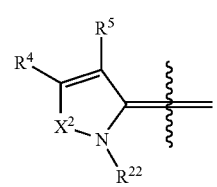

(b)

wherein $R^4$, $R^5$, $R^{22}$, and $X^2$ are as defined in the Summary and in embodiments herein.

In conjunction with any of the embodiments herein above and below, examples of $R^4$ include, but are not limited to, alkyl (e.g. $C_1$-$C_4$ alkyl such as, but not limited to, tert-butyl) or optionally substituted $C_3$-$C_6$ cycloalkyl. For example, $R^4$ is tert-butyl or optionally substituted cyclopropyl. In certain embodiments, $R^4$ is tert-butyl.

$R^5$, for example, is hydrogen, alkyl, or halogen. In certain embodiments, $R^5$ is hydrogen or halogen (e.g. Br). In certain embodiments, $R^5$ is hydrogen.

Certain embodiments include, but are not limited to, compounds wherein $R^4$ and $R^5$, together with the carbon atoms to which they are attached, form an optionally substituted monocyclic cycloalkyl ring (e.g. an optionally substituted cyclopentyl).

In certain embodiments, $X^2$ is O.

In yet other embodiments, $X^2$ is $N(R^{10})$ wherein $R^{10}$ is as disclosed in the Summary. For example, $R^{10}$ is $C_1$-$C_4$ alkyl such as, but not limited to, methyl.

Yet other embodiments direct to compounds of formula (I) wherein ring A is formula (c)

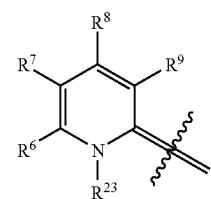

(c)

wherein $R^6$, $R^7$, $R^8$, $R^9$ and $R^{23}$ are as defined in the Summary and embodiments herein.

$R^6$ and $R^9$ are, for example, hydrogen.

$R^7$ and $R^8$ are, for example, each independently hydrogen or $C_1$-$C_4$ alkyl such as, but not limited to, methyl, ethyl, tert-butyl, and the like.

Yet still other embodiments provide compounds wherein ring A is formula (d)

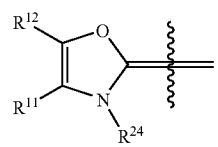

(d)

wherein $R^{11}$, $R^{12}$, and $R^{24}$ are as defined in the Summary.

For example, $R^{12}$ is alkyl (e.g. $C_1$-$C_4$ alkyl). For example, $R^{11}$ is tert-butyl.

Certain compounds include, but are not limited to, those wherein $R^{11}$ is hydrogen, alkyl, or halogen. In certain embodiments, $R^{11}$ is hydrogen.

$R^{21}$, $R^{22}$, $R^{23}$, and $R^{24}$ in formula (a), (b), (c), and (d) are as described generally in the Summary and in embodiments herein. For example, $R^{21}$, $R^{22}$, $R^{23}$, and $R^{24}$ are each independently -alkylene-$G^3$, and $G^3$, at each occurrence, is independently a 4-, 5-, or 6-membered monocyclic heterocycle containing zero or one double bond, one or two oxygen, and zero or one nitrogen as ring atoms, and each $G^3$ is optionally substituted as described in the Summary and in embodiments herein. For example, $G^3$ is a 4-, 5-, or 6-membered monocyclic heterocycle containing zero double bond, one or two oxygen, and zero or one nitrogen atom as ring atom, and each $G^3$ is optionally substituted as described in the Summary and in embodiments herein. Examples of such monocyclic heterocycle rings include, but are not limited to, oxetanyl (including but not limited thereto, oxetan-2-yl), oxazolidinyl (including but not limited thereto, 1,3-oxazolidin-4-yl), tetrahydrofuranyl (including but not limited thereto, tetrahydrofuran-2-yl and tetrahydrofuran-3-yl), tetrahydropyranyl (including but not limited thereto, tetrahydropyran-2-yl, tetrahydropyran-3-yl and tetrahydropyran-4-yl), 1,3-dioxalanyl (including but not limited thereto, 1,3-dioxalan-2-yl and 1,4-dioxalan-2-yl), and 1,4-dioxanyl (including but not limited thereto, 1,4-dioxan-2-yl). Each of these exemplary rings is independently unsubstituted or substituted as described in the Summary and in embodiments herein. For example, each can be unsubstituted or substituted with 1 or 2 groups selected from the group consisting of $C_1$-$C_4$ alkyl (such as, but not limited to, methyl), halogen (e.g. F), haloalkyl, oxo, —OH, —O(alkyl) (including, but not limited to —$OCH_3$), and —O(haloalkyl).

Other compounds include, but are not limited to, those wherein $R^{21}$, $R^{22}$, $R^{23}$, and $R^{24}$ are each independently -alkylene-$G^3$, and examples of $G^3$ include, but are not limited to, tetrahydrofuranyl (including but not limited thereto, tetrahydrofuran-2-yl and tetrahydrofuran-3-yl), tetrahydropyranyl (including but not limited thereto, tetrahydropyran-2-yl, tetrahydropyran-3-yl and tetrahydropyran-4-yl), and oxazolidinyl (including but not limited thereto, 1,3-oxazolidin-4-yl), each of which is optionally substituted as described in the Summary and in the preceding paragraph. Particularly, $R^{21}$, $R^{22}$, $R^{23}$, and $R^{24}$ are each tetrahydrofuranylmethyl, tetrahydropyranylmethyl, or oxazolidinylmethyl, wherein each of the tetrahydrofuranyl, tetrahydropyranyl, and oxazolidinyl moieties is independently unsubstituted or substituted as described in the Summary and in the preceding paragraph. More particularly, $R^{21}$, $R^{22}$, $R^{23}$ and $R^{24}$ are tetrahydrofuran-2-ylmethyl, tetrahydrofuran-3-ylmethyl, 1,3-oxazolidin-4-ylmethyl, or tetrahydropyran-2-ylmethyl wherein the tetrahydrofuran-2-yl, tetrahydrofuran-3-yl, 1,3-oxazolidin-4-yl, and the tetrahydropyran-2-yl moieties are each independently unsubstituted or substituted as described in the Summary and in the preceding paragraph.

Yet other exemplary compounds include, but are not limited to, those wherein $R^{21}$, $R^{22}$, $R^{23}$, and $R^{24}$ are each -alkylene-$G^3$, $G^3$ is furanyl, oxazolyl, isoxazolyl, or oxadiazolyl, and each $G^3$ is independently unsubstituted or substituted as described herein.

It is appreciated that compounds of formula (I) with combinations of the above embodiments, including particular, more particular and preferred embodiments are contemplated.

Accordingly, one aspect is directed to compounds of formula (I) wherein ring A is formula (a), or pharmaceutically acceptable salts, solvates, prodrugs, salts of prodrugs, or combinations thereof. Thus, it is understood that these compounds would have formula as represented by formula (Ia)

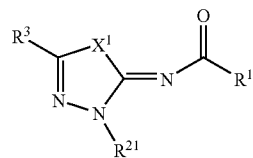

(Ia)

wherein $X^1$, $R^1$, $R^3$, and $R^{21}$ are as described for formula (I) in the Summary and the Detailed Description sections. In certain embodiments, $X^1$ is S.

Another aspect relates to compounds of formula (I) wherein ring A is formula (b), or pharmaceutically acceptable salts, solvates, prodrugs, salts of prodrugs, or combinations thereof. Such compounds are represented by formula (Ib)

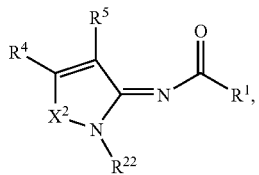

(Ib)

wherein $X^2$, $R^1$, $R^4$, $R^5$, and $R^{22}$ are as disclosed for formula (I) in the Summary and the Detailed Description sections. In certain embodiments, $X^2$ is O. In other embodiments, $X^2$ is $N(R^{10})$ wherein $R^{10}$ is alkyl (e.g. $C_1$-$C_4$ alkyl such as, but not limited to, methyl).

Yet another aspect relates to compounds of formula (I) wherein ring A is formula (c), or pharmaceutically acceptable salts, solvates, prodrugs, salts of prodrugs, or combinations thereof. Such compounds are represented by formula (Ic)

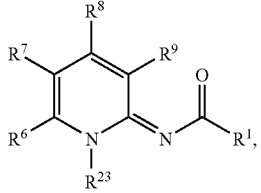

(Ic)

wherein $R^1$, $R^6$, $R^7$, $R^8$, $R^9$, and $R^{23}$ have values as disclosed for formula (I) in the Summary and the Detailed Description sections.

Yet another aspect contemplates compounds of formula (I) wherein ring A is formula (d), or pharmaceutically acceptable salts, solvates, prodrugs, salts of prodrugs, or combinations thereof. Such compounds are represented by formula (Id)

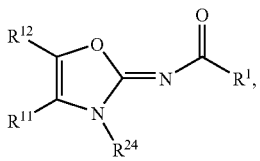

(Id)

wherein $R^1$, $R^{11}$, $R^{12}$, and $R^{24}$ are as described for formula (I) in the Summary and the Detailed Description sections.

For example, within each of the foregoing compounds, examples of a group of compounds include those having formula (I), (Ia), (Ib), (Ic), or (Id) wherein $R^{21}$, $R^{22}$, $R^{23}$, and $R^{24}$ are independently -alkylene-$G^3$, each $G^3$ is a 4-, 5-, or 6-membered monocyclic heterocycle containing zero or one double bond, one or two oxygen, and zero or one nitrogen as ring atoms, and each $G^3$ is optionally substituted as described in the Summary. For example, $G^3$ is a 4-, 5-, or 6-membered monocyclic heterocycle containing zero double bond, one or two oxygen, and zero or one nitrogen atom as ring atom, and $G^3$ is optionally substituted as described in the Summary. Examples of such monocyclic heterocycles include, but are not limited to, oxetanyl (including but not limited thereto, oxetan-2-yl), oxazolidinyl (including but not limited thereto, 1,3-oxazolidin-4-yl), tetrahydrofuranyl (including but not limited thereto, tetrahydrofuran-2-yl and tetrahydrofuran-3-yl), tetrahydropyranyl (including but not limited thereto, tetrahydropyran-2-yl, tetrahydropyran-3-yl, and tetrahydropyran-4-yl), 1,3-dioxalanyl (including but not limited thereto, 1,3-dioxalan-2-yl and 1,4-dioxalan-2-yl), and 1,4-dioxanyl (including but not limited thereto, 1,4-dioxan-2-yl). Each of these exemplary rings is independently unsubstituted or substituted as described in the Summary. For example, each can be independently unsubstituted or substituted with 1 or 2 substituents selected from the group consisting of $C_1$-$C_4$ alkyl (such as, but not limited to, methyl), halogen (e.g. F), haloalkyl, oxo, —OH, —O(alkyl) (e.g. $OCH_3$), and —O(haloalkyl).

Examples of another group of compounds having formula (I), (Ia), (Ib), (Ic), or (Id) include, but are not limited to, those wherein $R^{21}$, $R^{22}$, $R^{23}$, and $R^{24}$ are each independently -alkylene-$G^3$, and each $G^3$ is tetrahydrofuranyl (including but not limited thereto, tetrahydrofuran-2-yl and tetrahydrofuran-3-yl), tetrahydropyranyl (including but not limited thereto, tetrahydropyran-2-yl, tetrahydropyran-3-yl, and tetrahydropyran-4-yl), or oxazolidinyl (including but not limited thereto, 1,3-oxazolidin-4-yl), each of which is optionally substituted as described in the Summary and in the preceding paragraph.

Examples of yet another group of compounds having formula (I), (Ia), (Ib), (Ic), or (Id) include, but are not limited to, those wherein $R^{21}$, $R^{22}$, $R^{23}$, and $R^{24}$ are -alkylene-$G^3$, and -alkylene-$G^3$ is independently tetrahydrofuranylmethyl, tetrahydropyranylmethyl, or oxazolidinylmethyl wherein each of the tetrahydrofuranyl, tetrahyropyranyl, and oxazolidinyl moieties is independently unsubstituted or substituted as described in the Summary and in the preceding paragraph.

Further examples of a group of compounds having formula (I), (Ia), (Ib), (Ic), or (Id) include, but are not limited to, those wherein $R^{21}$, $R^{22}$, $R^{23}$, and $R^{24}$ are each independently tetrahydrofuran-2-ylmethyl, tetrahydrofuran-3-ylmethyl, 1,3-oxazolidin-4-ylmethyl, tetrahydropyran-2-ylmethyl, wherein the tetrahydrofuran-2-yl, tetrahydrofuran-3-yl, 1,3-oxazolidin-4-yl, and the tetrahydropyran-2-yl moieties are each independently unsubstituted or substituted as described in the Summary and in the preceding paragraph.

Within each group of compounds of formula (I), (Ia), (Ib), (Ic), or (Id) as described herein, $R^1$, $R^3$, $R^4$, $R^5$, $R^6$, $R^7$, $R^8$, $R^9$, $R^{11}$, $R^{12}$, $X^1$, and $X^2$ have values as disclosed in the Summary and the Detailed Description.

Thus, of each groups of compounds of formula (I), (Ia), (Ib), (Ic), or (Id) as described in the preceding paragraphs, examples of a subgroup include, but not limited to, those wherein $R^1$ is $G^1$ or —N($R^{1a}$)($R^z$) wherein $G^1$, $R^{1a}$ and $R^z$ are as defined in the Summary and in Detailed Description sections.

Other examples of a subgroup include, but not limited to, those wherein $R^1$ is $G^1$, and $G^1$ is as disclosed in the Summary and embodiments herein.

Other examples of a subgroup include, but are not limited to, those wherein $R^1$ is $G^1$, and $G^1$ is phenyl or naphthyl, each of which is optionally substituted as described in the Summary and the Detailed Description sections. For example, $G^1$ is optionally substituted phenyl.

Yet other examples of a subgroup include those wherein $R^1$ is $G^1$, and $G^1$ for example, is optionally substituted cycloalkyl (for example, adamantyl, bicyclo[2.2.1]heptyl, each of which is optionally substituted).

Still other examples of a subgroup include those wherein $R^1$ is $G^1$, and $G^1$ is heterocycle, optionally substituted as described in the Summary and in the Detailed Description. For example, $G^1$ is optionally substituted 2,3-dihydrobenzofuranyl (including optionally substituted 2,3-dihydro-1-benzofuran-7-yl).

Further examples of a subgroup include those wherein $R^1$ is $G^1$, and $G^1$ is heteroaryl, optionally substituted as described in the Summary and the Detailed Description. For example, $G^1$ is optionally substituted quinolinyl (including, but not limited to, optionally substituted quinolin-8-yl).

Examples of the optional substituents of $G^1$ are as described in the Summary and in embodiments herein above.

Yet other examples of a subgroup include those wherein $R^1$ is —N($R^{1a}$)($R^z$) wherein $R^{1a}$ and $R^z$ are as defined in the Summary and in Detailed Description sections. For example, $R^{1a}$ is hydrogen or alkyl. In certain embodiments, $R^{1a}$ is hydrogen. Examples of $R^z$ include, but are not limited to, alkyl (e.g. $C_4$-$C_8$ alkyl such as, but not limited to, neopentyl, 2-ethylhexyl, tert-butyl, 1,2-dimethylpropyl, 1-ethylpropyl, and the like); $G^2$ such as optionally substituted cycloalkyl (e.g. cyclopentyl, cyclohexyl, cycloheptyl, each of which is optionally substituted), or optionally substituted aryl (e.g. optionally substituted 1,2,3,4-tetrahydronaphthalenyl); —($CR^xR^y$)$_m$-$G^2$ ($G^2$, for example, is optionally substituted cycloalkyl such as, but not limited to, cyclohexyl, adamantyl or bicyclo[3.1.1]heptyl, each of which is optionally substituted; or optionally substituted aryl such as, but not limited to, optionally substituted phenyl; $R^x$ and $R^y$ are, for example, hydrogen or alkyl such as, but not limited to $C_1$-$C_4$ alkyl); —($CR^xR^y$)$_m$—C(O)N($R^{za}$)($R^{zb}$)(e.g. ($R^{za}$ and $R^{zb}$, are each independently hydrogen or $C_1$-$C_4$ alkyl such as, but not limited to, methyl, ethyl, $R^x$ is hydrogen, alkyl (e.g. $C_1$-$C_4$ alkyl such as, but not limited to, isopropyl, 1-methylpropyl, tert-butyl, isobutyl), or benzyl; $R^y$, for example, is hydrogen; m, for example, is 1 or 2); or —($CR^xR^y$)$_n$—$OR^{za}$ (e.g., $R^{za}$ is hydrogen, $R^x$ is hydrogen or alkyl (e.g. $C_1$-$C_4$ alkyl such as, but not limited to, isopropyl, 1-methylpropyl, tert-butyl, isobutyl); $R^y$ is, for example, hydrogen, and n, for example, is 2).

Of all examples of the groups and subgroups of compounds of formula (I), (Ia), (Ib), (Ic), or (Id) as discussed hereinabove, $R^3$, $R^4$, $R^5$, $R^6$, $R^7$, $R^8$, $R^9$, $R^{11}$, $R^{12}$, $X^1$, $X^2$, and the optional substituents of $G^1$ have values as defined in the Summary and the Detailed Description.

For example, for each of the foregoing groups and subgroups of compounds of formula (I) and (Ia), an example of $X^1$ is S. $R^3$ for compounds of formula (I) or (Ia) is, for example, alkyl (e.g. $C_1$-$C_4$ alkyl such as, but not limited to, methyl, isopropyl, tert-butyl, and the like), alkenyl, alkynyl (e.g. 1,1-dimethylprop-2-ynyl), haloalkyl, or optionally substituted cycloalkyl (e.g. optionally substituted $C_3$-$C_6$ cycloalkyl). In certain embodiments, $R^3$ is alkyl (e.g. $C_1$-$C_4$ alkyl such as, but not limited to, methyl, isopropyl, tert-butyl, and the like) or optionally substituted cycloalkyl (e.g. optionally substituted $C_3$-$C_6$ cycloalkyl). In certain embodiments, $R^3$ is alky (e.g. $C_1$-$C_4$ alkyl such as, but not limited to, methyl, isopropyl, tert-butyl, and the like). In certain embodiments, $R^3$ is optionally substituted cycloalkyl (e.g. optionally substituted $C_3$-$C_6$ cycloalkyl). Particular examples of $R^3$ include, but are not limited to, methyl, isopropyl, tert-butyl, 1,1-dimethylprop-2-ynyl, 2,2,2-trifluoro-1,1-dimethylethyl, cyclopropyl, and cyclobutyl, wherein the cyclopropyl and cyclobutyl are independently unsubstituted or substituted as described in the Summary and in the Detailed Description sections. Examples of the optional substituents of said cycloalkyl include, but are not limited to, alkyl (e.g. $C_1$-$C_4$ alkyl such as, but not limited to, methyl, ethyl), haloalkyl (e.g. trifluoromethyl), and halogen (e.g. F, Cl, Br).

For each of the foregoing groups and subgroups of compounds of formula (I) and (Ib), $R^4$, for example, is alkyl (e.g. $C_1$-$C_4$ alkyl) or optionally substituted cycloalkyl. Particularly, $R^4$ is tert-butyl or optionally substituted cyclopropyl. In certain embodiments, $R^4$ is tert-butyl. $R^5$, for example, is hydrogen, alkyl, or halogen (e.g. Br). In certain embodiments, $R^5$ is hydrogen. In certain embodiments, $X^2$ is O. In other embodiments, $X^2$ is $N(R^{10})$ wherein $R^{10}$ is as disclosed in the Summary. For example, $R^{10}$ is $C_1$-$C_4$ alkyl such as, but not limited to, methyl. Certain embodiments of the foregoing groups and subgroups of compounds of formula (I) or (Ib) described in the preceding paragraphs include those wherein $R^4$ and $R^5$, together with the carbon atoms to which they are attached, form an optionally substituted monocyclic cycloalkyl ring (e.g. an optionally substituted cyclopentyl).

For each of the foregoing groups and subgroups of compounds of formula (I) and (Ic), $R^6$ and $R^9$ are, for example, hydrogen. $R^7$ and $R^8$ are, for example, each independently hydrogen or $C_1$-$C_4$ alkyl such as, but not limited to, methyl, tert-butyl, and the like.

For each of the foregoing groups and subgroups of compounds of formula (I) and (Id), $R^{12}$, for example, is alkyl (e.g. $C_1$-$C_4$ alkyl such as, but not limited to, tert-butyl and the like). $R^{11}$, for example, is hydrogen, alkyl, or halogen. In certain embodiments, $R^{11}$ is hydrogen.

Exemplary compounds of formula (I) include, but are not limited to, those wherein ring A is formula (a), $R^1$ is $G^1$, and $G^1$ is phenyl or naphthyl, each of which is independently unsubstituted or substituted, $X^1$ is S, $R^3$ is alkyl or optionally substituted cycloalkyl, $R^{21}$ is -alkylene-$G^3$ and -alkylene-$G^3$ is independently tetrahydrofuranylmethyl, tetrahydropyranylmethyl, or oxazolidinylmethyl wherein each of the tetrahydrofuranyl, tetrahyropyranyl, and oxazolidinyl moieties is independently unsubstituted or substituted as described in the Summary and in the preceding paragraph.

Exemplary compounds of formula (I) also include, but are not limited to, those wherein ring A is formula (b), $R^1$ is $G^1$, and $G^1$ is phenyl or naphthyl, each of which is independently unsubstituted or substituted, $X^2$ is $N(R^{10})$, $R^{10}$ is $C_1$-$C_4$ alkyl, $R^4$ is tert-butyl or optionally substituted cyclopropyl, $R^5$ is hydrogen, $R^{22}$ is -alkylene-$G^3$ and -alkylene-$G^3$ is independently tetrahydrofuranylmethyl, tetrahydropyranylmethyl, or oxazolidinylmethyl wherein each of the tetrahydrofuranyl, tetrahyropyranyl, and oxazolidinyl moieties is independently unsubstituted or substituted as described in the Summary and in the preceding paragraph.

Exemplary compounds of formula (I) also include, but are not limited to, those wherein ring A is formula (c), $R^1$ is $G^1$, and $G^1$ is phenyl or naphthyl, each of which is independently unsubstituted or substituted, $R^6$ and $R^9$ are hydrogen, $R^7$ and $R^8$ are each independently hydrogen or $C_1$-$C_4$ alkyl, $R^{23}$ is -alkylene-$G^3$ and -alkylene-$G^3$ is independently tetrahydrofuranylmethyl, tetrahydropyranylmethyl, or oxazolidinylmethyl wherein each of the tetrahydrofuranyl, tetrahyropyranyl, and oxazolidinyl moieties is independently unsubstituted or substituted as described in the Summary and in the preceding paragraph.

Exemplary compounds of formula (I) include, but are not limited to:

5-chloro-2-methoxy-N-[(2Z)-3-[(2R)-tetrahydrofuran-2-ylmethyl]-5-[1-(trifluoromethyl)cyclopropyl]-1,3,4-thiadiazol-2(3H)-ylidene]benzamide;

5-chloro-N-[(2Z)-5-cyclopropyl-3-(tetrahydrofuran-2-ylmethyl)-1,3,4-thiadiazol-2(3H)-ylidene]-2-methoxybenzamide;

N-[(2Z)-5-cyclopropyl-3-(tetrahydrofuran-2-ylmethyl)-1,3,4-thiadiazol-2(3H)-ylidene]-2-ethoxybenzamide;

N-[(2Z)-5-tert-butyl-3-[(2R)-tetrahydrofuran-2-ylmethyl]-1,3,4-thiadiazol-2(3H)-ylidene]-5-chloro-2-methoxybenzamide;

5-chloro-2-methoxy-N-[(2Z)-5-(1-methylcyclopropyl)-3-[(2R)-tetrahydrofuran-2-ylmethyl]-1,3,4-thiadiazol-2 (3H)-ylidene]benzamide;

5-chloro-N-[(2Z)-5-(1,1-dimethylprop-2-ynyl)-3-[(2R)-tetrahydrofuran-2-ylmethyl]-1,3,4-thiadiazol-2(3H)-ylidene]-2-methoxybenzamide;

5-chloro-2-methoxy-N-[(2Z)-5-(2,2,3,3-tetrafluoro-1-methylcyclobutyl)-3-[(2R)-tetrahydrofuran-2-ylmethyl]-1,3,4-thiadiazol-2(3H)-ylidene]benzamide;

5-chloro-2-methoxy-N-[(2Z)-3-[(2R)-tetrahydrofuran-2-ylmethyl]-5-[1-(trifluoromethyl)cyclobutyl]-1,3,4-thiadiazol-2(3H)-ylidene]benzamide;

5-chloro-2-methoxy-N-[(2Z)-3-[(2R)-tetrahydrofuran-2-ylmethyl]-5-(2,2,2-trifluoro-1,1-dimethylethyl)-1,3,4-thiadiazol-2(3H)-ylidene]benzamide;

5-chloro-2-methoxy-N-[(2E)-5-methyl-1-(tetrahydrofuran-2-ylmethyl)pyridin-2(1H)-ylidene]benzamide;

N-[(3E)-5-tert-butyl-2-[(2R)-tetrahydrofuran-2-ylmethyl] isoxazol-3 (2H)-ylidene]-5-chloro-2-methoxybenzamide;

N-{(3E)-5-tert-butyl-1-methyl-2-[(2S)-tetrahydrofuran-2-ylmethyl]-1,2-dihydro-3H-pyrazol-3-ylidene}-5-chloro-2-methoxybenzamide;

N-[(2Z)-5-tert-butyl-3-[(2R)-tetrahydrofuran-2-ylmethyl]-1,3-oxazol-2(3H)-ylidene]-5-chloro-2-methoxybenzamide;

N-{(3E)-5-tert-butyl-1-methyl-2-[(2R)-tetrahydrofuran-2-ylmethyl]-1,2-dihydro-3H-pyrazol-3-ylidene}-2-ethoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-(pentafluoro-lambda~6~-sulfanyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(cis-3-hydroxycyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3-oxocyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(cis-3-methoxycyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3,3-difluorocyclobutypmethoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-methoxy-3-methylbutoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2,2,2-trifluoroethoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-hydroxy-5-(trifluoromethyl)benzamide;
2-tert-butoxy-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[2-(dimethylamino)ethoxy]-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(dimethylamino)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-{[(2S)-2-methoxypropyl]oxy}-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(3-ethoxypropoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(3-methoxypropoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(2-ethoxyethoxy)-5-(trifluoromethyl)benzamide;
2-methoxy-N-[(3E)-1-methyl-2-[(2R)-tetrahydrofuran-2-ylmethyl]-1,4,5,6-tetrahydrocyclopenta[c]pyrazol-3(2H)-ylidene]-5-(trifluoromethyl)benzamide;
2-methoxy-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[(2-methoxyethyl)amino]-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(2,2-difluoroethoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[(3R)-tetrahydrofuran-3-yloxy]-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[(3S)-tetrahydrofuran-3-yloxy]-5-(trifluoromethyl)benzamide;
(E)-N-(5-tert-butyl-2-(((2R,3R)-3-fluorotetrahydrofuran-2-yl)methyl)-1-methyl-1H-pyrazol-3(2H)-ylidene)-2-methoxy-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[(2-fluoroethyl)amino]-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(2-fluoropropoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-{[(2R)-2-fluoropropyl]oxy}-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(2-fluoro-1-methylethoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(3-fluoro-3-methylbutoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[(1-hydroxycyclobutyl)methoxy]-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-5-chloro-2-methoxybenzamide;
N-{(3E)-5-tert-butyl-1-methyl-2-[(2R)-tetrahydrofuran-2-ylmethyl]-1,2-dihydro-3H-pyrazol-3-ylidene}-2-fluoro-3-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-methoxy-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-5-cyano-2-methoxybenzamide;
5-bromo-N-{(3E)-5-tert-butyl-1-methyl-2-[(2R)-tetrahydrofuran-2-ylmethyl]-1,2-dihydro-3H-pyrazol-3-ylidene}-2-methoxybenzamide;
N-{(3E)-5-tert-butyl-1-methyl-2-[(2R)-tetrahydrofuran-2-ylmethyl]-1,2-dihydro-3H-pyrazol-3-ylidene}-2-chloro-5-fluorobenzamide;
N-{(3E)-5-tert-butyl-1-methyl-2-[(2R)-tetrahydrofuran-2-ylmethyl]-1,2-dihydro-3H-pyrazol-3-ylidene}-2,3,5-trifluorobenzamide;
N-{(3E)-5-tert-butyl-1-methyl-2-[(2R)-tetrahydrofuran-2-ylmethyl]-1,2-dihydro-3H-pyrazol-3-ylidene}-3-chloro-2-fluoro-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-3-chloro-2-methoxy-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-chloro-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-3,5-difluoro-2-methoxybenzamide;
N-{(3E)-5-tert-butyl-1-methyl-2-[(2R)-tetrahydrofuran-2-ylmethyl]-1,2-dihydro-3H-pyrazol-3-ylidene}-3-chloro-2-(2-methoxyethoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-3-chloro-2-(2-fluoro ethoxy)-5-(trifluoromethyl)benzamide;
5-bromo-N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)benzamide;
5-bromo-N-{(3E)-5-tert-butyl-1-methyl-2-[(2R)-tetrahydrofuran-2-ylmethyl]-1,2-dihydro-3H-pyrazol-3-ylidene}-2-(2-fluoro ethoxy)benzamide;
5-bromo-N-{(3E)-5-tert-butyl-1-methyl-2-[(2R)-tetrahydrofuran-2-ylmethyl]-1,2-dihydro-3H-pyrazol-3-ylidene}-2,3-dihydro-1-benzofuran-7-carboxamide;
N-[(2E)-4-tert-butyl-1-[(2R)-tetrahydrofuran-2-ylmethyl]pyridin-2(1H)-ylidene]-5-chloro-2-methoxybenzamide;
N-[(2E)-4-tert-butyl-1-[(2R)-tetrahydrofuran-2-ylmethyl]pyridin-2(1H)-ylidene]-2-methoxy-5-(trifluoromethyl)benzamide;
N-[(3E)-5-tert-butyl-1-methyl-2-(tetrahydro-2H-pyran-2-ylmethyl)-1,2-dihydro-3H-pyrazol-3-ylidene]-2-methoxy-5-(trifluoromethyl)benzamide;
N-((3E)-5-tert-butyl-1-methyl-2-{[(5R)-5-methyltetrahydrofuran-2-yl]methyl}-1,2-dihydro-3H-pyrazol-3-ylidene)-2-methoxy-5-(trifluoromethyl)benzamide;

N-((3E)-5-tert-butyl-1-methyl-2-{[(5S)-5-methyltetrahydrofuran-2-yl]methyl}-1,2-dihydro-3H-pyrazol-3-ylidene)-2-methoxy-5-(trifluoromethyl)benzamide;

N-[(2Z)-5-tert-butyl-3-[(2R)-tetrahydrofuran-2-ylmethyl]-1,3-oxazol-2(3H)-ylidene]-2-methoxy-5-(trifluoromethyl)benzamide;

N-[(2Z)-5-tert-butyl-3-[(2R)-tetrahydrofuran-2-ylmethyl]-1,3,4-thiadiazol-2(3H)-ylidene]-N'-(4-methylcyclohexyl)urea;

N-(1-adamantylmethyl)-N'-[(2Z)-5-tert-butyl-3-[(2R)-tetrahydrofuran-2-ylmethyl]-1,3,4-thiadiazol-2(3H)-ylidene]urea;

N-[(2Z)-5-tert-butyl-3-[(2R)-tetrahydrofuran-2-ylmethyl]-1,3,4-thiadiazol-2(3H)-ylidene]-N'-{[(1S,2R,5S)-6,6-dimethylbicyclo[3.1.1]hept-2-yl]methyl}urea;

N-[(2Z)-5-tert-butyl-3-[(2R)-tetrahydrofuran-2-ylmethyl]-1,3,4-thiadiazol-2(3H)-ylidene]-N'-[1-(hydroxymethyl)-3-methylbutyl]urea;

N-[(2Z)-5-tert-butyl-3-[(2R)-tetrahydrofuran-2-ylmethyl]-1,3,4-thiadiazol-2(3H)-ylidene]-N'-(1,2-dimethylpropyl)urea;

N-[(2Z)-5-tert-butyl-3-[(2R)-tetrahydrofuran-2-ylmethyl]-1,3,4-thiadiazol-2(3H)-ylidene]-N'-(1-ethylpropyl)urea;

N-[(2Z)-5-tert-butyl-3-[(2R)-tetrahydrofuran-2-ylmethyl]-1,3,4-thiadiazol-2(3H)-ylidene]-N'-1,2,3,4-tetrahydronaphthalen-1-ylurea;

N-[(2Z)-5-tert-butyl-3-[(2R)-tetrahydrofuran-2-ylmethyl]-1,3,4-thiadiazol-2(3H)-ylidene]-N'-[(1S)-1-cyclohexylethyl]urea;

N-(tert-butyl)-N'-[(2Z)-5-tert-butyl-3-[(2R)-tetrahydrofuran-2-ylmethyl]-1,3,4-thiadiazol-2(3H)-ylidene]urea;

N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2,2-dimethylpropyl]urea;

N-[(2Z)-5-tert-butyl-3-[(2R)-tetrahydrofuran-2-ylmethyl]-1,3,4-thiadiazol-2(3H)-ylidene]-N'-cycloheptylurea;

N-[(2Z)-5-tert-butyl-3-[(2R)-tetrahydrofuran-2-ylmethyl]-1,3,4-thiadiazol-2(3H)-ylidene]-N'-(2-ethylhexyl)urea;

N-[(2Z)-5-tert-butyl-3-[(2R)-tetrahydrofuran-2-ylmethyl]-1,3,4-thiadiazol-2(3H)-ylidene]-N'-(1-methyl-3-phenylpropyl)urea;

N-({[(2Z)-5-tert-butyl-3-[(2R)-tetrahydrofuran-2-ylmethyl]-1,3,4-thiadiazol-2(3H)-ylidene]amino}carbonyl)-L-phenylalaninamide;

$N^2$-({[(2Z)-5-tert-butyl-3-[(2R)-tetrahydrofuran-2-ylmethyl]-1,3,4-thiadiazol-2(3H)-ylidene]amino}1 carbonyl)-L-isoleucinamide;

$N^2$-({[(2Z)-5-tert-butyl-3-[(2R)-tetrahydrofuran-2-ylmethyl]-1,3,4-thiadiazol-2(3H)-ylidene]amino}carbonyl)-$N^1$,3-dimethyl-L-valinamide;

N-[(2Z)-5-tert-butyl-3-[(2R)-tetrahydrofuran-2-ylmethyl]-1,3,4-thiadiazol-2(3H)-ylidene]-N'-neopentylurea;

N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2-methylpropyl]urea;

N-[(3E)-5-tert-butyl-1-methyl-2-(tetrahydrofuran-3-ylmethyl)-1,2-dihydro-3H-pyrazol-3-ylidene]-2-methoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide;

N-{(3E)-4-bromo-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide;

2-bromo-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(1E)-3-methoxyprop-1-enyl]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-methoxypropyl)-5-(trifluoromethyl)benzamide;

N-[(2Z)-5-tert-butyl-3-{[(4S)-2-oxo-1,3-oxazolidin-4-yl]methyl}-1,3,4-thiadiazol-2(3H)-ylidene]-5-chloro-2-methoxybenzamide;

2-(2-amino-2-methylpropoxy)-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3-methylbut-2-enyl)oxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[2-(1-hydroxycyclopentypethoxy)-5-(trifluoromethyl)benzamide;

2-(azetidin-3-yloxy)-N-[(2Z)-5-tert-butyl-3-[(2R)-tetrahydrofuran-2-ylmethyl]-1,3-oxazol-2(3H)-ylidene]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-fluoro-5-(trifluoromethyl)benzamide;

N-[(2Z)-5-tert-butyl-3-[(2R)-tetrahydrofuran-2-ylmethyl]-1,3,4-thiadiazol-2(3H)-ylidene]-2-{[(3S)-1-methylpyrrolidin-3-yl]oxy}-5-(trifluoromethyl)benzamide;

N-[(2Z)-5-tert-butyl-3-[(2R)-tetrahydrofuran-2-ylmethyl]-1,3-oxazol-2(3H)-ylidene]-2-{[(3S)-1-methylpyrrolidin-3-yl]oxy}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(1E)-prop-1-enyl]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(1E)-3-hydroxy-3-methylbut-1-enyl]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-hydroxy-3-methylbutyl)-5-(trifluoromethyl)benzamide;

2-[(1-hydroxycyclobutyl)methoxy]-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-hydroxy-5-(trifluoromethyl)benzamide;

3-bromo-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-(2-fluoroethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-nitro-5-(trifluoromethyl)benzamide;

3-amino-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-[(2Z)-5-tert-butyl-3-[(2R)-tetrahydrofuran-2-ylmethyl]-1,3-oxazol-2(3H)-ylidene]-2-[2-(dimethylamino)ethoxy]-5-(trifluoromethyl)benzamide;

2-[(Z)-(tert-butoxyimino)methyl]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(methoxymethyl)-5-(trifluoromethyl)benzamide;

tert-butyl [2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl]acetate;

2-amino-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(methylsulfonyl)amino]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-5-cyano-2-fluorobenzamide;

methyl 3-[({(3E)-5-tert-butyl-1-methyl-2-[(2R)-tetrahydrofuran-2-ylmethyl]-1,2-dihydro-3H-pyrazol-3-ylidene}amino)carbonyl]benzoate;

N-{(3E)-5-tert-butyl-1-methyl-2-[(2R)-tetrahydrofuran-2-ylmethyl]-1,2-dihydro-3H-pyrazol-3-ylidene}-5-chloro-2-fluorobenzamide;

methyl 4-[({(3E)-5-tert-butyl-1-methyl-2-[(2R)-tetrahydrofuran-2-ylmethyl]-1,2-dihydro-3H-pyrazol-3-ylidene}amino)carbonyl]bicyclo[2.2.1]heptane-1-carboxylate;

methyl 3-({[(3E)-5-tert-butyl-1-methyl-2-[(2R)-tetrahydrofuran-2-ylmethyl]-1,2-dihydro-3H-pyrazol-3-ylidene]amino}carbonyl)adamantane-1-carboxylate;

N-{(3E)-5-tert-butyl-1-methyl-2-[(2R)-tetrahydrofuran-2-ylmethyl]-1,2-dihydro-3H-pyrazol-3-ylidene}-2-{[3-(hydroxyimino)cyclobutyl]methoxy}-5-(trifluoromethyl)benzamide;

tert-butyl 2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenylcarbamate;

N-{(3E)-5-tert-butyl-1-methyl-2-[(2R)-tetrahydrofuran-2-ylmethyl]-1,2-dihydro-3H-pyrazol-3-ylidene}-2-{[(dimethylamino)sulfonyl]amino}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-5-(trifluoromethyl)-2-vinylbenzamide;

N-{(3E)-5-tert-butyl-1-methyl-2-[(2R)-tetrahydrofuran-2-ylmethyl]-1,2-dihydro-3H-pyrazol-3-ylidene}-2-morpholin-4-yl-5-(trifluoromethyl)benzamide;

2-[bis(2-ethoxyethyl)amino]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(isobutylsulfonyl)amino]-5-(trifluoromethyl)benzamide;

3-acetyl-N-{(3E)-5-tert-butyl-1-methyl-2-[(2R)-tetrahydrofuran-2-ylmethyl]-1,2-dihydro-3H-pyrazol-3-ylidene}benzamide;

N-{(3E)-5-tert-butyl-1-methyl-2-[(2R)-tetrahydrofuran-2-ylmethyl]-1,2-dihydro-3H-pyrazol-3-ylidene}-3-(methylsulfonyl)benzamide;

methyl [2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl]acetate;

N-{(3E)-5-tert-butyl-1-methyl-2-[(2R)-tetrahydrofuran-2-ylmethyl]-1,2-dihydro-3H-pyrazol-3-ylidene}-2-fluoro-5-nitrobenzamide;

N-{(3E)-5-tert-butyl-1-methyl-2-[(2R)-tetrahydrofuran-2-ylmethyl]-1,2-dihydro-3H-pyrazol-3-ylidene}-3-cyanobenzamide;

ethyl 3-[2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl]propanoate;

5-bromo-N-{(3E)-5-tert-butyl-1-methyl-2-[(2R)-tetrahydrofuran-2-ylmethyl]-1,2-dihydro-3H-pyrazol-3-ylidene}-2-fluorobenzamide; and N-{(3E)-5-tert-butyl-1-methyl-2-[(2R)-tetrahydrofuran-2-ylmethyl]-1,2-dihydro-3H-pyrazol-3-ylidene}-2-phenoxy-5-(trifluoromethyl)benzamide.

Other examples of compounds of formula (I) that are contemplated include, but are not limited to, N-{5-tert-butyl-1-methyl-2-[(2R)-tetrahydrofuran-2-ylmethyl]-1,2-dihydro-3H-pyrazol-3-ylidene}-2-chloro-3-(trifluoromethyl)benzamide;

N-{5-tert-butyl-1-methyl-2-[(2R)-tetrahydrofuran-2-ylmethyl]-1,2-dihydro-3H-pyrazol-3-ylidene}-5-fluoro-2-methoxybenzamide;

N-{5-tert-butyl-1-methyl-2-[(2R)-tetrahydrofuran-2-ylmethyl]-1,2-dihydro-3H-pyrazol-3-ylidene}-4-chloro-5-fluoro-2-methoxybenzamide;

N-{5-tert-butyl-1-methyl-2-[(2R)-tetrahydrofuran-2-ylmethyl]-1,2-dihydro-3H-pyrazol-3-ylidene}-5-iodo-2-methoxybenzamide;

N-{5-tert-butyl-1-methyl-2-[(2R)-tetrahydrofuran-2-ylmethyl]-1,2-dihydro-3H-pyrazol-3-ylidene}-6-chloroquinoline-8-carboxamide;

N-{5-tert-butyl-1-methyl-2-[(2R)-tetrahydrofuran-2-ylmethyl]-1,2-dihydro-3H-pyrazol-3-ylidene}-2-chloronicotinamide;

N-{5-tert-butyl-1-methyl-2-[(2R)-tetrahydrofuran-2-ylmethyl]-1,2-dihydro-3H-pyrazol-3-ylidene}-5-chloro-2-(2,2,2-trifluoroethoxy)benzamide;

N-{5-tert-butyl-1-methyl-2-[(2R)-tetrahydrofuran-2-ylmethyl]-1,2-dihydro-3H-pyrazol-3-ylidene}-5-chloro-2-(2-methoxyethoxy)benzamide;

N-{5-tert-butyl-1-methyl-2-[(2R)-tetrahydrofuran-2-ylmethyl]-1,2-dihydro-3H-pyrazol-3-ylidene}-1-benzofuran-5-carboxamide;

N-{5-tert-butyl-1-methyl-2-[(2R)-tetrahydrofuran-2-ylmethyl]-1,2-dihydro-3H-pyrazol-3-ylidene}-2,3-dichlorobenzamide;

N-{5-tert-butyl-1-methyl-2-[(2R)-tetrahydrofuran-2-ylmethyl]-1,2-dihydro-3H-pyrazol-3-ylidene}-2-chloro-3-(trifluoromethyl)benzamide;

N-{5-tert-butyl-1-methyl-2-[(2R)-tetrahydrofuran-2-ylmethyl]-1,2-dihydro-3H-pyrazol-3-ylidene}-3-chloro-2-methylbenzamide;

3-bromo-N-{5-tert-butyl-1-methyl-2-[(2R)-tetrahydrofuran-2-ylmethyl]-1,2-dihydro-3H-pyrazol-3-ylidene}-2-methylbenzamide;

2-bromo-N-{5-tert-butyl-1-methyl-2-[(2R)-tetrahydrofuran-2-ylmethyl]-1,2-dihydro-3H-pyrazol-3-ylidene}-3-methylbenzamide;

N-{5-tert-butyl-1-methyl-2-[(3-methyloxetan-3-yl)methyl]-1,2-dihydro-3H-pyrazol-3-ylidene}-2-fluoro-3-(trifluoromethyl)benzamide;

N-[5-tert-butyl-1-methyl-2-(oxetan-2-ylmethyl)-1,2-dihydro-3H-pyrazol-3-ylidene]-2-fluoro-3-(trifluoromethyl)benzamide;

N-[5-tert-butyl-1-methyl-2-(tetrahydrofuran-3-ylmethyl)-1,2-dihydro-3H-pyrazol-3-ylidene]-2-fluoro-3-(trifluoromethyl)benzamide;

N-[5-tent-butyl-2-(1,3-dioxolan-2-ylmethyl)-1-methyl-1,2-dihydro-3H-pyrazol-3-ylidene]-2-fluoro-3-(trifluoromethyl)benzamide;

N-{5-tert-butyl-1-methyl-2-[(3-methyl-4,5-dihydroisoxazol-5-yl)methyl]-1,2-dihydro-3H-pyrazol-3-ylidene}-2-fluoro-3-(trifluoromethyl)benzamide;

N-(5-tent-butyl-2-{[(4R)-2,2-dimethyl-1,3-dioxolan-4-yl]methyl}-1-methyl-1,2-dihydro-3H-pyrazol-3-ylidene)-2-fluoro-3-(trifluoromethyl)benzamide;

N-(5-tent-butyl-2-{[(4S)-2,2-dimethyl-1,3-dioxolan-4-yl]methyl}-1-methyl-1,2-dihydro-3H-pyrazol-3-ylidene)-2-fluoro-3-(trifluoromethyl)benzamide;

N-(5-tert-butyl-1-methyl-2-{[(2R)-5-oxotetrahydrofuran-2-yl]methyl}-1,2-dihydro-3H-pyrazol-3-ylidene)-2-fluoro-3-(trifluoromethyl)benzamide;

N-(5-tert-butyl-1-methyl-2-{[(2S)-5-oxotetrahydrofuran-2-yl]methyl}-1,2-dihydro-3H-pyrazol-3-ylidene)-2-fluoro-3-(trifluoromethyl)benzamide;

N-{5-tert-butyl-1-methyl-2-[(5-methyltetrahydrofuran-2-yl)methyl]-1,2-dihydro-3H-pyrazol-3-ylidene}-2-fluoro-3-(trifluoromethyl)benzamide;

N-[5-tert-butyl-1-methyl-2-(tetrahydro-2H-pyran-4-ylmethyl)-1,2-dihydro-3H-pyrazol-3-ylidene]-2-fluoro-3-(trifluoromethyl)benzamide;

N-[5-tert-butyl-1-methyl-2-(tetrahydro-2H-pyran-2-ylmethyl)-1,2-dihydro-3H-pyrazol-3-ylidene]-2-fluoro-3-(trifluoromethyl)benzamide;

N-[5-tert-butyl-1-methyl-2-(tetrahydro-2H-pyran-3-ylmethyl)-1,2-dihydro-3H-pyrazol-3-ylidene]-2-fluoro-3-(trifluoromethyl)benzamide; and N-[5-tert-butyl-2-(1,4-dioxan-2-ylmethyl)-1-methyl-1,2-dihydro-3H-pyrazol-3-ylidene]-2-fluoro-3-(trifluoromethyl)benzamide.

Compounds described herein can exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

For example, compounds of formula (Ia), (Ib), (Ic), and (Id) wherein $R^{21}$, $R^{22}$, $R^{23}$, and $R^{24}$ are each tetrahydrofuran-2-ylmethyl, can have stereoisomers including, but not limited to, those shown below:

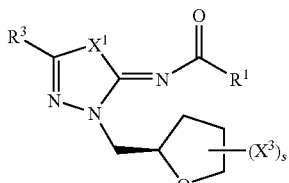
(Iaa)

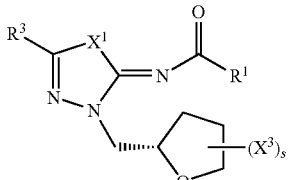
(Iab)

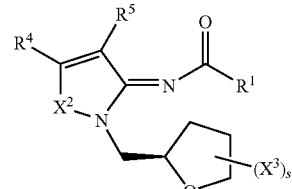
(Iba)

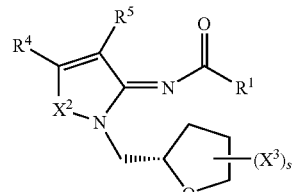
(Ibb)

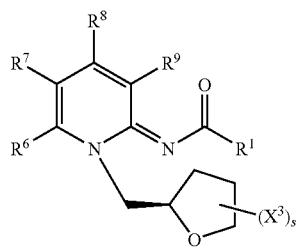
(Ica)

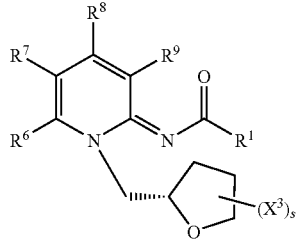
(Icb)

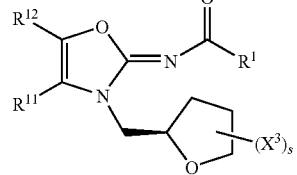
(Ida)

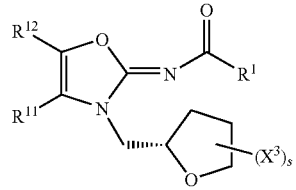
(Idb)

wherein s is 1, 2, 3, 4, 5, or 6, $X^3$ is oxo, alkyl, halogen, OH, O(alkyl), O(haloalkyl), or haloalkyl, and $R^1$, $R^3$, $R^4$, $R^5$, $R^6$, $R^7$, $R^8$, $R^9$, $R^{11}$, $R^{12}$, $X^1$, and $X^2$ are as disclosed in the Summary and the Detailed Description sections. It is understood that embodiments for $R^1$, $R^3$, $R^4$, $R^5$, $R^6$, $R^7$, $R^8$, $R^9$, $R^{11}$, $R^{12}$, $X^1$, and $X^2$, and combinations of embodiments, including particular, and more particular embodiments as described for formula (Ia), (Ib), (Ic), and (Id) are also contemplated for compounds of formula (Iaa), (Iab), (Iba), (Ibb), (Ica), (Icb), (Ida), and (Idb).

It can be appreciated two or more asymmetric centers can be present in the present compounds, hence several diastereomers and enantiomers of the exemplified structures can often be possible, and that pure diastereomers and enantiomers represent preferred embodiments. It is intended that pure diasteromers, pure enantiomers, and mixtures thereof, are within the scope of the invention.

Various stereoisomers (including enantiomers and diastereomers) and mixtures thereof (including racemates) are contemplated. Individual stereoisomers of present compounds can be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers can exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed herein can exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds can be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention can be used as standards to determine the effectiveness of $CB_2$ ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10):927-932 (1995); Kushner et al., *Can. J. Physiol. Pharmacol.*, 77, 79-88 (1999)).

In addition, non-radio active isotope containing drugs, such as deuterated drugs called "heavy drugs," can be used for the treatment of diseases and conditions related to CB2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom can be stronger than the same bond between the light isotope and that atom. Accordingly, the incorporation of an isotope at a site of metabolism or enzymatic transformation can slow said reactions potentially altering the pharmcokinetic profile or efficacy relative to the non-isotopic compound.

c. Biological Data (i) In Vitro Methods—Human $CB_2$ and $CB_3$ Radioligand Binding Assays:

The $CB_1$ and $CB_2$ radioligand binding assays described herein are utilized to determine the selectivity of compounds of the present invention for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing ([$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 μg/well for rat $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H] CP-55,940 and five concentrations of displacing ligands selected from the range of 0.01 nM to 10 The addition of 10 μM unlabeled CP-55,940 (Tocris, Ellisville, Mo.) was used to assess nonspecific binding.

Certain compounds tested bound to $CB_2$ receptors with a $K_i$ of less than about 1,000 nM, for example, less than 400 nM, or less than 200 nM and, or lower than 100 nM.

HEK293 human $CB_1$ membranes were purchased from Perkin Elmer. Binding was initiated by the addition of membranes (8-12 μg per well) into wells (Scienceware 96-well DeepWell plate, VWR, West Chester, Pa.) containing [$^3$H] CP-55,940 (120 Ci/mmol, Perkin Elmer, Boston, Ma.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 4. After incubation (30° C. for 90 minutes), binding was terminated by the addition of 300 per well of cold assay buffer and rapid vacuum filtration (FilterMate Cell Harvester, Perkin Elmer, Boston, Ma.) through a UniFilter-96 GF/C filter plate (Perkin Elmer, Boston, Ma.) (pre-soaked in 0.3% PEI at least 3 hours), followed by five washes with cold assay buffer. The bound activity was counted in the TopCount using Microscint-20 (both from Perkin Elmer, Boston, Ma.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding. Certain compounds tested bound to $CB_1$ receptors with $K_i$ of about 10 fold to about 500-fold higher than that for $CB_2$ receptors. These results show that these compounds preferably bind to $CB_2$ receptors, therefore are selective ligands for the $CB_2$ receptor.

TABLE 1

| Example | human $CB_2$ $K_i$ (nM) | rat $CB_2$ $K_i$ (nM) |
|---|---|---|
| 1 | 51 | 2.9 |
| 2 | 17 | 12 |
| 3 | 114 | 71 |
| 4 | 6.9 | 1.2 |
| 5 | 9.1 | 0.9 |
| 6 | 20 | 3.3 |
| 7 | 38 | 1.6 |
| 8 | | 0.8 |
| 9 | 33 | 1.4 |
| 10 | 360 | |
| 11 | 4.8 | 2.6 |
| 13 | 4.8 | 1.9 |
| 14 | 35 | 24 |
| 15 | 2.8 | 1.2 |
| 16 | 147 | 84 |
| 17 | 230 | 58 |
| 18 | 51 | 99 |
| 19 | 22 | 11 |
| 20 | 25 | 23 |
| 21 | 63 | 22 |
| 22 | 24 | 10 |
| 23 | 30 | 19 |
| 24 | 260 | 29 |
| 25 | 101 | 40 |
| 28 | 101 | 44 |
| 29 | 4.8 | 14 |
| 30 | 3.8 | 11 |
| 31 | 11 | 6.2 |
| 32 | 261 | 114 |
| 33 | 81 | 14 |
| 34 | 11 | 5.5 |
| 35 | 17 | 5.5 |
| 39 | 8.9 | 3.8 |
| 40 | 32 | 22 |
| 41 | 132 | 18 |
| 42 | 139 | 30 |
| 43 | 19 | 10 |
| 44 | 17 | 18 |
| 45 | 8.2 | 4.9 |
| 46 | 0.7 | 1.3 |
| 47 | 17 | 3.7 |
| 48 | 143 | 29 |
| 49 | 56 | 20 |
| 50 | 63 | 54 |
| 51 | 68 | 67 |
| 52 | 6.6 | 1.3 |
| 53 | 16 | 4.3 |
| 54 | 17 | 9.5 |
| 55 | 152 | 143 |
| 58 | 31 | 69 |
| 59 | 28 | 27 |
| 60 | 66 | 46 |
| 61 | 103 | 13 |
| 62 | 20 | 4.0 |
| 63 | 36 | 20 |
| 64 | 30 | 6.2 |
| 65 | 65 | 5.7 |
| 66 | 2.1 | 0.8 |
| 67 | 16 | 10 |

TABLE 1-continued

| Example | human $CB_2$ $K_i$ (nM) | rat $CB_2$ $K_i$ (nM) |
|---|---|---|
| 73 | 45 | 8.2 |
| 79 | 32 | 11 |
| 80 | 28 | 38 |
| 82 | 3.8 | 10 |
| 84 | 199 | 73 |
| 85 | 87 | 13 |
| 86 | 11 | 3.3 |
| 88 | 20 | 5.4 |
| 89 | 9.8 | 5.8 |
| 90 | 3.5 | 3.0 |
| 91 | 203 | 30 |
| 93 | 17 | 15 |
| 94 | 2.6 | 3.3 |
| 96 | 13 | 3.7 |
| 97 | 63 | 46 |
| 98 | 261 | 88 |
| 99 | 12 | 3.5 |
| 100 | 3.2 | 1.1 |
| 101 | 49 | 34 |
| 102 | 21 | 11 |
| 103 | 16 | 4.4 |
| 104 | 46 | 9.3 |
| 105 | 69 | 10 |
| 106 | 168 | 63 |
| 107 | 11 | 4.8 |
| 108 | 148 | 55 |
| 109 | 23 | 15 |
| 110 | 12 | 3.0 |
| 111 | 14 | 12 |
| 112 | 3.3 | 2.4 |
| 113 | 110 | 40 |
| 114 | 41 | 20 |
| 115 | 25 | 5.4 |
| 116 | 26 | 11 |
| 118 | 42 | 14 |
| 119 | 70 | 25 |
| 120 | 1.7 | 2.1 |
| 121 | 53 | 15 |
| 122 | 8.2 | 1.4 |
| 125 | 32 | 25 |
| 128 | 243 | 107 |
| 129 | 8.6 | 2.3 |
| 130 | 72 | 17 |
| 131 | 23 | 18 |
| 132 | 15 | 7.1 |
| 133 | 107 | 39 |

(ii) In Vivo Data:

Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Incisional Model of Postoperative Pain

A skin incision model of postoperative pain was produced using the procedures described in Brennan et al., 1996, Pain, 64, 493. All rats were anesthetized with isoflurane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as described in Chaplan, S. R., F. W. Bach, J. W. Pogrel, J. M. Chung and T. L. Yaksh, 1994, Quantitative Assessment of Tactile Allodynia in the Rat Paw, J. Neurosci. Methods, 53, 55. Rats were placed into inverted individual plastic cage (20×12.5×20 cm) on top of a suspended wire mesh grid, and were acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient Analysis of Experimental Observations, Ann. Rev. Pharmacol. Toxicol., 20, 441).

Certain compounds tested showed a statistically significant change in paw withdrawal latency versus a saline vehicle at less than about 300 micromoles/kg. Certain compounds measured showed efficacy at less than about 50 micromoles/kg.

Capsaicin-Induced Secondary Mechanical Hypersensitivity:

Rats were allowed to acclimate to the study room for 1 hour. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds are injected (i.p.) 30 min before testing (150 min post-capsaicin).

Tactile allodynia was measured as described above.

Certain compounds tested showed a statistically significant change in paw withdrawal latency versus a saline vehicle at less than about 300 micromoles/kg. Certain compounds measured showed efficacy at less than about 50 micromoles/kg.

MIA-induced Knee Joint Osteoarthritic Pain Model

Unilateral knee joint osteoarthritis was induced in the rats by a single intra-articular (i.a.) injection of sodium monoiodoacetate (MIA, 3 mg in 0.05 mL sterile isotonic saline) into the right knee joint cavity under light isoflurane anesthesia using a 26G needle. The dose of the MIA (3 mg/i.a.injection) was selected based on results obtained from preliminary studies wherein an optimal pain behavior was observed at this dose. Pain behavioral assessment of hind limb grip force were conducted by recording the maximum compressive force exerted on the hind limb strain gauge setup, in a commercially available grip force measurement system (Columbus Instruments, Columbus, Ohio). The grip force data was converted to a maximum hind limb cumulative compressive force (CFmax) (gram force)/kg body weight for each animal. The analgesic effects of test compounds were determined 20 days following the i.a. injection of MIA. The vehicle control group for each compound being tested was assigned 0% whereas the age matched naïve group was assigned as being 100% (normal). The % effects for each dose group was then expressed as % return to normalcy compared to the naïve group. Compounds were administered either orally (p.o.) or intraperitoneally (i.p.). The assessment of the analgesic effects of test compounds is typically made anytime between about 1 hour and about 5 hours following oral administration. The assessment of the analgesic effects of test compounds is typically made anytime between about 0.5 hour and about 2 hours following i.p. administration. Selection of the preferred time points for measuring the analgesic effects of test compounds was based upon consideration of the individual pharmacokinetic characteristics of test compounds in the rat. Time points that were known or expected to provide higher plasma concentrations of test compounds were preferred over those that were known or expected to provide lower concentrations. The assessment of the analgesic effects of test compounds can be made following a single dose or following repeated dosing of test compounds wherein the frequency of dosing is 1 to 2 times daily. The duration of such repeated daily dosing can last for any time greater than or equal to one day. A typical duration of repeated daily dosing is about 5 days to about 12 days.

Certain compounds tested showed a statistically significant change in hind limb grip force strength versus a saline vehicle at less than about 300 micromoles/kg in the MIA model of osteoarthritic pain following a single dose. Certain compounds tested showed a statistically significant change in hind limb grip force strength versus a saline vehicle at less than about 50 micromoles/kg in the MIA model of osteoarthritic pain following a single dose.

d. Methods of Using the Compounds

One embodiment of the present invention provides a method for treating pain (for example, inflammatory pain, chronic pain, neuropathic pain, nociceptive pain, osteoarthritic pain, post-operative pain, cancer pain, lower back pain, eye pain) in a mammal (including human) in need of such treatment. The method comprises administering to the mammal a therapeutically effective amount of a compound as described herein, or a pharmaceutically acceptable salt, solvate, salt of a solvate, or solvate of a salt thereof, alone or in combination with a pharmaceutically acceptable carrier. The method further comprises administration of present compounds as a single dose. The method also comprises repeated or chronic administration of present compounds over a period of days, weeks, months, or longer. Compounds described herein can be administered alone, or in combination with one or more other compounds described herein, or in combination (i.e. co-administered) with one or more additional pharmaceutical agents. For example, one or more compounds described herein, or pharmaceutically acceptable salts, solvates, salts of solvates, or solvates of salts thereof, can be administered in combination with an analgesic (e.g. acetaminophen or opioid), or with one or more nonsteroidal anti-inflammatory drug (NSAID) such as, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac; or administered with a combination of acetaminophen and one or more NSAID. In certain embodiments, the nonsteroidal anti-inflammatory drug (NSAID) is ibuprofen.

Another embodiment provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal therapeutically effective amount of a compound of formula (I) or pharmaceutically acceptable salts, solvates, salts of solvates, or solvates of salts thereof, alone or in combination with a pharmaceutically acceptable carriers.

Yet another embodiment relates to a method for providing neuroprotection in a mammal in need of such treatment. This method comprises administering to the mammal therapeutically effective amount of one or more compound(s) described herein or pharmaceutically acceptable salts, solvates, salts of solvates, or solvates of salts thereof, alone or in combination with a pharmaceutically acceptable carrier.

Another embodiment provides a method of increasing the therapeutic effectiveness or potency of compounds described herein by repeated or chronic administration over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $^9$-THC are absent in the $CB_2$ receptor knockout mice, providing evidence for the involvement of $CB_2$ receptors in immunomodulation. As such, selective $CB_2$ modulators can be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system.-Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands can be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators can provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators can possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators can represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators can represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators can have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators can be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor can be clinically useful for the treatment of atherscelorsis.

$CB_2$ receptors are expressed on malignant cells of the immune system and targeting $CB_2$ receptors to induce apoptosis can constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators can have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators can have utility for the treatment or prophylaxis of cardiovascular disease and the development of myocardial infarction.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level can depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of compounds can be required to achieve the desired therapeutic response. "Repeated or chronic administration" refers to the administration of compounds daily (i.e., every day) or intermittently (i.e., not every day) over a period of days, weeks, months, or longer. In particular, the treatment of chronic painful conditions is anticipated to require such repeated or chronic administration of the compounds. Compounds described herein can become more effective upon repeated or chronic administration such that the therapeutically effective doses on repeated or chronic administration can be lower than the therapeutically effective dose from a single administration.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a single oral dosage composition having a fixed ratio of each active ingredient, such as a tablet or capsule; or each agent can be administered in separate oral dosage formulations.

Where separate dosage formulations are used, present compounds and one or more additional pharmaceutical agents can be administered at essentially the same time (e.g., concurrently) or at separately staggered times (e.g., sequentially).

Compounds described herein can also be administered as a pharmaceutical composition comprising the compounds of interest in combination with one or more pharmaceutically acceptable carriers. The phrase "therapeutically effective amount" of the present compounds means sufficient amounts of the compounds to treat disorders, at a reasonable benefit/risk ratio applicable to any medical treatment. It can be understood, however, that the total daily usage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds administered to a human or other animal range from about 0.01 mg/kg body weight to about 100 mg/kg body weight. More preferable doses can be in the range of from about 0.03 mg/kg body weight to about 30 mg/kg body weight. If desired, the effective daily dose can be divided into multiple doses for purposes of administration. Consequently, single dose compositions can contain such amounts or submultiples thereof to make up the daily dose. It is understood that the effective daily dose can vary with the duration of the treatment.

e. Pharmaceutical Compositions

Pharmaceutical compositions comprise compounds described herein or pharmaceutically acceptable salts or solvates thereof are also described. The pharmaceutical compositions comprising compounds described herein can be formulated together with one or more non-toxic pharmaceutically acceptable carriers.

Another aspect relates to pharmaceutical compositions comprising present compounds, or pharmaceutically acceptable salts or solvates thereof, and one or more pharmaceutically acceptable carriers, alone or in combination with one or more nonsteroidal anti-inflammatory drug (NSAID), or other analgesics (for example, acetaminophen), or combinations thereof.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds with suitable non-irritating carriers or carriers such as cocoa butter, polyethylene glycol or a suppository wax which are solid at room temperature but liquid at body temperature and therefore melt in the rectum or vaginal cavity and release the active compound.

The compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to compounds described herein, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of compounds described herein include powders, sprays, ointments and inhalants. The active compounds can be mixed under sterile conditions with a pharmaceutically acceptable carrier and any needed preservatives, buffers or propellants which can be required. Opthalmic formulations, eye ointments, powders and solutions are also contemplated as being within the scope.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

f. General Synthesis

Encompassed herein are compounds prepared by synthetic processes or by metabolic processes. Preparation of the compounds by metabolic processes includes those occurring in the human or animal body (in vivo) or processes occurring in vitro.

Compounds described herein can be prepared by a variety of processes well known for the preparation of compounds of this class. For example, compounds described herein wherein the groups $R^1$, $R^{21}$, $R^{22}$, $R^{24}$, $R^3$, $R^4$, $R^5$, $R^6$, $R^7$, $R^8$, $R^9$, $R^{10}$, $R^{11}$, $R^{12}$, $R^{1a}$, $R^z$, Ring A, $X^1$, and $X^2$ have the meanings as set forth in the summary section unless otherwise noted, can be prepared by general procedures such as, but not limited to, those outlined in Schemes 1-11.

As used in the descriptions of the schemes and the examples, certain abbreviations are intended to have the following meanings DAST for diethylaminosulfur trifluoride, DMAP for 4-(dimethylamino)pyridine, DME for dimethoxyethane, DMSO for dimethyl sulfonamide, EtOAc for ethyl acetate, Et$_3$N for triethylamine, MeOH for methanol, dppf for 1,1'-bis(diphenylphosphino)ferrocene, OMs or mesylate for methanesulfonate, t-Bu for tert-butoxide, THF for tetrahydrofuran, and OTs or tosylate for p-toluenesulfonate.

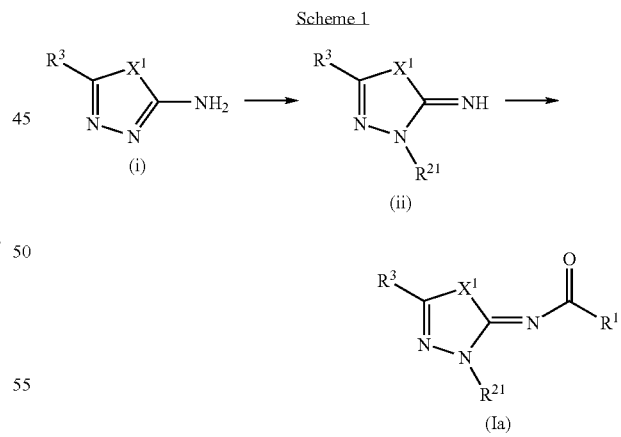

Compounds of formula (Ia) can be prepared according to the 2-step method illustrated in Scheme 1. Amino compounds of formula (i) can be first reacted with compounds of formula $R^{21}$—$X^{101}$, wherein $X^{101}$ is Cl, Br, I, OTs, or OMs, to form the intermediate (ii). This reaction can be performed either neat or in a solvent such as, but not limited to, tetrahydrofuran, dimethylformamide, dimethylsulfoxide, or dioxane, at about room temperature or up to 150° C., and optionally in the presence of a catalyst such as but not limited to tetrabutylammonium iodide, or sodium iodide. In certain cases, it can be beneficial to conduct this reaction in the presence of a base such as, but not limited to, triethylamine, potassium carbonate, potassium tert-butoxide, or sodium hydride. The intermediate (ii) can be converted to the product (Ia) by reaction with an acid chloride ($R^1COCl$) or carboxylic acid ($R^1CO_2H$) under appropriate conditions. For example, intermediate (ii) can be reacted with $R^1COCl$ in a solvent such as, but not limited to, tetrahydrofuran, dimethylformamide or dichloromethane at a temperature from about 25° C. to about 50° C. in the presence of a base such as, but not limited to, triethylamine, diisopropylethylamine or potassium carbonate, and optionally in the presence of a catalyst such as 4-dimethylaminopyridine. Alternatively, intermediate (ii) can be reacted with $R^1CO_2H$ in a solvent such as, but not limited to, tetrahydrofuran or dimethylformamide in the presence of a coupling reagent such as 1,1'-carbonyldiimidazole (CDI), bis (2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), or O-benzotriazol-1-yl-N,N,N',N'-tetramethyluronium tetrafluoroborate (TBTU), in the presence or absence of a coupling auxiliary such as, but not limited to, 1-hydroxy-7-azabenzotriazole (HOAT) or 1-hydroxybenzotriazole hydrate (HOBT). The reaction is generally conducted in the presence or absence of a base such as, but not limited to, N-methyl morpholine, triethylamine, or diisopropylethylamine.

Alternatively, compounds of formula (Ia) can be prepared according to the general procedures as outlined in Scheme 2.

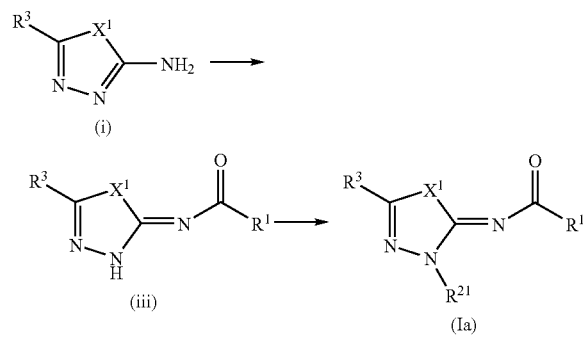

Compounds of formula (i) can be converted to intermediate (iii) by reaction with $R^1COCl$ or $R^1CO_2H$ using reaction conditions as described in Scheme 1. The intermediate (iii) can be converted to (Ia) by reaction with $R^{21}$—$X^{101}$, wherein $X^{101}$ is Cl, Br, I, OTs, or OMs, using reaction conditions as described in Scheme 1 for the transformation of (i) to (ii).

Similarly, compounds of general formula (I) wherein Ring A represents formula (b) or (c) can be prepared from the appropriate heteroarylamines using general procedures as illustrated in Scheme 1 or 2.

Heteroarylamines used to prepare compounds of formula (I) can be obtained from commercial sources or can be prepared using methods well-known to those skilled in the art. For example, heteroaryl amines of formula (i) wherein $X^1$ is sulfur can be prepared using general procedures as illustrated in Scheme 3.

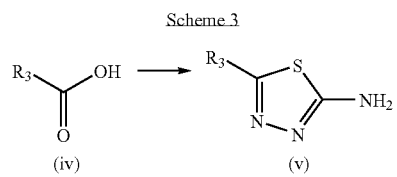

Carboxylic acids of formula (iv) can be treated with thiosemicarbazide and phosphorus oxychloride at a temperature of about 90° C., in a solvent such as, but not limited to, dioxane to provide compounds of formula (v).

Compounds of general formula (I) wherein $R^1$ is —$N(R^{1a})$ ($R^z$) can be prepared, for example, as illustrated in Scheme 4.

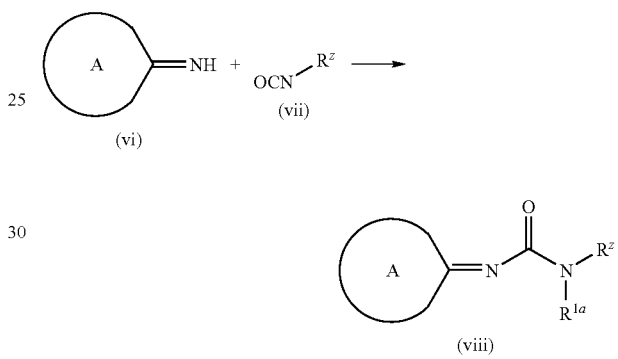

Reaction of compounds of formula (vi) with isocyanates of formula (vii) in a solvent such as, but not limited to, dichloromethane, toluene, dioxane, or dimethylformamide, at a temperature from about 25° C. to about 150° C. provides compounds of formula (viii) wherein $R^{1a}$ is hydrogen. Alternatively, treatment of compounds of formula (vii) with carbamylchlorides of formula $ClCONR^{1a}R^z$ in a solvent such as, but not limited to, dichloromethane, toluene, dioxane, or dimethylformamide, at a temperature from about 25° C. to about 150° C. provides compounds of formula (viii) wherein $R^{1a}$ is other than hydrogen.

Alternatively, compounds of formula (viii) can be prepared using general procedures as shown in Scheme 5.

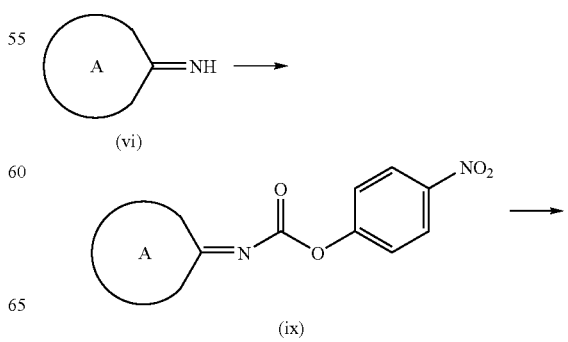

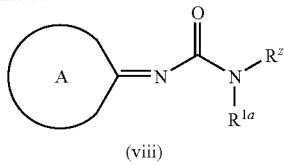

(viii)

Reaction of compounds of formula (vi) with 4-nitrophenylcarbonochloridate in a solvent such as, but not limited to, tetrahydrofuran in the presence of a base such as, but not limited to, diisopropylethylamine, at about room temperature provides the intermediate (ix). The intermediate (ix) can be converted to (viii) by reaction with amines of formula $HNR^{1a}R^z$ in a solvent such as, but not limited to, tetrahydrofuran or dimethylformamide, at temperatures from about 25° C. to about 150° C.

Many other methods for the preparation of ureas are known in the art and can be found, for example, in the following references: Chem. Rev., 1972, 72, 457-496; J. Org. Chem., 1994, 59, 1937-38; Synthesis, 1996, 553-76; Angew. Chem. Int. Ed. Engl., 1987, 26, 894-95; J. Org. Chem., 2003, 68, 7289-97; J. Org. Chem., 1997, 62, 4155-58; Tet. Lett., 1995, 36, 2583-86; Tet. Lett., 1994, 35, 4055-58; Tet. Lett., 1997, 38, 5335-38; Angew. Chem. Int. Ed. Engl., 1995, 34, 2497-2500; Synlett., 1996, 507-08; Synlett., 1996, 502-03; Tet. Lett., 1983, 24, 4569-72; Synthesis, 1989, 423-425; J. Org. Chem., 1996, 61, 4175-79; Tet. Lett., 1998, 39, 7811-14; J. Org. Chem., 1998, 63, 4802-07; and J. Comb. Chem., 1999, 1, 163-172.

Compounds of general formula (I) wherein $X^2$ is $N(R^{10})$ can be synthesized, for example, using the general procedures as outlined in Scheme 6.

Scheme 6

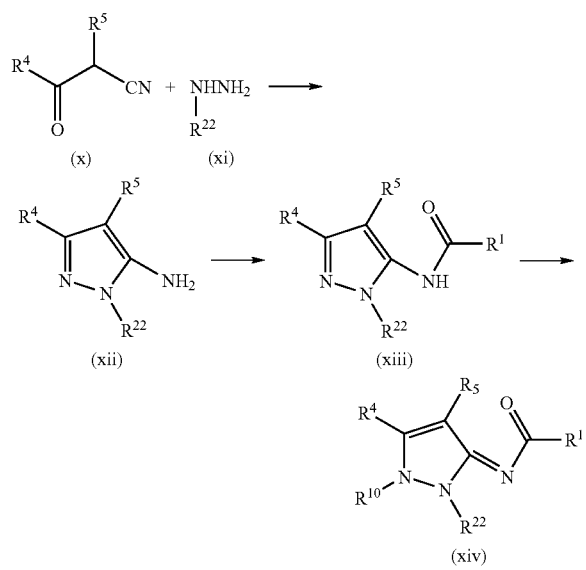

Hydrazines of formula (xi) can be reacted with ketonitriles (x) in a solvent such as, but not limited to, ethanol, at a temperature of between about 0° C. to about 80° C., to provide intermediates of formula (xii). These intermediate aminopyrazoles (xii) can be treated with carboxylic acids of formula $R^1COOH$, acid chlorides of formula $R^1COCl$, or isocyanates of formula $R^1NCO$ according to the methods outlined in Schemes 1, 2, and 4 to provide pyrazoles (xiii). (xiii) can be converted to (xiv) by reaction with an appropriate alkylating agent such as, but not limited to, a halide, mesylate, tosylate, sulfate, or diphenylmethylsulfonium tetrafluoroborate either neat or in a solvent such as but not limited to tetrahydrofuran, toluene, acetonitrile, or dioxane. This reaction can be conducted from about 0° C. to about 150° C. In certain cases the addition of a base can be beneficial. Examples of bases that can be used include triethylamine, diisopropylethylamine, potassium carbonate, sodium hydride, sodium hydroxide and lithium diisopropylamide.

Scheme 7 outlines general procedure for synthesizing compounds of general formula (Id).

Scheme 7

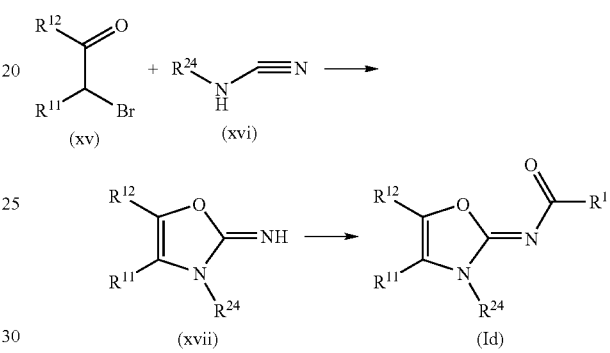

Compounds of formula (xv) when treated with compounds of formula (xvi), in the presence of potassium carbonate or sodium carbonate and in a solvent such as, but not limited to, methyl ethyl ketone, at a temperature from about 25° C. to about 100° C. provides intermediates of formula (xvii). Intermediates of formula (xvii) can be converted to compounds of formula (Id) by reaction with $R^1COCl$ or $R^1CO_2H$ using reaction conditions as described in Scheme 1.

Compounds of formula (xvi) can be obtained from reaction of amines of formula $R^{24}NH_2$ with cyanogen bromide in the presence of sodium carbonate or potassium carbonate in a solvent such as, but not limited to, ether, and at a temperature from about −25° C. to about 0° C.

Alternative method of synthesis for compounds of formula (xiv) is shown in Scheme 8.

Scheme 8

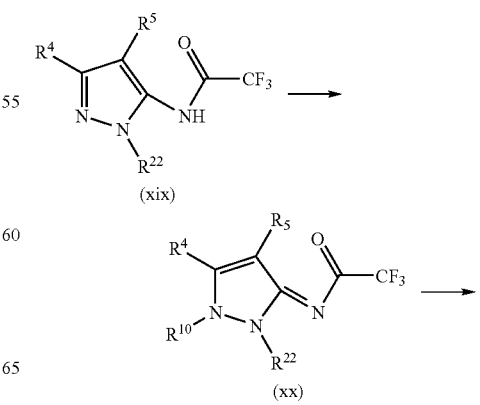

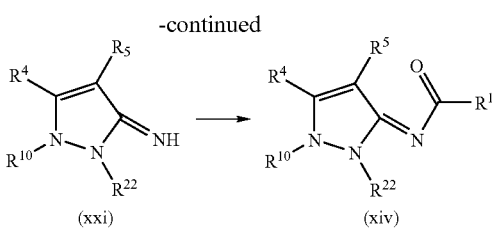

Compounds of formula (xix) (prepared from (xii) by reaction with trifluoroacetic anhydride in solvents such as, but not limited to, dichloromethane and in the presence of a base such as, but not limited to, pyridine, or triethylamine) can be converted to compounds of formula (xx) using the alkylation conditions of Scheme 6 for the conversion of (xiii) to (xiv). Compounds of formula (xx) can be converted to (xxi) by reaction with aqueous potassium or sodium hydroxide with methanol or ethanol as a co-solvent at temperatures from about room temperature to about 70° C. Compounds (xxi), in turn, can be treated with carboxylic acids of formula $R^1COOH$ or acid chlorides of formula $R^1COCl$ according to the methods outlined in Scheme 1 to give compounds of formula (xiv).

Compounds of formula (xii) can also be prepared using the methods shown in Scheme 9.

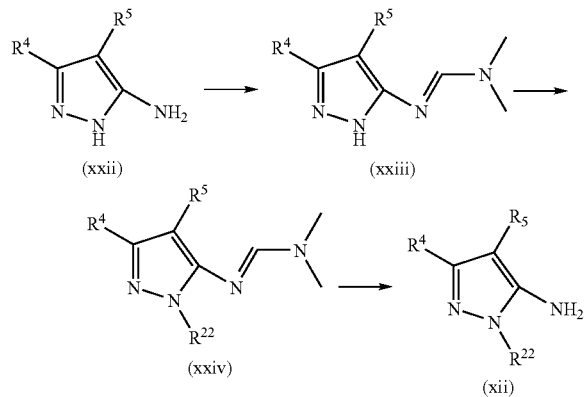

Aminopyrazoles (xxii) can be converted to the amidine intermediates (xxiii) by refluxing in dimethylformamide dimethylacetal or refluxing with a 2- to 3-fold excess of dimethylformamide dimethylacetal in dioxane or other aprotic solvent. Compounds (xxiii), in turn, can be alkylated with reagents $R^{22}$—$X^{202}$ wherein $X^{202}$ is Cl, Br, I, OTs, or OMs under phase transfer conditions such as, but not limited to, conducting the reaction in a toluene/water mixture with a phase transfer reagent like tetrabutylammonium hydrogensulfate or tetrabutylammonium iodide at a temperature from about 50° C. to about 110° C., with potassium carbonate as a base to provide the intermediates (xxiv). The intermediates (xxiv) can be converted to the intermediates (xii) by reaction with hydrazine hydrate and in the presence of acetic acid in a solvent such as, but not limited to, dioxane at temperatures from about 50° C. to about 100° C. The foregoing sequence to install the $R^{22}$ group can also be accomplished by first placing a triphenylmethyl (trityl) group on the exocyclic nitrogen of (xxii) instead of the amidine, followed by alkylation. Typical conditions for effecting the analogous alkylation in the presence of a trityl group include, but are not limited to, reaction with an alkylating agent $R^{22}$—$X^{202}$ in the presence of a base such as sodium hydride or potassium tert-butoxide in a solvent such as dimethylformamide or tetrahydrofuran. The trityl protecting group can be removed using methods well-known to those skilled in the art such as, for example, treatment of the compound with an acid such as, but not limited to, hydrochloric acid.

Certain compounds wherein $G^1$ is phenyl and said phenyl is substituted with the group —$OR^e$ can be prepared using the methods described in Scheme 10.

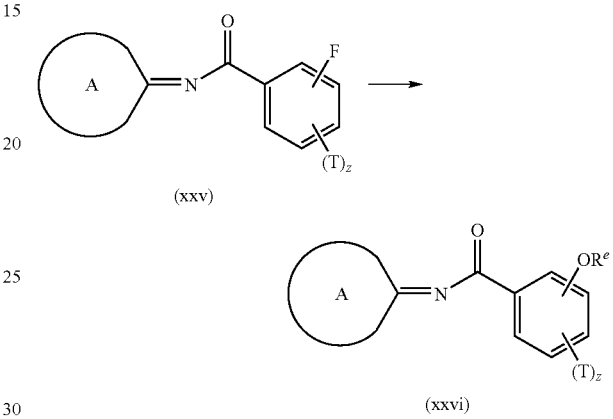

Compounds of formula (xxvi), wherein the ring A is as defined in formula (I), T represents the optional substituents of $G^1$ as defined in formula (I), and z is 0, 1, 2, 3, or 4, can be prepared from compounds of formula (xxv) by reaction with an alcohol $HOR^e$ in the presence of a base such as, but not limited to, potassium tert-butoxide or sodium tert-butoxide in a solvent such as, but not limited to, tetrahydrofuran or dimethylformamide at temperatures between about 0° C. and about 50° C. In certain instances, a protecting group can be attached to a functional group present in $R^e$. Such protecting groups can be removed using methods well-known to those skilled in the art. The group $R^e$ can also be further transformed to provide other compounds of the invention using standard chemical techniques well-known to those skilled in the art such as alkylation, acylation, sulfonylation, oxidation followed by reductive amination and the like.

Certain compounds wherein $G^1$ is phenyl and said phenyl is substituted with a group $R^{GA}$, wherein $R^{GA}$ is attached to said phenyl through a carbon atom of $R^{GA}$, can be prepared according to the carbon-carbon bond forming reactions described in Scheme 11.

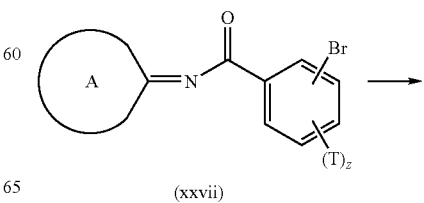

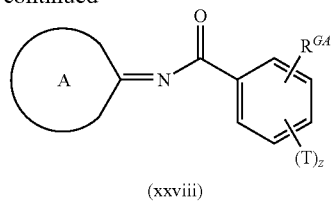

(xxviii)

Compounds of formula (xxviii), wherein ring A is as described in formula (I), T is an optional substituent of $G^1$ as defined in formula (I), z is 0, 1, 2, 3, or 4, and $R^{GA}$ is selected from the group consisting of alkyl, alkenyl, alkynyl, alkoxyalkenyl, hydroxyalkenyl, haloalkyl, $-(CR^jR^k)_q-CN$, $-(CR^jR^k)_q-OR^e$, $-(CR^jR^k)_q-OC(O)R^e$, $-(CR^jR^k)_q-SR^e$, $-(CR^jR^k)_q-S(O)R^f$, $-(CR^jR^k)_q-S(O)_2R^f$, $-(CR^jR^k)_q-N(R^e)(R^g)$, $-(CR^jR^k)_q-N(R^g)C(O)R^e$, $-(CR^jR^k)_q-N(R^g)S(O)_2R^f$, $-(CR^jR^k)_q-N(R^g)C(O)N(R^e)(R^g)$, $-(CR^jR^k)_q-N(R^g)S(O)_2N(R^e)(R^g)$, $-(CR^jR^k)_q-C(O)R^e$, $-(CR^jR^k)_q-C(O)O(R^e)$, $-(CR^jR^k)_q-C(O)N(R^e)(R^g)$, and $-C(R^w)=N-OR^w$, can be prepared from compounds of formula (xxvii). Reactions well-known in the chemical literature for effecting these transformations include the Suzuki, Heck, Stille, Sonogashira, and Negishi reactions. Typical reaction conditions for can be found in the following references: Negishi, E. A. Handbook of Organopalladium Chemistry for Organic Synthesis; Wiley-Interscience: New York, 2002; Miyaura, N. Cross-Coupling Reactions: A Practical Guide; Springer: New York, 2002. More specifically, where $R^{GA}$ is alkoxyalkenyl or alkenyl, compounds can be prepared using palladium tetrakistriphenyl phosphine as catalyst, cesium fluoride as base with the corresponding boronic acid or boronic ester under microwave conditions at temperatures from about 100° C. to about 140° C. In the conversion of (xxvii) to (xxviii), the —Br of (xxvii) can also be a triflate, —I, —Cl, a boronic acid (or derivative), stannyl or the like.

Compounds of formula (Ib) wherein $X^2$ is O and compounds of formula (Ic) can be prepared respectively from isoxazole-3-amines and pyridine-2-amines using synthetic methods that are analogous to those in Schemes 1, 2, 4, and 5. The starting isoxazole-3-amines and pyridine-2-amines are either commercially available or can be prepared by known synthetic methods described in the chemical literature.

It can be appreciated that the synthetic schemes and specific examples as illustrated in the Examples section are illustrative and are not to be read as limiting the scope as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

The skilled artisan can also appreciate that not all of the substituents in the compounds of formula (I) can tolerate certain reaction conditions employed to synthesize the compounds. Routine experimentations, including appropriate manipulation of the reaction conditions, reagents and sequence of the synthetic route, protection of any chemical functionality that can not be compatible with the reaction conditions, and deprotection at a suitable point in the reaction sequence of the method, followed by further transformation of the molecules using standard chemical techniques well known to those skilled in the art such as alkylation, acylation, reductive amination, sulfonylation, oxidation, reduction and the like, are included within the scope. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety.

Furthermore, the skilled artisan can appreciate that in many circumstances, the order in which moieties are introduced can not be critical. The particular order of steps required to produce the compounds of formula (I) is dependent upon the particular compounds being synthesized, the starting compound, and the relative lability of the substituted moieties. Thus, synthesis of the present compounds can be accomplished by methods analogous to those described in the synthetic schemes described hereinabove and in specific examples, and routine experimentations, including appropriate manipulation of the reaction conditions, reagents and sequence of the synthetic route are within the scope.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

Following Examples can be used for illustrative purposes and should not be deemed to narrow the scope.

g. Examples

Example 1

5-chloro-2-methoxy-N-[(2Z)-3-[(2R)-tetrahydrofuran-2-ylmethyl]-5-[1-(trifluoromethyl)cyclopropyl]-1,3,4-thiadiazol-2(3H)-ylidene]benzamide Example 1A 5-[1-(trifluoromethyl)cyclopropyl]-1,3,4-thiadiazol-2-amine A mixture of 1-(trifluoromethyl)cyclopropanecarboxylic acid (1 g, 6.5 mmol) and thiosemicarbazide (0.6 g, 6.5 mmol)

in dioxane (8 mL) was heated to 90° C. To the hot reaction mixture was added phosphorus oxychloride (0.6 mL, 6.5 mmol). The reaction mixture was stirred at 90° C. for 16 h. The reaction mixture was then cooled, diluted with ethyl acetate (10 mL) and quenched with saturated NaHCO$_3$ (10 mL). The aqueous layer was extracted with ethyl acetate (2×10 mL). The combined organic extracts were washed with water (15 mL), dried (Na$_2$SO$_4$), filtered and concentrated. The residue was triturated in hot hexanes to afford 0.5 g (37%) of the title compound. LC/MS (ESI$^+$) m/z 210 (M+H)$^+$.

Example 1B

(2R)-tetrahydrofuran-2-ylmethyl 4-methylbenzenesulfonate

The title compound was prepared from commercially available (R)-(tetrahydrofuran-2-yl) methanol (Fluka) according to the procedure as described in Ebata, T.; Kawakami, H.; Koseki, K.; Matsushita, H. Agricultural and Biological Chemistry, 1991, 55(6), 1685-6. MS (ESI$^+$) m/z 257 (M+H)$^+$.

Example 1C

3-[(2R)-tetrahydrofuran-2-ylmethyl]-5-[1-(trifluoromethyl)cyclopropyl]-1,3,4-thiadiazol-2(3H)-imine A mixture of Example 1A (0.15 g, 0.7 mmol), Example 1B (0.20 g, 0.8 mmol) and tetrabutylammonium iodide (0.13 g, 0.36 mmol) in N,N-dimethylformamide (0.2 mL) was heated at 95° C. for 16 hr, cooled to room temperature and quenched with 1M NaHCO$_3$ (10 mL). The aqueous layer was extracted with dichloromethane (3×10 mL). The combined organic extracts were dried (Na$_2$SO$_4$), filtered and concentrated to afford 0.2 g (crude) of the title compound. LC/MS (ESI$^+$) m/z 294 (M+H)$^+$.

Example 1D

5-chloro-2-methoxy-N-[(2Z)-3-[(2R)-tetrahydrofuran-2-ylmethyl]-5-[1-(trifluoromethyl)cyclopropyl]-1,3,4-thiadiazol-2(3H)-ylidene]benzamide To a solution of Example 1C (crude, 0.2 g, 0.7 mmol) in tetrahydrofuran (10 mL) was added triethylamine (0.3 mL), 4-dimethylaminopyridine (2 mg) and the product from step A of Example 11C (0.15 g, 0.7 mmol). The reaction mixture was stirred at room temperature overnight, diluted with ethyl acetate (10 mL), washed with 1M NaHCO$_3$ (10 mL), and the layers were separated. The aqueous layer was extracted with ethyl acetate (2×10 mL). The combined organic extracts were dried (Na$_2$SO$_4$), filtered and concentrated. The residue was purified by column chromatography using an Analogix® Intelliflash280™ (SiO$_2$, 0-100% ethyl acetate in hexanes) to afford 16 mg (5%) of the title compound. $^1$H NMR (300 MHz, DMSO-d$_6$) δ ppm 1.53-1.59 (m, 2H), 1.59-1.64 (m, 2H), 1.67-1.79 (m, 1H), 1.79-1.91 (m, 2H), 1.91-2.04 (m, 1H), 3.59-3.70 (m, 1H), 3.71-3.79 (m, 1H), 3.81 (s, 3H), 4.21-4.42 (m, 2H), 4.45-4.57 (m, 1H), 7.16 (d, J=8.7 Hz, 1H), 7.53 (dd, J=9.1, 2.8 Hz, 1H), 7.79 (d, J=2.8 Hz, 1H); MS (ESI$^+$) m/z 462 (M+H)$^+$.

Example 2

5-chloro-N-[(2Z)-5-cyclopropyl-3-(tetrahydrofuran-2-ylmethyl)-1,3,4-thiadiazol-2(3 H)-ylidene]-2-methoxybenzamide

Example 2A

5-cyclopropyl-3-(tetrahydrofuran-2-ylmethyl)-1,3,4-thiadiazol-2(3H)-imine 5-cyclopropyl-1,3,4-thiadiazol-2-amine (ASD) and 2-(bromomethyl)tetrahydrofuran (Acros) were processed using the method described in Example 1C to afford the title compound.

Example 2B

5-chloro-N-[(2Z)-5-cyclopropyl-3-(tetrahydrofuran-2-ylmethyl)-1,3,4-thiadiazol-2(3 H)-ylidene]-2-methoxybenzamide A mixture of the compound from Example 2A (70 mg, 0.31 mmol), 5-chloro-2-methoxy-benzoic acid (64 mg, 0.34 mmol), O-(7-azabenzotriazol-1-yl)-N,N,N',N'-tetramethyluronium hexafluorophosphate (HATU) (185 mg, 0.46 mmol) and triethylamine (130 L, 0.93 mmol) in N,N-dimethylformamide (5 mL) was stirred at room temperature for 12 hour. The mixture was diluted with water, and extracted with ethyl acetate (3×30 mL). The combined organic layers were dried over MgSO$_4$, filtered and concentrated under reduced pressure. The residue was purified by flash chromatography (silica gel, eluting with ethyl acetate/hexanes 2:3) to provide the title compound. $^1$H NMR (300 MHz, DMSO-d$_6$) δ ppm 0.95-1.01 (m, 2H) 1.14-1.21 (m, 2H) 1.67-1.78 (m, 1H) 1.79-1.93 (m, 2H) 1.91-2.00 (m, 1H) 2.30-2.39 (m, 1H) 3.65 (dd, J=13.81, 7.06 Hz, 1H) 3.77 (dd, J=13.50, 6.75 Hz, 1H) 3.80 (s, 3H) 4.21 (dd, J=13.20, 4.60 Hz, 1H) 4.31-4.38 (m, 1H) 4.43 (dd, J=12.89, 7.36 Hz, 1H) 7.13 (d, J=8.90 Hz, 1H) 7.49 (dd, J=8.90, 2.76 Hz, 1H) 7.73 (d, J=2.76 Hz, 1H); MS (ESI$^+$) m/z 394 (M+H)$^+$.

Example 3

N-[(2Z)-5-cyclopropyl-3-(tetrahydrofuran-2-ylmethyl)-1,3,4-thiadiazol-2(3H)-ylidene]-2-ethoxybenzamide The product from Example 2A and 2-ethoxybenzoic acid (Aldrich) were processed using the method described in Example 2B to afford the title compound. $^1$H NMR (300 MHz, DMSO-d$_6$) δ ppm 0.95-1.02 (m, 2H) 1.13-1.19 (m, 2H) 1.32 (t, J=7.02 Hz, 3 H) 1.65-1.73 (m, 1H) 1.79-1.90 (m, 2H) 1.92-2.00 (m, 1H) 2.30-2.37 (m, 1H) 3.64 (dd, J=13.73, 7.63 Hz, 1H) 3.77 (dd, J=14.34, 7.32 Hz, 1H) 4.07 (q, J=7.02 Hz, 2H) 4.21 (dd, J=13.12, 4.58 Hz, 1H) 4.32-4.39 (m, 1H) 4.44 (dd, J=13.43, 7.63 Hz, 1H) 6.98 (td, J=7.63, 0.92 Hz, 1H) 7.08 (d, J=7.93 Hz, 1H) 7.40-7.45 (m, 1H) 7.77 (dd, J=7.63, 1.83 Hz, 1H); MS (ESI$^+$) m/z 374 (M+H)$^+$.

Example 4

N-[(2Z)-5-tert-butyl-3-[(2R)-tetrahydrofuran-2-ylmethyl]-1,3,4-thiadiazol-2(3H)-ylidene]-5-chloro-2-methoxybenzamide

Example 4A

N-(5-tert-butyl-1,3,4-thiadiazol-2-yl)-5-chloro-2-methoxybenzamide

To a solution of 2-amino-5-tert-butyl-1,3,4-thiadiazole (Aldrich) (2.5 g, 16.3 mmol) in tetrahydrofuran (30 mL) were added 5-chloro-2-methoxybenzoic acid (Aldrich) (3.65 g, 19.6 mmol), triethylamine (5.5 mL, 39.5 mmol), and 1-propanephosphonic acid cyclic anhydride 50% solution in ethyl acetate (Aldrich) (11.6 mL, 19.6 mmol). The reaction mixture was stirred at about room temperature for 14 hours, cooled with external ice bath while quenching with saturated aqueous $NaHCO_3$ (20 mL). The aqueous layer was extracted with ethyl acetate (2×40 mL). The combined organic extracts were dried over anhydrous $Na_2SO_4$, filtered and concentrated under reduced pressure. The residue was purified by column chromatography using an Analogix® Intelliflash280™ ($SiO_2$, 0-100% ethyl acetate in hexanes) to afford 4.65 g of the title compound. $^1$H NMR (300 MHz, DMSO-$d_6$) δ ppm 1.43 (s, 9H), 3.88 (s, 3H), 7.22 (d, J=8.7 Hz, 1H), 7.55-7.64 (m, 2H), 12.41 (s, 1H); MS (ESI$^+$) m/z 326 (M+H)$^+$.

Example 4B

N-[(2Z)-5-tert-butyl-3-[(2R)-tetrahydrofuran-2-ylmethyl]-1,3,4-thiadiazol-2(3H)-ylidene]-5-chloro-2-methoxybenzamide To a solution of Example 4A (200 mg, 0.62 mmol) in N,N-dimethylformamide/tetrahydrofuran (1:4, 10 mL) were added a solution of potassium tert-butoxide (Aldrich, 103 mg, 0.92 mmol) and Example 1B (189 mg, 0.74 mmol). The reaction mixture was stirred at 80° C. for 16 h, cooled to room temperature, quenched with saturated aqueous $NaHCO_3$ (10 mL). The aqueous layer was extracted with ethyl acetate (3×10 mL). The combined organic extracts were dried over anhydrous $Na_2SO_4$, filtered and concentrated under reduced pressure. The residue was purified by column chromatography using an Analogix® Intelliflash280™ ($SiO_2$, 0-1% methanol in dichloromethane) to afford the title compound. $^1$H NMR (300 MHz, DMSO-$d_6$) δ ppm 1.39 (s, 9H), 1.69-2.04 (m, 4H), 3.60-3.70 (m, 1H), 3.73-3.79 (m, 1H), 3.80 (s, 3H), 4.24 (dd, J=4.7, 15.0 Hz, 1H), 4.31-4.42 (m, 1H), 4.49 (dd, J=15.0, 7.5 Hz, 1H), 7.14 (d, J=8.8 Hz, 1H), 7.50 (dd, J=8.8, 2.7 Hz, 1H), 7.73 (d, J=3.1 Hz, 1H); MS (ESI$^+$) m/z 410 (M+H)$^+$.

Example 5

5-chloro-2-methoxy-N-[(2Z)-5-(1-methylcyclopropyl)-3-[(2R)-tetrahydrofuran-2-ylmethyl]-1,3,4-thiadiazol-2(3H)-ylidene]benzamide

Example 5A 5-(1-methylcyclopropyl)-1,3,4-thiadiazol-2-amine

Commercially available, 1-methyl-cyclopropane-1-carboxylic acid (Aldrich), thiosemicarbazide (Aldrich) and phosphorus oxychloride (Aldrich) were processed as described for Example 1A to obtain the title compound. $^1$H NMR (300 MHz, DMSO-$d_6$) δ ppm 0.84-0.93 (m, 2H), 0.93-1.03 (m, 2H), 1.41 (s, 3H), 6.94 (s, 2H); MS (ESI$^+$) m/z 156 (M+H)$^+$.

Example 5B 5-chloro-2-methoxy-N-[5-(1-methylcyclopropyl)-1,3,4-thiadiazol-2-yl]benzamide Example 5A and 5-chloro-2-methoxybenzoic acid (Aldrich) were processed as described for Example 4A to obtain the title compound. $^1$H NMR (300 MHz, DMSO-$d_6$) δ ppm 1.01-1.06 (m, 2H), 1.15-1.22 (m, 2H), 1.54 (s, 3H), 3.87 (s, 3H), 7.22 (d, J=8.8 Hz, 1H), 7.55-7.64 (m, 2H), 12.39 (s, 1H); MS (ESI$^+$) m/z 324 (M+H)$^+$.

Example 5C 5-chloro-2-methoxy-N-[(2Z)-5-(1-methylcyclopropyl)-3-[(2R)-tetrahydrofuran-2-ylmethyl]-1,3,4-thiadiazol-2(3H)-ylidene]benzamide Example 5B and Example 1B were processed as described for Example 4B to obtain the title compound. $^1$H NMR (300 MHz, DMSO-$d_6$) δ ppm 1.03-1.10 (m, 2H), 1.12-1.19 (m, 2H), 1.50 (s, 3H), 1.68-2.01 (m, 4H), 3.60-3.70 (m, 1H), 3.72-3.78 (m, 1H), 3.80 (s, 3H), 4.22 (dd, J=12.9, 4.4 Hz, 1H), 4.30-4.41 (m, 1H), 4.45 (dd, J=12.0, 7.5 Hz, 1H), 7.14 (d, J=8.8 Hz, 1H), 7.50 (dd, J=9.0, 2.9 Hz, 1H), 7.74 (d, J=3.1 Hz, 1H): MS (ESI$^+$) m/z 408 (M+H).

Example 6

5-chloro-N-[(2Z)-5-(1,1-dimethylprop-2-ynyl)-3-[(2R)-tetrahydrofuran-2-ylmethyl]-1,3,4-thiadiazol-2(3H)-ylidene]-2-methoxybenzamide

Example 6A 5-(1,1-dimethylprop-2-ynyl)-1,3,4-thiadiazol-2-amine

Commercially available, 2,2-dimethylbut-3-ynoic acid (Betapharma), thiosemicarbazide (Aldrich) and phosphorus oxychloride (Aldrich) were processed as described for Example 1A to obtain the title compound. MS (ESI$^+$) m/z 168 (M+H)$^+$.

Example 6B 5-chloro-N-[5-(1,1-dimethylprop-2-ynyl)-1,3,4-thiadiazol-2-yl]-2-methoxybenzamide To a solution of Example 6A (0.46 g, 2.8 mmol) in tetrahydrofuran (10 mL) was added the product from step A of Example 11C (0.62 g, 3.0 mmol), triethylamine (1.1 mL, 8.2 mmol), and 4-dimethylaminopyridine (3 mg). The reaction mixture was stirred at 60° C. for 14 h, cooled, and quenched with saturated aqueous $NaHCO_3$ (20 mL). The aqueous layer was extracted with ethyl acetate (3×30 mL). The combined organic extracts were dried over anhydrous $Na_2SO_4$, filtered and concentrated under reduced pressure. The residue was purified by column chromatography using an Analogix® Intelliflash280™ ($SiO_2$, 0-100% ethyl acetate in hexanes) to afford 0.85 g (44%) of the title compound. MS (ESI$^+$) m/z 336 (M+H)$^+$.

Example 6C 5-chloro-N-[(2Z)-5-(1,1-dimethylprop-2-ynyl)-3-[(2R)-tetrahydrofuran-2-ylmethyl]-1,3,4-thiadiazol-2(3H)-ylidene]-2-methoxybenzamide To a solution of Example 6B (250 mg, 0.75 mmol) in N,N-dimethylformamide/tetrahydrofuran (1:4, 10 mL) was added a solution of potassium tert-butoxide (Aldrich, 125 mg, 1.1 mmol) and Example 1B (285 mg, 1.1 mmol). The reaction mixture was stirred at 80° C. for 16 h, cooled to room temperature, quenched with saturated aqueous $NaHCO_3$ (10 mL). The aqueous layer was extracted with ethyl acetate (3×10 mL). The combined organic extracts were dried over anhydrous $Na_2SO_4$, filtered and concentrated under reduced pressure. The residue was purified by column chromatography using an Analogix® Intelliflash280™ ($SiO_2$, 0-1% methanol in dichloromethane) to afford 90 mg (29%) of the title compound. $^1$H NMR (300 MHz, DMSO-$d_6$) δ ppm 1.65 (s, 6H), 1.69-1.81 (m, 1H), 1.80-1.92 (m, 2H), 1.92-2.05 (m, 1H), 3.57 (s, 1H), 3.59-3.72 (m, 1H), 3.72-3.79 (m, 1H), 3.81 (s, 3H), 4.21-4.31 (m, 1H), 4.31-4.43 (m, 1H), 4.44-4.58 (m, 1H), 7.15 (d, J=9.1 Hz, 1H), 7.52 (dd, J=8.9, 3.0 Hz, 1H), 7.77 (d, J=2.8 Hz, 1 H); MS (ESI$^+$) m/z 420 (M+H)$^+$.

Example 7

5-chloro-2-methoxy-N-[(2Z)-5-(2,2,3,3-tetrafluoro-1-methylcyclobutyl)-3-[(2 R)-tetrahydrofuran-2-ylmethyl]-1,3,4-thiadiazol-2(3H)-ylidene]benzamide

Example 7A 5-(2,2,3,3-tetrafluoro-1-methylcyclobutyl)-1,3,4-thiadiazol-2-amine A mixture of 2,2,3,3-tetrafluoro-1-methylcyclobutanecarbonyl chloride (ABCR) (2 g, 9.78 mmol) and thiosemicarbazide (Aldrich) (0.891 g, 9.78 mmol) in 10 mL of dioxane was heated at 90° C. for 12 h. The solvent was evaporated under reduced pressure. The residue was dissolved in dichloromethane and washed with saturated $NaHCO_3$. The organic extract was dried over $Na_2SO_4$ and concentrated. The residue was purified by flash chromatography on $SiO_2$ (2% methanol in dichloromethane) to give the title compound. MS (ESI$^+$) m/z 242 (M+H)$^+$.

Example 7B 5-chloro-2-methoxy-N-[5-(2,2,3,3-tetrafluoro-1-methylcyclobutyl)-1,3,4-thiadiazol-2-yl]benzamide Example 7A and the product from step A of Example 11C were processed as described for Example 6B to obtain the title compound. LC/MS (ESI$^+$) m/z 410 (M+H)$^+$.

Example 7C 5-chloro-2-methoxy-N-[(2Z)-5-(2,2,3,3-tetrafluoro-1-methylcyclobutyl)-3-[(2 R)-tetrahydrofuran-2-ylmethyl]-1,3,4-thiadiazol-2(3H)-ylidene]benzamide Example 7B and Example 1B were processed as described for Example 6C to obtain the title compound. $^1$H NMR (300 MHz, DMSO-$d_6$) δ ppm 1.71 (s, 3H), 1.73-1.99 (m, 4 H), 2.91-3.15 (m, 1H), 3.38-3.59 (m, 1H), 3.61-3.71 (m, 1H), 3.71-3.80 (m, 1H), 3.82 (s, 3H), 4.26-4.45 (m, 2H), 4.48-4.64 (m, 1H), 7.17 (d, J=8.8 Hz, 1H), 7.53 (dd, J=9.0, 2.9 Hz, 1H), 7.80 (d, J=3.4 Hz, 1H); MS (ESI$^+$) m/z 494 (M+H)$^+$.

Example 8

5-chloro-2-methoxy-N-[(2Z)-3-[(2R)-tetrahydrofuran-2-ylmethyl]-5-[1-(trifluoromethyl)cyclobutyl]-1,3,4-thiadiazol-2(3H)-ylidene]benzamide

Example 8A

5-[1-(trifluoromethyl)cyclobutyl]-1,3,4-thiadiazol-2-amine

Commercially available, 1-(trifluoromethyl)cyclobutanecarboxylic acid (Oakwood), thiosemicarbazide (Aldrich) and phosphorus oxychloride (Aldrich) were processed as described for Example 1A to obtain the title compound. MS (ESI$^+$) m/z 224 (M+H)$^+$.

Example 8B

3-[(2R)-tetrahydrofuran-2-ylmethyl]-5-[1-(trifluoromethyl)cyclobutyl]-1,3,4-thiadiazol-2(3H)-imine Example 8A and Example 1B were processed as described for Example 1C to obtain the title compound. LC/MS (ESI$^+$) m/z 308 (M+H)$^+$.

Example 8C 5-chloro-2-methoxy-N-[(2Z)-3-[(2R)-tetrahydrofuran-2-ylmethyl]-5-[1-(trifluoromethyl)cyclobutyl]-1,3,4-thiadiazol-2(3H)-ylidene]benzamide Example 8B and the product from step A of Example 11C were processed as described for Example 1D to obtain the title compound. $^1$H NMR (300 MHz, DMSO-$d_6$) δ ppm 1.68-2.17 (m, 6H), 2.70 (t, J=8.1 Hz, 4H), 3.60-3.72 (m, 1H), 3.73-3.80 (m, J=6.6, 6.6 Hz, 1H), 3.81 (s, 3H), 4.27-4.48 (m, 2H), 4.51-4.62 (m, 1H), 7.17 (d, J=8.8 Hz, 1H), 7.53 (dd, J=9.0, 2.9 Hz, 1H), 7.79 (d, J=2.7 Hz, 1H); MS (ESI$^+$) m/z 476 (M+H)$^+$.

Example 9

5-chloro-2-methoxy-N-[(2Z)-3-[(2R)-tetrahydrofuran-2-ylmethyl]-5-(2,2,2-trifluoro-1,1-dimethylethyl)-1,3,4-thiadiazol-2(3H)-ylidene]benzamide

Example 9A 5-(2,2,2-trifluoro-1,1-dimethylethyl)-1,3,4-thiadiazol-2-amine

Commercially available, 3,3,3-trifluoro-2,2-dimethylpropanoic acid (Matrix), thiosemicarbazide (Aldrich) and phosphorus oxychloride (Aldrich) were processed as described for Example 1A to obtain the title compound. MS (ESI$^+$) m/z 212 (M+H)$^+$.

Example 9B

3-[(2R)-tetrahydrofuran-2-ylmethyl]-5-(2,2,2-trifluoro-1,1-dimethylethyl)-1,3,4-thiadiazol-2(3H)-imine Example 9A and Example 1B were processed as described for Example 1C to obtain the title compound. LC/MS (ESI$^+$) m/z 296 (M+H)$^+$.

Example 9C 5-chloro-2-methoxy-N-[(2Z)-3-[(2R)-tetrahydrofuran-2-ylmethyl]-5-(2,2,2-trifluoro-1,1-dimethylethyl)-1,3,4-thiadiazol-2(3H)-ylidene]benzamide Example 9B and the product from step A of Example 11C were processed as described for Example 1D to obtain the title compound. $^1$H NMR (300 MHz, DMSO-d$_6$) δ ppm 1.64 (s, 6H), 1.69-2.03 (m, 4H), 3.60-3.71 (m, 1H), 3.71-3.79 (m, J=7.5, 7.5 Hz, 1 H), 3.81 (s, 3H), 4.23-4.43 (m, 2H), 4.56 (d, 1H), 7.16 (d, J=8.8 Hz, 1H), 7.53 (dd, J=8.8, 2.7 Hz, 1H), 7.79 (d, J=2.7 Hz, 1H); MS (ESI$^+$) m/z 464 (M+H)$^+$.

Example 10

5-chloro-2-methoxy-N-[(2E)-5-methyl-1-(tetrahydrofuran-2-ylmethyl)pyridin-2(1 H)-ylidene]benzamide

Example 10A 5-methyl-1-(tetrahydrofuran-2-ylmethyl)pyridin-2(1H)-imine

To a 25 mL, round-bottomed flask containing a magnetic stir bar were added solid 5-methylpyridin-2-amine (1.08 g, 10.0 mmol) and liquid (±)-2-(bromomethyl)tetrahydrofuran (Acros) (2.46 g, 15.0 mmol). A reflux condenser with N$_2$-inlet was attached and a heating mantle was applied. The mixture was heated to 60° C. and stirred overnight. The reaction mixture changed to a brown slurry while heating. After cooling to room temperature, ethyl acetate (20 mL) was added to precipitate the product. The tan solid was collected by vacuum filtration on a glass frit and dried under vacuum to give 2.68 g of the hydrobromide salt of the title compound. The crude product was used without further purification for the next step.

Example 10B 5-chloro-2-methoxy-N-[(2E)-5-methyl-1-(tetrahydrofuran-2-ylmethyl)pyridin-2(1 H)-ylidene]benzamide The product of Example 10A (273 mg, 1.00 mmol), solid 5-chloro-2-methoxybenzoic acid (224 mg, 1.20 mmol), and solid 2-(1H-benzo[d][1,2,3]triazol-1-yl)-1,1,3,3-tetramethylisouronium tetrafluoroborate (TBTU) (385 mg, 1.20 mmol) were added to a 20-mL scintillation vial. Anhydrous acetonitrile (8 mL) was added via syringe. Neat triethylamine (486 mg, 669 mL, 4.80 mmol) was added via syringe and the mixture was stirred at room temperature for 24 h. The solvents/volatiles were removed by rotary evaporator. The crude product was dissolved in dichloromethane (10 mL) and washed with saturated NaHCO$_3$ solution (10 mL). The product was purified by flash chromatography (silica gel, 30% ethyl acetate in hexanes) to give 37.9 mg (10%) of the title compound as a white powder. $^1$H NMR (300 MHz, DMSO-d$_6$) δ 1.59-1.68 (m, 1H), 1.78-1.96 (m, 3 H), 2.18 (s, 3H), 3.61-3.68 (m, 1H), 3.75 (s, 3H), 3.76-3.84 (m, 1H), 4.03 (dd, J=12.5, 8.1 Hz, 1H), 4.29-4.37 (m, 1H), 4.57 (dd, J=12.9, 3.4 Hz, 1H), 7.03 (d, J=8.8 Hz, 1H), 7.33 (dd, J=8.6, 2.9 Hz, 1H), 7.50 (d, J=2.7 Hz, 1H), 7.65 (dd, J=9.3, 2.2 Hz, 1H), 7.89 (br s, 1H), 8.20 (d, J=9.2 Hz, 1H). (MS (ESI$^+$) m/z 362.1 (M+H)$^+$. Anal. calcd for C$_{19}$H$_{21}$ClN$_2$O$_3$: C, 63.24; H, 5.87; N, 7.76. Found: C, 63.19; H, 5.83; N, 7.82.

Example 11

N-[(3E)-5-tert-butyl-2-[(2R)-tetrahydrofuran-2-ylmethyl]isoxazol-3(2H)-ylidene]-5-chloro-2-methoxybenzamide

Example 11A (2R)-tetrahydrofuran-2-ylmethyl 4-methylbenzenesulfonate

To (R)-(tetrahydrofuran-2-yl)methanol (1.0 g, 9.8 mmol) in CH$_2$Cl$_2$ (3 mL) and pyridine (3 mL) at ambient temperature was added 4-methylbenzene-1-sulfonyl chloride (2.0 g, 10.3 mmol) portion-wise over 5 minutes. This mixture was stirred for 16 hours at ambient temperature then was quenched with 10 mL of 5% aqueous HCl and was extracted with 3×5 mL CH$_2$Cl$_2$. The combined organics were dried over anhydrous Na$_2$SO$_4$, filtered and concentrated under reduced pressure. The crude material was purified by column chromatography (SiO$_2$, 75% hexanes in ethyl acetate) to give the title compound (1.7 g, 6.8 mmol, 69% yield). MS (DCI/NH$_3$) m/z 257 (M+H)$^+$ and 274 (M+NH$_4$)$^+$.

Example 11B 5-tert-butyl-2-[(2R)-tetrahydrofuran-2-ylmethyl]isoxazol-3(2H)-imine A mixture of 5-tert-butylisoxazol-3-amine (1 g, 7.1 mmol) and the product from Example 11A (1.7 g, 6.8 mmol) in 1.5 mL N,N-dimethylformamide was warmed to 85° C. and was allowed to stir for 70 hours. The mixture was cooled to ambient temperature, concentrated under reduced pressure and purified by column chromatography (SiO$_2$, 50% hexanes in ethyl acetate then 10% CH$_3$OH in ethyl acetate) to provide the p-toluenesulfonate salt of the title compound (0.48 g, 1.2 mmol, 17% yield). MS (DCI/NH$_3$) m/z 225 (M+H)$^+$.

Example 11C

N-[(3E)-5-tert-butyl-2-[(2R)-tetrahydrofuran-2-ylmethyl]isoxazol-3(2H)-ylidene]-5-chloro-2-methoxybenzamide Step A: 5-chloro-2-methoxybenzoyl chloride A mixture of 5-chloro-2-methoxybenzoic acid (0.24 g, 1.3 mmol) and thionyl chloride (5 mL) was warmed to reflux and was allowed to stir for 2 hours. The mixture was cooled to ambient temperature, concentrated under reduced pressure and diluted with 10 mL toluene. The reaction mixture was again concentrated under reduced pressure and was again diluted with 10 mL toluene. This concentration and dilution was repeated and the crude product was used without further purification.

Step B

To a solution of the product of Example 11B (0.48 g, 1.2 mmol) in tetrahydrofuran (10 mL) was added triethylamine (0.68 mL, 4.8 mmol) followed by a solution of the product from Step A (1.3 mmol) in tetrahydrofuran (5 mL) via cannula. This mixture was warmed to 50° C. and was allowed to stir for 3 hours. The mixture was cooled to ambient temperature, was quenched with saturated, aqueous NH$_4$Cl (5 mL) and was diluted with ethyl acetate (5 mL). The layers were separated and the aqueous layer was extracted with ethyl acetate (3×5 mL). The combined organic extracts were dried over Na$_2$SO$_4$, filtered and concentrated under reduced pressure. The crude material was purified by column chromatography (SiO$_2$, 60% hexanes in ethyl acetate) to give the title compound (0.34 g, 0.87 mmol, 72% yield). $^1$H NMR (CDCl$_3$, 300 MHz) δ ppm 1.34 (s, 9H), 1.74-1.97 (m, 3H), 1.98-2.11 (m, 1H), 3.74-3.84 (m, 1H), 3.85-3.96 (m, 1H), 3.87 (s, 3H), 4.17-4.25 (m, 1H), 4.27-4.43 (m, 2H), 6.87 (d, J=8.7 Hz, 1H), 7.22 (s, 1H), 7.27-7.32 (m, 1H), 7.82 (d, J=2.8 Hz, 1H); MS (DCI/NH$_3$) m/z 393 (M+H)$^+$; Anal. (C$_{20}$H$_{25}$ClN$_2$O$_4$) Calc: C, 61.14; H, 6.41; N, 7.13.
Found: C, 60.97; H, 6.57; N, 7.13.

Example 12

N-{(3E)-5-tert-butyl-1-methyl-2-[(2S)-tetrahydrofuran-2-ylmethyl]-1,2-dihydro-3H-pyrazol-3-ylidene}-5-chloro-2-methoxybenzamide Example 12A (2S)-tetrahydrofuran-2-ylmethyl 4-methylbenzenesulfonate To (S)-(tetrahydrofuran-2-yl)methanol (2.0 g, 20 mmol) in CH$_2$Cl$_2$ (10 mL) at about 0° C. was added p-toluenesulfonyl chloride (4.2 g, 22.00 mmol), followed by drop-wise addition of triethylamine (5.6 mL, 40.0 mmol). The resulting solution was kept at 0° C. for 2 hours, and then at room temperature for another 2 hours. The reaction mixture was concentrated to dryness and diethylether (200 mL) and water (100 mL) were added. The organic layer was separated, dried over magnesium sulfate, filtered, and concentrated to yield the title compound (2.3 g, 13.00 mmol, 64%) as a colorless oil, which was used in the next step without purification.

Example 12B

[(2S)-tetrahydrofuran-2-ylmethyl]hydrazine

To the product from Example 12A (720 mg, 4.0 mmol) in ethanol (2 mL) was gradually added ice-cooled liquid hydrazine (2560 mg, 80 mmol). The temperature was allowed to rise to room temperature where it was kept for 2 hours before warming to 40° C. and kept at that temperature for 2 hours. The reaction solution was allowed to stand overnight at room temperature and concentrated. The residue was extracted with diethylether (3×60 mL). The combined ether layers were dried over MgSO$_4$, filtered, and concentrated to yield the title compound as a colorless oil (385 mg, 83%).

Example 12C 3-tert-butyl-1-[(2S)-tetrahydrofuran-2-ylmethyl]-1H-pyrazol-5-amine

To a stirred solution of the product from Example 12B (232 mg, 2.0 mmol) in ethanol (4 mL) was added 4,4-dimethyl-3-oxopentanenitrile (250 mg, 2.0 mmol). The mixture was refluxed for 2 hours. The ethanol was removed by evaporation under reduced pressure and the crude product was dissolved in CH$_2$Cl$_2$ (10 mL), which was used directly for the next step.

Example 12D

N-{3-tert-butyl-1-[(2S)-tetrahydrofuran-2-ylmethyl]-1H-pyrazol-5-yl}-5-chloro-2-methoxybenzamide To the mixture of the product from Example 12C (447 mg, 2.0 mmol) and the product from Step A of Example 11C (410 mg, 2.0 mmol) in CH$_2$Cl$_2$ (8 mL) at about 0° C. was added triethylamine (0.34 mL, 2.4 mmol) dropwise. After stirring for 1 hour at room temperature, water (10 mL) was added to quench the reaction, and CH$_2$Cl$_2$ (20 mL) was added. The organic layer was separated, washed with brine, dried over MgSO$_4$, filtered, and concentrated. The residue was purified by chromatography using an Analogix® IT280™ eluting with ethyl acetate/Hexanes in 0-50% gradient to yield the title compound (330 mg, 42%). $^1$H NMR (300 MHz, DMSO-d$_6$) δ ppm 10.26 (s, 1H), 7.81 (d, J=2.71 Hz, 1 H), 7.62 (dd, J=8.98, 2.88 Hz, 1H), 7.28 (d, J=9.15 Hz, 1H), 6.31 (s, 1H), 4.05-4.23 (m, 3H), 3.97 (s, 3H), 3.54-3.72 (m, 2H), 1.83-2.01 (m, 1H), 1.62-1.82 (m, 2H), 1.43-1.60 (m, 1H), 1.24 (s, 9H). MS (ESI) m/z 392 (M+H)$^+$.

Example 12E

N-{(3E)-5-tert-butyl-1-methyl-2-[(2S)-tetrahydrofuran-2-ylmethyl]-1,2-dihydro-3H-pyrazol-3-ylidene}-5-chloro-2-methoxybenzamide To the product from Example 12D (298 mg, 0.76 mmol) in toluene (6 mL) was added dimethylsulfate (0.145 mL, 1.52 mmol). The mixture was heated at 110° C. for 48 hours and concentrated under reduced pressure. The residue was dissolved in 1:1 dimethylsulfoxide/methanol and purified by reverse phase preparative HPLC on a Waters Nova-Pak® HR C18 6 um 60 Å Prep-Pak® cartridge column (40 mm×100 mm) using a gradient of 0% to 70% acetonitrile: 10 mM ammonium acetate over 8 min (10 min run time) at a flow rate of 70 mL/min to yield the title compound (150 mg, 48.6%). $^1$H NMR (300 MHz, DMSO-d$_6$) δ ppm 7.36 (d, J=2.74 Hz, 1H), 7.27 (dd, J=8.77, 2.82 Hz, 1H), 6.98 (d, J=8.69 Hz, 1H), 6.80 (s, 1H), 4.26-4.37 (m, 2H), 4.12-4.20 (m, 1H), 3.87 (m, 9H). MS 3.78 (m, 1H), 3.72 (s, 3H), 3.59-3.66 (m, 1H), 1.67-1.92 (m, 4H), 1.37 (m, 9H). MS (ESI) m/z 406 (M+H)$^+$.

Example 13

N-[(2Z)-5-tert-butyl-3-[(2R)-tetrahydrofuran-2-ylmethyl]-1,3-oxazol-2(3H)-ylidene]-5-chloro-2-methoxybenzamide Example 13A (R)-tetrahydrofuran-2-ylmethyl-cyanamide To a stirred mixture of cyanogen bromide (2.2 g, 20.8 mmol) and anhydrous Na$_2$CO$_3$ (4.2 g, 39.6 mmol) in dry ether (30 mL) at about −20 to about −10° C. was added (R)-(tetrahydro-furan-2-yl)-methylamine (Aldrich) (2.0 g, 9.8 mmol) over 10 minutes. Stirring was continued for an additional 1.5 hours at about −20 to about −10° C. Then the mixture was filtered and concentrated to provide 2.21 g of the title product. MS (DCI/NH$_3$) m/z 127 (M+H)$^+$.

Example 13B (R)-5-tert-butyl-3-((tetrahydrofuran-2-yl)methyl) oxazol-2(3H)-imine A mixture of Example 13A (2.35 g, 18.63 mmol), 1-bromo-3,3-dimethylbutan-2-one (Aldrich) (2.52 mL, 18.63 mmol) and potassium carbonate (2.57 g, 18.63 mmol) in 2-butanone (75 mL) was stirred at 80° C. overnight. The mixture was cooled, poured into water, and extracted with ethyl acetate (2×). The combined organic extracts were dried over $Na_2SO_4$, filtered, and concentrated under reduced pressure to afford the title compound. LC/MS (ESI$^+$) m/z 224 (M+H)$^+$.

Example 13C

N-[(2Z)-5-tert-butyl-3-[(2R)-tetrahydrofuran-2-ylmethyl]-1,3-oxazol-2(3H)-ylidene]-5-chloro-2-methoxybenzamide To a solution of Example 13B (1.24 g, 5.53 mmol) in tetrahydrofuran (10 mL) was added N-(3-dimethylaminopropyl)-N-ethylcarbodiimide hydrochloride (1.06 g, 5.53 mmol), 1-hydroxybenzotriazole (0.85 g, 5.55 mmol), triethylamine (0.45 mL, 3.2 mmol) and 5-chloro-2-methoxybenzoic acid (Aldrich) (1.03 g, 5.55 mmol). The mixture was stirred at 80° C. overnight, cooled to room temperature, diluted with ethyl acetate, washed with 1 M aqueous $NaHCO_3$, dried ($Na_2SO_4$), filtered and concentrated. The residue was purified by column chromatography using an Analogix® Intelliflash280™ ($SiO_2$, 0-50% ethyl acetate in hexanes) to provide the title product. MS (ESI$^+$) m/z 393 (M+H)$^+$; $^1$H NMR (300 MHz, CDCl$_3$) δ ppm 1.20 (s, 9H), 1.59-1.71 (m, 1H), 1.83-1.97 (m, 2H), 2.02-2.14 (m, 1H), 3.66 (dd, J=14.2, 7.5 Hz, 1H), 3.75-3.82 (m, 1H), 3.82 (s, 3H), 3.82-3.92 (m, 1H), 4.07 (dd, J=14.2, 2.7 Hz, 1H), 4.13-4.24 (m, 1H), 6.52 (s, 1H), 6.83 (d, J=8.8 Hz, 1H), 7.27 (dd, J=9.0, 2.7 Hz, 1H), 7.74 (d, J=2.7 Hz, 1H).

Example 14

N-{(3E)-5-tert-butyl-1-methyl-2-[(2R)-tetrahydrofuran-2-ylmethyl]-1,2-dihydro-3H-pyrazol-3-ylidene}-2-ethoxy-5-(trifluoromethyl)benzamide

Example 14A (R)—N-(3-tert-butyl-1-((tetrahydrofuran-2-yl)methyl)-1H-pyrazol-5-yl)-2,2,2-trifluoroacetamide To a solution of the product of Example 45B (4.15 g, 18.6 mmol) and triethylamine (7.8 mL, 55.8 mmol) in $CH_2Cl_2$ (30 mL) at 0° C. was added 2,2,2-trifluoroacetic anhydride (2.6 mL, 18.6 mmol) dropwise via syringe pump over 20 min. The ice-bath was removed after the addition was complete and the mixture was stirred at ambient temperature for 1 hour. The mixture was concentrated under reduced pressure and was purified by column chromatography ($SiO_2$, 40% hexanes/EtOAc) to provide the title compound (5.3 g, 16.6 mmol, 89% yield). MS (DCI/NH$_3$) m/z 320 (M+H)$^+$.

Example 14B

N-{(3E)-5-tert-butyl-1-methyl-2-[(2R)-tetrahydrofuran-2-ylmethyl]-1,2-dihydro-3H-pyrazol-3-ylidene}-2,2,2-trifluoroacetamide A mixture of the product of Example 14A (5.3 g, 16.6 mmol) and dimethyl sulfate (4.8 mL, 49.8 mmol) in toluene (7 mL) was warmed to 90° C. and was allowed to stir for 72 hours then was cooled to ambient temperature and was concentrated under reduced pressure. The mixture was purified by column chromatography ($SiO_2$, 50% hexanes/EtOAc to 100% EtOAc to 9:1:0.1 EtOAc:MeOH:Et$_3$N) to give the title compound (2.8 g, 8.4 mmol, 51% yield). MS (DCI/NH$_3$) m/z 334 (M+H)$^+$.

Example 14C 5-tert-butyl-1-methyl-2-[(2R)-tetrahydrofuran-2-ylmethyl]-1,2-dihydro-3H-pyrazol-3-imine To a solution of the product of Example 14B (2.3 g, 6.8 mmol) in MeOH (12 mL) was added sodium hydroxide (1.4 g, 34.0 mmol) in water (2.5 mL). This mixture was warmed to 50° C. and was allowed to stir for 16 hours then was cooled to ambient temperature. The mixture was concentrated under reduced pressure and then was diluted with 10 mL $CH_2Cl_2$ and 5 mL $H_2O$. The layers were separated and the aqueous layer was extracted with $CH_2Cl_2$ (3×5 mL). The combined organics were dried over anhydrous $Na_2SO_4$, filtered and concentrated under reduced pressure. The crude material was recrystallized from methanol and ethyl acetate to give the title compound (1.6 g, 6.7 mmol, 99% yield). MS (DCI/NH$_3$) m/z 238 (M+H)$^+$.

Example 14D

N-{(3E)-5-tert-butyl-1-methyl-2-[(2R)-tetrahydrofuran-2-ylmethyl]-1,2-dihydro-3H-pyrazol-3-ylidene}-2-ethoxy-5-(trifluoromethyl)benzamide A mixture of 2-ethoxy-5-(trifluoromethyl)benzoic acid (0.20 g, 0.84 mmol) and SOCl$_2$ (5 mL) was warmed to 90° C. for 2 hours and then was cooled to ambient temperature and concentrated under reduced pressure. The crude material was diluted with 10 mL toluene and was concentrated again. This dilution/concentration was repeated two additional times to provide 2-ethoxy-5-(trifluoromethyl)benzoyl chloride that was used directly below.

To a solution of the product of Example 14C (0.20 g, 0.84 mmol) in THF (10 mL) at ambient temperature was added Et$_3$N (0.47 mL, 3.4 mmol) followed by 2-ethoxy-5-(trifluoromethyl)benzoyl chloride (0.84 mmol). This mixture was warmed to 50° C. and was allowed to stir for 2 hours then was cooled to ambient temperature and was quenched with 5 mL saturated, aqueous NaHCO$_3$. EtOAc (10 mL) was added, the layers were separated and the aqueous layer was extracted with EtOAc (3×5 mL). The combined organics were dried over anhydrous Na$_2$SO$_4$, filtered, concentrated under reduced pressure and purified by column chromatography (SiO$_2$, 100% CH$_2$Cl$_2$ to 9:1:0.1 CH$_2$Cl$_2$:CH$_3$OH:NH$_4$OH) to give the title compound (0.11 g, 0.24 mmol, 29% yield). $^1$H NMR (300 MHz, CDCl$_3$) δ ppm 1.41-1.44 (m, 3H), 1.42 (s, 9H), 1.69-1.90 (m, 3H), 1.94-2.08 (m, 1H), 3.66-3.80 (m, 2H), 3.86 (s, 3H), 4.11-4.26 (m, 3H), 4.28-4.38 (m, 1H), 4.45-4.55 (m, 1H), 6.95 (d, J=8.7 Hz, 1H), 7.06 (s, 1H), 7.48 (dd, J=8.7, 2.4 Hz, 1H), 7.98 (d, J=2.4 Hz, 1H); MS (DCI/NH$_3$) 3.80 (m, 2H), m/z 454 (M+H)$^+$; Anal. calculated for C$_{23}$H$_{30}$F$_3$N$_3$O$_3$; Calc: C, 60.91; H, 6.67; N, 9.27. Found: C, 60.75; H, 6.75; N, 9.13.

Example 15

N-{(3E)-5-tert-butyl-1-methyl-2-[(2R)-tetrahydrofuran-2-ylmethyl]-1,2-dihydro-3H-pyrazol-3-ylidene}-3-(pentafluoro-lambda~6~sulfanyl)benzamide A mixture of 3-(pentafluorothio)benzoic acid (Apollo Scientific, 0.42 g, 1.7 mmol) and SOCl$_2$ (1.2 mL, 16.9 mmol)

was warmed to reflux and was allowed to stir for 2 hours. The mixture was cooled to ambient temperature and concentrated under reduced pressure. The residue was dissolved in toluene (5 mL) and was concentrated under reduced pressure. This dilution with toluene and concentration was repeated two additional times to remove residual thionyl chloride and afford 3-(pentafluoro-$\lambda^6$-sulfanyl)benzoyl chloride that was used directly below.

To a mixture of the product of Example 14C (0.20 g, 0.84 mmol) in THF (5 mL) was added Et$_3$N (0.47 mL, 3.4 mmol) followed by 3-(pentafluoro-$\lambda^6$-sulfanyl)benzoyl chloride (1.7 mmol). This mixture was stirred at ambient temperature for 16 h then the mixture was quenched with saturated, aqueous NaHCO$_3$ (5 mL) and diluted with EtOAc (10 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 50% hex/EtOAc to 100% EtOAc to 15% MeOH in EtOAc) to provide the title compound (0.22 g, 0.47 mmol, 56% yield). $^1$H NMR (300 MHz, CDCl$_3$) δ ppm 1.43 (s, 9H), 1.74-1.92 (m, 3H), 2.01-2.10 (m, 1H), 3.68-3.84 (m, 2H), 3.90 (s, 3H), 4.20-4.30 (m, 1H), 4.37 (dd, J=15.3, 5.8 Hz, 1H), 4.60 (dd, J=15.3, 3.1 Hz, 1H), 7.08 (s, 1H), 7.46 (t, J=8.0 Hz, 1H), 7.75 (ddd, J=8.2, 2.3, 1.0 Hz, 1 H), 8.38 (d, J=7.8 Hz, 1H), 8.72 (dd, J=2.2, 1.5 Hz, 1H); MS (DCI/NH$_3$) m/z 468 (M+H)$^+$. Anal. calculated for C$_{20}$H$_{26}$F$_5$N$_3$O$_2$S; Calc: C, 51.38; H, 5.61; N, 8.99. Found: C, 51.35; H, 5.58; N, 8.82.

Example 16

N-{(3E)-5-tert-butyl-1-methyl-2-[(2R)-tetrahydrofuran-2-ylmethyl]-1,2-dihydro-3H-pyrazol-3-ylidene}-2-[(cis-3-hydroxycyclobutyl)methoxy]-5-(trifluoromethyl)benzamide Example 16A N-{3-tert-butyl-1-[(2R)-tetrahydrofuran-2-ylmethyl]-1H-pyrazol-5-yl}-2-fluoro-5-(trifluoromethyl)benzamide To a solution of the product of Example 45B (7.8 g, 35.0 mmol) and triethylamine (14.6 mL, 105 mmol) in THF (60 mL) at ambient temperature was added 2-fluoro-5-(trifluoromethyl)benzoyl chloride (5.3 mL, 35.0 mmol) dropwise over 10 min. The mixture was stirred at ambient temperature for 3 hours. The mixture was quenched with saturated, aqueous NaHCO$_3$ (20 mL) and diluted with EtOAc (20 mL). The layers were separated and the aqueous layer was extracted with EtOAc (3×10 mL). The combined organics were dried over anhydrous Na$_2$SO$_4$, filtered and concentrated under reduced pressure. Purification by column chromatography (SiO$_2$, 40% hexanes/EtOAc) gave the title compound (11.0 g, 26.6 mmol, 76% yield). MS (DCI/NH$_3$) m/z 414 (M+H)$^+$.

Example 16B

N-{(3E)-5-tert-butyl-1-methyl-2-[(2R)-tetrahydrofuran-2-ylmethyl]-1,2-dihydro-3H-pyrazol-3-ylidene}-2-fluoro-5-(trifluoromethyl)benzamide A mixture of the product of Example 16A (14.2 g, 34.3 mmol) and dimethyl sulfate (9.9 mL, 103 mmol) in toluene (40 mL) was warmed to 90° C. and was allowed to stir for 18 hours then was cooled to ambient temperature. The mixture was concentrated under reduced pressure and was purified by column chromatography (SiO$_2$, 50% hexanes/EtOAc to 100% EtOAc to 9:1:0.1 EtOAc:MeOH:Et$_3$N) to give the title compound (10.0 g, 23.4 mmol, 68% yield). MS (DCI/NH$_3$) m/z 428 (M+H)$^+$.

Example 16C (cis-3-(benzyloxymethyl)cyclobutoxy)(tert-butyl)dimethylsilane

To a solution of cis-3-(benzyloxymethyl)cyclobutanol (Albany Molecular, 1.0 g, 5.2 mmol) in CH$_2$Cl$_2$ (20 mL) was added imidazole (0.71 g, 10.4 mmol), DMAP (64 mg, 0.52 mmol) and tert-butyldimethylsilylchloride (TBSCl) (1.6 g, 10.4 mmol). This mixture was stirred at ambient temperature for 16 h, quenched with saturated, aqueous NH$_4$Cl (5 mL) and diluted with EtOAc (10 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 50% hexanes/EtOAc) to give the title compound (1.15 g, 3.8 mmol, 72% yield). MS (DCI/NH$_3$) m/z 307 (M+H)$^+$.

Example 16D (cis-3-(tert-butyldimethylsilyloxy)cyclobutyl)methanol

A solution of the product of Example 16C (1.15 g, 3.8 mmol) in ethanol (20 mL) was degassed three times with a N$_2$ back-flush each time. Palladium on carbon (0.080 g, 0.75 mmol) was added and the mixture was degassed three times with an N$_2$ back-flush each time. The system was put under 1 atm of H$_2$ (balloon) and was allowed to stir at ambient temperature for 72 hours at which time the mixture was degassed three times with a N$_2$ backflush each time. The mixture was filtered through Celite, concentrated under reduced pressure and purified via column chromatography (SiO$_2$, 50% hexanes/EtOAc) to give the title product (0.75 g, 3.5 mmol, 92% yield). MS (DCI/NH$_3$) m/z 217 (M+H)$^+$.

Example 16E

2-[(cis-3-{[tert-butyl(dimethyl)silyl]oxy}cyclobutyl)methoxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide To a solution of the product of Example 16D (0.16 g, 0.75 mmol) in THF (5 mL) was added KOt-Bu (0.13 g, 1.1 mmol). This mixture was stirred at ambient temperature for 20 min then the product of Example 16B (0.16 g, 0.37 mmol) in THF (5 mL) was added via cannula. The mixture was stirred at ambient temperature for 6 hours. The mixture was quenched with saturated, aqueous NaHCO$_3$ (5 mL) and diluted with EtOAc (5 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 100% EtOAc to 10% MeOH in EtOAc) to provide the title compound (0.12 g, 0.19 mmol, 51% yield). MS (DCI/NH$_3$) m/z 624 (M+H)$^+$.

Example 16F

N-{(3E)-5-tert-butyl-1-methyl-2-[(2R)-tetrahydrofuran-2-ylmethyl]-1,2-dihydro-3H-pyrazol-3-ylidene}-2-[(cis-3-hydroxycyclobutyl)methoxy]-5-(trifluoromethyl)benzamide To a solution of the product of Example 16E (0.12 g, 0.19 mmol) in THF (5 mL) was added tetrabutylammonium fluoride (TBAF) (1M in THF, 0.39 mL, 0.39 mmol). This mixture was stirred at ambient temperature for 3 h then the mixture was concentrated under reduced pressure and purified via column chromatography (SiO$_2$, 50% hex/EtOAc to 100% EtOAc to 9:1:0.1 EtOAc, MeOH: Et$_3$N) to give the title compound (40 mg, 0.078 mmol, 41% yield). $^1$H NMR (300 MHz, CDCl$_3$) δ ppm 1.42 (s, 9H), 1.70-1.94 (m, 3H), 1.98-2.12 (m, 1H), 2.22-2.43 (m, 3H), 2.48-2.63 (m, 2H), 3.68-3.83 (m, 2H), 3.86 (s, 3H), 4.00 (d, J=2.0 Hz, 2H), 4.07-4.18 (m, 1H), 4.18-4.26 (m, 1H), 4.25-4.34 (m, 1H), 4.35-4.47 (m, 1H), 4.53 (dd, J=15.3, 3.1 Hz, 1H), 6.92 (d, J=8.8 Hz, 1H), 7.03 (s, 1H), 7.51 (dd, J=8.5, 1.7 Hz, 1H), 8.11 (d, J=2.0 Hz, 1H); MS (DCI/NH$_3$) m/z 510 (M+H)$^+$; Anal. calculated for C$_{26}$H$_{34}$F$_3$N$_3$O$_4$; Calc: C, 61.28; H, 6.73; N, 8.25. Found: C, 61.34; H, 6.80; N, 8.21.

Example 17

N-{(3E)-5-tert-butyl-1-methyl-2-[(2R)-tetrahydrofuran-2-ylmethyl]-1,2-dihydro-3H-pyrazol-3-ylidene}-2-[(3-oxocyclobutyl)methoxy]-5-(trifluoromethyl)benzamide To a solution of the product of Example 16F (0.38 g, 0.75 mmol) in CH$_2$Cl$_2$ (10 mL) at ambient temperature was added N-methylmorpholine N-oxide (0.44 g, 3.7 mmol) and a small amount of 4 Å powdered molecular sieves (~200 mg). The mixture was stirred for 10 min then was cooled to 0° C. Tetrapropylammonium perruthenate (TPAP, 0.039 g, 0.11 mmol) was added portion-wise and the mixture was stirred at 0° C. for 30 min then was allowed to warm to ambient temperature and was stirred for 2 hours. The mixture was filtered through Celite and the filtrate was concentrated under reduced pressure. The crude material was purified via column chromatography (SiO$_2$, 50% hexanes/EtOAc to 100% EtOAc to 9:1:0.1 EtOAc/MeOH/Et$_3$N) to give the title compound (0.19 g, 0.37 mmol, 50% yield). $^1$H NMR (300 MHz, CDCl$_3$) δ ppm 1.43 (s, 9H), 1.66-1.90 (m, 3H), 1.94-2.06 (m, 1H), 2.82-2.99 (m, 1H), 3.10-3.17 (m, 4H), 3.65-3.79 (m, 2H), 3.86 (s, 3H), 4.13-4.20 (m, 1H), 4.24 (d, J=5.8 Hz, 2H), 4.26-4.33 (m, 1H), 4.47 (dd, J=15.3, 3.4 Hz, 1H), 6.96 (s, 1H), 6.98 (d, J=8.8 Hz, 1H), 7.49 (dd, J=8.8, 2.0 Hz, 1H), 7.93 (d, J=2.4 Hz, 1H); MS (DCI/NH$_3$) m/z 508 (M+H)$^+$. Anal. calculated for C$_{26}$H$_{32}$F$_3$N$_3$O$_4$.0.5H$_2$O; Calc: C, 60.45; H, 6.44; N, 8.13. Found: C, 60.22; H, 6.28; N, 8.06.

Example 18

N-{(3E)-5-tert-butyl-1-methyl-2-[(2R)-tetrahydrofuran-2-ylmethyl]-1,2-dihydro-3H-pyrazol-3-ylidene}-2-[cis-3-methoxycyclobutyl)methoxy]-5-(trifluoromethyl)benzamide

Example 18A (((cis-3-methoxycyclobutyl)methoxy)methyl)benzene

To a solution of cis-3-(benzyloxymethyl)cyclobutanol (Albany Molecular, 0.76 g, 4.0 mmol) in THF (10 mL) at 0° C. was added sodium hydride (0.47 g, 11.9 mmol). The mixture was stirred at 0° C. for 15 minutes then iodomethane (0.37 mL, 5.9 mmol) was added. The mixture was stirred for 5 minutes then the ice-bath was removed and the mixture was stirred at ambient temperature for 16 hours. The mixture was quenched with 5 mL saturated, aqueous NaHCO$_3$ and diluted with 5 mL EtOAc. The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 75% hexanes/EtOAc) to provide the title compound (0.69 g, 3.3 mmol, 85% yield). MS (DCI/NH$_3$) m/z 207 (M+H)$^+$.

Example 18B (cis-3-methoxycyclobutyl)methanol

A solution of the product of Example 18A (0.69 g, 3.3 mmol) in ethyl acetate (10 mL) was degassed three times with a N$_2$ back-flush each time. Palladium on carbon (0.071 g, 0.067 mmol) was added and the mixture was again degassed three times with a nitrogen back-flush each time. The reaction mixture was put under 1 atm of hydrogen (balloon) and was allowed to stir for 70 hours. The mixture was degassed three times with a nitrogen back-flush each time then was filtered through Celite and the filtrate was concentrated under reduced pressure to give the title compound (0.38 g, 3.3 mmol, 98% yield). MS (DCI/NH$_3$) m/z 117 (M+H)$^+$.

Example 18C

N-{(3E)-5-tert-butyl-1-methyl-2-[(2R)-tetrahydrofuran-2-ylmethyl]-1,2-dihydro-3H-pyrazol-3-ylidene}-2-[(cis-3-methoxycyclobutyl)methoxy]-5-(trifluoromethyl)benzamide To a solution of the product of Example 18B (0.2 g, 1.7 mmol) in THF (10 mL) was added KOt-Bu (1 M in THF, 2.6 mL, 2.6 mmol). This mixture was stirred at ambient temperature for 20 min then the product of Example 16B (0.37 g, 0.86 mmol) in THF (5 mL) was added via cannula. The mixture was stirred at ambient temperature for 6 hours then was quenched with saturated, aqueous NaHCO$_3$ (5 mL) and diluted with EtOAc (5 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 50% hexanes/EtOAc to 100% EtOAc to 9:1:0.1 EtOAc/MeOH/Et$_3$N) to provide the title compound (0.39 g, 0.75 mmol, 87% yield). $^1$H NMR (300 MHz, CDCl$_3$) δ ppm 1.43 (s, 9H), 1.70-1.80 (m, 4H), 1.82-1.89 (m, 1H), 1.95-2.09 (m, 1H), 2.30-2.45 (m, 3H), 3.20 (s, 3H), 3.67-3.80 (m, 3H), 3.85 (s, 3H), 4.07 (d, J=6.1 Hz, 2H), 4.13-4.23 (m, 1H), 4.30 (dd, J=15.3, 5.8 Hz, 1H), 4.49 (dd, J=15.3, 3.1 Hz, 1H), 6.93 (d, J=8.8 Hz, 1H), 7.01 (s, 1H), 7.46 (dd, J=8.5, 2.0 Hz, 1H), 7.94 (d, J=2.4 Hz, 1H); MS (DCI/NH$_3$) m/z 524 (M+H)$^+$; Anal. calculated for C$_{27}$H$_{36}$F$_3$N$_3$O$_4$.0.2H$_2$O; Calc: C, 61.51; H, 6.96; N, 7.97. Found: C, 61.33; H, 7.19; N, 8.10.

Example 19

N-{(3E)-5-tert-butyl-1-methyl-2-[(2R)-tetrahydrofuran-2-ylmethyl]-1,2-dihydro-3H-pyrazol-3-ylidene}-2-[(3,3-difluorocyclobutyl)methoxy]-5-(trifluoromethyl)benzamide

Example 19A (3,3-difluorocyclobutyl)methanol

To a solution of 3,3-difluorocyclobutanecarboxylic acid (Parkway Scientific, 1.0 g, 7.4 mmol) in THF (20 mL) at −10° C. was added N-methylmorpholine (0.81 mL, 7.4 mmol). The mixture was stirred for 1 minute then ethyl chloroformate (0.70 mL, 7.4 mmol) was added dropwise. This mixture was stirred at −10° C. for 15 minutes then was filtered through Celite and the filtrate was added dropwise via syringe to a mixture of $NaBH_4$ (0.63 g, 16.5 mmol) in water (10 mL) at 5° C. The ice-bath was removed after the addition was complete and the mixture was stirred at ambient temperature for 2 hours. The mixture was quenched with saturated, aqueous $NH_4Cl$ (10 mL) and diluted with EtOAc (10 mL). The layers were separated and the aqueous layer was extracted with EtOAc (3×5 mL). The combined organics were dried over anhydrous $Na_2SO_4$, filtered and concentrated under reduced pressure to give the title compound (1.0 g, 8.2 mmol, 111% yield) which was used without further purification. $^1$H NMR (300 MHz, $CDCl_3$) δ ppm 1.81-1.89 (m, 1H), 2.26-2.43 (m, 2H), 2.57-2.70 (m, 2H), 3.70 (t, J=5.2 Hz, 2H), 3.72-3.77 (m, 1H).

Example 19B

N-{(3E)-5-tert-butyl-1-methyl-2-[2R)-tetrahydrofuran-2-ylmethyl]-1,2-dihydro-3H-pyrazol-3-ylidene}-2-[(3,3-difluorocclobutyl)methoxy]-5-(trifluoromethyl)benzamide To a solution of the product of Example 19A (0.21 g, 1.8 mmol) in THF (5 mL) was added KOt-Bu (0.33 g, 2.9 mmol). This mixture was stirred at ambient temperature for 20 minutes then the product of Example 16B (0.25 g, 0.59 mmol) in THF (5 mL) was added via cannula. The mixture was stirred at ambient temperature for 1 hour then was quenched with saturated, aqueous $NaHCO_3$ (5 mL) and diluted with EtOAc (5 mL). The layers were separated and the aqueous layer was extracted with EtOAc (3×5 mL). The combined organics were dried over anhydrous $Na_2SO_4$, filtered, concentrated under reduced pressure and purified via column chromatography ($SiO_2$, 100% EtOAc to 10% MeOH in EtOAc) to provide the title compound (0.20 g, 0.34 mmol, 65% yield). $^1$H NMR (300 MHz, $CDCl_3$) δ ppm 1.43 (s, 9H), 1.69-1.80 (m, 2H), 1.81-1.91 (m, 1H), 1.95-2.03 (m, 1 H), 2.49-2.72 (m, 5H), 3.69-3.80 (m, 2H), 3.86 (s, 3H), 4.08-4.14 (m, 2H), 4.14-4.20 (m, 1H), 4.29 (dd, J=15.3, 5.4 Hz, 1H), 4.48 (dd, J=15.3, 3.1 Hz, 1H), 6.94 (d, J=8.8 Hz, 1H), 6.98 (s, 1 H), 7.48 (dd, J=8.8, 1.7 Hz, 1H), 7.91 (d, J=2.0 Hz, 1H); MS (DCI/$NH_3$) m/z 530 (M+H)$^+$; Anal. calculated for $C_{26}H_{32}F_5N_3O_3$: Calc: C, 58.97; H, 6.09; N, 7.94. Found: C, 58.78; H, 6.16; N, 7.86.

Example 20

N-{(3E)-5-tert-butyl-1-methyl-2-[(2R)-tetrahydrofuran-2-ylmethyl]-1,2-dihydro-3H-pyrazol-3-ylidene}-2-(3-methoxy-3-methylbutoxy)-5-(trifluoromethyl)benzamide Potassium t-butoxide (0.47 mL, 1M in THF) was added to 3-methoxy-3-methylbutan-1-ol (58 mg, 0.49 mmol) in 0.25 mL of THF and stirred for 10 minutes. Example 16B (0.1 g, 0.23 mmol) in 0.6 mL of THF was added and the mixture stirred for 3 hours. The mixture was diluted with dichloromethane, 15 μL of glacial acetic acid was added and the resulting mixture filtered, loaded onto silica and chromatographed (0 to 25% MeOH in EtOAc) to afford the title compound (0.05 g, 0.1 mmol, 41% yield). $^1$H NMR (300 MHz, $CDCl_3$) δ ppm 1.21 (s, 6H), 1.42 (s, 9H), 1.70-1.93 (m, 3H), 1.96-2.11 (m, 3H), 3.19 (s, 3H), 3.63-3.81 (m, 2H), 3.86 (s, 3H), 4.13-4.24 (m, 3H), 4.26-4.37 (m, 1H), 4.44-4.56 (m, 1H), 6.98 (d, J=8.8 Hz, 1H), 7.03 (s, 1H), 7.49 (dd, J=8.8, 1.7 Hz, 1H), 7.95 (d, J=2.4 Hz, 1H). MS (DCI/$NH_3$) m/z 526.3 (M+H)$^+$. Analytical calculated for $C_{27}H_{38}F_3N_3O_4$: C, 61.70; H, 7.29; N, 7.99. Found: C, 61.43; H, 7.38; N, 7.84.

Example 21

N-{(3E)-5-tert-butyl-1-methyl-2-[(2R)-tetrahydrofuran-2-ylmethyl]-1,2-dihydro-3H-pyrazol-3-ylidene}-2-(2,2,2-trifluoroethoxy)-5-(trifluoromethyl)benzamide Potassium tert-butoxide (0.47 mL, 1M in THF) was added to 2,2,2-trifluoroethanol (35 μL, 0.49 mmol) in 0.25 mL THF and stirred for 10 minutes. Example 16B (0.1 g, 0.23 mmol) in 0.25 mL of THF was added and the resulting mixture stirred for 3 hours. The mixture was diluted with dichloromethane, 25 μL glacial acetic acid was added, the mixture filtered, loaded onto silica and chromatographed (0 to 25% MeOH in EtOAc) to afford the title compound (0.05 g, 0.1 mmol, 42% yield). $^1$H NMR (300 MHz, $CDCl_3$) δ ppm 1.44 (s, 9 H), 1.61-1.81 (m, 2H), 1.81-1.94 (m, 1H), 1.96-2.10 (m, 1H), 3.63-3.84 (m, 2H), 3.90 (s, 3H), 4.12-4.24 (m, 1H), 4.26-4.39 (m, 1H), 4.46-4.57 (m, 2H), 4.53-4.63 (m, 1H), 7.01 (s, 1H), 7.08 (d, J=8.5 Hz, 1H), 7.49-7.56 (m, 1H), 8.11 (d, J=2.4 Hz, 1H). MS (DCI/$NH_3$) m/z 508.2 (M+H)$^+$. Analytical calculated for $C_{23}H_{27}F_6N_3O_3$: C, 54.44; H, 5.36; N, 8.28. Found: C, 54.05; H, 5.35; N, 7.86.

Example 22

N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)-5-(trifluoromethyl)benzamide To potassium tert-butoxide (0.47 mL, 1M in THF) was added 2-fluoroethanol (30 μL, 0.49 mmol) and stirred for 10 minutes. Example 16B (0.1 g, 0.23 mmol) in 0.6 mL of THF was added and the mixture stirred at ambient temperature for 2 hours. The mixture was diluted with dichloromethane, 15 μL of glacial acetic acid was added, the solution filtered, loaded onto silica and chromatographed (0 to 20% MeOH in EtOAc (0.1% $NH_4OH$)) to afford the title compound (0.04 g, 0.09 mmol, 36% yield). $^1$H NMR (300 MHz, $CDCl_3$) δ ppm 1.43 (s, 9H), 1.68-1.79 (m, 2H), 1.79-1.93 (m, 1H), 1.94-2.09 (m, 1H), 3.66-3.82 (m, 2H), 3.88 (s, 3H), 4.14-4.25 (m, 1H), 4.26-4.37 (m, 2H), 4.37-4.43 (m, 1H), 4.47-4.58 (m, 1H), 4.64-4.73 (m, 1H), 4.78-4.90 (m, 1H), 7.00 (d, J=9.1 Hz, 1 H), 7.02 (s, 1 H), 7.50 (dd, J=8.5, 2.6 Hz, 1H), 8.01 (d, J=2.0 Hz, 1H). MS (DCI/$NH_3$) m/z 472.3 (M+H)$^+$. Analytical calculated for $C_{23}H_{29}F_4N_3O_3$: C, 58.59; H, 6.20; N, 8.91. Found: C, 58.48; H, 6.25; N, 8.79.

Example 23

N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)-5-(trifluoromethyl)benzamide Potassium tert-butoxide (0.47 mL, 1M in THF) was added to 2-methoxyethanol (39 μL, 0.49 mmol) and stirred for 10 minutes. Example 16B (0.1 g, 0.23 mmol) in 0.6 mL of THF was added and the mixture stirred for 2 hours. The mixture was diluted with dichloromethane, 15 µL of glacial acetic acid was added and the resulting mixture filtered, loaded onto silica and chromatographed (0 to 20% MeOH in $CH_2Cl_2$ (0.1% $NH_4OH$)) to afford the title compound (0.04 g, 0.08 mmol, 35% yield). $^1$H NMR (300 MHz, $CDCl_3$) δ ppm 1.43 (s, 9H), 1.70-1.82 (m, 2H), 1.81-1.94 (m, 1H), 1.95-2.09 (m, 1H), 3.41 (s, 3H), 3.66-3.75 (m, 2H), 3.78 (t, J=5.4 Hz, 2H), 3.86 (s, 3H), 4.14-4.23 (m, 1H), 4.23-4.28 (m, 2H), 4.28-4.37 (m, 1H), 4.45-4.55 (m, 1H), 6.98-7.05 (m, 2H), 7.49 (dd, J=8.5, 1.7 Hz, 1H), 7.99 (d, J=2.4 Hz, 1H). MS (DCI/$NH_3$) m/z 484.3 $(M+H)^+$. Analytical calculated for $C_{24}H_{32}F_3N_3O_4$: C, 59.62; H, 6.67; N, 8.69. Found: C, 59.50; H, 6.73; N, 8.52.

Example 24

N-{(3E)-5-tert-butyl-1-methyl-2-[(2R)-tetrahydrofuran-2-ylmethyl]-1,2-dihydro-3H-pyrazol-3-ylidene}-2-hydroxy-5-(trifluoromethyl)benzamide The title compound was obtained as the unexpected product in the reaction of 3-(hydroxymethyl)cyclobutanone with Example 16B using the method of Example 23. The crude product was chromatographed (solvent A—hexane:EtOAc:triethylamine (5:15:1); solvent B—hexane:EtOAc:MeOH:triethylamine (4:12:4:1); solvent A:solvent B (100:0 gradient to 0:100) over 240 mL then isocratic with solvent B for 300 mL) to afford the title compound. (0.05 g, 0.12 mmol, 71% yield). $^1$H NMR (300 MHz, $CDCl_3$) δ ppm 1.45 (s, 9H), 1.60-1.74 (m, 1H), 1.78-2.01 (m, 2H), 2.14-2.30 (m, 1H), 3.69-3.84 (m, 2H), 3.96 (s, 3H), 4.09-4.32 (m, 2H), 4.44-4.57 (m, 1H), 6.92 (d, J=8.8 Hz, 1H), 7.11 (s, 1H), 7.50 (dd, J=8.3, 2.2 Hz, 1H), 8.40 (d, J=2.4 Hz, 1H). MS (DCI/$NH_3$) m/z 426.2 $(M+H)^+$.

Example 25

2-tert-butoxy-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide The title compound was obtained as the unexpected product in the reaction of (S)-5-(hydroxymethyl)pyrrolidin-2-one (0.02 g, 0.17 mmol) with Example 16B using the general method of Example 23. The reaction was diluted with dichloromethane, loaded onto silica gel and chromatographed. (solvent A—hexane:EtOAc:triethylamine (5:15:1); solvent B—hexane:EtOAc:MeOH:triethylamine (4:12:4:1); solvent A to solvent B over 240 mL then isocratic for 300 mL) to afford the title compound. (15 mg, 0.03 mmol, 38% yield). $^1$H NMR (500 MHz, pyridine-$d_5$) δ ppm 1.18 (s, 9H), 1.53 (s, 9H), 1.54-1.62 (m, 2H), 1.63-1.72 (m, 1H), 1.74-1.83 (m, 1H), 3.54-3.61 (m, 1H), 3.68-3.75 (m, 1H), 3.79 (s, 3H), 4.23 (ddd, J=13.5, 6.8, 3.2 Hz, 1H), 4.34 (dd, J=15.3, 6.4 Hz, 1H), 4.57 (dd, J=15.3, 3.1 Hz, 1H), 7.33 (d, J=8.5 Hz, 1H), 7.47 (s, 1H), 7.60 (dd, J=8.5, 2.4 Hz, 1H), 8.43 (d, J=2.4 Hz, 1H). MS (DCI/$NH_3$) m/z 482.3 $(M+H)^+$.

Example 26

N-{(3E)-5-tert-butyl-1-methyl-2-[(2R)-tetrahydrofuran-2-ylmethyl]-1,2-dihydro-3H-pyrazol-3-ylidene}-2-[2-dimethylamino)ethoxy]-5-trifluoromethyl)benzamide Potassium tert-butoxide (1.2 mL, 1M in THF) was added to 2-(dimethylamino)ethanol (0.12 mL, 1.2 mmol) and the solution stirred for 10 minutes. Example 16B (0.25 g, 0.59 mmol) in 1 mL of THF was added and the mixture stirred at ambient temperature for 1 hour. Saturated $NH_4Cl$ (0.5 mL) was added and the mixture diluted with EtOAc, washed with 2N NaOH, water, brine, dried with $MgSO_4$ and the solvent removed. The residue was chromatographed (solvent A—hexane:EtOAc:triethylamine (1:3:0.1) solvent B—hexane:EtOAc:MeOH:triethylamine (1:3:1:0.1); 100% solvent A to 100% solvent B over 240 mL then isocratic for 300 mL) to afford the title compound (0.13 g, 0.26 mmol, 45% yield). $^1$H NMR (300 MHz, $CDCl_3$) δ ppm 1.43 (s, 9H), 1.75-1.81 (m, 2H), 1.82-1.92 (m, 1H), 1.94-2.13 (m, 1H), 2.31 (s, 6H), 2.79 (t, J=6.6 Hz, 2H), 3.65-3.82 (m, 2H), 3.85 (s, 3H), 4.13-4.24 (m, 3H), 4.25-4.35 (m, 1H), 4.42-4.56 (m, 1H), 6.98 (d, J=8.5 Hz, 1H), 7.02 (s, 1H), 7.49 (ddd, J=8.6, 2.5, 0.7 Hz, 1H), 7.96 (d, J=2.4 Hz, 1H). MS (DCI/$NH_3$) m/z 497.3 $(M+H)^+$. Analytical calculated for $C_{25}H_{35}F_3N_4O_3$: C, 60.47; H, 7.10; N, 11.28. Found: C, 60.46; H, 7.17; N, 11.02.

Example 27

N-{(3E)-5-tert-butyl-1-methyl-2-[(2R)-tetrahydrofuran-2-ylmethyl]-1,2-dihydro-3H-pyrazol-3-ylidene}-2-(dimethylamino)-5-(trifluoromethyl)benzamide Sodium hydride (0.09 g, 2.3 mmol, 60% in mineral oil) was added to (R)-5-(hydroxymethyl)pyrrolidin-2-one (0.14 g, 1.2 mmol) in 0.75 mL of dimethylformamide and stirred at ambient temperature for 10 minutes. Example 16B (0.25 g, 0.59 mmol) in 0.3 mL of DMF was added and the mixture stirred at 50° C. for 4 hours. The mixture was diluted with EtOAc, washed with 2N NaOH, water, brine, dried with $MgSO_4$ and the solvent removed under reduced pressure. The residue was chromatographed (solvent A—hexane:EtOAc:triethylamine (1:3:0.1) solvent B—hexane:EtOAc:MeOH:triethylamine (1:3:1:0.1); 100% solvent A to 100% solvent B over 240 mL then isocratic for 300 mL) to afford the title compound as an unexpected by-product. (20 mg, 0.04 mmol, 8% yield) $^1$H NMR (300 MHz, $CDCl_3$) δ ppm 1.43 (s, 9H), 1.72-1.83 (m, 2H), 1.84-1.93 (m, 1H), 1.96-2.10 (m, 1H), 2.95 (s, 6H), 3.69-3.82 (m, 2H), 3.86 (s, 3H), 4.14-4.23 (m, 1H), 4.26-4.36 (m, 1H), 4.49-4.56 (m, 1H), 6.84 (d, J=8.3 Hz, 1H), 7.05 (s, 1H), 7.38 (dd, J=8.7, 2.4 Hz, 1H), 7.87 (d, J=2.4 Hz, 1H). MS (DCI/$NH_3$) m/z 453.3 $(M+H)^+$.

Example 28

N-{(3E)-5-tert-butyl-1-methyl-2-[(2R)-tetrahydrofuran-2-ylmethyl]-1,2-dihydro-3H-pyrazol-3-ylidene}-2-{[(2S)-2-methoxypropyl]oxy}-5-(trifluoromethyl)benzamide Potassium tert-butoxide (1.2 mL, 1M in THF) was added to (S)-2-methoxypropan-1-ol (0.11 g, 1.2 mmol) in 0.5 mL of THF and stirred for 10 minutes. Example 16B (0.25 g, 0.6 mmol) in 1 mL of THF was added and the mixture stirred for 1 hour. The mixture was diluted with dichloromethane (10 mL), filtered, and chromatographed. (solvent A—hexane:EtOAc:triethylamine (1:3:0.1); solvent B—hexane:EtOAc:MeOH:triethylamine (1:3:1:0.1) 100% solvent A to 100% solvent B over 450 mL then isocratic for 300 mL) to afford the title compound. (0.16 g, 0.32 mmol, 55% yield). $^1$H NMR (500 MHz, pyridine-$d_5$) δ ppm 1.17 (s, 9 H), 1.31 (d, J=6.4 Hz, 3H), 1.53-1.61 (m, 2H), 1.64-1.72 (m, 1H), 1.78 (ddd, J=19.4, 7.0, 6.9 Hz, 1H), 3.40 (s, 3H), 3.55-3.61 (m, 1H), 3.69-3.76 (m, 1H), 3.79 (s, 3H), 3.80-3.84 (m, 1H), 4.09 (dd, J=9.9, 5.0 Hz, 1H), 4.21-4.28 (m, 2H), 4.37 (dd, J=15.1, 6.6

Hz, 1 H), 4.59 (dd, J=15.1, 3.2 Hz, 1H), 7.17 (d, J=8.5 Hz, 1H), 7.47 (s, 1H), 7.64 (dd, J=8.5, 2.1 Hz, 1H), 8.48 (d, J=2.4 Hz, 1H). MS (DCI/NH$_3$) m/z 498.3 (M+H)$^+$. Analytical calculated for C$_{25}$H$_{34}$F$_3$N$_3$O$_4$: C, 60.35; H, 6.89; N, 8.45. Found: C, 60.16; H, 7.04; N, 8.48.

Example 29

N-{(3E)-5-tert-butyl-1-methyl-2-[(2R)-tetrahydrofuran-2-ylmethyl]-1,2-dihydro-3H-pyrazol-3-ylidene}-2-(3-ethoxypropoxy)-5-(trifluoromethyl)benzamide Potassium tert-butoxide (1.2 mL, 1M in THF) was added to 3-ethoxypropan-1-ol (0.13 g, 1.2 mmol) in 0.5 mL of THF and stirred for 10 minutes. Example 16B (0.25 g, 0.6 mmol) in 1 mL of THF was added and the mixture stirred for 1 hour. The mixture was diluted with dichloromethane (10 mL), filtered, and chromatographed (solvent A—hexane:EtOAc:triethylamine (1:3:0.1); solvent B—hexane:EtOAc:MeOH:triethylamine (1:3:1:0.1); 100% solvent A to 100% solvent B over 450 mL then isocratic for 300 mL) to afford the title compound (0.13 g, 0.25 mmol, 43% yield). $^1$H NMR (500 MHz, pyridine-d$_5$) δ ppm 1.10 (t, J=7.0 Hz, 3H), 1.17 (s, 9H), 1.53-1.62 (m, 2H), 1.65-1.72 (m, 1H), 1.75-1.82 (m, 1H), 2.09-2.15 (m, 2H), 3.36 (q, J=7.0 Hz, 2H), 3.55-3.60 (m, 1H), 3.65 (t, J=6.3 Hz, 2H), 3.69-3.75 (m, 1H), 3.78 (s, 3H), 4.21-4.28 (m, 3H), 4.37 (dd, J=15.0, 6.4 Hz, 1H), 4.59 (dd, J=15.1, 3.2 Hz, 1H), 7.14 (d, J=8.5 Hz, 1H), 7.48 (s, 1H), 7.62 (dd, J=8.5, 2.1 Hz, 1H), 8.46 (d, J=2.4 Hz, 1H). MS (DCI/NH$_3$) m/z 512.3 (M+H)$^+$. Analytical calculated for C$_{26}$H$_{36}$F$_3$N$_3$O$_4$: C, 61.04; H, 7.09; N, 8.21. Found: C, 60.97; H, 7.19; N, 8.31.

Example 30

N-{(3E)-5-tert-butyl-1-methyl-2-[(2R)-tetrahydrofuran-2-ylmethyl]-1,2-dihydro-3H-pyrazol-3-ylidene}-2-(3-methoxypropoxy)-5-(trifluoromethyl)benzamide Potassium tert-butoxide (0.64 mL, 1M in THF) was added to 3-methoxypropan-1-ol (0.063 g, 0.7 mmol) in 0.25 mL of THF and stirred for 10 minutes. Example 16B (0.25 g, 0.59 mmol) in 1.0 mL of THF was added and the mixture stirred at ambient temperature for 3 hours. The mixture was diluted with dichloromethane (10 mL), filtered and chromatographed (solvent A—hexane:EtOAc:triethylamine (1:3:0.1); solvent B—hexane:EtOAc:MeOH:triethylamine (1:3:1:0.1); 100% solvent A to 100% solvent B over 450 mL then isocratic for 300 mL) to afford the title compound (0.12 g, 0.24 mmol, 41% yield). $^1$H NMR (500 MHz, pyridine-d$_5$) δ ppm 1.17 (s, 9H), 1.53-1.61 (m, 2H), 1.65-1.72 (m, 1 H), 1.75-1.82 (m, 1H), 2.07-2.13 (m, 2H), 3.21 (s, 3H), 3.55-3.61 (m, 3H), 3.69-3.75 (m, 1H), 3.78 (s, 3H), 4.21-4.26 (m, 3H), 4.37 (dd, J=15.1, 6.6 Hz, 1H), 4.59 (dd, J=15.1, 3.2 Hz, 1H), 7.13 (d, J=8.5 Hz, 1H), 7.48 (s, 1H), 7.62 (dd, J=8.5, 2.4 Hz, 1H), 8.47 (d, J=2.1 Hz, 1H). MS (DCI/NH$_3$) m/z 498.3 (M+H)$^+$. Analytical calculated for C$_{26}$H$_{36}$F$_3$N$_3$O$_4$: C, 61.04; H, 7.09; N, 8.21. Found: C, 60.97; H, 7.19; N, 8.31.

Example 31

N-{(3E)-5-tert-butyl-1-methyl-2-[(2R)-tetrahydrofuran-2-ylmethyl]-1,2-dihydro-3H-pyrazol-3-ylidene}-2-(2-ethoxyethoxy)-5-(trifluoromethyl)benzamide Potassium tert-butoxide (09.4 mL, 1M in THF) was added to 2-ethoxyethanol (0.09 g, 0.98 mmol) in 0.5 mL of THF and the mixture stirred for 10 minutes. Example 16B (0.2 g, 0.47 mmol) in 0.8 mL of THF was added and the mixture stirred at ambient temperature for 1 hour. The mixture was diluted with 10 mL of dichloromethane, 50 μL of glacial acetic acid was added, the resulting solution was filtered and chromatographed (solvent A—hexane:EtOAc:triethylamine (1:3:0.1); solvent B—hexane:EtOAc:MeOH:triethylamine (1:3:1:0.1); 100% solvent A to solvent A:solvent B (25:75) over 450 mL then isocratic for 180 mL) to afford the title compound (0.13 g, 0.26 mmol, 56% yield). $^1$H NMR (500 MHz, pyridine-d$_5$) δ ppm 1.09 (t, J=7.0 Hz, 3H), 1.18 (s, 9H), 1.52-1.62 (m, 2H), 1.64-1.73 (m, 1H), 1.74-1.84 (m, 1H), 3.48 (q, J=7.0 Hz, 2H), 3.54-3.62 (m, 1H), 3.69-3.75 (m, 1 H), 3.79 (s, 3 H), 3.80-3.85 (m, 2H), 4.19-4.28 (m, 1H), 4.32-4.41 (m, 3H), 4.59 (dd, J=15.1, 3.2 Hz, 1H), 7.19 (d, J=8.5 Hz, 1H), 7.46 (s, 1H), 7.61 (dd, J=8.5, 2.1 Hz, 1H), 8.47 (d, J=2.4 Hz, 1 H). MS (DCI/NH$_3$) m/z 498.3 (M+H)$^+$. Analytical calculated for C$_{25}$H$_{34}$F$_3$N$_3$O$_4$: C, 60.35; H, 6.89; N, 8.45. Found: C, 60.07; H, 7.00; N, 8.39.

Example 32

2-methoxy-N-[(3E)-1-methyl-2-[(2R)-tetrahydrofuran-2-ylmethyl]-1,4,5,6-tetrahydrocyclopenta[c]pyrazol-3(2H)-ylidene]-5-(trifluoromethyl)benzamide Example 32A (S)-2-((tetrahydrofuran-2-yl)methyl)-2,4,5,6-tetrahydrocyclopenta[c]pyrazol-3-amine The title compound was prepared from Example 45A using the procedure as described in Example 45B substituting 2-oxocyclopentanecarbonitrile for 4,4-dimethyl-3-oxopentanenitrile. MS (DCI/NH$_4$$^+$) m/z 208 (M+H)$^+$.

Example 32B 2-methoxy-N-{2-[(2R)-tetrahydrofuran-2-ylmethyl]-2,4,5,6-tetrahydrocyclopenta[c]pyrazol-3-yl}-5-(trifluoromethyl)benzamide To a solution of the product of Example 32A (340 mg, 1.64 mmol) and pyridine (535 μL, 6.56 mmol) in CH$_2$Cl$_2$ (20 mL) was added 2-methoxy-5-(trifluoromethyl)benzoyl chloride (470 mg, 1.97 mmol) dropwise. The mixture was stirred at ambient temperature for 1 h. The mixture was concentrated under reduced pressure and was purified by column chromatography (SiO$_2$, 40% hexanes/EtOAc) to provide the title compound 550 mg (82%). MS (DCI/NH$_3$) m/z 410 (M+H)$^+$.

Example 32C 2-methoxy-N-[(3E)-1-methyl-2-[(2R)-tetrahydrofuran-2-ylmethyl]-1,4,5,6-tetrahydrocyclopenta[c]pyrazol-3(2H)-ylidene]-5-(trifluoromethyl)benzamide A mixture of the product of Example 32B (550 mg, 1.34 mmol) and dimethyl sulfate (512 μL, 5.37 mmol) in toluene (5 mL) was warmed to 90° C. and was allowed to stir for 12 h then was cooled to ambient temperature and was concentrated under reduced pressure. The mixture was purified by column chromatography (SiO$_2$, 50% hexanes/EtOAc to 100% EtOAc to 9:1:0.1 EtOAc:MeOH:Et$_3$N) to give the title compound 73 mg (13%). $^1$H NMR (400 MHz, CDCl$_3$) δ ppm 1.66-1.78 (m, 1H) 1.80-1.93 (m, 2H) 2.03 (m, 1H) 2.39-2.50 (m, 2 H) 2.73 (t, J=7.36 Hz, 2H) 3.02 (t, J=7.36, 6.75 Hz, 2H) 3.65 (s, 3H) 3.68-3.76 (m, 1H) 3.77-3.85 (m, 1H) 3.89 (s, 3H) 4.09 (dd, J=14.73, 6.14 Hz, 1H) 4.13-4.19 (m, 1H) 4.45 (dd, J=15.04, 2.76 Hz, 1H) 6.94 (d, J=8.59 Hz, 1H) 7.50 (dd, J=10.13, 1.53 Hz, 1H) 7.96 (d, J=2.15 Hz, 1H); MS (DCI/NH$_3$) m/z 424 (M+H)$^+$.

Example 33

2-methoxy-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide

Example 33A 3-(1-methylcyclopropyl)-3-oxopropanenitrile

To a solution of diisopropylamine (7.43 mL, 52.6 mmol) in 60 mL of THF was added n-BuLi (2.5M) (21.03 mL, 52.6 mmol) at −78° C. The reaction was stirred at −78° C. for 30 min, then acetonitrile (2.76 mL, 52.6 mmol) was added at −78° C. and the reaction was stirred for 30 min, then methyl 1-methylcyclopropanecarboxylate (3 g, 52.6 mmol) was added at −78° C. The reaction was stirred at −78° C. for 1 hour and then allowed to warm up at room temperature overnight. The solvent was evaporated and the solid dissolved in water. The aqueous layer was washed with ether and then acidified with 6N HCl to pH 2-3. The aqueous layer was extracted with ether. The organic layer was dried with MgSO$_4$ and concentrated to afford the title compound (2.89 g, 89%). MS (DCI/NH$_3$) m/z 124 (M+H)$^+$.

Example 33B (R)-3-(1-methylcyclopropyl)-1-((tetrahydrofuran-2-yl)methyl)-1H-pyrazol-5-amine The title compound was prepared from Example 45A using the procedure as described in Example 45B substituting Example 33A for 4,4-dimethyl-3-oxopentanenitrile. MS (DCI/NH$_3$) m/z 222 (M+H)$^+$.

Example 33C 2-methoxy-N-{3-(1-methylcyclopropyl)-1-[(2R)-tetrahydrofuran-2-ylmethyl]-1H-pyrazol-5-yl}-5-(trifluoromethyl)benzamide The title compound was prepared using the procedure as described in Example 32B substituting Example 33B for Example 32A. MS (DCI/NH$_3$) m/z 424 (M+H)$^+$.

Example 33D 2-methoxy-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide The title compound was prepared using the procedure as described in Example 32C substituting Example 33C for Example 32B. $^1$H NMR (400 MHz, CDCl$_3$) δ ppm 0.78-0.85 (m, 2H) 0.91-1.00 (m, 2H) 1.37 (s, 3H) 1.72-1.85 (m, 2H) 1.83-1.92 (m, 1H) 1.97-2.09 (m, 1H) 3.68-3.80 (m, 2H) 3.84 (s, 3H) 3.91 (s, 3H) 4.16-4.32 (m, 2 H) 4.50 (d, J=12.58 Hz, 1H) 6.96 (d, J=8.90 Hz, 1H) 7.04 (s, 1H) 7.51 (dd, J=8.90, 1.84 Hz, 1H) 7.99 (d, J=2.15 Hz, 1H) MS (DCI/NH$_3$) m/z 438 (M+H)$^+$.

Example 34

N-{(3E)-5-tert-butyl-1-methyl-2-[(2R)-tetrahydrofuran-2-ylmethyl]-1,2-dihydro-3H-pyrazol-3-ylidene}-2-[2-methoxyethyl)amino]-5-(trifluoromethyl)benzamide A mixture of the product from Example 16B (100 mg, 0.234 mmol), 2-methoxyethanamine (52.7 mg, 0.702 mmol) and triethylamine (71 mg, 0.702 mmol) in THF (1 mL) was heated at 120° C. with microwave irradiation (Discover, CEM) for 60 min. The reaction mixture was diluted with H$_2$O and extracted with EtOAc (2×). The organic layer was dried over MgSO$_4$, filtered and concentrated. The residue was purified by column chromatography using an Analogix® Intelliflash280™ (SiO$_2$, 50% hexanes/EtOAc to 100% EtOAc to 9:1:0.1 EtOAc:MeOH:Et$_3$N) to afford 79 mg (70%) of the title compound. $^1$H NMR (400 MHz, CDCl$_3$) δ ppm 1.42 (s, 9H) 1.72-1.82 (m, 2H) 1.81-1.90 (m, 1 H) 1.98-2.11 (m, 1H) 3.39 (s, 3H) 3.45 (q, J=5.52 Hz, 2H) 3.63 (t, J=5.83 Hz, 2H) 3.68-3.82 (m, 2 H) 3.86 (s, 3H) 4.18-4.26 (m, 1H) 4.33 (dd, J=15.65, 5.83 Hz, 1H) 4.55 (dd, J=15.65, 3.38 Hz, 1H) 6.67 (d, J=8.59 Hz, 1H) 7.41 (dd, J=8.59, 2.15 Hz, 1H) 8.60 (d, J=1.84 Hz, 1H) 9.54 (brs, 1H) MS (DCI/NH$_3$) m/z 483 (M+H)$^+$.

Example 35

N-{(3E)-5-tert-butyl-1-methyl-2-[(2R)-tetrahydrofuran-2-ylmethyl]-1,2-dihydro-3H-pyrazol-3-ylidene}-2-(2,2-difluoroethoxy)-5-(trifluoromethyl)benzamide A mixture of the product from Example 16B (100 mg, 0.234 mmol), 2,2-difluoroethanol (38.4 mg, 0.468 mmol) and sodium tert-butoxide (45 mg, 0.468 mmol) in THF (2 mL) was heated at 40° C. for 12 hrs. The reaction mixture was diluted with H$_2$O and extracted with EtOAc (2×). The organic layer was dried over MgSO$_4$, filtered and concentrated. The residue was purified by column chromatography using an Analogix® Intelliflash280™ (SiO$_2$, 50% hexanes/EtOAc to 100% EtOAc to 9:1:0.1 EtOAc:MeOH:Et$_3$N) to afford 89 mg (80%) of the title compound. $^1$H NMR (500 MHz, CDCl$_3$) δ ppm 1.44 (m, 9H) 1.67-1.80 (m, 2H) 1.81-1.91 (m, 1H) 1.97-2.05 (m, 1H) 3.68-3.80 (m, 2H) 3.88 (s, 3H) 4.15-4.21 (m, 1H) 4.32 (td, J=13.12, 4.27 Hz, 3H) 4.51 (dd, J=15.26, 3.05 Hz, 1H) 6.15 (tt, J=55.23, 4.27 Hz, 1H) 7.00 (d, J=9.76 Hz, 1H) 7.02 (s, 1H) 7.52 (dd, J=8.54, 1.83 Hz, 1H) 8.05 (d, J=2.14 Hz, 1H) MS (DCI/NH$_3$) m/z 490 (M+H)$^+$.

Example 36

N-{(3E)-5-tert-butyl-1-methyl-2-[(2R)-tetrahydrofuran-2-ylmethyl]-1,2-dihydro-3H-pyrazol-3-ylidene}-2-[(3R)-tetrahydrofuran-3-yloxy]-5-trifluoromethyl)benzamide The title compound was prepared using the procedure as described in Example 35 substituting (R)-tetrahydrofuran-2-ol for 2,2-difluoroethanol. $^1$H NMR (400 MHz, CDCl$_3$) δ ppm 1.43 (s, 9H) 1.69-1.80 (m, 2H) 1.81-1.90 (m, 1H) 1.96-2.04 (m, 1H) 2.12-2.27 (m, 2H) 3.67-3.80 (m, 2H) 3.85 (s, 3H) 3.84-3.91 (m, 1H) 3.92-4.01 (m, 1H) 4.00-4.04 (m, 2H) 4.15-4.22 (m, 1H) 4.31 (dd, J=15.34, 5.52 Hz, 1H) 4.48 (dd, J=15.04, 3.07 Hz, 1H) 4.99-5.07 (m, 1H) 6.89 (d, J=8.59 Hz, 1H) 6.98 (s, 1H) 7.48 (dd, J=8.59, 2.46 Hz, 1H) 7.97 (d, J=2.46 Hz, 1H)MS (DCI/NH$_3$) m/z 496 (M+H)$^+$.

Example 37

N-{(3E)-5-tert-butyl-1-methyl-2-[(2R)-tetrahydrofuran-2-ylmethyl]-1,2-dihydro-3H-pyrazol-3-ylidene}-2-[(3S)-tetrahydrofuran-3-yloxy]-5-(trifluoromethyl)benzamide The title compound was prepared using the procedure as described in Example 35 substituting (S)-tetrahydrofuran-2-ol for 2,2-difluoroethanol. $^1$H NMR (400 MHz, CDCl$_3$) δ ppm 1.42 (s, 9H) 1.69-1.79 (m, 2H) 1.80-1.89 (m, 1H) 1.96-2.03 (m, 1H) 2.12-2.27 (m, 2H) 3.66-3.81 (m, 2H) 3.85 (s, 3H) 3.85-3.90 (m, 1H) 3.92-4.01 (m, 1H) 4.00-4.04 (m, 2H) 4.15-4.23 (m, 1H) 4.31 (dd, J=15.34, 5.52 Hz, 1H) 4.48 (dd, J=15.04, 3.07 Hz, 1H) 4.99-5.06 (m, 1H) 6.90 (d, J=8.59 Hz, 1H) 6.98 (s, 1H) 7.47 (dd, J=8.59, 2.46 Hz, 1H) 7.97 (d, J=2.46 Hz, 1H); MS (DCI/NH$_3$) m/z 496 (M+H)$^+$.

Example 38

(E)-N-(5-tert-butyl-2-(((2R,3R)-3-fluorotetrahydro furan-2-yl)methyl)-1-methyl-1 H-pyrazol-3(2H)-ylidene)-2-methoxy-5-(trifluoromethyl)benzamide

Example 38A (2R,3S)-pentane-1,2,3,5-tetraol

Water (50 mL) and Ra—Ni, water-wet (5.03 g, 38.6 mmol) were added to (3S,4R)-3,4,5-trihydroxypentanal (25.19 g, 188 mmol) in a 300 mL SS reactor. The mixture was stirred for 1.5 hr at 70° C. under 800 psi of hydrogen. The mixture was filtered through a nylon membrane, the reactor was rinsed with water, and the filtrate was concentrated and afforded 25.8 g of the title compound. $^1$H NMR (400 MHz, DMSO-d$_6$) δ ppm 1.36-1.48 (m, 1H) 1.66-1.77 (m, 1H) 3.20-3.27 (m, 1H) 3.33 (dd, J=11.66, 6.14 Hz, 1H) 3.38-3.59 (m, 4H) 4.25-4.33 (m, 3H) 4.40 (d, J=5.22 Hz, 1H); MS (ESI) m/z 137 (M+H)$^+$.

Example 38B (2R,3S)-2-(hydroxymethyl)tetrahydrofuran-3-ol

A mixture of the product from Example 38A (25.8 g, 190 mmol) and 4-methylbenzenesulfonic acid monohydrate (710 mg, 3.73 mmol) was refluxed and the water removed as an azeotropic mixture with toluene by using a Dean-Stark apparatus. After 4 hrs of reflux, the reaction mixture was cooled and treated with solid NaHCO$_3$ (3.9 mmol) to neutralize the acid catalyst followed by removing the solid material by filtration. The filtrate was distilled and the fraction at 95-98° C. under a pressure of 0.6 Torr was collected as a colorless oil (15.3 g, 68%). $^1$H NMR (400 MHz, DMSO-d$_6$) δ ppm 1.63-1.74 (m, 1H) 1.84-1.98 (m, 1H) 3.28-3.35 (m, 1H) 3.52-3.59 (m, 1H) 3.69-3.82 (m, 2H) 4.00-4.08 (m, 1H) 4.57 (t, J=5.52 Hz, 1H) 4.82 (d, J=3.99 Hz, 1H).

Example 38C (2R,3S)-2-((bis(4-methoxyphenyl)(phenyl)methoxy)methyl)tetrahydrofuran-3-ol The product from 38B (1.6 g, 13.54 mmol) in pyridine (20 mL) was treated with 4,4'-(chloro(phenyl)methylene)bis(methoxybenzene) (5.05 g, 14.9 mmol) for 12 hrs at rt. The solvent was removed in vacuo. The residue was diluted with CH$_2$Cl$_2$, washed with saturated NaHCO$_3$ and brine. The organic was dried over MgSO$_4$, filtered and concentrated. The residue was purified by column chromatography using an Analogix® Intelliflash280™ (SiO$_2$, 0-100% ethyl acetate in hexanes) to afford 4.25 g (75%) of the title compound. $^1$H NMR (400 MHz, CDCl$_3$) δ ppm 1.73 (d, J=3.99 Hz, 1H) 1.84-1.94 (m, 1H) 2.09-2.22 (m, 1H) 3.08 (dd, J=9.51, 6.14 Hz, 1H) 3.25 (dd, J=9.51, 4.60 Hz, 1H) 3.78 (s, 6H) 3.84-7.24 (m, 1H) 3.97 (dd, J=8.29, 5.52 Hz, 2H) 4.26-4.32 (m, 1H) 6.78-6.86 (m, 4H) 7.17-7.24 (m, 1H) 7.27-7.36 (m, 6H) 7.39-7.46 (m, 2H).

Example 38D (2R,3R)-3-fluoro-2-(((3-methoxyphenyl)(4-methoxyphenyl(phenyl)methoxy)methyl)tetrahydrofuran The product from Example 38C (1.1 g, 2.62 mmol) in CH$_2$Cl$_2$ (10 mL) was treated dropwise with diethylaminosulfur trifluoride (DAST) (508 mg, 3.14 mmol) at −78° C. The reaction was allowed to warm up to room temperature for 12 hours. The reaction mixture was quenched with saturated aqueous NaHCO$_3$ and extracted with CH$_2$Cl$_2$. The organic extract was dried (Na$_2$SO$_4$), filtered and concentrated. The residue was purified by column chromatography using an Analogix® Intelliflash280™ (SiO$_2$, 0-100% ethyl acetate in hexanes) to afford the title compound. $^1$H NMR (400 MHz, CDCl$_3$) δ ppm 2.05-2.27 (m, 2 H) 3.32 (dd, J=9.21, 6.14 Hz, 1H) 3.35-3.43 (m, 1H) 3.79 (s, 6H) 3.84-3.95 (m, 2H) 4.03 (dd, J=15.96, 8.59 Hz, 1H) 5.20 (d, J=55.54 Hz, 1H) 6.77-6.86 (m, 4H) 7.17-7.23 (m, 1H) 7.24-7.30 (m, 2H) 7.31-7.38 (m, 4H) 7.44-7.49 (m, 2H).

Example 38E ((2R,3R)-3-fluorotetrahydrofuran-2-yl)methanol

The product from Example 38D (600 mg, 1.42 mmol) in CH$_2$Cl$_2$ (10 mL) and MeOH (10 mL) was treated with 4-methylbenzenesulfonic acid monohydrate (135 mg, 0.71 mmol). The mixture was stirred at room temperature for 1 hour. The mixture was neutralized with excess Et$_3$N. The solvent was removed and the residue was purified by column chromatography using an Analogix® Intelliflash280™ (SiO$_2$, 0-50% MeOH in ethyl acetate) to afford 35 mg (21%) of the title compound. $^1$H NMR (400 MHz, CDCl$_3$) δ ppm 2.02-2.42 (m, 2H) 3.51-3.79 (m, 1H) 3.81-3.94 (m, 3H) 4.03-4.15 (m, 1H) 5.24 (d, J=59.84 Hz, 1H).

Example 38F (((2R,3R)-3-fluorotetrahydrofuran-2-yl)methyl)hydrazine

The title compound was prepared using the 2-step procedure as described in Example 45A substituting Example 38E for (R)-(tetrahydrofuran-2-yl)methanol. MS (DCI/NH$_3$) m/z 135 (M+H)$^+$.

Example 38G 3-tert-butyl-1-(((2R,3R)-3-fluorotetrahydrofuran-2-yl)methyl)-1H-pyrazol-5-amine The title compound was prepared using the procedure as described in Example 45B substituting Example 38F for Example 45A. MS (DCI/NH$_3$) m/z 241 (M+H)$^+$.

Example 38H

N-(3-tert-butyl-1-(((2R,3R)-3-fluorotetrahydro furan-2-yl)methyl)-1H-pyrazol-5-yl)-2-fluoro-5-(trifluoromethyl)benzamide The title compound was prepared using the procedure as described in Example 32B substituting Example 38G for Example 32A and 2-fluoro-5-(trifluoromethyl)benzoyl chloride for 2-methoxy-5-(trifluoromethyl)benzoyl chloride. MS (DCI/NH$_3$) m/z 432 (M+H)$^+$.

Example 38I (E)-N-(5-tert-butyl-2-(((2R,3R)-3-fluorotetrahydro-furan-2-yl)methyl)-1-methyl-1 H-pyrazol-3(2H)-ylidene)-2-fluoro-5-(trifluoromethyl)benzamide The title compound was prepared using the procedure as described in Example 32C substituting Example 38H for Example 32B. MS (DCI/NH$_3$) m/z 446 (M+H)$^+$.

Example 38J (E)-N-(5-tert-butyl-2-(((2R,3R)-3-fluorotetrahydro-furan-2-yl)methyl)-1-methyl-1 H-pyrazol-3(2H)-ylidene)-2-methoxy-5-(trifluoromethyl)benzamide The title compound was prepared using the procedure as described in Example 35 substituting Example 38I for Example 16B and methanol for 2,2-difluoroethanol. $^1$H NMR (400 MHz, CDCl$_3$) δ ppm 1.41 (s, 9H) 2.14-2.25 (m, 1H) 2.24-2.35 (m, 1H) 3.77-3.85 (m, 1H) 3.86 (s, 3H) 3.92 (s, 3H) 4.05-4.28 (m, 3H) 4.96 (d, J=15.65 Hz, 1 H) 5.22 (d, J=53.70 Hz, 1H) 6.97 (d, J=8.59 Hz, 1H) 7.06 (s, 1H) 7.52 (d, J=7.67 Hz, 1 H) 8.06 (s, 1 H); MS (DCI/NH$_3$) m/z 458 (M+H)$^+$.

Example 39

N-{(3E)-5-tert-butyl-1-methyl-2-[(2R)-tetrahydrofuran-2-ylmethyl]-1,2-dihydro-3H-pyrazol-3-ylidene}-2-[(2-fluoroethyl)amino]-5-(trifluoromethyl)benzamide The title compound was prepared using the procedure as described in Example 34 substituting 2-fluoroethanamine for 2-methoxyethanamine. $^1$H NMR (400 MHz, CDCl$_3$) δ ppm 1.42 (s, 9H) 1.68-1.91 (m, 3H) 1.98-2.11 (m, 1H) 3.57 (dd, J=24.86, 8.29 Hz, 2H) 3.66-3.84 (m, 2H) 3.87 (s, 3H) 4.16-4.27 (m, 1H) 4.32 (dd, J=21.17, 5.83 Hz, 1H) 4.50-4.58 (m, 1H) 4.58 (t, J=5.22 Hz, 1H) 4.70 (t, J=5.22 Hz, 1H) 6.66 (d, J=8.59 Hz, 1H) 6.94-7.01 (m, 1H) 7.41 (dd, J=8.59, 2.15 Hz, 1H) 8.62 (s, 1H) 9.71 (s, 1H); MS (DCI/NH$_3$) m/z 471 (M+H)$^+$.

Example 40

N-{(3E)-5-tert-butyl-1-methyl-2-[(2R)-tetrahydro furan-2-ylmethyl]-1,2-dihydro-3H-pyrazol-3-ylidene}-2-(2-fluoropropoxy)-5-(trifluoromethyl)benzamide The title compound was prepared using the procedure as described in Example 35 substituting 2-fluoropropan-1-ol for 2,2-difluoroethanol. $^1$H NMR (500 MHz, CDCl$_3$) δ ppm 1.39-1.49 (m, 3H) 1.42-1.45 (m, 9H) 1.68-1.79 (m, 1H) 1.80-1.91 (m, 1 H) 2.02-2.09 (m, 3H) 3.67-3.81 (m, 2H) 3.90 (s, 3H) 4.08-4.27 (m, 3H) 4.34 (ddd, J=6.10, 1.83 Hz, 1 H) 4.58 (dd, J=15.56, 2.75 Hz, 1H) 5.07 (d, J=7.15 Hz 1H) 6.99 (s, 1H) 7.51 (dd, J=8.54, 2.14 Hz, 1H) 7.98 (s, 1H); MS (DCI/NH$_3$) m/z 486 (M+H)$^+$.

Example 41

N-{(3E)-5-tert-butyl-1-methyl-2-[(2R)-tetrahydrofuran-2-ylmethyl]-1,2-dihydro-3H-pyrazol-3-ylidene}-2-{[(2R)-2-fluoropropyl]oxy}-5-(trifluoromethyl)benzamide The title compound was prepared using the procedure as described in Example 35 substituting (R)-2-fluoropropan-1-ol for 2,2-difluoroethanol. $^1$H NMR (400 MHz, CDCl$_3$) δ ppm 1.48 (s, 9H) 1.37-1.49 (m, 3H) 1.66-1.78 (m, 2H) 1.79-1.90 (m, 1 H) 2.03-2.07 (m, 1H) 3.64-3.80 (m, 2H) 3.88 (s, 3H) 4.06-4.27 (m, 3H) 4.33 (dd, J=17.80, 5.83 Hz, 1 H) 4.57 (dd, J=15.34, 3.07 Hz, 1H) 4.94-5.15 (m, 1H) 6.98 (d, J=7.06 Hz, 1H) 7.00 (s, 1 H) 7.50 (dd, J=7.67, 1.23 Hz, 1H) 7.99 (d, J=1.84 Hz, 1H); MS (DCI/NH$_3$) m/z 486 (M+H)$^+$.

Example 42

N-{(3E)-5-tert-butyl-1-methyl-2-[(2R)-tetrahydrofuran-2-ylmethyl]-1,2-dihydro-3H-pyrazol-3-ylidene}-2-(2-fluoro-1-methylethoxy)-5-(trifluoromethyl)benzamide The title compound was prepared using the procedure as described in Example 35 substituting 1-fluoropropan-2-ol for 2,2-difluoroethanol. $^1$H NMR (500 MHz, CDCl$_3$) δ ppm 1.39 (d, J=7.63 Hz, 3H) 1.44 (s, 9H) 1.64-1.81 (m, 2H) 1.81-1.91 (m, 1 H) 2.00-2.10 (m, 1H) 3.66-3.80 (m, 2H) 3.92 (s, 3H) 4.14-4.22 (m, 1H) 4.30-4.40 (m, 1H) 4.44-4.68 (m, 3H) 4.67-4.78 (m, 1H) 6.99 (s, 1H) 7.04 (d, J=8.85 Hz, 1H) 7.52 (dd, J=8.54, 2.14 Hz, 1H) 7.96 (s, 1H); MS (DCI/NH$_3$) m/z 486 (M+H)$^+$.

Example 43

N-{(3E)-5-tert-butyl-1-methyl-2-[(2R)-tetrahydrofuran-2-ylmethyl]-1,2-dihydro-3H-pyrazol-3-ylidene}-2-(3-fluoro-3-methylbutoxy)-5-(trifluoromethyl)benzamide

Example 43A

N-{(3E)-5-tert-butyl-1-methyl-2-[(2R)-tetrahydrofuran-2-ylmethyl]-1,2-dihydro-3H-pyrazol-3-ylidene}-2-(3-hydroxy-3-methylbutoxy)-5-(trifluoromethyl)benzamide The title compound was prepared using the procedure as described in Example 35 substituting 3-methylbutane-1,3-diol for 2,2-difluoroethanol. MS (DCI/NH$_3$) m/z 512 (M+H)$^+$.

Example 43B

N-{(3E)-5-tert-butyl-1-methyl-2-[(2R)-tetrahydrofuran-2-ylmethyl]-1,2-dihydro-3H-pyrazol-3-ylidene}-2-(3-fluoro-3-methylbutoxy)-5-(trifluoromethyl)benzamide The product from Example 43A (215 mg, 0.42 mmol) in CH$_2$Cl$_2$ (10 mL) was treated dropwise with DAST (66 μL, 0.504 mmol) at −78° C. The reaction mixture was allowed to warm up to room temperature for 4 hrs. The mixture was quenched with saturated NaHCO$_3$ and extracted with EtOAc (2×). The organic layer was dried over MgSO$_4$, filtered and concentrated. The residue was purified by column chromatography using an Analogix® Intelliflash280™ (SiO$_2$, 50% hexanes/EtOAc to 100% EtOAc to 9:1:0.1 EtOAc:MeOH: Et$_3$N) to afford 48 mg (22%) of the title compound. $^1$H NMR (400 MHz, CDCl$_3$) δ ppm 1.45 (d, J=21.48 Hz, 6H) 1.50 (s, 9H) 1.82-1.99 (m, 3H) 2.19-2.37 (m, 3 H) 3.67-3.83 (m, 2H) 4.14-4.23 (m, 1H) 4.24 (s, 3H) 4.48 (t, J=7.36 Hz, 2 H) 4.80-4.97 (m, 1H) 5.48 (d, J=17.18 Hz, 1H) 6.97 (s, 1H) 7.13 (d, J=8.59 Hz, 1H) 7.74 (dd, J=7.98, 1.84 Hz, 1H) 8.08 (d, J=2.15 Hz, 1H); MS (DCI/NH$_3$) m/z 514 (M+H)$^+$.

Example 44

N-{(3E)-5-tert-butyl-1-methyl-2-[(2R)-tetrahydrofuran-2-ylmethyl]-1,2-dihydro-3H-pyrazol-3-ylidene}-2-[(1-hydroxycyclobutyl)methoxy]-5-(trifluoromethyl)benzamide Example 44A 1-(hydroxymethyl)cyclobutanol Methylenecyclobutane (2.5 g, 36.7 mmol) in acetone (150 mL) and water (25 mL) was treated with osmium(VIII) oxide (467 mg, 1.835 mmol). The mixture was stirred at room temperature for 20 minutes. To the above mixture was added, in portions, 4-methylmorpholine N-oxide (12.9 g, 110 mmol). The reaction was stirred at room temperature for 12 hrs. The mixture was quenched with saturated Na$_2$S$_2$O$_3$, dried over MgSO$_4$, filtered and concentrated. The residue was purified by distillation (65-68° C. under 0.6 Torr) to provide the title compound (760 mg, 20%). $^1$H NMR (400 MHz, DMSO-d$_6$) δ ppm 1.30-1.48 (m, 1H) 1.55-1.66 (m, 1H) 1.76-1.89 (m, 2H) 1.91-2.04 (m, 2H) 4.41 (s, 1H) 4.60 (s, 1H).

Example 44B

N-{(3E)-5-tert-butyl-1-methyl-2-[(2R)-tetrahydrofuran-2-ylmethyl]-1,2-dihydro-3H-pyrazol-3-ylidene}-2-[(1-hydroxycyclobutyl)methoxy]-5-(trifluoromethyl)benzamide The title compound was prepared using the procedure as described in Example 35 substituting Example 44A for 2,2-difluoroethanol. $^1$H NMR (400 MHz, CDCl$_3$) δ ppm 1.42 (s, 9H) 1.50-1.64 (m, 2H) 1.65-1.91 (m, 4H) 1.97-2.06 (m, 1H) 2.05-2.21 (m, 3H) 3.66-3.81 (m, 2H) 3.87 (s, 3H) 4.13-4.20 (m, 1H) 4.24 (s, 2H) 4.28 (dd, J=15.34, 5.83 Hz, 1H) 4.53 (dd, J=15.34, 3.07 Hz, 1H) 7.00 (s, 1H) 7.09 (d, J=8.59 Hz, 1H) 7.52 (dd, J=8.29, 2.45 Hz, 1H) 8.13 (d, J=2.15 Hz, 1H); MS (DCI/NH$_3$) m/z 510 (M+H)$^+$.

Example 45

N-{(3E)-5-tert-butyl-1-methyl-2-[(2R)-tetrahydrofuran-2-ylmethyl]-1,2-dihydro-3H-pyrazol-3-ylidene}-5-chloro-2-methoxybenzamide Example 45A (R)-((tetrahydrofuran-2-yl)methyl)hydrazine dihydrochloride To (R)-(tetrahydrofuran-2-yl)methanol (4.0 g, 39.2 mmol), di-tert-butyl hydrazine-1,2-dicarboxylate (3.64 g, 15.67 mmol) and triphenylphosphine (15.41 g, 58.7 mmol) in THF (100 mL) was added (E)-di-tert-butyl diazene-1,2-dicarboxylate (13.5 g, 5.87 mmol). The mixture was stirred at ambient temperature for 3 h then diluted with water and extracted with EtOAc (100 mL×2). The organic extract was washed with brine and concentrated. Purification by flash chromatography (silica gel, 5-30% EtOAc/hexane) afforded 10.2 g (82%) of (R)-di-tert-butyl 1-((tetrahydrofuran-2-yl)-methyl)-hydrazine-1,2-dicarboxylate, which was dissolved in a solution of 4M HCl in dioxane (40 mL) and stirred at ambient temperature overnight. The solvent was removed under reduced pressure and ethyl acetate (20 mL) was added with stirring. The solid precipitate was filtered, washed with ether (10 mL) and dried under vacuum to yield 7.8 g (97%) of the title compound as a white solid. $^1$H NMR (300 MHz, DMSO-d$_6$) δ ppm 1.48-1.63 (m, 1H), 1.73-1.88 (m, 2H), 1.90-2.02 (m, 1H), 2.84-3.01 (m, 2H), 3.61-3.71 (m, 1H), 3.72-3.83 (m, 1H), 3.97-4.08 (m, 1H), 5.76 (br, 5H); MS (ESI) m/z 117 (M+H)$^+$.

Example 45B (R)-3-tert-butyl-1-((tetrahydrofuran-2-yl)methyl)-1H-pyrazol-5-amine hydrochloride A mixture of Example 45A (7.8 g, 41.3 mmol) and 4,4-dimethyl-3-oxopentanenitrile (5.68 g, 45.4 mmol) in ethanol (50 mL) was refluxed at 90° C. for 6 hours, then the solvent was removed under reduced pressure and ethyl acetate (10 mL) was added with stirring. The white solid that precipitated was collected, washed with ether and dried to yield 10.4 g (97%) of the title compound. $^1$H NMR (300 MHz, DMSO-d$_6$) δ ppm 1.14 (s, 9H), 1.60-1.97 (m, 4 H), 3.50-3.66 (m, 1H), 3.67-3.79 (m, 1H), 3.83 (d, J=5.16 Hz, 2H), 3.99-4.16 (m, 1H), 4.85 (s, 2H), 5.15 (s, 1H); MS (ESI) m/z 224 (M+H)$^+$, 222 (M−H)$^−$.

Example 45C

N-{3-tert-butyl-1-[(2R)-tetrahydrofuran-2-ylmethyl]-1H-pyrazol-5-yl}-5-chloro-2-methoxybenzamide To the mixture of Example 45B (1.25 g, 5.6 mmol) in CH$_2$Cl$_2$ (50 mL) cooled with an ice-bath was added triethylamine (2.3 mL, 16.8 mmol), and 5-chloro-2-methoxybenzoyl chloride (the product from Step A of Example 11C) (1.15 g, 5.6 mmol) dropwise. The mixture was stirred at ambient temperature for 2 hours, then treated with water (50 mL) and CH$_2$Cl$_2$ (50 mL). The organic layer was washed with brine and concentrated. Purification by flash chromatography (silica gel, Et$_3$N/MeOH/EtOAc, (1:10:90) in hexane in 10-40% gradient) afforded 1.75 g (80%) of the title compound. $^1$H NMR (300 MHz, DMSO-d$_6$) δ ppm 1.24 (s, 9H), 1.46-1.59 (m, 1H), 1.61-1.82 (m, 2H), 1.84-1.97 (m, 1 H), 3.54-3.76 (m, 2H), 3.97 (s, 3H), 4.01-4.23 (m, 3H), 6.31 (s, 1H), 7.28 (d, J=8.72 Hz, 1H), 7.62 (dd, J=8.73, 2.78 Hz, 1H), 7.81 (d, J=2.78 Hz, 1H), 10.25 (s, 1H)); MS (ESI) m/z 392 [M+H]$^+$, 390 [M−H].

Example 45D

N-{(3E)-5-tert-butyl-1-methyl-2-[(2R)-tetrahydrofuran-2-ylmethyl]-1,2-dihydro-3H-pyrazol-3-ylidene}-5-chloro-2-methoxybenzamide A mixture of Example 45C (392 mg, 1.0 mmol) and dimethyl sulfate (0.38 mL, 4.0 mmol) in toluene (2 mL) was heated in a microwave at 130° C. for 1 hour. The solvent was removed under reduced pressure and the residue was purified by flash chromatography (silica gel, MeOH/Et$_3$N (90:10) in EtOAc in 10-60% gradient) to yield 223 mg (55%) of the title compound. $^1$H NMR (300 MHz, DMSO-d$_6$) δ ppm 1.44 (s, 9H), 1.51-1.68 (m, 1H), 1.79-1.97 (m, 2H), 2.01-2.18 (m, 1H), 3.62-3.84 (m, 2H), 3.92 (s, 3H), 4.07-4.12 (s, 3H), 4.14-4.26 (m, 1H), 4.50-4.63 (m, 1H), 4.65-4.79 (m, 1H), 6.92-7.02 (m, 1H), 7.31 (d, J=8.82 Hz, 1H), 7.63-7.75 (m, 2H); MS (ESI) m/z 406 [M+H]$^+$, 404 [M−H].

Example 46

N-{(3E)-5-tert-butyl-1-methyl-2-[(2R)-tetrahydrofuran-2-ylmethyl]-1,2-dihydro-3H-pyrazol-3-ylidene}-2-fluoro-3-(trifluoromethyl)benzamide The title compound was prepared from Example 45B according to the procedures described in Example 45C and Example 45D, substituting 2-fluoro-3-(trifluoromethyl)benzoyl chloride for 2-methoxy-5-chlorobenzoyl chloride. $^1$H NMR (300 MHz, DMSO-d$_6$) δ ppm 1.44 (s, 9H) 1.51-1.67 (m, 1H), 1.75-1.95 (m, 2H), 2.01-2.14 (m, 1H), 3.71-3.87 (m, 2H), 4.12 (s, 3H), 4.13-4.27 (m, 1H), 4.56-4.76 (m, 2H), 6.98 (s, 1H), 7.63 (t, J=7.73 Hz, 1H), 8.01-8.11 (m, 2H); MS (ESI) m/z 428 [M+H]$^+$.

Example 47

N-{(3E)-5-tert-butyl-1-methyl-2-[(2R)-tetrahydrofuran-2-ylmethyl]-1,2-dihydro-3H-pyrazol-3-ylidene}-2-methoxy-5-(trifluoromethyl)benzamide The title compound was prepared from Example 45B according to the procedures described in Example 45C and Example 45D, substituting 2-methoxy-5-(trifluoromethyl)benzoyl chloride for 2-methoxy-5-chlorobenzoyl chloride. $^1$H NMR (300 MHz, DMSO-d$_6$) δ ppm 1.38 (s, 9H), 1.65-1.93 (m, 4H), 3.58-3.67 (m, 1H), 3.69-3.76 (m, 1H), 3.80 (s, 3H), 3.88 (s, 3H), 4.12-4.22 (m, 1H), 4.31 (dd, J=4.96, 2.58 Hz, 2H), 6.81 (s, 1H), 7.15 (d, J=8.72 Hz, 1H), 7.59 (dd, J=8.92, 2.18 Hz, 1H), 7.68 (d, J=2.38 Hz, 1 H); MS (ESI) m/z 440 [M+H]$^+$, 438 [M−H].

Example 48

N-{(3E)-5-tert-butyl-1-methyl-2-[2R)-tetrahydrofuran-2-ylmethyl]-1,2-dihydro-3H-pyrazol-3-ylidene}-5-cyano-2-methoxybenzamide The title compound was prepared from Example 45B according to the procedures described in Example 45C and Example 45D, substituting 2-methoxy-5-cyanobenzoyl chloride for 2-methoxy-5-chlorobenzoyl chloride. $^1$H NMR (300 MHz, DMSO-d$_6$) δ ppm 1.38 (s, 9H), 1.62-1.86 (m, 4H), 3.57-3.66 (m, 1H), 3.70-3.76 (m, 1H), 3.81 (s, 3H), 3.88 (s, 3H), 4.12-4.21 (m, 1H), 4.27-4.35 (m, 2H), 6.80 (s, 1H), 7.10-7.18 (m, 1H) 7.68-7.78 (m, 2H); MS (ESI) m/z 397 [M+H]$^+$, 395 [M−H].

Example 49

5-bromo-N-{(3E)-5-tert-butyl-1-methyl-2-[(2R)-tetrahydrofuran-2-ylmethyl]-1,2-dihydro-3H-pyrazol-3-ylidene}-2-methoxybenzamide The title compound was prepared from Example 45B according to the procedures described in Example 45C and Example 45D, substituting 2-methoxy-5-bromobenzoyl chloride for 2-methoxy-5-chlorobenzoyl chloride. $^1$H NMR (300 MHz, DMSO-d$_6$) δ ppm 1.37 (s, 9H), 1.63-1.94 (m, 4H), 3.58-3.67 (m, 1H), 3.71 (s, 3H), 3.71-3.79 (m, 1H), 3.87 (s, 3H), 4.11-4.21 (m, 1H), 4.31 (dd, J=5.09, 2.71 Hz, 2H), 6.79 (s, 1 H), 6.93 (d, J=8.82 Hz, 1H), 7.38 (dd, J=8.82, 2.71 Hz, 1H), 7.47 (d, J=2.71 Hz, 1H); MS (ESI) m/z 452 [M+H].

Example 50

N-{(3E)-5-tert-butyl-1-methyl-2-[(2R)-tetrahydrofuran-2-ylmethyl]-1,2-dihydro-3H-pyrazol-3-ylidene}-2-chloro-5-fluorobenzamide The title compound was prepared from Example 45B according to the procedures described in Example 45C and Example 45D, substituting 2-chloro-5-fluorobenzoyl chloride for 2-methoxy-5-chlorobenzoyl chloride. $^1$H NMR (300 MHz, DMSO-d$_6$) δ ppm 1.38 (s, 9 H), 1.63-1.94 (m, 4H), 3.57-3.67 (m, 1H), 3.69-3.78 (m, 1H), 3.90 (s, 3 H), 4.12-4.20 (m, 1H), 4.27-4.44 (m, 2H), 6.81 (s, 1H), 7.10-7.19 (m, 1H), 7.30-7.43 (m, 2H); MS (ESI) m/z 394 [M+H]$^+$.

Example 51

N-{(3E)-5-tert-butyl-1-methyl-2-[(2R)-tetrahydrofuran-2-ylmethyl]-1,2-dihydro-3H-pyrazol-3-ylidene}-2,3,5-trifluorobenzamide The title compound was prepared from Example 45B according to the procedures described in Example 45C and Example 45D, substituting 2,3,5-trifluorobenzoyl chloride for 2-methoxy-5-chlorobenzoyl chloride. $^1$H NMR (300 MHz, DMSO-d$_6$) δ ppm 1.38 (s, 9H), 1.65-1.82 (m, 3H), 1.84-1.95 (m, 1H), 3.58-3.69 (m, 1H), 3.69-3.81 (m, 1H), 3.91 (s, 3H), 4.11-4.25 (m, 1H), 4.30-4.46 (m, 2H), 6.82 (s, 1H), 7.34-7.53 (m, 2H); MS (ESI) m/z 396 [M+H]$^+$, 394 [M−H].

Example 52

N-{(3E)-5-tert-butyl-1-methyl-2-[(2R)-tetrahydrofuran-2-ylmethyl]-1,2-dihydro-3H-pyrazol-3-ylidene}-3-chloro-2-fluoro-5-(trifluoromethyl)benzamide The title compound was prepared from Example 45B according to the procedures described in Example 45C and Example 45D, substituting 3-chloro-2-fluoro-5-(trifluoromethyl)benzoyl chloride for 2-methoxy-5-chlorobenzoyl chloride. $^1$H NMR (300 MHz, DMSO-d$_6$) δ ppm 1.39 (s, 9H), 1.64-1.95 (m, 4H), 3.57-3.68 (m, 1H), 3.70-3.81 (m, 1H), 3.93 (s, 3H), 4.14-4.25 (m, 1H), 4.39 (t, J=5.16 Hz, 2H), 6.83 (s, 1H), 8.01-8.14 (m, 2H); MS (ESI) m/z 462 [M+H]$^+$, 460 [M−H].

Example 53

N-{(3E)-5-tert-butyl-1-methyl-2-[(2R)-tetrahydrofuran-2-ylmethyl]-1,2-dihydro-3H-pyrazol-3-ylidene}-3-chloro-2-methoxy-5-(trifluoromethyl)benzamide To methanol (48.1 mg, 1.5 mmol) in THF (4 mL) was added sodium tert-butoxide (144 mg, 1.5 mmol). The reaction mixture was stirred at ambient temperature for 10 minutes, then Example 52 (231 mg, 0.500 mmol) was added. The mixture was stirred for 2 hours and monitored by LC/MS. Saturated aqueous NaHCO$_3$ (10 mL) and ethyl acetate (10 mL) were added and the layers were separated. The organic layer was washed with brine and concentrated. Purification by flash chromatography (Et$_3$N/MeOH/EtOAc (1:10:90) in hexane at 10-60% gradient) afforded the title compound as a white solid (194 mg, 82%). $^1$H NMR (300 MHz, DMSO-d$_6$) δ ppm 1.39 (s, 9H), 1.62-1.94 (m, 4H), 3.56-3.68 (m, 1 H), 3.69-3.79 (m, 1H), 3.89 (s, 3H), 3.91 (s, 3H), 4.08-4.23 (m, 1H), 4.35 (dd, J=5.16, 3.17 Hz, 2 H), 6.83 (s, 1H), 7.74-7.83 (m, 2H); MS (ESI) m/z 474 [M+H]$^+$.

Example 54

N-{(3E)-5-tert-butyl-1-methyl-2-[(2R)-tetrahydrofuran-2-ylmethyl]-1,2-dihydro-3H-pyrazol-3-ylidene}-2-chloro-5-(trifluoromethyl)benzamide The title compound was prepared from Example 45B according to the procedures described in Example 45C and Example 45D, substituting 2-chloro-5-(trifluoromethyl)benzoyl chloride for 2-methoxy-5-chlorobenzoyl chloride. $^1$H NMR (300 MHz, DMSO-d$_6$) δ ppm 1.39 (s, 9H), 1.63-1.95 (m, 4H), 3.58-3.67 (m, 1H), 3.70-3.80 (m, 1H), 3.91 (s, 3H), 4.13-4.23 (m, 1H), 4.27-4.42 (m, 2H), 6.83 (s, 1 H), 7.58-7.70 (m, 2H), 7.89 (s, 1H); MS (ESI) m/z 444 [M+H]$^+$, 442 [M−H].

Example 55

N-{(3E)-5-tert-butyl-1-methyl-2-[(2R)-tetrahydrofuran-2-ylmethyl]-1,2-dihydro-3H-pyrazol-3-ylidene}-3,5-difluoro-2-methoxybenzamide The title compound was prepared from Example 51 and methanol according to the procedure described in Example 53. $^1$H NMR (300 MHz, DMSO-d$_6$) δ ppm 1.38 (s, 9H), 1.59-1.94 (m, 4H), 3.55-3.66 (m, 1H), 3.73 (t, J=7.14 Hz, 1H), 3.80 (s, 3 H), 3.89 (s, 3 H), 4.10-4.22 (m, 1H), 4.28-4.45 (m, 2H), 6.83 (s, 1H) 7.10 (dd, J=9.12, 1.98 Hz, 1H), 7.17-7.29 (m, 1H); MS (ESI) m/z 408 [M+H]$^+$, 406 [M−H].

Example 56

N-{(3E)-5-tert-butyl-1-methyl-2-[(2R)-tetrahydrofuran-2-ylmethyl]-1,2-dihydro-3H-pyrazol-3-ylidene}-3-chloro-2-(2-methoxyethoxy)-5-(trifluoromethyl)benzamide The title compound was prepared from Example 52 and 2-methoxyethanol according to the procedure described in Example 53. $^1$H NMR (300 MHz, DMSO-d$_6$) δ ppm 1.39 (s, 9 H), 1.62-1.86 (m, 4H), 3.26 (s, 3H), 3.54-3.68 (m, 3H) 3.73 (t, J=7.14 Hz, 3.91 (s, 3H), 4.16 (d, J=5.55 Hz, 1H), 4.19-4.26 (m, 2H), 4.37-4.39 (m, 2H), 6.81 (s, 1H), 7.72-7.85 (m, 2H); MS (ESI) m/z 518 [M+H]$^+$, 516 [M−H].

Example 57

N-{(3E)-5-tert-butyl-1-methyl-2-[(2R)-tetrahydrofuran-2-ylmethyl]-1,2-dihydro-3H-pyrazol-3-ylidene}-3-chloro-2-(2-fluoroethoxy)-5-(trifluoromethyl)benzamide The title compound was prepared from Example 52 and 2-fluoroethanol according to the procedure described in Example 53. $^1$H NMR (300 MHz, DMSO-d$_6$) δ ppm 1.39 (s, 9H), 1.63-1.93 (m, 4H), 3.59-3.68 (m, 1H), 3.73 (t, J=7.14 Hz, 1H), 3.91 (s, 3 H), 4.10-4.22 (m, 1H), 4.28-4.38 (m, 3H), 4.39-4.46 (m, 1H), 4.58-4.63 (m, 1H), 4.73-4.79 (m, 1 H), 6.82 (s, 1H), 7.82 (s, 2H); MS (ESI) m/z 506 [M+H]$^+$, 504 [M−H].

Example 58

5-bromo-N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)benzamide Example 58A 5-bromo-N-{(3E)-5-tert-butyl-1-methyl-2-[(2R)-tetrahydrofuran-2-ylmethyl]-1,2-dihydro-3H-pyrazol-3-ylidene}-2-fluorobenzamide The title compound was prepared from Example 45B according to the procedure described in Example 45C and Example 45D, substituting 5-bromo-2-fluorobenzoyl chloride for 2-methoxy-5-chlorobenzoyl chloride. $^1$H NMR (300 MHz, DMSO-d$_6$) δ ppm 1.38 (s, 9 H), 1.65-1.96 (m, 4H), 3.59-3.69 (m, 1H), 3.74 (t, J=7.14 Hz, 1H), 3.90 (s, 3H), 4.13-4.24 (m, 1H), 4.32-4.44 (m, 2H), 6.81 (s, 1H), 7.13 (dd, J=10.31, 8.72 Hz, 1H), 7.48-7.57 (m, 1H), 7.92 (dd, J=6.74, 2.78 Hz, 1H); MS (ESI) m/z 438 [M+H]$^+$.

Example 58B 5-bromo-N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)benzamide The title compound was prepared from Example 58A and 2-methoxyethanol according to the procedure described in Example 53. $^1$H NMR (300 MHz, DMSO-d$_6$) δ ppm 1.37 (s, 9H), 1.65-1.92 (m, 4H), 3.27 (s, 3H), 3.57-3.67 (m, 3H), 3.70-3.78 (m, 1H), 0.87 (s, 3H), 4.07 (dd, J=5.43, 4.07 Hz, 2H), 4.10-4.20 (m, 1H), 4.29-4.36 (m, 2H), 6.77 (s, 1H), 6.94 (d, J=8.82 Hz, 1H), 7.36 (dd, J=8.82, 2.71 Hz, 1H), 7.49 (d, J=2.37 Hz, 1H); MS (ESI) m/z 496 [M+H]$^+$, 494 [M−H].

Example 59

5-bromo-N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)benzamide The title compound was prepared from Example 58A and 2-fluoroethanol according to the procedure described in Example 53. $^1$H NMR (300 MHz, DMSO-d$_6$) δ ppm 1.38 (s, 9 H), 1.60-1.96 (m, 4H), 3.54-3.66 (m, 1H), 3.69-3.80 (m, 1H), 3.87 (s, 3 H), 4.11-4.18 (m, 2H), 4.23-4.36 (m, 3H), 4.56-4.62 (m, 1H), 4.72-4.78 (m, 1H), 6.79 (s, 1H), 6.96 (d, J=8.82 Hz, 1H), 7.38 (dd, J=8.48, 2.71 Hz, 1H), 7.53 (d, J=2.71 Hz, 1H); MS (ESI) m/z 484 [M+H]$^+$, 482 [M−H].

Example 60

5-bromo-N-{(3E)-5-tert-butyl-1-methyl-2-[(2R)-tetrahydrofuran-2-ylmethyl]-1,2-dihydro-3H-pyrazol-3-ylidene}-2,3-dihydro-1-benzofuran-7-carboxamide The title compound was prepared from Example 45B according to the procedure described in Example 45C and Example 45D, substituting 5-bromo-2,3-dihydrobenzofuran-7-carbonyl chloride for 2-methoxy-5-chlorobenzoyl chloride. ¹H NMR (300 MHz, DMSO-d₆) δ ppm 1.37 (s, 9H), 1.73-1.97 (m, 4H), 3.12-3.28 (m, 2H), 3.59-3.69 (m, 1 H), 3.72-3.81 (m, 1H), 3.87 (s, 3H), 4.22 (dd, J=5.35, 3.77 Hz, 1H), 4.27-4.37 (m, 1H), 4.39-4.47 (m, 1H), 4.52 (t, J=8.72 Hz, 2H), 6.77 (s, 1H), 7.34 (d, J=2.38 Hz, 1H), 7.76 (d, J=1.98 Hz, 1 H); MS (ESI) m/z 464 [M+H].

Example 61

N-[(2E)-4-tert-butyl-1-[(2R)-tetrahydrofuran-2-ylmethyl]pyridin-2(1H)-ylidene]-5-chloro-2-methoxybenzamide Example 61A (R)-4-tert-butyl-1-((tetrahydrofuran-2-yl)methyl)pyridin-2(1H)-imine A mixture of 4-tert-butylpyridin-2-amine (1.0 g, 6.7 mmol, LeadGen Labs), Example 11A (2.0 g, 8.0 mmol), and tetrabutylammonium iodide (1.2 g, 3.3 mmol) in N,N-dimethylformamide (1.3 mL) was heated at 95° C. for 16 hours. The reaction was incomplete as monitored by LC/MS. One more equivalent of both Example 11A and tetrabutylammonium iodide were added. After stirring at 95° C. for 16 hours, the reaction mixture was cooled and quenched with saturated NaHCO₃ (10 mL). The aqueous layer was extracted with dichloromethane (3×30 mL). The combined organic extracts were dried over anhydrous Na₂SO₄, filtered and concentrated under reduced pressure to provide the title compound. MS (ESI⁺) m/z 235 (M+H)⁺.

Example 61B

N-[(2E)-4-tert-butyl-1-[(2R)-tetrahydrofuran-2-ylmethyl]pyridin-2(1H)-ylidene]-5-chloro-2-methoxybenzamide To a solution of the crude product of Example 61A (0.8 g, 1.7 mmol) in tetrahydrofuran (10 mL) were added 5-chloro-2-methoxybenzoyl chloride (0.4 g, 1.9 mmol) and triethylamime (0.7 mL, 5.1 mmol). After stirring at 60° C. for 14 hours, the reaction mixture was cooled and quenched with saturated NaHCO₃ (10 mL). The aqueous layer was extracted with ethyl acetate (3×20 mL). The combined organic extracts were dried over anhydrous Na₂SO₄, filtered and concentrated under reduced pressure. The residue was purified by column chromatography using an Analogix® Intelliflash280™ (SiO₂, 0-5% methanol in dichloromethane) to provide 60 mg of the title compound. ¹H NMR (300 MHz, DMSO-d₆) δ ppm 1.26 (s, 9H), 1.50-1.69 (m, 1H), 1.69-2.09 (m, 3H), 3.57-3.70 (m, 1 H), 3.75 (s, 3H), 3.76-3.86 (m, 1H), 4.00 (dd, J=12.9, 8.5 Hz, 1H), 4.30 (dd, 1H), 4.57 (dd, J=12.7, 3.2 Hz, 1H), 6.87 (dd, J=7.0, 2.2 Hz, 1H), 7.03 (d, J=8.8 Hz, 1H), 7.34 (dd, J=8.8, 2.7 Hz, 1H), 7.53 (d, J=2.7 Hz, 1H), 7.95 (d, J=7.1 Hz, 1H), 8.28 (d, J=2.4 Hz, 1H) MS (ESI⁺) m/z 403 (M+H)⁺.

Example 62

N-[(2E)-4-tert-butyl-[(2R)-tetrahydrofuran-2-ylmethyl]pyridin-2(1H)-ylidene]-2-methoxy-5-(trifluoromethyl)benzamide Example 61A, 2-methoxy-5-(trifluoromethyl)benzoyl chloride (JRD Fluorochemicals) and triethylamine were processed as described for Example 61B to provide the title compound. ¹H NMR (300 MHz, DMSO-d₆) δ ppm 1.27 (s, 9H), 1.52-1.69 (m, 1H), 1.71-2.01 (m, 3H), 3.55-3.70 (m, 1H), 3.72-3.82 (m, 1H), 3.84 (s, 3H), 3.93-4.12 (m, 1H), 4.24-4.43 (m, 1H), 4.60 (dd, J=12.7, 3.2 Hz, 1H), 6.89 (dd, J=7.0, 2.2 Hz, 1H), 7.21 (d, J=8.5 Hz, 1H), 7.67 (dd, J=8.6, 2.5 Hz, 1H), 7.88 (d, J=2.4 Hz, 1H), 7.97 (d, J=7.1 Hz, 1 H), 8.34 (d, J=2.0 Hz, 1H); MS (ESI⁺) m/z 437 (M+H)⁺

Example 63

N-[(3E)-5-tert-butyl-1-methyl-2-(tetrahydro-2H-pyran-2-ylmethyl)-1,2-dihydro-3H-pyrazol-3-ylidene]-2-methoxy-5-(trifluoromethyl)benzamide Example 63A (E)-N'-(3-tert-butyl-1H-pyrazol-5-yl)-N,N-dimethylformimidamide A mixture of 3-tert-butyl-1H-pyrazol-5-amine (5 g, 36 mmol, Alfa-aesar) and N,N-dimethylformamide dimethylacetal (153 mL, 1078 mmol, Aldrich) was refluxed overnight. The reaction mixture was then cooled, concentrated under reduced pressure and the residue was purified by column chromatography using an Analogix® Intelliflash280™ (SiO₂, 0-5% methanol in dichloromethane) to provide 6.9 g (99%) of the title compound. MS (ESI⁺) m/z 195 (M+H)⁺.

Example 63B (E)-N'-(3-tert-butyl-1-((tetrahydro-2H-pyran-2-yl)methyl)-1H-pyrazol-5-yl)-N,N-dimethylformimidamide To a solution of Example 63A (1.0 g, 5.2 mmol) in N,N-dimethylformamide (10 mL) were added sodium hydride (0.52 g, 12.9 mmol, 60% in mineral oil, Aldrich), 2-(bromomethyl)tetrahydro-2H-pyran (0.8 mL, 6.2 mmol) and sodium iodide (0.23 g, 1.5 mmol). After stirring at 65° C. for 16 hours, the reaction mixture was cooled and quenched with saturated NaHCO₃ (10 mL). The aqueous layer was extracted with ethyl acetate (3×20 mL). The combined organic extracts were dried over anhydrous Na₂SO₄, filtered and concentrated under reduced pressure. The residue was purified by column chromatography using an Analogix® Intelliflash280™ (SiO₂, 0-10% methanol in dichloromethane) to provide 0.82 g (55%) of the title compound. ¹H NMR (501 MHz, CDCl₃) δ ppm 1.22-1.33 (m, 1H), 1.27 (s, 9H), 1.34-1.49 (m, 3H), 1.51-1.62 (m, 1H), 1.72-1.83 (m, 1H), 2.87 (s, 3H), 2.95 (s, 3H), 3.36-3.49 (m, 1H), 3.73-3.83 (m, 1H), 3.95 (dd, J=11.3, 3.0 Hz, 1 H), 4.02 (dd, J=13.4, 7.7 Hz, 1H), 4.17 (dd, J=13.4, 5.8 Hz, 1H), 5.55 (s, 1H), 8.00 (s, 1H). MS (ESI⁺) m/z 293 (M+H)⁺.

Example 63C 3-tert-butyl-1-((tetrahydro-2H-pyran-2-yl)methyl)-1H-pyrazol-5-amine To a solution of Example 63B (0.9 g, 3.1 mmol) in dioxane (10 mL) were added hydrazine (0.12 mL, 3.7 mmol, Aldrich) and acetic acid (0.35 mL, 6.2 mmol). After stirring at 85° C. for 16 hours, the reaction mixture was cooled and quenched with saturated NaHCO₃ (10 mL). The aqueous layer was extracted with ethyl acetate (3×20 mL). The combined organic extracts were dried over anhydrous Na₂SO₄, filtered

Example 63D

N-(3-tert-butyl-1-((tetrahydro-2H-pyran-2-yl)methyl)-1H-pyrazol-5-yl)-2-methoxy-5-(trifluoromethyl)benzamide To a solution of Example 63C (0.73 g, 3.1 mmol) in tetrahydrofuran (20 mL) were added 2-methoxy-5-(trifluoromethyl)benzoic acid (0.68 g, 3.1 mmol, JRD Fluorochemicals), 1-hydroxybenzotriazole (0.47 g, 3.1 mmol, Aldrich), N-(3-dimethylaminopropyl)-N-ethylcarbodimide hydrochloride (0.59 g, 3.1 mmol) and triethylamine (1.3 mL, 9.2 mmol). After stirring at 60° C. for 16 hours, the reaction mixture was cooled and quenched with saturated $NaHCO_3$ (20 mL). The aqueous layer was extracted with ethyl acetate (3×20 mL). The combined organic extracts were dried over anhydrous $Na_2SO_4$, filtered and concentrated under reduced pressure. The residue was purified by column chromatography using an Analogix® Intelliflash280™ ($SiO_2$, 0-50% ethyl acetate in hexanes) to provide 0.2 g of the title compound. MS ($ESI^+$) m/z 440 $(M+H)^+$.

Example 63E

N-[(3E)-5-tert-butyl-1-methyl-2-(tetrahydro-2H-pyran-2-ylmethyl)-1,2-dihydro-3H-pyrazol-3-ylidene]-2-methoxy-5-(trifluoromethyl)benzamide To a solution Example 63D (0.2 g, 0.455 mmol) in toluene (2.0 mL) was added dimethyl sulfate (0.130 mL, 1.365 mmol). The reaction mixture was heated at 150° C. with microwave irradiation for 60 minutes. The reaction mixture was then purified by column chromatography using an Analogix® Intelliflash280™ ($SiO_2$, 0-100% of 7N methanol/dichloromethane (1:10) in dichloromethane) to provide the title compound. $^1$H NMR (300 MHz, DMSO-$d_6$) δ ppm 1.21-1.32 (m, 2H), 1.37 (s, 9H), 1.39-1.48 (m, 2H), 1.49-1.57 (m, 1H), 1.73-1.85 (m, 1H), 3.60-3.70 (m, 1H), 3.81 (s, 3H), 3.86 (s, 3H), 3.87-3.90 (m, 1H), 4.16 (s, 1H), 4.17-4.23 (m, 1H), 4.24-4.34 (m, 1H), 6.78 (s, 1H), 7.15 (d, J=8.6 Hz, 1H), 7.60 (dd, J=8.6, 2.5 Hz, 1H), 7.75 (d, J=2.5 Hz, 1H); MS($ESI^+$) m/z 454 $(M+H)^+$.

Example 64

N-((3E)-5-tert-butyl-1-methyl-2-{[(5R)-5-methyltetrahydrofuran-2-yl]methyl}-1,2-dihydro-3H-pyrazol-3-ylidene)-2-methoxy-5-(trifluoromethyl)benzamide

Example 64A ((5R)-5-methyltetrahydrofuran-2-yl)methanol

To a solution of (R)-hex-5-en-2-ol (5.0 g, 50.0 mmol, Aldrich) in chloroform (100 mL) were added methyltrioxorhenium(VII) (0.37 g, 1.5 mmol, Aldrich) and hydrogen peroxide (5.7 g, 50.0 mmol, 30% in water, Aldrich). After stirring at room temperature for 16 hours, the reaction mixture was quenched with potassium carbonate, and extracted with diethyl ether (2×50 mL). The combined organic extracts were dried over anhydrous $MgSO_4$, filtered and concentrated under reduced pressure to provide 7.7 g (75%) of the title compound MS ($DCI^+$) m/z 134 $(M+NH_4)^+$.

Example 64B ((5R)-5-methyltetrahydrofuran-2-yl)methyl 4-methylbenzenesulfonate To a solution of Example 64A (4.0 g, 25.8 mmol) in dichloromethane (100 mL) were added triethylamine (10.8 mL, 77.0 mmol) and p-toluenesulfonyl chloride (4.9 g, 25.8 mmol). The reaction mixture was stirred at room temperature overnight and then washed with water (50 mL) and brine (50 mL). The organic layer was dried ($Na_2SO_4$), filtered and concentrated under reduced pressure. The residue was purified by column chromatography using an Analogix® Intelliflash280™ ($SiO_2$, 0-25% ethyl acetate in hexanes) to provide 3.5 g (50%) of the title compound. MS ($DCI^+$) m/z 288 $(M+NH_4)^+$.

Example 64C (E)-N'-(3-tert-butyl-1-(((5R)-5-methyltetrahydrofuran-2-yl)methyl)-1H-pyrazol-5-yl)-N,N-dimethylformimidamide To a solution of Example 63A (1.6 g, 8.2 mmol) in toluene (100 mL) were added potassium carbonate (2.3 g, 16.5 mmol), Example 64B (2.7 g, 9.9 mmol), tetrabutylammonium iodide (70 mg), tetraethylammonium iodide (70 mg) and tetrabutylammonium hydrogensulfate (70 mg). The reaction mixture was refluxed for 16 h, cooled, filtered and concentrated under reduced pressure. The residue was purified by column chromatography using an Analogix® Intelliflash280™ ($SiO_2$, 0-10% methanol in dichloromethane) to provide 0.6 g (25%) of the title compound. MS ($ESI^+$) m/z 293 $(M+H)^+$.

Example 64D 3-tert-butyl-1-(((5R)-5-methyltetrahydrofuran-2-yl)methyl)-1H-pyrazol-5-amine Example 64C, hydrazine and acetic acid were processed as described for Example 63C to provide the title compound. LCMS ($APCI^+$) m/z 237 $(M+H)^+$.

Example 64E

N-(3-tert-butyl-1-{[(5R)-5-methyltetrahydrofuran-2-yl]methyl}-1H-pyrazol-5-yl)-2-methoxy-5-(trifluoromethyl)benzamide Example 64D, 2-methoxy-5-(trifluoromethyl)benzoic acid, 1-hydroxybenzotriazole, N-(3-dimethylaminopropyl)-N-ethylcarbodimide hydrochloride and triethylamine were processed as described in Example 63D to provide the title compound. MS ($ESI^+$) m/z 440 $(M+H)^+$.

Example 64F

N-((3E)-5-tert-butyl-1-methyl-2-{[(5R)-5-methyltetrahydrofuran-2-yl]methyl}-1,2-dihydro-3H-pyrazol-3-ylidene)-2-methoxy-5-(trifluoromethyl)benzamide Example 64E and dimethyl sulfate were processed as described in Example 63E to provide the title compound as a mixture of diastereomers (the NMR spectrum has duplicate signals for a few protons). $^1$H NMR (300 MHz, DMSO-$d_6$) δ ppm 1.09 (d, J=5.9 Hz, 3H), 1.09 (d, J=5.9 Hz, 3H), 1.19-1.27

(m, 1H), 1.29-1.37 (m, 2H), 1.38 (s, 18H), 1.67-1.81 (m, 1H), 1.82-1.97 (m, 4H), 3.80 (s, 6H), 3.88 (s, 3H), 3.90 (s, 3H), 3.94-4.04 (m, 2H), 4.10-4.19 (m, 1H), 4.25-4.38 (m, 5H), 6.81 (s, 1H), 6.82 (s, 1H), 7.14 (d, J=8.7 Hz, 2H), 7.59 (dd, J=8.7, 2.4 Hz, 2H), 7.67 (d, J=1.6 Hz, 2H); MS (ESI$^+$) m/z 454 (M+H)$^+$.

Example 65

N-((3E)-5-tert-butyl-1-methyl-2-{[(5S)-5-methyltetrahydrofuran-2-yl]methyl}-1,2-dihydro-3H-pyrazol-3-ylidene)-2-methoxy-5-(trifluoromethyl)benzamide

Example 65A ((5S)-5-methyltetrahydrofuran-2-yl)methanol

Commercially available (S)-hex-5-en-2-ol (Aldrich), methyltrioxorhenium(VII) (Aldrich) and hydrogen peroxide (Aldrich) were processed as described for Example 64A to provide the title compound MS (DCI$^+$) m/z 134 (M+NH$_4$)$^+$.

Example 65B ((5S)-5-methyltetrahydrofuran-2-yl)methyl 4-methylbenzenesulfonate Example 65A, triethylamine and p-toluenesulfonyl chloride were processed as described for Example 64B to provide the title compound. MS (DCI$^+$) m/z 288 (M+NH$_4$)$^+$.

Example 65C (E)-N'-(3-tert-butyl-1-(((5S)-5-methyltetrahydrofuran-2-yl)methyl)-1H-pyrazol-5-yl)-N,N-dimethylformimidamide Example 63A, Example 65B and potassium carbonate were processed as described for Example 64C to provide the title compound. MS (ESI$^+$) m/z 293 (M+H)$^+$.

Example 65D 3-tert-butyl-1-(((5S)-5-methyltetrahydrofuran-2-yl)methyl)-1H-pyrazol-5-amine Example 65C, hydrazine and acetic acid were processed as described for Example 63C to provide the title compound. LCMS (APCI$^+$) m/z 237 (M+H)$^+$.

Example 65E

N-(3-tert-butyl-1-{[(5S)-5-methyltetrahydrofuran-2-yl]methyl}-1H-pyrazol-5-yl)-2-methoxy-5-(trifluoromethyl)benzamide Example 65D, 2-methoxy-5-(trifluoromethyl)benzoic acid, 1-hydroxybenzotriazole, N-(3-dimethylaminopropyl)-N-ethylcarbodiimide hydrochloride and triethylamine were processed as described for Example 63D to provide the title compound. MS (ESI$^+$) m/z 440 (M+H)$^+$.

Example 65F

N-((3E)-5-tert-butyl-1-methyl-2-{[(5S)-5-methyltetrahydrofuran-2-yl]methyl}-1,2-dihydro-3H-pyrazol-3-ylidene)-2-methoxy-5-(trifluoromethyl)benzamide Example 65E and dimethyl sulfate were processed as described for Example 63E to provide the title compound as a diasteriomeric mixture (the NMR spectrum has duplicated signals for few proton types). $^1$H NMR (300 MHz, DMSO-d$_6$) δ ppm 1H NMR (400 MHz, DMSO-d$_6$) δ ppm 1.09 (d, J=6.1 Hz, 3H), 1.09 (d, J=5.8 Hz, 3H), 1.19-1.26 (m, 1H), 1.32-1.37 (m, 1H), 1.38 (s, 18H), 1.69-1.78 (m, 1H), 1.81-1.98 (m, 5H), 3.80 (s, 6H), 3.87 (s, 3H), 3.90 (s, 3H), 3.96-4.06 (m, 2H), 4.10-4.20 (m, 1H), 4.23-4.39 (m, 5H), 6.81 (s, 1H), 6.82 (s, 1H), 7.14 (d, J=8.6 Hz, 2H), 7.59 (dd, J=8.6, 2.1 Hz, 2H), 7.68 (d, J=2.1 Hz, 2H); MS (ESI$^+$) m/z 454 (M+H)$^+$.

Example 66

N-[(2Z)-5-tert-butyl-3-[(2R)-tetrahydrofuran-2-ylmethyl]-1,3-oxazol-2(3H)-ylidene]-2-methoxy-5-(trifluoromethyl)benzamide

Example 66A (R)-5-tert-butyl-3-((tetrahydrofuran-2-yl)methyl)oxazol-2(3H)-imine A mixture of Example 13A (500 mg, 3.96 mmol), 1-bromo-3,3-dimethylbutan-2-one (Aldrich) (535 μL, 3.96 mmol) and cesium carbonate (2.58 g, 7.93 mmol) in 1,2-dimethoxyethane (8 mL) was stirred at 60° C. for 4 hours. The mixture was cooled, poured into water, and extracted with ethyl acetate (2×). The combined organic extracts were dried over MgSO$_4$, filtered, and concentrated under reduced pressure to afford the title compound. LC/MS (ESI$^+$) m/z 225 (M+H)$^+$.

Example 66B

N-[(2Z)-5-tert-butyl-3-[(2R)-tetrahydrofuran-2-ylmethyl]-1,3-oxazol-2(3H)-ylidene]-2-methoxy-5-(trifluoromethyl)benzamide To a solution of Example 66A (100 mg, 0.45 mmol) in tetrahydrofuran (4 mL) was added N-(3-dimethylaminopropyl)-N-ethylcarbodiimide hydrochloride (85.0 mg, 0.45 mmol), 1-hydroxybenzotriazole (68.3 mg, 0.45 mmol), triethylamine (93 μL, 0.67 mmol) and 2-methoxy-5-trifluoromethylbenzoic acid (Alfa) (98.0 mg, 0.45 mmol). The mixture was stirred at 60° C. overnight, cooled to room temperature, diluted with ethyl acetate, washed with 1 M aqueous NaHCO$_3$, dried (MgSO$_4$), filtered and concentrated. The residue was purified by column chromatography using an Analogix® Intelliflash280™ (SiO$_2$, 0-50% ethyl acetate in hexanes) to provide the title product. MS (ESI$^+$) m/z 428 (M+H)$^+$; $^1$H NMR (300 MHz, CDCl$_3$) δ ppm 1.15-1.19 (m, 1H), 1.20 (s, 9H), 1.61-1.72 (m, 1H), 1.83-1.96 (m, 2H), 2.02-2.15 (m, 1H), 3.68 (dd, J=14.3, 7.1 Hz, 1H), 3.75-3.87 (m, 2H), 3.89 (s, 3 H), 4.02-4.12 (m, 1H), 4.14-4.25 (m, 1H), 6.53 (s, 1H), 6.97 (d, J=8.7 Hz, 1H), 7.58 (dd, J=8.7, 2.4 Hz, 1H), 8.06 (d, J=2.0 Hz, 1H).

Example 67

N-[(2Z)-5-tert-butyl-3-[(2R)-tetrahydrofuran-2-ylmethyl]-1,3,4-thiadiazol-2(3 H)-ylidene]-N'-(4-methylcyclohexyl)urea

Example 67A

Tert-butyl 5-tert-butyl-1,3,4-thiadiazol-2-ylcarbamate

To mixture of 5-tert-butyl-1,3,4-thiadiazol-2-amine (Aldrich) (20.0 g, 127 mmol) and $N^1,N^1,N^2,N^2$-tetramethylethane-1,2-diamine (0.19 mL, 1.27 mmol) in dichloromethane was added di-tertbutyl dicarbonate (30.5 g, 140 mmol). The reaction was stirred at room temperature for 12 hours. The mixture was washed with aq. sodium bicarbonate, dried over $Na_2SO_4$ and concentrated under reduced pressure. The residue was purified by column chromatography using an Analogix® Intelliflash280™ ($SiO_2$, 0-15% ethyl acetate in hexanes) to give the title product. MS (ESI$^+$) m/z 258 (M+H)$^+$.

Example 67B tert-butyl [(2Z)-5-tert-butyl-3-[(2R)-tetrahydrofuran-2-ylmethyl]-1,3,4-thiadiazol-2(3H)-ylidene]carbamate To a mixture of Example 67A (1.88 g, 7.31 mmol) and Example 11A (2.25 g, 8.77 mmol) in THF/DMF (4/1) was added potassium tert-butoxide (1.12 g, 9.50 mmol). The reaction was heated at 75° C. for 16 hours. The mixture was cooled to room temperature and diluted with ether, washed with aq. $NaHCO_3$, dried over $MgSO_4$ and concentrated under reduced pressure. The residue was purified by column chromatography using an Analogix® Intelliflash280™ ($SiO_2$, 0-50% ethyl acetate in hexanes) to give the title compound. MS (ESI$^+$) m/z 342 (M+H)$^+$.

Example 67C (R)-5-tert-butyl-3-((tetrahydrofuran-2-yl)methyl)-1,3,4-thiadiazol-2(3H)-imine Example 67B (619 mg, 1.81 mmol) and trifluoroacetic acid (1.12 mL, 14.5 mmol) were stirred at 22° C. for 8 hours. The trifluoroacetic acid was evaporated and the residue was dissolved in dichloromethane and washed with saturated aq. $NaHCO_3$. The organic extract was dried over $Na_2SO_3$ and concentrated to dryness to yield the title compound. MS (ESI$^+$) m/z 242 (M+H)$^+$.

Example 67D

N-[(2Z)-5-tert-butyl-3-[(2R)-tetrahydrofuran-2-ylmethyl]-1,3,4-thiadiazol-2(3 H)-ylidene]-N'-(4-methylcyclohexyl)urea To a solution of Example 67C (33 mg, 0.14 mmol) in tetrahydrofuran (0.3 mL), was added triethylamine (28 mg, 0.27 mmol). After shaking a solution of p-nitrophenyl carbamoyl chloride (28 mg, 0.14 mmol) was added in tetrahydrofuran (0.3 mL). A precipitate was formed and after shaking for 30 minutes a solution of 4-methylcyclohexanamine (21 mg, 0.19 mmol) in tetrahydrofuran (0.6 mL) was added. The mixture was heated to 50° C. overnight. The mixture was cooled to ambient temperature, and filtered through Si-Carbonate cartridge, washed with methanol checked by LC/MS and concentrated to dryness. The residue was dissolved in 1:1 DMSO/Methanol and purified by preparative HPLC on a Phenomenex Luna C8(2) 5 μm 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-6.0 min linear gradient 10-100% A, 6.0-7.0 min 100% A, 7.0-8.0 min linear gradient 100-10% A) to afford the title compound. $^1$H NMR (500 MHz, DMSO/D$_2$O) δ ppm 0.83-0.93 (m, 3H), 0.93-1.01 (m, 1H), 1.15-1.25 (m, 1H), 1.26-1.35 (m, 10H), 1.41-1.99 (m, 10H), 3.59-3.67 (m, 2H), 3.75-3.80 (m, 1H), 3.96-4.08 (m, 1H), 4.19-4.32 (m, 2H); MS (ESI) m/z 381 (M+H)$^+$.

Example 68

N-(1-adamantylmethyl)-N'-[(2Z)-5-tert-butyl-3-[(2R)-tetrahydrofuran-2-ylmethyl]-1,3,4-thiadiazol-2(3H)-ylidene]urea Example 67C (33 mg, 0.14 mmol) and adamantanemethylamine (31 mg, 0.19 mmol) were processed and the product purified according to the methods of Example 67D to afford the title compound. $^1$H NMR (500 MHz, DMSO/D$_2$O) δ ppm 1.24-1.40 (m, 9H), 1.40-2.03 (m, 19H), 2.75-2.85 (m, 2H), 3.59-3.67 (m, 1H), 3.74-3.81 (m, 1H), 3.98-4.07 (m, 1 H), 4.22-4.36 (m, 2H); MS (ESI) m/z 433 (M+H)$^+$.

Example 69

N-[(2Z)-5-tert-butyl-3-[(2R)-tetrahydrofuran-2-ylmethyl]-1,3,4-thiadiazol-2(3 H)-ylidene]-N'-{[(1S,2R,5S)-6,6-dimethylbicyclo[3.1.1]hept-2-yl]methyl}urea Example 67C (33 mg, 0.14 mmol) and ((1S,2R,5S)-6,6-dimethylbicyclo[3.1.1]heptan-2-yl)methanamine (29 mg, 0.19 mmol) were processed and the product purified according to the methods of Example 67D to afford the title compound. $^1$H NMR (500 MHz, DMSO/D$_2$O) δ ppm 1.00-1.35 (m, 15H), 1.38-2.37 (m, 13H), 2.88-3.20 (m, 2H), 3.61-3.67 (m, 1H), 3.76-3.80 (m, 1H), 3.94-4.08 (m, 1H), 4.20-4.34 (m, 2H); MS (ESI) m/z 421 (M+H)$^+$.

Example 70

N-[(2Z)-5-tert-butyl-3-[(2R)-tetrahydrofuran-2-ylmethyl]-1,3,4-thiadiazol-2(3 H)-ylidene]-N'-[1-(hydroxymethyl)-3-methylbutyl]urea Example 67C (33 mg, 0.14 mmol) and (S)-2-amino-4-methylpentan-1-ol (22 mg, 0.19 mmol) were processed and the product purified according to the methods of Example 67D to afford the title compound. $^1$H NMR (500 MHz, DMSO/D$_2$O) δ ppm 0.80-0.93 (m, 6H), 1.26-1.35 (m, 11H), 1.49-1.72 (m, 2H), 1.76-2.01 (m, 3H), 3.21-3.38 (m, 2H), 3.60-3.66 (m, 1H), 3.69-3.75 (m, 1H), 3.78-3.82 (m, 1H), 3.97-4.13 (m, 1H), 4.18-4.34 (m, 2H); MS (ESI) m/z 385 (M+H)$^+$.

Example 71

N-[(2Z)-5-tert-butyl-3-[(2R)-tetrahydrofuran-2-ylmethyl]-1,3,4-thiadiazol-2(3 H)-ylidene]-N'-(1,2-dimethylpropyl)urea Example 67C (33 mg, 0.14 mmol) and 3-methylbutan-2-amine (16 mg, 0.19 mmol) were processed and the product purified according to the methods of Example 67D to afford the title compound. $^1$H NMR (500 MHz, DMSO/D$_2$O) δ ppm 0.79-0.88 (m, 6H), 0.98-1.06 (m, 3H), 1.27-1.36 (m, 9H), 1.60-1.76 (m, 2H), 1.76-2.02 (m, 3H), 3.47-3.55 (m, 1H), 3.59-3.67 (m, 1H), 3.77-3.80 (m, 1H), 3.95-4.05 (m, 1H), 4.19-4.32 (m, 2H); MS (ESI) m/z 355 (M+H)$^+$.

Example 72

N-[(2Z)-5-tert-butyl-3-[(2R)-tetrahydrofuran-2-ylmethyl]-1,3,4-thiadiazol-2(3H)-ylidene]-N'-(1-ethylpropyl)urea Example 67C (33 mg, 0.14 mmol) and pentan-3-amine (16 mg, 0.19 mmol) were processed and the product purified according to the methods of Example 67D to afford the title compound. $^1$H NMR (500 MHz, DMSO/D$_2$O) δ ppm 0.72-0.87 (m, 6H), 1.24-1.33 (m, 9H), 1.33-1.57 (m, 4H), 1.58-1.76 (m, 1H), 1.74-2.05 (m, 3H), 3.36-3.48 (m, 1H), 3.59-3.69 (m, 1H), 3.77-3.82 (m, 1H), 3.93-4.11 (m, 1H), 4.20-4.31 (m, 2H); MS (ESI) m/z 355 (M+H)$^+$.

Example 73

N-[(2Z)-5-tert-butyl-3-[(2R)-tetrahydrofuran-2-ylmethyl]-1,3,4-thiadiazol-2(3H)-ylidene]-N'-1,2,3,4-tetrahydronaphthalen-1-ylurea Example 67C (33 mg, 0.14 mmol) and 1,2,3,4-tetrahydronaphthalen-1-amine (28 mg, 0.19 mmol) were processed and the product purified according to the methods of Example 67D to afford the title compound. $^1$H NMR (500 MHz, DMSO/D$_2$O) δ ppm 1.27-1.40 (m, 9H), 1.58-2.06 (m, 8H), 2.63-2.83 (m, 2H), 3.57-3.69 (m, 1H), 3.74-3.78 (m, 1H), 3.96-4.09 (m, 1H), 4.17-4.39 (m, 2H), 4.81-4.97 (m, 1H), 7.00-7.24 (m, 4H); MS (ESI) m/z 415 (M+H)$^+$.

Example 74

N-[(2Z)-5-tert-butyl-3-[(2R)-tetrahydrofuran-2-ylmethyl]-1,3,4-thiadiazol-2(3H)-ylidene]-N'-[(1S)-1-cyclohexylethyl]urea Example 67C (33 mg, 0.14 mmol) and (S)-1-cyclohexylethanamine (24 mg, 0.19 mmol) were processed and the product purified according to the methods of Example 67D to afford the title compound. $^1$H NMR (500 MHz, DMSO/D$_2$O) δ ppm 0.85-0.97 (m, 2H), 0.99-1.04 (m, 3H), 1.05-1.25 (m, 3H), 1.27-1.34 (m, 9H), 1.55-1.74 (m, 6H), 1.77-2.00 (m, 3H), 3.46-3.55 (m, 1H), 3.60-3.67 (m, 1H), 3.74-3.81 (m, 2H), 3.97-4.06 (m, 1H), 4.18-4.33 (m, 2H); MS (ESI) m/z 395 (M+H)$^+$.

Example 75

N-(tert-butyl)-N'-[(2Z)-5-tert-butyl-3-[(2R)-tetrahydrofuran-2-ylmethyl]-1,3,4-thiadiaol-2(3H)-ylidene]urea Example 67C (33 mg, 0.14 mmol) and 2-methylpropan-2-amine (14 mg, 0.19 mmol) were processed and the product purified according to the methods of Example 67D to afford the title compound. $^1$H NMR (500 MHz, DMSO-d$_6$/D$_2$O) δ ppm 1.25-1.34 (m, 18H), 1.60-1.72 (m, 1H), 1.77-2.03 (m, 3H), 3.59-3.66 (m, 1H), 3.75-3.80 (m, 1H), 3.97-4.05 (m, 1H), 4.21-4.30 (m, 2H); MS (ESI) m/z 341 (M+H)$^+$.

Example 76

N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2,2-dimethylpropyl]urea Example 67C (33 mg, 0.14 mmol) and (S)-2-amino-3,3-dimethylbutan-1-ol (22 mg, 0.19 mmol) were processed and the product purified according to the methods of Example 67D to afford the title compound. $^1$H NMR (500 MHz, DMSO/D$_2$O) δ ppm 0.85-0.93 (m, 9H), 1.28-1.35 (m, 9H), 1.63-1.75 (m, 1H), 1.79-2.05 (m, 3H), 3.34-3.40 (m, 1H), 3.50-3.55 (m, 1H), 3.57-3.69 (m, 2H), 3.77-3.80 (m, 1H), 3.99-4.09 (m, 1H), 4.24-4.33 (m, 2H); MS (ESI) m/z 385 (M+H)$^+$.

Example 77

N-[(2Z)-5-tert-butyl-3-[(2R)-tetrahydrofuran-2-ylmethyl]-1,3,4-thiadiazol-2(3H)-ylidene]-N'-cycloheptylurea Example 67C (33 mg, 0.14 mmol) and cycloheptanamine (21 mg, 0.19 mmol) were processed and the product purified according to the methods of Example 67D to afford the title compound. $^1$H NMR (500 MHz, DMSO/D$_2$O) δ ppm 1.27-1.33 (m, 9H), 1.33-2.02 (m, 16H), 3.58-3.69 (m, 2H), 3.75-3.80 (m, 1H), 3.95-4.06 (m, 1H), 4.20-4.31 (m, 2H); MS (ESI) m/z 381 (M+H)$^+$.

Example 78

N-[(2Z)-5-tert-butyl-3-[(2R)-tetrahydrofuran-2-ylmethyl]-1,3,4-thiadiazol-2(3H)-ylidene]-N'-(2-ethylhexyl)urea Example 67C (33 mg, 0.14 mmol) and 2-ethylhexan-1-amine (25 mg, 0.19 mmol) were processed and the product purified according to the methods of Example 67D to afford the title compound. $^1$H NMR (500 MHz, DMSO/D$_2$O) δ ppm 1.12-1.36 (m, 23H), 1.38-1.48 (m, 1H), 1.59-1.73 (m, 1H), 1.76-2.00 (m, 3H), 2.88-3.04 (m, 3H), 3.58-3.72 (m, 1H), 3.94-4.07 (m, 1H), 4.20-4.34 (m, 2H); MS (ESI) m/z 397 (M+H)$^+$.

Example 79

N-[(2Z)-5-tert-butyl-3-[(2R)-tetrahydrofuran-2-ylmethyl]-1,3,4-thiadiazol-2(3H)-ylidene]-N'-(1-methyl-3-phenylpropyl)urea Example 67C (33 mg, 0.14 mmol) and 4-phenylbutan-2-amine (28 mg, 0.19 mmol) were processed and the product purified according to the methods of Example 67D to afford the title compound. $^1$H NMR (500 MHz, DMSO/D$_2$O) δ ppm 1.07-1.12 (m, 3H), 1.29-1.35 (m, 9H), 1.58-2.14 (m, 6H), 2.56-2.67 (m, 2H), 3.56-3.72 (m, 2H), 3.77-3.82 (m, 1H), 3.94-4.07 (m, 1H), 4.20-4.34 (m, 2H), 7.09-7.33 (m, 5H); MS (ESI) m/z 417 (M+H)$^+$.

Example 80

N-({[(2Z)-5-tert-butyl-3-[(2R)-tetrahydrofuran-2-ylmethyl]-1,3,4-thiadiazol-2(3H)-ylidene]amino}carbonyl)-L-phenylalaninamide Example 67C (33 mg, 0.14 mmol) and (S)-2-amino-3-phenylpropanamide (31 mg, 0.19 mmol) were processed and the product purified according to the methods of Example 67D to afford the title compound. $^1$H NMR (500 MHz, DMSO/D$_2$O) δ ppm 1.26-1.41 (m, 9 H), 1.60-1.73 (m, 1H), 1.79-2.03 (m, 3H), 2.77-2.89 (m, 1H), 2.99-3.06 (m, 1H), 3.59-3.66 (m, 1H), 3.71-3.76 (m, 1H), 3.95-4.04 (m, 1H), 4.21-4.29 (m, 2H), 4.31-4.38 (m, 1H), 7.19-7.30 (m, 5H); MS (ESI) m/z 432 (M+H)$^+$.

Example 81

N$^2$-({[(2Z)-5-tert-butyl-3-[(2R)-tetrahydrofuran-2-ylmethyl]-1,3,4-thiadiazol-2(3H)-ylidene]amino}carbonyl)-L-isoleucinamide Example 67C (33 mg, 0.14 mmol) and (2S,3S)-2-amino-3-methylpentanamide (32 mg, 0.19 mmol) were processed and the product purified according to the methods of Example 67D to afford the title compound. $^1$H NMR (500 MHz, DMSO/D$_2$O) δ ppm 0.77-0.91 (m, 6H), 1.05-1.17 (m, 1H), 1.28-1.34 (m, 9H), 1.40-1.47 (m, 1H), 1.59-2.05 (m, 5H), 3.57-3.70 (m, 1H), 3.76-3.81 (m, 1H), 3.95-4.10 (m, 2H), 4.22-4.37 (m, 2H); MS (ESI) m/z 398 (M+H)$^+$.

Example 82

N$^2$-({[(2Z)-5-tert-butyl-3-[(2R)-tetrahydrofuran-2-ylmethyl]-1,3,4-thiadiazol-2(3H)-ylidene]amino}carbonyl)-N$^1$,3-dimethyl-L-valinamide Example 67C (30 mg, 0.12 mmol) and (S)-2-amino-N,3,3-trimethylbutanamide (24 mg, 0.17 mmol) were processed and the product purified according to the methods of Example 67D to afford the title compound. $^1$H NMR (500 MHz, DMSO/D$_2$O) δ ppm 0.90-0.95 (m, 9H), 1.29-1.33 (m, 9H), 1.61-1.76 (m, 1H), 1.78-2.02 (m, 3H), 2.58-2.61 (m, 3H), 3.59-3.68 (m, 1H), 3.74-3.77 (m, 1H), 4.03-4.05 (m, 1H), 4.05 (m, 1H), 4.24-4.31 (m, 2H); MS (ESI) m/z 412 (M+H)$^+$.

Example 83

N-[(2Z)-5-tert-butyl-3-[(2R)-tetrahydrofuran-2-ylmethyl]-1,3,4-thiadiazol-2(3 H)-ylidene]-N'-neopentylurea Example 67C (30 mg, 0.12 mmol) and 2,2-dimethylpropan-1-amine (15 mg, 0.17 mmol) were processed and the product purified according to the methods of Example 67D to afford the title compound. $^1$H NMR (500 MHz, DMSO/D$_2$O) δ ppm 0.75-0.93 (m, 9H), 1.28-1.33 (m, 9H), 1.61-1.75 (m, 1H), 1.74-2.06 (m, 3H), 2.84-3.00 (m, 2H), 3.59-3.68 (m, 1H), 3.76-3.82 (m, 1H), 3.97-4.09 (m, 1H), 4.22-4.31 (m, 2H); MS (ESI) m/z 355 (M+H)$^+$.

Example 84

N-[(2Z)-5-tert-butyl-3-[(2R)-tetrahydrofuran-2-ylmethyl]-1,3,4-thiadiazol-2(3 H)-ylidene]-N'-[(1S)-1-(hydroxymethyl)-2-methylpropyl]urea Example 67C (33 mg, 0.14 mmol) and (S)-2-amino-3-methylbutan-1-ol (19 mg, 0.19 mmol) were processed and the product purified according to the methods of Example 67D to afford the title compound. $^1$H NMR (500 MHz, DMSO/D$_2$O) δ ppm 0.81-0.90 (m, 6H), 1.28-1.34 (m, 9H), 1.61-1.74 (m, 1H), 1.78-2.00 (m, 4H), 3.40-3.45 (m, 2H), 3.46-3.53 (m, 1H), 3.61-3.66 (m, 1H), 3.77-3.79 (m, 1H), 4.00-4.09 (m, 1H), 4.23-4.33 (m, 2H); MS (ESI) m/z 371 (M+H)$^+$.

Example 85

N-[(3E)-5-tert-butyl-1-methyl-2-(tetrahydrofuran-3-ylmethyl)-1,2-dihydro-3H-pyrazol-3-ylidene]-2-methoxy-5-(trifluoromethyl)benzamide Example 85A 3-tert-butyl-N-trityl-1H-pyrazol-5-amine In a 20 mL vial, to a solution of 3-tert-butyl-1H-pyrazol-5-amine (150 mg, 1.078 mmol) in dichloromethane (2 mL) and triethylamine (0.180 mL, 1.293 mmol) was added (chloromethanetriyl)tribenzene (300 mg, 1.078 mmol). The reaction was stirred at 20° C. for 10 hours before toluene (5 mL) and ethyl acetate (10 mL) were added. The solid was filtered and the filtrate was concentrated to provide the crude title compound (320 mg). $^1$H NMR (300 MHz, DMSO-d$_6$) δ ppm 0.95-1.02 (m, 9H) 4.82 (s, 1H) 5.75 (s, 1H) 7.15-7.37 (m, 15H) 11.13 (s, 1H); MS (DCI/NH$_3$) m/z 382 (M+H)$^+$.

Example 85B (tetrahydrofuran-3-yl)methyl 4-methylbenzenesulfonate

To a solution of (tetrahydrofuran-3-yl)methanol (5.15 g, 50.4 mmol) in dichloromethane (200 mL) were added triethylamine (21.08 mL, 151 mmol) and p-toluenesulfonyl chloride (9.61 g, 50.4 mmol) and the mixture was stirred at room temperature overnight. The reaction mixture was washed with water (100 mL) and brine (100 mL). The organic layer was dried with sodium sulfate, filtered and concentrated. The crude product was purified by column chromatography using an Analogix® Intelliflash280™ (SiO$_2$, 0-40% ethyl acetate in hexane) to provide the title compound (12.5 g, 97%) as colorless viscous liquid. $^1$H NMR (300 MHz, DMSO-d$_6$) δ ppm 1.40-1.51 (m, 1H) 1.83-1.95 (m, 1H) 2.43 (s, 3H) 3.28-3.31 (m, 1H) 3.31-3.37 (m, 1H) 3.51-3.67 (m, 3H) 3.90-4.00 (m, 2H) 7.48-7.51 (m, 2H) 7.78-7.82 (m, 2H); MS (DCI/NH$_3$) m/z 274 (M+NH$_4$)$^+$.

Example 85C (3-tert-butyl-1-((tetrahydrofuran-3-yl)methyl)-N-trityl-1H-pyrazol-5-amine In a 200 mL round-bottomed flask, to a solution of Example 85A (5 g, 13.11 mmol) in N,N-dimethyl formamide (25 mL) was added sodium iodide (0.786 g, 5.24 mmol), Example 85B (4.03 g, 15.73 mmol), followed by addition of sodium hydride (1.310 g, 32.8 mmol) and the mixture was stirred at 60° C. for 6 hours. LC-MS, m/z 466 (M+H)$^+$ indicated an almost complete reaction. Water (150 mL) was added and the mixture was extracted with ethyl acetate (3×40 mL). The organics were combined, dried and concentrated in vacuo. The residue was purified by column chromatography using an Analogix® Intelliflash280™ (SiO$_2$, 10-70% ethyl acetate in hexanes) to afford the title compound (5.9 g, 97%) which was carried on without further spectral characterization.

Example 85D

3-tert-butyl-1-((tetrahydrofuran-3-yl)methyl)-1H-pyrazol-5-amine

In a 200 mL round-bottomed flask, to a solution of Example 85C (6.24 g, 13.4 mmol) in ethyl acetate (20 mL) was added hydrogen chloride (4 N in dioxane, 20 mL) and stirred at 20° C. for 2 hours. The reaction was concentrated and triturated with ethyl acetate. The solid was collected and dried to provide the title compound as the hydrogen chloride salt (2.12 g, 61%). $^1$H NMR (500 MHz, DMSO-$d_6$) δ ppm 1.28 (s, 9H) 1.61-1.69 (m, 1H) 1.81-1.89 (m, 1H) 2.73-2.81 (m, 1H) 3.45 (dd, J=8.85, 5.80 Hz, 1H) 3.61-3.67 (m, 3H) 3.78-3.84 (m, 1H) 4.17-4.26 (m, 2H) 5.53 (s, 1H) 7.07 (s, 2H); MS (DCI/NH$_3$) m/z 224 (M+H)$^+$.

Example 85E

N-(3-tert-butyl-1-((tetrahydrofuran-3-yl)methyl)-1H-pyrazol-5-yl)-2-methoxy-5-(trifluoromethyl)benzamide In a 40 mL vial, Example 85D (757 mg, 2.91 mmol) in tetrahydrofuran (3.2 mL) and sodium hydroxide (256 mg, 6.4 mmol) in water (3.20 mL) were mixed and treated with 2-methoxy-5-(trifluoromethyl)benzoyl chloride (695 mg, 2.91 mmol) and the reaction was stirred at 25° C. for 12 hours. The reaction was concentrated, extracted with ethyl acetate (3×10 mL), the organic layers were combined, dried with sodium sulfate, concentrated and the residue was purified by column chromatography using an Analogix® Intelliflash280™ (SiO$_2$, 0-100% ethyl acetate in hexanes) to afford the title compound (450 mg, 36.3%). $^1$H NMR (300 MHz, DMSO-$d_6$) δ ppm 1.24 (s, 9H) 1.56-1.67 (m, 1H) 1.83-1.95 (m, 1H) 2.61-2.73 (m, 1H) 3.47-3.53 (m, 1H) 3.58-3.66 (m, 2H) 3.70-3.78 (m, 1 H) 3.90-4.04 (m, 5H) 6.21 (s, 1H) 7.40 (d, J=8.73 Hz, 1H) 7.87-7.93 (m, 2H) 10.15 (s, 1 H); MS (DCI/NH$_3$) m/z 440 (M+H)$^+$.

Example 85F

N-[(3E)-5-tert-butyl-1-methyl-2-(tetrahydrofuran-3-ylmethyl)-1,2-dihydro-3H-pyrazol-3-ylidene]-2-methoxy-5-(trifluoromethyl)benzamide In a microwave vial a solution of Example 85E (100 mg, 0.24 mmol) and dimethyl sulfate (104 mg, 0.823 mmol) in toluene (0.8 mL) was heated at 140° C. for 1 hour. The reaction was concentrated, dissolved in dichloromethane, and purified by column chromatography using an Analogix® Intelliflash280™ (SiO$_2$, 0-10% solvent A in dichloromethane; Solvent A: 10% 7M ammonia in MeOH) to collect fractions containing the desired molecule. The fractions were combined and purified further by preparative HPLC on a Waters Symmetry C8 column (25 mm×100 mm, 7 μm particle size) using a gradient of 10% to 100% acetonitrile:10 mM ammonium acetate over 8 min (10 min run time) at a flow rate of 40 mL/min to provide the title compound (25 mg, 25%). $^1$H NMR (300 MHz, DMSO-$d_6$) δ ppm 1.38 (s, 9H) 1.67-1.76 (m, 1H) 1.79-1.88 (m, 1H) 2.63-2.73 (m, 1H) 3.51-3.66 (m, 3H) 3.73-3.79 (m, 1H) 3.80 (s, 3H) 3.86 (s, 3H) 4.16-4.24 (m, 1 H) 4.27-4.35 (m, 1H) 6.82 (s, 1H) 7.15 (d, J=8.82 Hz, 1H) 7.60 (dd, J=8.65, 1.86 Hz, 1H) 7.68-7.69 (m, 1H); MS (DCI/NH$_3$) m/z 440 (M+H)$^+$.

Example 86

N-{(3E)-5-tert-butyl-1-methyl-2-[2R)-tetrahydrofuran-2-ylmethyl]-1,2-dihydro-3H-pyrazol-3-ylidene}-2-methyl-5-(trifluoromethyl)benzamide To a solution of Example 14C (237 mg, 1 mmol) in tetrahydrofuran (1.5 mL) and sodium hydroxide (120 mg, 3.00 mmol) in water (1.5 mL) was added 2-methyl-5-(trifluoromethyl)benzoyl chloride (445 mg, 2.0 mmol) and stirred for 4 hours at ambient temperature. The mixture was extracted with ethyl acetate. The organic layers were combined, dried, concentrated, and the residue was purified by column chromatography using an Analogix® Intelliflash280™ (SiO$_2$, 0-10% solvent A in dichloromethane; Solvent A: 10% 7M ammonia in methyl alcohol) to provide the title compound (205 mg, 0.484 mmol, 48.4% yield). $^1$H NMR (300 MHz, DMSO-$d_6$) δ ppm 1.39 (s, 9H) 1.67-1.83 (m, 3H) 1.86-1.94 (m, 1H) 2.59 (s, 3H) 3.60-3.68 (m, 1H) 3.72-3.80 (m, 1H) 3.89 (s, 3 H) 4.13-4.22 (m, 1H) 4.29-4.44 (m, 2H) 6.86 (s, 1H) 7.37 (d, J=7.80 Hz, 1H) 7.53 (dd, J=7.97, 1.86 Hz, 1H) 8.05 (d, J=2.03 Hz, 1H); MS (DCI/NH$_3$) m/z 424 (M+H)$^+$. Anal. calcd $C_{22}H_{28}F_3N_3O_2$·0.4H$_2$O: C, 61.35; H, 6.74; N, 9.76. Found: 61.65; H, 6.89; N, 9.76.

Example 87

N-{(3E)-4-bromo-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide In a 5 mL vial, a solution of Example 86 (34 mg, 0.080 mmol), N-bromosuccinimide (14.29 mg, 0.080 mmol) and -2,2'-azobisisobutyronitrile (0.659 mg, 4.01 μmol) in carbon tetrachloride (0.3 mL) was heated at 80° C. for 4 hours. The reaction mixture was concentrated and purified by preparative HPLC on a Waters Symmetry C8 column (25 mm×100 mm, 7 μm particle size) using a gradient of 10% to 100% acetonitrile:10 mM ammonium acetate over 8 min (10 min run time) at a flow rate of 40 mL/min to provide the title compound (19 mg, 0.038 mmol, 47.1% yield). $^1$H NMR (300 MHz, DMSO-$d_6$) δ ppm 1.55 (s, 9H) 1.61-1.67 (m, 1H) 1.71-1.87 (m, 3H) 2.58 (s, 3H) 3.58-3.69 (m, 1H) 3.70-3.78 (m, 1H) 3.97 (s, 3H) 4.13 (t, J=6.27 Hz, 1H) 4.34 (d, J=5.43 Hz, 2H) 7.37 (d, J=7.80 Hz, 1H) 7.53 (dd, J=7.97, 1.86 Hz, 1H) 7.93 (d, J=1.70 Hz, 1H); MS (DCI/NH$_3$) m/z 502 (M+H)$^+$.

Example 88

2-bromo-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide The title compound was prepared and isolated as described in Example 86, substituting 2-bromo-5-trifluoromethyl benzoyl chloride for 2-methyl-5-trifluoromethyl benzoyl chloride in 62% yield. $^1$H NMR (300 MHz, DMSO-$d_6$) δ ppm 1.39 (s, 9H) 1.65-1.81 (m, 3H) 1.84-1.92 (m, 1H) 3.59-3.67 (m, 1H) 3.71-3.78 (m, 1H) 3.91 (s, 3H) 4.13-4.21 (m, 1H) 4.27-4.43 (m, 2H) 6.82 (s, 1H) 7.55 (dd, J=8.33, 2.38 Hz, 1H) 7.78-7.84 (m, 2H); MS (DCI/NH$_3$) m/z 488 (M+H)$^+$. Anal. calcd $C_{21}H_{25}BrF_3N_3O_2$: C, 51.65; H, 5.16; N, 8.60. Found: C, 51.37; H, 5.30; N, 8.54

Example 89

N-{(3E)-5-tert-butyl-1-methyl-2-[(2R)-tetrahydrofuran-2-ylmethyl]-1,2-dihydro-3H-pyrazol-3-ylidene}-2-[(1E)-3-methoxyprop-1-enyl]-5-(trifluoromethyl)benzamide To a solution of Example 88 (146 mg, 0.299 mmol) and (E)-2-(3-methoxyprop-1-enyl)-4,4,5,5-tetramethyl-1,3,2-dioxaborolane (148 mg, 0.747 mmol) in dimethoxyethane (1 mL) and methanol (0.5 mL) was added palladium tetrakistriphenyl phosphine (86 mg, 0.075 mmol) and cesium fluoride (159 mg, 1.05 mmol). This mixture was microwaved at 100° C. for 10 minutes. To the reaction was added ethyl acetate and the mixture was filtered through celite and purified by column chromatography using an Analogix® Intelliflash280™ (SiO$_2$, 0-100% solvent A in hexanes, solvent A: 10% MeOH in ethyl acetate) to afford the title compound (74 mg, 52%). $^1$H NMR (300 MHz, CDCl$_3$) δ ppm 1.44 (s, 9H) 1.71-1.85 (m, 3 H) 1.98-2.07 (m, 1H) 3.37 (s, 3H) 3.69-3.82 (m, 2H) 3.88 (s, 3H) 4.11-4.13 (m, 2H) 4.18-4.32 (m, 2H) 4.48-4.58 (m, 1H) 6.22 (dt, J=15.96, 6.30 Hz, 1H) 7.03 (s, 1H) 7.46-7.53 (m, 1H) 7.57-7.65 (m, 2H) 8.20 (s, 1H); MS (DCI/NH$_3$) m/z 480 (M+H)$^+$.

Example 90

N-{(3E)-5-tert-butyl-1-methyl-2-[(2R)-tetrahydrofuran-2-ylmethyl]-1,2-dihydro-3H-pyrazol-3-ylidene}-2-(3-methoxypropyl)-5-(trifluoromethyl)benzamide A mixture of Example 89 (245 mg, 0.51 mmol) and platinum(IV) oxide (40 mg) in ethyl acetate (1 mL) and methanol (0.5 mL) was hydrogenated under a balloon filled with hydrogen at ambient temperature for 5 hours. The reaction mixture was filtered through celite, concentrated and the residue was purified by column chromatography using an Analogix® Intelliflash280™ (SiO$_2$, 0-100% solvent A in hexanes, solvent A: 10% MeOH in ethyl acetate) to afford the title compound (178 mg, 72%). $^1$H NMR (300 MHz, CDCl$_3$) δ ppm 1.44 (s, 9H) 1.70-1.89 (m, 3H) 1.91-2.07 (m, 3H) 3.08-3.22 (m, 2H) 3.32 (s, 3H) 3.40 (t, J=6.61 Hz, 2H) 3.68-3.82 (m, 2H) 3.87 (s, 3H) 4.15-4.31 (m, 2H) 4.54 (dd, J=14.92, 2.71 Hz, 1H) 7.00 (s, 1H) 7.30 (s, 1H) 7.46 (d, J=7.46 Hz, 1H) 8.10 (s, 1H); MS (DCI/NH$_3$) m/z 482 (M+H)$^+$.

Example 91

N-[(2Z)-5-tert-butyl-3-{[(4S)-2-oxo-1,3-oxazolidin-4-yl]methyl}-1,3,4-thiadiazol-2(3H)-ylidene]-5-chloro-2-methoxybenzamide A mixture of Example 4A (195 mg, 0.6 mmol), (S)-(2-oxazolidin-4-yl)methyl 4-methylbenzenesulfonate (190 mg, 0.7 mmol), potassium carbonate (170 mg, 1.23 mmol), tetrabutylammonium iodide (10 mg, 0.03 mmol), tetrabutylammonium hydrogen sulfate (10 mg, 0.03 mmol) and tetraethylammonium iodide (10 mg, 0.04 mmol) in toluene (25 mL) was refluxed for 12 hours. The mixture was washed with water, brine, dried with MgSO$_4$ and concentrated under reduced pressure. The residue was purified by silica gel chromatography eluting with CH$_2$Cl$_2$:EtOAc (4:1) to afford 115 mg of the title compound. $^1$H NMR (300 MHz, CDCl$_3$) δ ppm 1.42 (s, 9H), 3.94 (s, 3H), 4.34-4.42 (m, 3H), 4.53-4.76 (m, 2H), 6.08 (s, 1H), 6.95 (d, J=8.8 Hz, 1H), 7.39 (dd, J=8.8, 2.7 Hz, 1H), 7.86 (d, J=2.7 Hz, 1H). MS (DCI/NH$_3$) m/z 425 (M+H)$^+$.

Example 92

2-(2-amino-2-methylpropoxy)-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide Potassium tert-butoxide (1.2 mL, 1M in THF) was added to 2-amino-2-methylpropan-1-ol (0.11 g, 1.2 mmol) in 0.5 mL of THF and stirred for 10 minutes. Example 16B (0.25 g, 0.59 mmol) in 1.0 mL of THF was added and the mixture stirred for 1 hour. EtOAc (15 mL) was added and the organic phase washed with saturated NaHCO$_3$, water, brine, dried with MgSO$_4$ and the solvent removed. The residue was chromatographed to afford the title compound. (solvent A-hexane: EtOAc:triethylamine 1:3:0.2; solvent B-hexane:EtOAc:MeOH:triethylamine 1:3:1:0.2; 100% solvent A to 100% solvent B in a gradient over 600 mL then isocratic for 180 mL). (0.2 g, 0.4 mmol, 69% yield). $^1$H NMR (500 MHz, PYRIDINE-d$_5$) δ ppm 1.15 (s, 9H), 1.32 (s, 6H), 1.54-1.61 (m, 2H), 1.63-1.70 (m, 1H), 1.76-1.82 (m, 1H), 3.53-3.61 (m, 1H), 3.69-3.75 (m, 1H), 3.79 (s, 3H), 3.94 (s, 2 H), 4.23 (qd, J=6.7, 3.4 Hz, 1H), 4.37 (dd, J=15.1, 6.6 Hz, 1H), 4.61 (dd, J=15.3, 3.1 Hz, 1 H), 7.12 (d, J=8.5 Hz, 1H), 7.45 (s, 1H), 7.66 (dd, J=8.5, 2.4 Hz, 1H), 8.55 (d, J=2.4 Hz, 1 H). MS (ESI) m/z 497.2 (M+H)$^+$.

Example 93

N-{(3E)-5-tert-butyl-1-methyl-2-[(2R)-tetrahydrofuran-2-ylmethyl]-1,2-dihydro-3H-pyrazol-3-ylidene}-2-[(3-methylbut-2-enyl)oxy]-5-(trifluoromethyl)benzamide Potassium tert-butoxide (1.2 mL, 1M in THF) was added to 3-methylbut-2-en-1-ol (0.11 g, 1.2 mmol) in 0.5 mL of THF and stirred for 10 minutes. Example 16B (0.25 g, 0.59 mmol) in 1.0 mL of THF was added and the mixture stirred for 1 hour. EtOAc (15 mL) was added and the organic phase washed with saturated NaHCO$_3$, water, brine, dried with MgSO$_4$ and the solvent removed. The residue was chromatographed to afford the title compound. (solvent A-hexane: EtOAc:triethylamine 1:3:0.2; solvent B-hexane:EtOAc:MeOH:triethylamine 1:3:1:0.2; solvent A to solvent B over 600 mL then isocratic for 180 mL). (0.16 g, 0.32 mmol, 55% yield). $^1$H NMR (300 MHz, DMSO-d$_6$) δ ppm 1.38 (s, 9H), 1.69-1.74 (m, 8H), 1.74-1.81 (m, 1H), 1.82-1.89 (m, 1H), 3.58-3.66 (m, 1H), 3.69-3.78 (m, 1H), 3.87 (s, 3H), 4.11-4.20 (m, 1H), 4.31 (dd, J=5.1, 2.0 Hz, 2H), 4.61 (d, J=6.4 Hz, 2H), 5.34-5.40 (m, 1H), 6.80 (s, 1H), 7.13 (d, J=8.5 Hz, 1H), 7.56 (dd, J=8.8, 2.0 Hz, 1H), 7.67 (d, J=2.4 Hz, 1H). MS (ESI) m/z 494.2 (M+H)$^+$. Analytical calculated for C$_{26}$H$_{34}$F$_3$N$_3$O$_3$: C, 63.27; H, 6.94; N, 8.51. Found: C, 63.22; H, 7.10; N, 8.47.

Example 94

N-{(3E)-5-tert-butyl-1-methyl-2-[(2R)-tetrahydrofuran-2-ylmethyl]-1,2-dihydro-3H-pyrazol-3-ylidene}-2-[2-(1-hydroxycyclopentyl)ethoxy]-5-(trifluoromethyl)benzamide

Example 94A 1-(2-hydroxyethyl)cyclopentanol 1,4-dibromobutane (10 g, 46.3 mmol) in THF (100 mL) was treated with magnesium (2.81 g, 116 mmol) and I$_2$ (100 mg) as initiator. The mixture was stirred at room temperature for 3 hours. To the mixture was added dropwise oxetan-2-one (3.34 g, 46.3 mmol) in THF (25 mL). The reaction was stirred at room temperature for 12 hours, quenched with saturated NH$_4$Cl, and the mixture was extracted with isopropanol/ CH$_2$Cl$_2$ (1:3) (2×100 mL). The organic layers were combined and dried over MgSO$_4$, filtered and concentrated. The residue was purified by distillation at 95-100° C. (0.6 torr) to provide the title compound (1.1 g, 18%) MS (DCI/NH$_3$) m/z 148 (M+NH$_4$)$^+$.

Example 94B

N-{(3E)-5-tert-butyl-1-methyl-2-[(2R)-tetrahydrofuran-2-ylmethyl]-1,2-dihydro-3H-pyrazol-3-ylidene}-2-[2-(1-hydroxycyclopentyl)ethoxy]-5-(trifluoromethyl)benzamide The title compound was prepared using the procedure as described in Example 35 substituting Example 94A for 2,2-difluoroethanol. $^1$H NMR (400 MHz, CDCl$_3$) δ ppm 1.42 (s, 9H) 1.50-1.61 (m, 5H) 1.64-1.75 (m, 1H) 1.76-1.90 (m, 6H) 2.13 (t, J=5.83 Hz, 2H) 3.67-3.81 (m, 2H) 3.91 (s, 3H) 4.12-4.21 (m, 1H) 4.32 (t, J=5.83 Hz, 2H) 4.37 (d, J=6.14 Hz, 1H) 4.65 (dd, J=15.65, 3.07 Hz, 1H) 6.97 (s, 1H) 7.01 (d, J=8.59 Hz, 1H), 7.56 (dd, J=8.59, 2.76 Hz, 1H) 8.19 (d, J=2.46 Hz, 1H); MS (DCI/NH$_3$) m/z 538 (M+H)$^+$.

Example 95

2-(azetidin-3-yloxy)-N-[(2Z)-5-tert-butyl-3-[(2R)-tetrahydrofuran-2-ylmethyl]-1,3-oxazol-2(3H)-ylidene]-5-(trifluoromethyl)benazmide

Example 95A

N-[(2Z)-5-tert-butyl-3-[(2R)-tetrahydrofuran-2-ylmethyl]-1,3-oxazol-2(3 H)-ylidene]-2-fluoro-5-(trifluoromethyl)benzamide The title compound was prepared using the procedure as described in Example 13C substituting 2-fluoro-5-(trifluoromethyl)benzoic acid for 2-methoxy-5-(trifluoromethyl)benzoic acid. MS (DCI/NH$_3$) m/z 415 (M+H)$^+$.

Example 95B tert-butyl 3-[2-{[(2Z)-5-tert-butyl-3-[(2R)-tetrahydrofuran-2-ylmethyl]-1,3-oxazol-2(3H)-ylidene]carbamoyl}-4-(trifluoromethyl)phenoxy]azetidine-1-carboxylate To a solution of tert-butyl 3-hydroxyazetidine-1-carboxylate (167 mg, 0.965 mmol) in THF (2 mL) was added sodium tert-butoxide (93 mg, 0.965 mmol). The reaction was stirred at room temperature for 20 min. The reaction was cooled to 0° C. and a solution of Example 95A (200 mg, 0.483 mmol) in THF (1 mL) was added. The reaction was stirred at 0-5° C. for 2 hours. The reaction mixture was diluted with H$_2$O and extracted with EtOAc (2×). The organic layer was combined and dried over MgSO$_4$, filtered and concentrated to afford the title compound 260 mg (93%). MS (DCI/NH$_3$) m/z 568 (M+H)$^+$.

Example 95C 2-(azetidin-3-yloxy)-N-[(2Z)-5-tert-butyl-3-[(2R)-tetrahydrofuran-2-ylmethyl]-1,3-oxazol-2(3H)-ylidene]-5-(trifluoromethyl)benzamide The product from Example 95B (260 mg, 0.458 mmol) in CH$_2$Cl$_2$ (6 mL) was treated with trifluoroacetic acid (1.5 mL). The mixture was stirred at room temperature for 30 minutes. The solvent was evaporated and the residue was dissolved in saturated NaHCO$_3$. The aqueous layer was extracted with EtOAc. The organic layer was dried with MgSO$_4$ and concentrated. The residue was purified by column chromatography (SiO$_2$, CH$_2$Cl$_2$ to 9:1:0.1 CH$_2$Cl$_2$:MeOH:Et$_3$N) to give the title compound (54 mg, 13%). $^1$H NMR (400 MHz, CDCl$_3$) δ ppm 1.22 (s, 9H) 1.59-1.70 (m, 1H) 1.85-1.96 (m, 3H) 2.06-2.14 (m, 1 H) 3.70 (dd, J=14.12, 7.36 Hz, 1H) 3.76-3.84 (m, 1H) 3.93-4.03 (m, 2H) 4.06 (dd, J=14.12, 2.76 Hz, 1H) 4.11-4.22 (m, 3H) 5.05-5.17 (m, 1H) 6.57 (s, 1H) 6.71 (d, J=8.29 Hz, 1H) 7.55 (d, J=8.29 Hz, 1H) 8.06 (s, 1H) MS (DCI/NH$_3$) m/z 468 (M+H)$^+$.

Example 96

N-{(3E)-5-tert-butyl-1-methyl-2-[(2R)-tetrahydrofuran-2-ylmethyl]-1,2-dihydro-3H-pyrazol-3-ylidene}-3-fluoro-5-(trifluoromethyl)benzamide The title compound was prepared according to the procedure described in Example 45C and Example 45D, substituting 3-fluoro-5-trifluorobenzoyl chloride for 2-methoxy-5-chlorobenzoyl chloride. $^1$H NMR (300 MHz, DMSO-d$_6$) δ ppm 1.44 (s, 9H), 1.65-2.20 (m, 4H), 3.69-3.82 (m, 2H), 3.91 (s, 3H), 4.24 (dd, J=5.43, 3.05 Hz, 1H), 4.33-4.45 (m, 1 H), 4.54-4.64 (m, 1H), 7.08 (s, 1H), 7.32 (d, J=8.48 Hz, 1H), 8.11 (d, J=10.17 Hz, 1H), 8.35 (s, 1H); MS (DCI) m/z 428 [M+H].

Example 97

N-[(2Z)-5-tert-butyl-3-[(2R)-tetrahydrofuran-2-ylmethyl]-1,3,4-thiadiazol-2(3 H)-ylidene]-2-{[(3S)-1-methylpyrrolidin-3-yl]oxy}-5-(trifluoromethyl)benazmide

Example 97A (S)-2-(1-methylpyrrolidin-3-yloxy)-5-(trifluoromethyl)benzonitrile To a solution of 2-fluoro-5-(trifluoromethyl)benzonitrile (8.0 g, 42.3 mmol, Aldrich) in tetrahydrofuran (50 mL) were added sodium hydride (1.9 g, 46.5 mmol, 60% in mineral oil) and (S)-1-methylpyrrolidin-3-ol (4.7 mL, 46.5 mmol, Aldrich). After stirring at room temperature for 3 hours, the reaction mixture was quenched with saturated NaHCO$_3$ (30 mL). The aqueous layer was extracted with ethyl acetate (3×30 mL). The combined organic extracts were dried over anhydrous Na$_2$SO$_4$, filtered and concentrated under reduced pressure to afford 10.9 g of the title compound. MS (ESI$^+$) m/z 271 (M+H)$^+$.

Example 97B (S)-2-(1-methylpyrrolidin-3-yloxy)-5-(trifluoromethyl)benzoic acid To a solution of Example 97A (10.9 g, 40.5 mmol) in ethanol (50 mL) and water (15 mL) at 40° C. was added sodium hydroxide (7.5 mL, 142 mmol, 50% aqueous solution), followed by hydrogen peroxide (7.0 mL, 122 mmol, 50% aqueous solution), which was added in 4 portions, each portion one hour apart. The reaction was stirred at 40° C. for 4 more hours. The reaction was monitored by LC/MS. After almost all the nitrile was converted to the amide, sodium hydroxide (6.4 mL, 122 mmol, 50% aqueous solution) was added followed by 10 mL of water. Then the reaction mixture was stirred at 80° C., cooled, concentrated and dissolved in 100 mL of water. The resultant solution was washed with diethyl ether (2×25 mL). The aqueous solution was neutralized to pH 7 with 6N HCl. and then concentrated to dryness. The precipitate was suspended in ethanol/dichloromethane (100 mL, 1:1), heated to 60° C. and filtered. This process was repeated 3 times. The combined filtrates were concentrated and azeotroped with toluene to obtain 8.5 g (80%) of the title compound. MS (ESI+) m/z 290 (M+H)+.

Example 97C

N-[(2Z)-5-tert-butyl-3-[(2R)-tetrahydrofuran-2-ylmethyl]-1,3,4-thiadiazol-2(3 H)-ylidene]-2-{[(3S)-1-methylpyrrolidin-3-yl]oxy}-5-(trifluoromethyl)benzamide Example 67C, Example 97B, 1-hydroxybenzotriazole, N-(3-dimethylaminopropyl)-N-ethylcarbodimide hydrochloride and triethylamine were processed as described for Example 63D to obtain the title compound. $^1$H NMR (300 MHz, DMSO-d$_6$) δ ppm 1.39 (s, 9H), 1.68-1.91 (m, 4H), 1.91-2.06 (m, 1H), 2.25 (s, 3H), 2.28-2.43 (m, 2H), 2.57-2.71 (m, 2H), 2.75-2.87 (m, 1H), 3.57-3.70 (m, 1H), 3.71-3.83 (m, 1H), 4.24 (dd, J=13.2, 4.7 Hz, 1 H), 4.30-4.42 (m, 1H), 4.44-4.59 (m, 1H), 4.90-5.14 (m, 1H), 7.22 (d, J=8.5 Hz, 1), 7.77 (dd, J=8.8, 2.7 Hz, 1H), 8.07 (d, J=2.7 Hz, 1H); MS (ESI+) m/z 513 (M+H)+.

Example 98

N-[(2Z)-5-tert-butyl-3-[(2R)-tetrahydrofuran-2-ylmethyl]-1,3-oxazol-2(3 H)-ylidene]-2-{[(3S)-1-methylpyrrolidin-3-yl]oxy}-5-(trifluoromethyl)benzamide Example 66A, Example 97B, 1-hydroxybenzotriazole, N-(3-dimethylaminopropyl)-N-ethylcarbodimide hydrochloride and triethylamine were processed as described for Example 63D to obtain the title compound. $^1$H NMR (400 MHz, DMSO-d$_6$) δ ppm 1.04-1.09 (m, 9H), 1.55-1.66 (m, 1H), 1.65-1.75 (m, 1H), 1.77-1.88 (m, 2H), 1.89-2.03 (m, 1H), 2.27 (s, 3H), 2.28-2.34 (m, 1H), 2.35-2.45 (m, 1H), 2.52-2.59 (m, 1H), 2.59-2.70 (m, 1H), 2.80 (dd, J=10.3, 6.0 Hz, 1H), 3.62-3.71 (m, 1H), 3.72-3.84 (m, 3H), 4.14-4.23 (m, 1H), 4.89-4.97 (m, 1H), 7.01 (s, 1H), 7.12 (d, J=8.6 Hz, 1H), 7.65 (dd, J=8.9, 2.5 Hz, 1H), 7.72 (d, J=2.5 Hz, 1H); MS (ESI+) m/z 496 (M+H)+.

Example 99

N-{(3E)-5-tert-butyl-1-methyl-2-[(2R)-tetrahydrofuran-2-ylmethyl]-1,2-dihydro-3H-pyrazol-3-ylidene}-2-[(1E)-prop-1-enyl]-5-(trifluoromethyl)benazmide The title compound was prepared and isolated as described in Example 89, substituting trans-1-propen-1-ylboronic acid for (E)-2-(3-methoxyprop-1-enyl)-4,4,5,5-tetramethyl-1,3,2-dioxaborolane in 62% yield. $^1$H NMR (300 MHz, CDCl$_3$) δ ppm 1.44 (s, 9 H) 1.65-1.88 (m, 3H) 1.88-1.92 (m, 3H) 1.98-2.11 (m, 1H) 3.69-3.82 (m, 2H) 3.88 (s, 3H) 4.18-4.33 (m, 2H) 4.48-4.58 (m, 1H) 6.14-6.26 (m, 1H) 7.05 (s, 1 H) 7.92-7.33 (m, 1H) 7.44-7.50 (m, 1H) 7.55-7.58 (m, 1H) 8.12 (s, 1H); MS (DCI/NH$_3$) m/z 450 (M+H)+.

Example 100

N-{(3E)-5-tert-butyl-1-methyl-2-[(2R)-tetrahydrofuran-2-ylmethyl]-1,2-dihydro-3H-pyrazol-3-ylidene}-2-[(1E)-3-hydroxy-3-methylbut-1-enyl]-5-(trifluoromethyl)benzamide Example 100A (E)-trimethyl(2-methyl-4-(4,4,5,5-tetramethyl-1,3,2-dioxaborolan-2-yl)but-3-en-2-yloxy)silane To a solution of trimethyl(2-methylbut-3-yn-2-yloxy)silane (1.5 g, 9.60 mmol) in tetrahydrofuran (15 mL) was added 4,4,5,5-tetramethyl-1,3,2-dioxaborolane (2.79 mL, 19.19 mmol), followed by addition of 9-BBN (9-borabicyclo[3.3.1] nonane) dimer (0.117 g, 0.480 mmol). This mixture was heated at 60° C. for 24 hours. The reaction was cooled and quenched carefully with saturated ammonium chloride solution. The reaction mixture was extracted with ethyl acetate (2×15 mL). The organics were combined, dried, concentrated and the residue was purified by column chromatography using an Analogix® Intelliflash280™ (SiO$_2$, 0-60% ethyl acetate in hexanes) to afford the title compound (600 mg, 22% yield). $^1$H NMR (300 MHz, DMSO-d$_6$) δ ppm 0.06-0.08 (m, 9H) 1.19 (s, 12H) 1.25 (s, 6H) 5.41 (d, J=17.85 Hz, 1H) 6.53 (d, J=17.85 Hz, 1H); MS (DCI/NH$_3$) m/z 285 (M+H)+.

Example 100B

N-{(3E)-5-tert-butyl-1-methyl-2-[2R)-tetrahydrofuran-2-ylmethyl]-1,2-dihydro-3H-pyrazol-3-ylidene}-2-[(1E)-3-hydroxy-3-methylbut-1-enyl]-5-(trifluoromethyl)benzamide The title compound was prepared and isolated as described in Example 89, substituting Example 100A for (E)-2-(3-methoxyprop-1-enyl)-4,4,5,5-tetramethyl-1,3,2-dioxaborolane in 79% yield. $^1$H NMR (300 MHz, CDCl$_3$) δ ppm 1.42 (s, 6H) 1.43 (s, 9H) 1.73-1.88 (m, 3H) 1.98-2.10 (m, 1H) 3.68-3.80 (m, 2H) 3.87 (s, 3H) 4.17-4.28 (m, 2 H) 4.49-4.56 (m, 1H) 6.29 (d, J=16.28 Hz, 1H) 6.99 (s, 1H) 7.47-7.60 (m, 3H) 8.17 (d, J=2.03 Hz, 1H); MS (DCI/NH$_3$) m/z 494 (M+H)+.

Example 101

N-{(3E)-5-tert-butyl-1-methyl-2-[(2R)-tetrahydrofuran-2-ylmethyl]-1,2-dihydro-3H-pyrazol-3-ylidene}-2-(3-hydroxy-3-methylbutyl)-5-(trifluoromethyl)benazmide The title compound was prepared and isolated as described in Example 90, substituting Example 100B for Example 89 in 68% yield. $^1$H NMR (300 MHz, CDCl$_3$) δ ppm 1.22 (s, 6H) 1.42 (s, 9H) 1.70-1.83 (m, 2H) 1.83-1.95 (m, 3H) 2.00-3.18 (m, 2H) 3.69-3.82 (m, 2H) 3.89 (s, 3H) 4.18-4.24 (ddd, J=9.52, 6.54, 2.97 Hz, 1 H) 4.25-4.35 (m, 1H) 4.56 (dd, J=15.07, 2.78 Hz, 1H) 7.02 (s, 1H) 7.29 (d, J=8.33 Hz, 1 H) 7.47 (dd, J=7.93, 1.59 Hz, 1H) 8.19 (d, J=1.59 Hz, 1H); MS (DCI/NH$_3$) m/z 496 (M+H)+.

Example 102

2-[(1-hydroxycyclobutyl)methoxy]-N-{(3E)-1-methyl-5-(1-methylcyclopropyl)-2-[(2 R)-tetrahydrofuran-2-ylmethyl]-1,2-dihydro-3H-pyrazol-3-ylidene}-5-(trifluoromethyl)benzamide

Example 102A (R)-2-fluoro-N-(3-(1-methylcyclopropyl)-1-((tetrahydrofuran-2-yl)methyl)-1H-pyrazol-5-yl)-5-(trifluoromethyl)benzamide The title compound was prepared using the procedure as described in Example 32B, substituting Example 33B for Example 32A and substituting 2-fluoro-5-(trifluoromethyl)benzoyl chloride for 2-methoxy-5-(trifluoromethyl)benzoyl chloride. MS (DCI/NH$_3$) m/z 412 (M+H)$^+$.

Example 102B

2-[(1-hydroxycyclobutyl)methoxy]-N-{(3E)-1-methyl-5-(1-methylcyclopropyl)-2-[(2 R)-tetrahydrofuran-2-ylmethyl]-1,2-dihydro-3H-pyrazol-3-ylidene}-5-(trifluoromethyl)benzamide The title compound was prepared using the procedure as described in Example 35, substituting Example 44A for 2,2-difluoroethanol.and substituting Example 102A for Example 16B. $^1$H NMR (400 MHz, CDCl$_3$) δ ppm 0.80-0.85 (m, 2H) 0.91-0.98 (m, 2 H) 1.36 (s, 3H) 1.68-1.92 (m, 5H) 1.99-2.22 (m, 6H) 3.68-3.80 (m, 2H) 3.85 (s, 3H) 4.22 (s, 2H) 4.23 (s, 2H) 4.52 (dd, J=14.73, 2.45 Hz, 1H) 6.95 (s, 1H) 7.08 (d, J=8.29 Hz, 1H) 7.52 (dd, J=8.59, 1.84 Hz, 1H) 8.12 (d, J=2.15 Hz, 1H); MS (DCI/NH$_3$) m/z 508 (M+H)$^+$.

Example 103

N-{(3E)-5-tert-butyl-1-methyl-2-[(2R)-tetrahydrofuran-2-ylmethyl]-1,2-dihydro-3H-pyrazol-3-ylidene}-3-hydroxy-5-(trifluoromethyl)benzamide To a mixture of Example 14C (0.7 g, 2.56 mmol in THF (10 mL) and water (5 mL) was added sodium hydroxide (0.409 g, 10.23 mmol) followed by a solution of 3-hydroxy-5-(trifluoromethyl)benzoyl chloride (0.689 g, 3.07 mmol; prepared from commercially available 3-hydroxy-5-(trifluoromethyl)benzoic acid) in THF (5 mL) dropwise at 0° C. The mixture was stirred at room temperature for 1 hour then diluted with water (20 mL) and ethyl acetate (30 mL). The organic extract was washed with brine, dried over MgSO$_4$, filtered, and concentrated. Purification by chromatography (SiO$_2$, 10-50% gradient of 1:10:90 Et$_3$N/MeOH/EtOAc in hexane) afforded 0.67 g (62%) of the title compound. $^1$H NMR (300 MHz, DMSO-d$_6$) δ ppm 1.38 (s, 9H), 1.67-2.02 (m, 4H), 3.58-3.69 (m, 1H), 3.71-3.82 (m, 1H), 3.90 (s, 3H), 4.16-4.27 (m, 1H), 4.35-4.51 (m, 2H), 6.86 (s, 1H), 7.03 (s, 1H), 7.77 (s, 1H), 7.85 (s, 1H), 10.01 (s, 1H); MS (ESI) m/z 426 [M+H]$^+$, 424[M−H]$^-$.

Example 104

3-bromo-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide The title compound was prepared as described in Example 103, substituting 3-bromo-5-(trifluoromethyl)benzoyl chloride for 3-hydroxy-5-(trifluoromethyl)benzoyl chloride in 64% yield. $^1$H NMR (300 MHz, DMSO-d$_6$) δ ppm 1.39 (s, 9H), 1.72-2.01 (m, 4H), 3.60-3.70 (m, 1H), 3.72-3.82 (m, 1H), 3.93 (s, 3H), 4.18-4.29 (m, 1H), 4.42-4.53 (m, 2H), 6.88 (s, 1H), 7.99 (s, 1H), 8.36 (s, 1H), 8.47 (s, 1H); MS (ESI) m/z 490 [M+H]$^+$, 488[M−H]$^-$.

Example 105

N-{(3E)-5-tert-butyl-1-methyl-2-[(2R)-tetrahydrofuran-2-ylmethyl]-1,2-dihydro-3H-pyrazol-3-ylidene}-3-(2-fluoroethoxy)-5-(trifluoromethyl)benazmide To the mixture of Example 103 (90 mg, 0.21 mmol), 2-fluoroethanol (27 mg, 0.42 mmol) and triphenylphosphine (110 mg, 0.42 mmol) in THF (3 mL) was added di-tert-butyl azodicarboxylate (97 mg, 0.42 mmol) at room temperature. The mixture was stirred at room temperature for 1 hour, then water (10 mL) and ethyl acetate (10 mL) were added. The organic extract was washed with brine and concentrated. Purification by flash chromatography (10-40% gradient of Et$_3$N/MeOH/EtOAc (1:10:90) in hexane) afforded 92 mg (92%) of the title compound. $^1$H NMR (300 MHz, DMSO-d$_6$) δ ppm 1.38 (s, 9H), 1.72-2.01 (m, 4H), 3.58-3.70 (m, 1H), 3.71-3.81 (m, 1H), 3.91 (s, 3H), 4.19-4.27 (m, 1H), 4.28-4.35 (m, 1H), 4.38-4.50 (m, 3H), 4.67-4.73 (m, 1H), 4.82-4.90 (m, 1H), 6.88 (s, 1H), 7.29 (s, 1H), 7.91 (s, 1H), 8.02 (s, 1H); MS (ESI) m/z 472 [M+H]$^+$, 470 [M−H]$^-$.

Example 106

N-{(3E)-5-tert-butyl-1-methyl-2-[(2R)-tetrahydrofuran-2-ylmethyl]-1,2-dihydro-3H-pyrazol-3-ylidene}-3-nitro-5-(trifluoromethyl)benzamide A solution of 3-nitro-5-(trifluoromethyl)benzoic acid (2.00 g, 8.51 mmol) in thionyl chloride (12.4 ml, 170 mmol) was heated at 90° C. for 2 hours. The solution was cooled to room temperature, concentrated, and azeotroped with toluene to provide 3-nitro-5-(trifluoromethyl)benzoyl chloride as a liquid.

The title compound was prepared and isolated as described in Example 86, substituting 3-nitro-5-(trifluoromethyl)benzoyl chloride for 2-methyl-5-trifluoromethyl benzoic chloride in 84% yield. $^1$H NMR (300 MHz, DMSO-d$_6$) δ ppm 1.40 (s, 9H), 1.77-1.87 (m, 3H) 1.89-2.01 (m, 1H) 3.62-3.71 (m, 1H) 3.72-3.84 (m, 1H) 3.95 (s, 3H) 4.19-4.31 (m, 1H) 4.42-4.56 (m, 2H) 6.91 (s, 1H) 8.50-8.52 (m, 1H) 8.72-8.76 (m, 1H) 9.06-9.08 (m, 1H); MS (DCI/NH$_3$) m/z 455 (M+H)$^+$. Anal. calcd C$_{21}$H$_{25}$F$_3$N$_4$O$_4$: C, 55.5; H, 5.54; N, 12.33. Found: C, 55.08; H, 5.46; N, 12.00.

Example 107

3-amino-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide A mixture of Example 106 (740 mg, 1.63 mmol) and palladium hydroxide (50 mg) in ethyl alcohol (10 mL) was stirred under an atmosphere of hydrogen (balloon) at room temperature for 4 hours. The reaction mixture was filtered and the filtrate was concentrated. The residue was purified on Analogix® Intelliflash280™ (SiO$_2$, 15-100% gradient of solvent A in hexanes, solvent A=10:1:0.5 ethyl acetate:methanol:triethylamine) to provide the title compound (540 mg, 78%). $^1$H NMR (300 MHz, DMSO-d$_6$) δ ppm 1.38 (s, 9H)

1.73-1.83 (m, 3H) 1.89-1.97 (m, 1H) 3.60-3.68 (m, 1H) 3.73-3.81 (m, 1H) 3.89 (s, 3H) 4.18-4.25 (m, 1H) 4.35-4.48 (m, 2H) 5.50 (s, 2H) 6.83-6.86 (m, 2H) 7.56 (d, J=1.70 Hz, 2H); MS (DCI/NH$_3$) m/z 425 (M+H)$^+$. Anal. calcd $C_{21}H_{27}F_3N_4O_2 \cdot 0.5H_2O$: C, 58.19; H, 6.51; N, 12.33. Found: C, 57.88; H, 6.56; N, 12.63.

Example 108

N-[(2Z)-5-tert-butyl-3-[(2R)-tetrahydrofuran-2-ylmethyl]-1,3-oxazol-2(3H)-ylidene]-2-[2-(dimethylamino)ethoxy]-5-(trifluoromethyl)benzamide The title compound was prepared as described in Example 95B, substituting 2-(dimethylamino)ethanol for tert-butyl 3-hydroxyazetidine-1-carboxylate. $^1$H NMR (500 MHz, CDCl$_3$) δ ppm 1.19 (s, 9H) 1.58-1.67 (m, 1H) 1.85-1.96 (m, 2H) 2.04-2.13 (m, 1H) 2.30 (s, 6H) 2.75 (t, J=6.10 Hz, 2H) 3.65 (dd, J=14.04, 7.32 Hz, 1H) 3.80 (dd, J=13.73, 6.71 Hz, 1H) 3.87 (dd, J=15.26, 7.02 Hz, 1H) 4.07 (dd, J=14.34, 2.75 Hz, 1H) 4.12-4.21 (m, 3H) 6.53 (s, 1H) 6.97 (d, J=8.54 Hz, 1H) 7.56 (dd, J=8.85, 2.44 Hz, 1H) 7.97 (d, J=2.44 Hz, 1H); MS (DCI/NH$_3$) m/z 484 (M+H)$^+$.

Example 109

2-[(Z)-(tert-butoxyimino)methyl]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide

Example 109A

2-formyl-5-(trifluoromethyl)benzoic acid

To a solution of n-butyl lithium (56.0 ml, 140 mmol) in tetrahydrofuran (100 mL) at −78° C. was added a solution of 2-bromo-5-(trifluoromethyl)benzoic acid (17.9 g, 66.7 mmol) in tetrahydrofuran (100 mL) over 0.5 hour, at which time the solution turned dark red. After stirring for 1 hour, N,N-dimethylformamide (50 mL, 646 mmol) was added dropwise and the reaction mixture was allowed to warm to room temperature over 6 hours. The mixture was cooled to 0° C. and then a solution of 2 N sodium hydroxide (120 mL) was added. The mixture was extracted with ether (2×50 mL). The aqueous layer was separated and concentrated hydrochloric acid was added to it until the pH was acidic. The mixture was extracted with ethyl acetate (3×80 mL). The organic extracts were combined, dried with sodium sulfate, filtered, and concentrated. The residue was purified on Analogix® Intelliflash280™ (SiO$_2$, 7-100% solvent A in hexanes, solvent A=3:1:0.1 hexane:ethyl aceate:acetic acid) over 1 hour to obtain the title compound (4.5 g, 20.6 mmol, 31% yield). $^1$H NMR (300 MHz, DMSO-d$_6$) δ ppm 6.78 (br, 1H) 7.93 (d, J=8.48 Hz, 1H) 8.13-8.20 (m, 2H) 8.38 (br, 1H); MS (DCI/NH$_3$) m/z 236 (M+NH$_4$)$^+$.

Example 109B

N-{(3E)-5-tert-butyl-1-methyl-2-[(2R)-tetrahydrofuran-2-ylmethyl]-1,2-dihydro-3H-pyrazol-3-ylidene}-2-formyl-5-(trifluoromethyl)benzamide A solution of Example 109A (0.6 g) and thionyl chloride (3.27 g, 27.5 mmol) was warmed to reflux for 2 hours. The reaction solution was concentrated and then the residue was azeotroped with toluene to provide 2-formyl-5-(trifluoromethyl)benzoyl chloride, which was used without further purification.

The title compound was prepared and isolated as described in Example 86, substituting 2-formyl-5-(trifluoromethyl)benzoyl chloride for 2-methyl-5-trifluoromethyl benzoic chloride. MS (APCI) m/z 438 (M+H)$^+$.

Example 109C

2-[(Z)-(tert-butoxyimino)methyl]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide In a 4 mL vial, Example 109C (65 mg, 0.15 mmol) was dissolved in ethyl alcohol (2 mL). O-tert-Butylhydroxylamine hydrochloride (37 mg, 0.30 mmol) was added followed by H$_2$O (0.1 mL). The mixture was stirred at room temperature for 2 hours then concentrated. The residue was diluted with ethyl acetate, filtered, and concentrated. Purification by preparative HPLC on a Waters Symmetry C8 column (25 mm×100 mm, 7 μm particle size) using a gradient of 10% to 100% acetonitrile:10 mM ammonium acetate over 8 min (10 min run time) at a flow rate of 40 mL/min provided the title compound (19 mg, 0.038 mmol, 25% yield). $^1$H NMR (300 MHz, CDCl$_3$) δ ppm 1.35 (s, 9H) 1.44 (s, 9H) 1.67-1.87 (m, 3H) 2.05-2.17 (m, 1H) 3.68-3.80 (m, 2H) 3.90 (s, 3H) 4.15-4.23 (m, 1H) 4.29-4.37 (m, 1H) 4.48-4.57 (m, 1H) 7.06 (s, 1H) 7.53 (dd, J=8.31, 1.86 Hz, 1H) 7.98 (d, J=8.14 Hz, 1H) 8.29 (s, 1H) 9.05 (s, 1H); MS (DCI/NH$_3$) m/z 509 (M+H)$^+$.

Example 110

N-{(3E)-5-tert-butyl-1-methyl-2-[(2R)-tetrahydrofuran-2-ylmethyl]-1,2-dihydro-3H-pyrazol-3-ylidene}-2-(methoxymethyl)-5-(trifluoromethyl)benzamide

Example 110A

6-(trifluoromethyl)isobenzofuran-1(3H)-one

Methyl 2-(hydroxymethyl)-5-(trifluoromethyl)benzoate (5.00 g, 21.4 mmol) in MeOH (50 mL) was added to Pd-dppf (Heraeus) (0.312 g, 0.427 mmol) and triethylamine (5.95 ml, 42.7 mmol) in a 250 mL stainless steel pressure bottle. The mixture was pressurized with carbon monoxide (60 psi), and stirred at 95° C. for 6 hours. The mixture was filtered through Celite, and the filtrate concentrated. The residue was purified by column chromatography using an Analogix® Intelliflash280™ (SiO$_2$, 0-100% ethyl acetate in hexanes) to afford the title compound (2.5 g, 63%). MS (DCI/NH$_3$) m/z 203 (M+H)$^+$.

Example 110B

2-(methoxymethyl)-5-(trifluoromethyl)benzoic acid

Example 110A (1.00 g, 4.95 mmol) in water (10 mL) was treated with 10% NaOH (36 mL) and dimethyl sulfate (4.29 ml, 45.2 mmol). The reaction mixture was heated at 100° C. for 16 hours. After cooling to ambient temperature, the mixture was extracted with Et$_2$O (50 mL), then acidified with 2 N aqueous HCl. The white precipitate was collected, washed with water and dried to afford the title compound. MS (DCI/NH$_3$) m/z 235 (M+H)$^+$.

Example 110C

N-{(3E)-5-tert-butyl-1-methyl-2-[(2R)-tetrahydrofuran-2-ylmethyl]-1,2-dihydro-3H-pyrazol-3-ylidene}-2-(methoxymethyl)-5-(trifluoromethyl)benazmide A mixture of Example 14C (200 mg, 0.73 mmol), Example 110B (205 mg, 0.88 mmol), triethylamine (612 µL, 4.38 mmol) and propylphosphonic anhydride (512 µL, 0.88 mmol) in THF (15 mL) was stirred at room temperature for 12 hours. The reaction mixture was quenched with saturated aqueous NaHCO$_3$ and extracted with EtOAc (2×). The organic extracts were dried over MgSO$_4$, filtered, and concentrated. The residue was purified by column chromatography using an Analogix® Intelliflash280™ (SiO$_2$, 50% hexanes/EtOAc to 100% EtOAc to 9:1:0.1 EtOAc:MeOH:Et$_3$N) to afford 228 mg (69%) of the title compound. $^1$H NMR (500 MHz, CDCl$_3$) δ ppm 1.44 (s, 9H) 1.70-1.83 (m, 2H) 1.84-1.94 (m, 1H) 2.02-2.12 (m, 1H) 3.47 (s, 3H) 3.74 (dd, J=13.73, 6.10 Hz, 1H) 3.80 (dd, J=14.65, 7.02 Hz, 1H) 3.89 (s, 3H) 4.22 (ddd, J=17.09, 7.02, 2.75 Hz, 1H) 4.29 (dd, J=15.26, 6.10 Hz, 1H) 4.58 (dd, J=14.95, 2.44 Hz, 1H) 5.10 (s, 2H) 7.01 (s, 1H) 7.60 (d, J=7.93 Hz, 1H) 7.74 (d, J=8.24 Hz, 1H) 8.35 (s, 1H); MS (DCI/NH$_3$) m/z 454 (M+H)$^+$.

Example 111 tert-butyl [2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl]acetate A solution of (2-tert-butoxy-2-oxoethyl)zinc(II) bromide (2.13 mL, 1.07 mmol) in ether (3 mL) was added to a mixture of Example 88 (260 mg, 0.532 mmol), palladium acetate (12.0 mg, 0.053 mmol), and dicyclohexyl(2',6'-dimethoxybiphenyl-2-yl)phosphine (82 mg, 0.20 mmol). The mixture was stirred at 50° C. overnight then quenched with saturated aqueous ammonium chloride and extracted with ethyl acetate (3×10 mL). The organic extracts were combined, washed with water, dried (MgSO$_4$), filtered, and concentrated. The residue was purified by column chromatography using an Analogix® Intelliflash280™ (SiO$_2$, 15-100% solvent A in hexanes, solvent A=10:1:0.5 ethyl acetate:methanol:triethylamine) to afford the title compound (0.19 g, 0.363 mmol, 68.2% yield). $^1$H NMR (300 MHz, CDCl$_3$) δ ppm 1.41 (s, 9H) 1.42 (s, 9H) 1.72-1.88 (m, 3H) 2.00-2.10 (m, 1H) 3.62 (q, J=7.27 Hz, 1H) 3.68-3.82 (m, 2H) 3.87 (s, 3H) 4.19 (d, J=7.93 Hz, 2H) 4.23-4.32 (m, 1 H) 4.53-4.61 (m, 1H) 7.01 (s, 1H) 7.30 (d, J=8.33 Hz, 1H) 7.51 (dd, J=8.13, 1.39 Hz, 1H) 8.38 (s, 1H); MS (DCI/NH$_3$) m/z 524 (M+H)$^+$.

Example 112

2-amino-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide Trifluoroacetic acid (1.8 ml, 23 mmol) was added to a solution of Example 120 (0.60 g, 1.1 mmol) in 5 mL of dichloromethane. After stirring at room temperature for 3 hours the volatiles were removed under reduced pressure. The residue was diluted with dichloromethane and then concentrated under reduced pressure twice. Purification of the residue by chromatography (solvent A=hexane:EtOAc:triethylamine (1:3:0.2); solvent B=hexane:EtOAc:MeOH:triethylamine (1:3:1:0.2); a gradient from 100% solvent A to 50% solvent B over 600 mL) afforded the title compound (0.32 g, 0.75 mmol, 66% yield). $^1$H NMR (500 MHz, pyridine-d$_5$) δ ppm 1.19 (s, 9H), 1.59-1.68 (m, 2H), 1.69-1.78 (m, 1H), 1.90-1.97 (m, 1H), 3.56-3.62 (m, 1H), 3.73-3.79 (m, 1H), 3.81 (s, 3H), 4.30 (qd, J=6.9, 3.1 Hz, 1H), 4.35-4.41 (m, 1H), 4.61 (dd, J=15.3, 3.1 Hz, 1H), 7.05 (d, J=8.5 Hz, 1H), 7.44 (s, 1H), 7.53 (dd, J=8.5, 2.4 Hz, 1H), 8.32 (s, 2H), 9.28 (d, J=2.1 Hz, 1H); MS (DCI/NH$_3$) m/z 425.3 (M+H)$^+$.

Example 113

N-{(3E)-5-tert-butyl-1-methyl-2-[(2R)-tetrahydrofuran-2-ylmethyl]-1,2-dihydro-3H-pyrazol-3-ylidene}-2-[(methylsulfonyl)amino]-5-(trifluoromethyl)benzamide Methanesulfonyl chloride (0.025 mL, 0.28 mmol) was added to Example 112 (0.10 g, 0.24 mmol) in 3.0 mL of THF followed by triethylamine (0.10 mL, 0.71 mmol). The mixture was stirred at ambient temperature for 3 hours then diluted with EtOAc, washed with saturated NaHCO$_3$, water, brine, dried with MgSO$_4$, filtered, and the solvent removed under reduced pressure. Purification by chromatography (SiO$_2$; solvent A=hexane:EtOAc:triethylamine (1:3:0.2); solvent B=hexane:EtOAc:MeOH:triethylamine (1:3:1:0.2); a gradient from 100% solvent A to 100% solvent B over 500 mL) afforded the title compound. (0.05 g, 0.10 mmol, 42% yield). $^1$H NMR (500 MHz, pyridine-d$_5$) δ ppm 1.23 (s, 9H), 1.62-1.69 (m, 2H), 1.76-1.84 (m, 1H), 2.17 (dq, J=13.0, 6.6 Hz, 1H), 3.30 (s, 3H), 3.56-3.61 (m, 1H), 3.71-3.76 (m, 1H), 3.99 (s, 3H), 4.34-4.40 (m, 1H), 4.65 (dd, J=16.2, 7.6 Hz, 1 H), 4.91 (dd, J=16.0, 2.6 Hz, 1H), 7.39 (s, 1H), 7.75 (dd, J=8.5, 2.1 Hz, 1H), 8.14 (d, J=8.8 Hz, 1H), 9.15 (d, J=2.1 Hz, 1H), 16.36 (s, 1H); MS (DCI/NH$_3$) m/z 503.3 (M+H)$^1$. Anal. calculated for C$_{22}$H$_{29}$F$_3$N$_4$O$_4$S: C, 52.58; H, 5.82; N, 11.15. Found: C, 52.74; H, 5.83; N, 11.09.

Example 114

N-{(3E)-5-tert-butyl-1-methyl-2-[(2R)-tetrahydrofuran-2-ylmethyl]-1,2-dihydro-3H-pyrazol-3-ylidene}-5-cyano-2-fluorobenzamide Oxalyl chloride (5.1 mL of a 2 M solution in CH$_2$Cl$_2$) was added to 5-cyano-2-fluorobenzoic acid (0.56 g, 3.4 mmol) suspended in 2 mL of CH$_2$Cl$_2$. To this was added a catalytic amount of dimethylformamide (10 µL) and the mixture was stirred at room temperature for 1 hour then concentrated under reduced pressure. The residue was diluted with toluene and then the volatiles were removed under reduced pressure (2×). The residue was suspended in 5 mL of THF and then Example 14C (0.80 g, 3.4 mmol) was added followed by triethylamine (2.8 mL, 20 mmol). The mixture was stirred at ambient temperature for 3 hours, diluted with EtOAc, and washed with saturated NaHCO$_3$, water, and brine, dried with MgSO$_4$, filtered, and concentrated. Purification by chromatography (SiO$_2$, hexane:EtOAc:triethylamine (1:3:0.2)) afforded the title compound (0.6 g, 1.6 mmol, 46% yield). $^1$H NMR (300 MHz, DMSO-d$_6$) δ ppm 1.38 (s, 9H), 1.67-1.83 (m, 3H), 1.84-1.99 (m, 1H), 3.59-3.67 (m, 1H), 3.70-3.79 (m, 1H), 3.91 (s, 3H), 4.13-4.25 (m, 1H), 4.32-4.47 (m, 2H), 6.82 (s, 1H), 7.38 (dd, J=10.3, 8.7 Hz, 1H), 7.87 (ddd, J=8.4, 4.5, 2.2 Hz, 1 H), 8.20 (dd, J=6.7, 2.4 Hz, 1H) MS (DCI/NH$_3$) m/z 385.3 (M+H)$^+$.

Example 115 methyl 3-[({3E)-5-tert-butyl-1-methyl-2-[2R)-tetrahydrofuran-2-ylmethyl]-1,2-dihydro-3H-pyrazol-3-ylidene}amino)carbonyl]benzoate A mixture of Example 14C (1.2 g, 4.4 mmol), triethylamine (5.00 mL, 35.8 mmol), 1-propanephosphonic acid cyclic anhydride (50% solution in ethyl acetate, 3.91 mL, 6.57 mmol) and 3-(methoxycarbonyl)benzoic acid (1.18 g, 6.57 mmol) in tetrahydrofuran (10 mL) was stirred at room temperature overnight. To the reaction mixture was added ethyl acetate (20 mL) and the mixture was washed with saturated aqueous sodium bicarbonate. The organic extract was dried ($MgSO_4$), filtered, and concentrated. The residue was purified by column chromatography using an Analogix® Intelliflash280™ ($SiO_2$, 15-100% solvent A in hexanes, solvent A=10:1:0.5 ethyl acetate:methanol:triethyl amine) to afford the title compound (920 mg, 2.30 mmol, 53% yield). $^1$H NMR (300 MHz, $CDCl_3$) δ ppm 1.43 (s, 9 H) 1.76-1.91 (m, 3H) 2.08-2.11 (m, 1H) 3.70-3.84 (m, 2H) 3.88 (s, 3H) 3.92 (s, 3H) 4.25-4.29 (m, 1H) 4.37-4.47 (m, 1H) 4.56-4.65 (m, 1H) 7.10 (s, 1H) 7.45 (t, J=7.73 Hz, 1H) 8.06 (d, J=7.53 Hz, 1H) 8.45 (d, J=7.54 Hz, 1H) 8.95 (s, 1H); MS (DCI/$NH_3$) m/z 400 (M+H)$^+$. Anal. calcd $C_{22}H_{29}N_3O_4 \cdot 0.2C_2H_5OH \cdot 0.5H_2O$: C, 64.41; H, 7.53; N, 10.06. Found: C, 64.75; H, 7.32; N, 9.72.

Example 116

N-{(3E)-5-tert-butyl-1-methyl-2-[2R)-tetrahydrofuran-2-ylmethyl]-1,2-dihydro-3H-pyrazol-3-ylidene}-5-chloro-2-fluorobenzamide Triethylamine (1.2 mL, 8.8 mmol) was added to a mixture of 5-chloro-2-fluorobenzoyl chloride (0.57 g, 2.95 mmol) and Example 14C (0.7 g, 2.95 mmol) in 6 mL of THF. The mixture was stirred at room temperature for 3 hours, diluted with EtOAc, washed with saturated $NaHCO_3$, water, brine, dried with $MgSO_4$, filtered, and concentrated. Purification by chromatography ($SiO_2$, solvent A=hexane:EtOAc:triethylamine (1:3:0.2); solvent B=hexane:EtOAc:MeOH:triethylamine (1:3:1:0.2); a gradient from 100% solvent A to 20% Solvent B over 300 mL then isocratic for 180 mL) afforded the title compound (0.6 g, 1.5 mmol, 52% yield). $^1$H NMR (300 MHz, DMSO-$d_6$) δ ppm 1.38 (s, 9H), 1.67-1.82 (m, 3H), 1.84-1.96 (m, 1H), 3.59-3.67 (m, 1H), 3.71-3.79 (m, 1H), 3.91 (s, 3H), 4.14-4.23 (m, 1H), 4.32-4.46 (m, 2H), 6.82 (s, 1H), 7.14-7.23 (m, 1H), 7.42 (ddd, J=8.5, 3.6, 3.4 Hz, 1H), 7.78 (dd, J=6.3, 3.2 Hz, 1H). MS (DCI/$NH_3$) m/z 394.2 (M+H)$^+$.

Example 117 methyl 4-[({(3E)-5-tert-butyl-1-methyl-2-[(2R)-tetrahydrofuran-2-ylmethyl]-1,2-dihydro-3H-pyrazol-3-ylidene}amino)carbonyl]bicyclo[2.2.1]heptane-1-carboxylate

Example 117A

Dimethyl bicyclo[2.2.1]heptane-1,4-dicarboxylate

The title compound was prepared in three steps from commercially available norbornene (Aldrich) as described in US 2007/0155738.

Example 117B bicyclo[2.2.1]heptane-1,4-dicarboxylic acid

A mixture of Example 117A (3.18 g, 15.0 mmol), solid potassium hydroxide (8.4 g, 150 mmol), and a mixture of ethanol (75 mL) and water (15 mL) was heated at about 60° C. overnight. After cooling, the pH of the mixture was adjusted to about 1 by addition of 1N aqueous hydrochloric acid. The mixture was extracted with ethyl acetate (4×50 mL). The combined organic extracts were dried over sodium sulfate, filtered, and concentrated by rotary evaporator to give a tan powder. The crude product was recrystallized from ethyl acetate/hexanes to give the title compound as a white solid that was used without further purification for the next step.

Example 117C methyl 4-[({(3E)-tert-butyl-1-methyl-2-[(2R)-tetrahydrofuran-2-ylmethyl]-1,2-dihydro-3H-pyrazol-3-ylidene}amino)carbonyl]bicyclo[2.2.1]heptane-1-carboxylate Example 117B (800 mg, 4.34 mmol) and hexanes (50 mL) was stirred at room temperature and solid phosphorus pentachloride (Aldrich, 1.81 g, 8.69 mmol) was added in portions. A condenser with $N_2$ inlet was attached and the mixture was stirred at room temperature overnight. The slurry changed to a yellow solution. The solvents/volatiles were removed by rotary evaporator to give bicyclo[2.2.1]heptane-1,4-dicarbonyl dichloride as a yellow oil.

A slurry of the hydrochloride salt of Example 14C (274 mg, 1.00 mmol), anhydrous tetrahydrofuran (10 mL), and triethylamine (0.836 mL, 6.00 mmol) was treated with a solution of bicyclo[2.2.1]heptane-1,4-dicarbonyl dichloride (332 mg, 1.50 mmol) in a few drops of dry tetrahydrofuran. The resulting brown mixture was stirred at room temperature for 4 hours. Methanol (10 mL) was added, and the mixture was stirred at room temperature for an additional 1 hour. Water (15 mL) was added, and the mixture was extracted with dichoromethane (3×10 mL). The combined organic extracts were dried over sodium sulfate, filtered, and concentrated by rotary evaporator to give a brown oil. Flash chromatography (silica gel, 20-50% ethyl acetate (with 10% methanol added) in hexanes) afforded a viscous oil. The oil solidified upon standing at room temperature to give 103 mg (25%) of the title compound $^1$H NMR (300 MHz, DMSO-$d_6$) δ ppm 1.33 (s, 9H), 1.47-1.98 (m, 14H), 3.58-3.64 (m, 4H), 3.68-3.75 (m, 1H), 3.80 (s, 3H), 4.10-4.17 (m, 1H), 4.26-4.28 (m, 2H), 6.67 (s, 1H). LC-MS (ESI$^+$) m/z 418 (M+H)$^+$.

Example 118 methyl 3-({[3E)-5-tert-butyl-1-methyl-2-((2R)-tetrahydrofuran-2-ylmethyl)-1,2-dihydro-3H-pyrazol-3-ylidene]amino}carbonyl)adamantane-1-carboxylate The title compound was prepared as described in Example 117C substituting adamantane-1,3-dicarboxylic acid (Aldrich) for Example 117B. $^1$H NMR (DMSO-$d_6$) δ 1.33 (s, 9H), 1.59-1.87 (m, 16H), 2.04 (br s, 2H), 3.58 (s, 3H), 3.59-3.65 (m, 1 H), 3.69-3.76 (m, 1H), 3.80 (s, 3H), 4.11-4.18 (m, 1H), 4.27-4.29 (m, 2H), 6.65 (s, 1H). MS (ESI+) m/z 458 (M+H)$^+$.

Example 119

N-{(3E)-5-tert-butyl-1-methyl-2-[(2R)-tetrahydrofuran-2-ylmethyl]-1,2-dihydro-3H-pyrazol-3-ylidene}-2-{[3-(hydroxyimino)cyclobutyl]methoxy}-5-(trifluoromethyl)benzamide A mixture of Example 17 (0.25 g, 0.49 mmol) and hydroxylamine hydrochloride (41 mg, 0.59 mmol) were combined in pyridine (5 mL) and the mixture was stirred at ambient temperature for 16 hours. The mixture was quenched with saturated aqueous $NaHCO_3$ (5 mL), diluted with EtOAc (5 mL), and the layers were separated. The aqueous layer was extracted with EtOAc (3×5 mL) and the combined organic extracts were dried over anhydrous $Na_2SO_4$, filtered, and concentrated under reduced pressure. Purification by column chromatography ($SiO_2$, 50% hexanes/EtOAc then 100% EtOAc, then 9:1:0.1 EtOAc:MeOH:$Et_3N$) afforded the title compound (0.21 g, 0.40 mmol, 82% yield). $^1$H NMR (500 MHz, $CDCl_3$) δ ppm 1.43 (s, 9H) 1.69-1.80 (m, 2H) 1.81-1.90 (m, 1H) 1.97-2.06 (m, 1H) 2.79-2.91 (m, 3H) 2.97-3.12 (m, 2H) 3.68-3.80 (m, 2H) 3.86 (s, 3H), 4.14 (d, J=6.1 Hz, 2H) 4.15-4.20 (m, 1H) 4.29 (dq, J=15.2, 3.1, 2.8 Hz, 1H) 4.49 (dd, J=15.1, 1.9 Hz, 1H) 6.96 (d, J=8.5 Hz, 1H) 6.99 (s, 1H) 7.48 (dd, J=8.6, 2.0 Hz, 1H) 7.93 (s, 1H); MS (DCI/$NH_3$) m/z 523 (M+H)$^+$; Anal. calculated for $C_{26}H_{33}F_3N_4O_4$: Calc: C. 59.76; H, 6.37; N, 10.72. Found: C, 59.73; H, 6.41; N, 10.56.

Example 120 tert-butyl 2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenylcarbamate Example 14C (0.45 g, 1.9 mmol), 2-(tert-butoxycarbonylamino)-5-(trifluoromethyl)benzoic acid (0.87 g, 2.8 mmol), 2-(7-aza-1H-benzotriazole-1-yl)-1,1,3,3-tetramethyluronium hexafluorophosphate (HATU) (1.4 g, 3.8 mmol) and diisopropylethylamine (1.3 mL, 7.6 mmol) were mixed in 4 mL of THF and stirred for 18 hours at room temperature. The mixture was diluted with EtOAc, washed with saturated $NaHCO_3$, water, brine, dried with $MgSO_4$, filtered, and concentrated. Purification by chromatography (Solvent A=hexane:EtOAc:triethylamine (2:2:0.2), Solvent B=hexane:EtOAc:MeOH:triethylamine (2:2:1:0.2). a gradient from 100% solvent A to 30% solvent B over 500 mL) afforded the title compound (0.6 g, 1.1 mmol, 60% yield). $^1$H NMR (500 MHz, pyridine-$d_5$) δ ppm 1.19 (s, 9H), 1.57 (s, 9H), 1.63-1.69 (m, 2H), 1.73-1.80 (m, 1 H), 1.92-2.00 (m, 1H), 3.59-3.65 (m, 1H), 3.73-3.78 (m, 1H), 3.92 (s, 3H), 4.31-4.37 (m, 1H), 4.53 (dd, J=15.6, 6.4 Hz, 1H), 4.75 (dd, J=15.4, 3.2 Hz, 1H), 7.41 (s, 1 H), 7.78 (dd, J=8.7, 2.3 Hz, 1H), 8.99 (d, J=8.8 Hz, 1H), 9.29 (d, J=2.1 Hz, 1H), 13.96 (s, 1H). MS (DCI/$NH_3$) m/z 525.4 (M+H)$^+$. Analytical calculated for $C_{26}H_{35}F_3N_4O_4$: C, 59.53; H, 6.73; N, 10.68. Found: C, 59.58; H, 6.82; N, 10.66.

Example 121

N-{(3E)-5-tert-butyl-1-methyl-2-[(2R)-tetrahydrofuran-2-ylmethyl]-1,2-dihydro-3H-pyrazol-3-ylidene}-2-{[(dimethylamino)sulfonyl]amino}-5-(trifluoromethyl)benzamide Sodium hydride (60% in mineral oil, 11 mg, 0.28 mmol) was added to a 0° C. solution of Example 112 (0.10 g, 0.24 mmol) in 0.5 mL of THF and stirred for 15 minutes. Dimethylsulfamoyl chloride (38 μL, 0.35 mmol) was added and the mixture stirred for 20 hours at ambient temperature. The mixture was concentrated and the residue was purified by chromatography (solvent A=dichloromethane, solvent B=10% MeOH in dichloromethane; a gradient of 100% solvent A to 50% solvent B over 600 mL) to afford the title compound (0.09 g, 0.17 mmol, 72% yield). $^1$H NMR (500 MHz, pyridine-$d_5$) δ ppm 1.22 (s, 9H), 1.62-1.68 (m, 2H), 1.75-1.83 (m, 1H), 2.17 (dq, J=12.9, 6.6 Hz, 1H), 2.89 (s, 6H), 3.56-3.62 (m, 1H), 3.71-3.77 (m, 1H), 3.98 (s, 3H), 4.38 (qd, J=7.2, 2.6 Hz, 1H), 4.64 (dd, J=15.9, 7.3 Hz, 1H), 4.89 (dd, J=15.9, 2.7 Hz, 1H), 7.43 (s, 1H), 7.77 (dd, J=8.7, 2.3 Hz, 1H), 8.15 (d, J=8.5 Hz, 1H), 9.18 (d, J=2.1 Hz, 1H), 16.09 (s, 1H). MS (DCI/$NH_3$) m/z 523.3 (M+H)$^+$. Analytical calculated for $C_{23}H_{32}F_3N_5O_4S$: C, 51.97; H, 6.07; N, 13.17. Found: C, 52.33; H, 6.12; N, 12.91.

Example 122

N-{(3E)-5-tert-butyl-1-methyl-2-[(2R)-tetrahydrofuran-2-ylmethyl]-1,2-dihydro-3H-pyrazol-3-ylidene}-5-(trifluoromethyl)-2-vinylbenzamide To the mixture of Example 88, tetrakis(triphenylphosphine)palladium (0.231 g, 0.200 mmol), dibutyl vinylboronate (0.863 ml, 4.00 mmol) and cesium fluoride (1.82 g, 12.0 mmol) in MeOH (1 mL) and DME (2 mL) was added tetrakis(triphenylphosphine)palladium (0.231 g, 0.200 mmol). The mixture was heated in a sealed tube at 130° C. for 20 min. After cooling to ambient temperature, the solvent was removed under reduced pressure and the residue was diluted with EtOAc and water. The organic layer was washed with saturated aqueous $NaHCO_3$ and brine and then concentrated. Purification by column chromatography (silica gel, 5-30% gradient of 9:1 MeOH/$Et_3N$ in EtOAC) provided the title compound 1.5 g (86% yield). $^1$H NMR (300 MHz, DMSO-$d_6$) δ ppm 1.39 (s, 9H) 1.62-1.95 (m, 4H) 3.59-3.68 (m, 1H) 3.70-3.81 (m, J=7.14, 7.14 Hz, 1H) 3.90 (s, 3H) 4.11-4.22 (m, J=6.15, 4.16 Hz, 1H) 4.26-4.46 (m, 2H) 5.31 (d, J=12.29 Hz, 1H) 5.76 (d, J=17.85 Hz, 1H) 6.85 (s, 1H) 7.54-7.68 (m, 2H) 7.76 (d, J=8.33 Hz, 1H) 8.04 (d, J=1.59 Hz, 1H); MS (ESI) m/z 436 (M+H)$^+$, 434 (M–H)$^-$.

Example 123

N-{(3E)-5-tert-butyl-1-methyl-2-[(2R)-tetrahydrofuran-2-ylmethyl]-1,2-dihydro-3H-pyrazol-3-ylidene}-2-morpholin-4-yl-5-(trifluoromethyl)benazmide To a 20-mL vial were added Example 16B (325 mg, 0.600 mmol), solid potassium carbonate (Aldrich, 105 mg, 1.20 mmol), and anhydrous pyridine (6 mL). Morpholine (Aldrich, 166 mg, 1.20 mmol) was added. The reaction mixture was heated at 60° C. overnight. After cooling, water (10 mL) was added and the mixture was extracted with dichloromethane (3×10 mL). The combined organic extracts were dried over sodium sulfate, filtered, and concentrated by rotary evaporator. Flash chromatography (silica gel, 5-25% methanol in dichloromethane) afforded 210 mg (71%) of the title compound. $^1$H NMR (300 MHz, DMSO-$d_6$) δ 1.38 (s, 9H), 1.66-1.91 (m, 4H), 3.09-3.12 (m, 4H), 3.59-3.65 (m, 5H), 3.71-3.78 (s, 1H), 3.87 (s, 3H), 4.15-4.22 (m, 1H), 4.32-4.34 (m, 2H), 6.75 (s, 1H). 7.00 (d, J=8.3 Hz, 1H), 7.47 (dd, J=8.3, 2.0 Hz, 1H), 7.62 (d, J=2.0 Hz, 1H). MS (ESI+) m/z 495 (M+H)$^+$.

Example 124

2-[bis(2-ethoxyethyl)amino]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide Commercially available bis(2-ethoxytheyl)amine (TCI) and Example 16B were processed as described in Example 123 to afford the title compound. $^1$H NMR (300 MHz, DMSO-d$_6$) δ 1.03 (t, J=7.0 Hz, 6H), 1.36 (s, 9H), 1.63-1.91 (m, 3H), 2.72-2.76 (m, 2H), 3.32-3.48 (m, 11H), 3.59-3.66 (m, 1H), 3.70-3.77 (m, 1H), 3.88 (s, 3H), 4.10-4.18 (m, 1H), 4.27-4.40 (m, 2H), 6.79 (s, 1H), 7.01 (d, J=8.5 Hz, 1H), 7.38 (d, J=8.5 Hz 1H), 7.48 (s, 1H). MS (ESI+) m/z 569 (M+H)$^+$.

Example 125

N-{(3E)-5-tert-butyl-1-methyl-2-[(2R)-tetrahydrofuran-2-ylmethyl]-1,2-dihydro-3H-pyrazol-3-ylidene}-2-[(isobutylsulfonyl)amino]-5-(trifluoromethyl)benzamide Sodium hydride (20 mg, 0.47 mmol) was added to a 0° C. solution of Example 112 (0.1 g, 0.24 mmol) in THF (0.5 mL) and the mixture was stirred for 10 minutes. Then 2-methylpropane-1-sulfonyl chloride (0.30 mL, 2.4 mmol) was added. The mixture was stirred for 30 minutes at 0° C., then the ice bath was removed and stirring was continued for 18 hours at ambient temperature. The mixture was concentrated and the residue purified by chromatography (SiO$_2$, solvent A=CH$_2$Cl$_2$, solvent B=10% MeOH in CH$_2$Cl$_2$, gradient from 0-50% solvent A:solvent B) to afford the title compound. (25 mg, 0.05 mmol, 20% yield). $^1$H NMR (500 MHz, pyridine-d$_5$) δ ppm 1.09 (d, J=6.7 Hz, 6H), 1.21 (s, 9H), 1.63-1.69 (m, 2H), 1.76-1.84 (m, 1H), 2.15-2.22 (m, 1H), 2.48-2.56 (m, 1H), 3.34 (dd, J=6.6, 1.1 Hz, 2H), 3.57-3.62 (m, 1H), 3.72-3.77 (m, 1H), 3.97 (s, 3H), 4.39 (qd, J=7.1, 2.4 Hz, 1H), 4.65 (dd, J=15.9, 7.3 Hz, 1H), 4.90 (dd, J=16.0, 2.6 Hz, 1H), 7.42 (s, 1H), 7.76 (dd, J=8.5, 2.1 Hz, 1H), 8.17 (d, J=8.5 Hz, 1H), 9.21 (d, J=2.1 Hz, 1H), 16.13 (s, 1H). MS (DCI/NH$_3$) m/z 545.4 (M+H)$^+$. Anal. calculated for C$_{25}$H$_{35}$F$_3$N$_4$O$_4$S: C, 55.13; H, 6.48; N, 10.29. Found: C, 55.39; H, 6.64; N, 9.92.

Example 126

3-acetyl-N-{(3E)-5-tert-butyl-1-methyl-2-[(2R)-tetrahydrofuran-2-ylmethyl]-1,2-dihydro-3H-pyrazol-3-ylidene}benzamide The title compound was prepared as described in Example 115, substituting 3-acetylbenzoic acid for 3-(methoxycarbonyl)benzoic acid. $^1$H NMR (300 MHz, CDCl$_3$) δ ppm 1.44 (s, 9H) 1.77-1.90 (m, 3H) 2.03-2.14 (m, 1H) 2.67 (s, 3H) 3.73-3.84 (m, 2H) 3.92 (s, 3H) 4.24-4.28 (m, 1H) 4.40-4.50 (m, 1H) 4.64-4.68 (m, 1H) 7.10 (s, 1H) 7.49 (t, J=7.73 Hz, 1H) 8.03 (d, J=7.93 Hz, 1H) 8.47 (d, J=7.93 Hz, 1H) 8.85 (s, 1 H); MS (DCI/NH$_3$) m/z 384 (M+H)$^+$. Anal. calcd C$_{22}$H$_{29}$N$_3$O$_3$.0.5 EtOAc: C, 67.42; H, 7.78; N, 9.83. Found: C, 67.03; H, 7.96; N, 9.99.

Example 127

N-{(3E)-5-tert-butyl-1-methyl-2-[2R)-tetrahydrofuran-2-ylmethyl]-1,2-dihydro-3H-pyrazol-3-ylidene}-3-(methylsulfonyl)benzamide The title compound was prepared as described in Example 115, substituting 3-(methylsulfonyl)benzoic acid for 3-(methoxycarbonyl)benzoic acid. $^1$H NMR (300 MHz, CDCl$_3$) δ ppm 1.44 (s, 9H) 1.75-1.91 (m, 3H) 2.05-2.15 (m, 1H) 3.07 (s, 3H) 3.69-3.83 (m, 2H) 3.91 (s, 3H) 4.24-4.28 (m, 1H) 4.35-4.48 (m, 1H) 4.54-4.66 (m 1H) 7.08 (s, 1 H) 7.58 (t, J=7.73 Hz, 1H) 7.95 (d, J=7.54 Hz, 1H) 8.52 (d, J=7.54 Hz, 1H) 8.86 (s, 1H); MS (DCI/NH$_3$) m/z 420 (M+H)$^+$. Anal. calcd C$_{21}$F$_{29}$N$_3$O$_4$S.0.5 EtOAc.0.1H$_2$O: C, 59.45; H, 7.15; N, 9.20. Found: C, 59.18; H, 6.77; N, 9.31.

Example 128 methyl [2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl]acetate

Example 128A

[2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl] acetic acid To a solution of Example 111 (450 mg, 0.859 mmol) in CH$_2$Cl$_2$ (3 mL) was added trifluoroacetic acid (980 mg, 8.59 mmol). The mixture was stirred at 20° C. overnight then concentrated under reduced pressure to provide the title compound. MS (APCI) m/z 468 (M+H)$^+$.

Example 128B methyl [2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl]acetate To a solution of Example 128A (400 mg, 0.856 mmol) in MeOH (3 mL) was added (diazomethyl)trimethylsilane (4.28 ml, 8.56 mmol). The mixture was stirred at 20° C. overnight then concentrated. The residue was purified by column chromatography using an Analogix® Intelliflash280™ (SiO$_2$, gradient 20-100% solvent A in hexane; solvent A=10:1:0.5 ethyl acetate:methanol:triethylamine) to afford the title compound (250 mg, 0.519 mmol, 60.7% yield). $^1$H NMR (300 MHz, CDCl$_3$) δ ppm 1.43 (s, 9H) 1.71-1.85 (m, 3H) 1.99-2.12 (m, 1H) 3.66 (s, 3H) 3.70-3.82 (m, 2H) 3.87 (s, 3H) 4.17-4.23 (m, 1H) 4.25-4.33 (m, 3H) 4.52-4.59 (m, 1H) 6.99 (s, 1H) 7.31 (d, J=7.80 Hz, 1H) 7.52 (dd, J=7.97, 1.53 Hz, 1H) 8.40 (d, J=1.70 Hz, 1H); MS (DCI/NH$_3$) m/z 482 (M+H)$^+$.

Example 129

N-{(3E)-5-tert-butyl-1-methyl-2-[(2R)-tetrahydrofuran-2-ylmethyl]-1,2-dihydro-3H-pyrazol-3-ylidene}-2-fluoro-5-nitrobenzamide The title compound was prepared as described in Example 115, substituting 2-fluoro-5-nitrobenzoic acid for 3-(methoxycarbonyl)benzoic acid. $^1$H NMR (300 MHz, CDCL$_3$) δ ppm 1.44 (s, 9H) 1.76-1.90 (m, 3H) 2.04-2.17 (m, 1H) 3.70-3.82 (m, 2H) 3.92 (s, 3H) 4.22-4.26 (m, 1H) 4.30-4.38 (m, 1H) 4.55-4.62 (m, 1H) 7.09 (s, 1H) 7.17 (t, J=9.32 Hz, 1H) 8.19 (ddd, J=8.72, 3.97, 3.57 Hz, 1H) 8.95 (dd, J=6.35, 3.17 Hz, 1H); MS (DCI/NH$_3$) m/z 405 (M+H)$^+$. Anal. calcd C$_{20}$H$_{25}$FN$_4$O$_4$.0.4H$_2$O: C, 58.36; H, 6.32; N, 13.61. Found: C, 58.59; H, 6.32; N, 13.47.

Example 130

N-{(3E)-5-tert-butyl-1-methyl-2-[(2R)-tetrahydrofuran-2-ylmethyl]-1,2-dihydro-3H-pyrazol-3-ylidene}-3-cyanobenzamide The title compound was prepared as described in Example 14D, substituting 3-cyanobenzoyl chloride for 2-ethoxy-5-(trifluoromethyl)benzoyl chloride. $^1$H NMR (300 MHz, CDCl$_3$) δ ppm 1.43 (s, 9H) 1.72-1.85 (m, 3H) 2.02-2.08 (m, 1H) 3.69-3.82 (m, 2 H) 3.91 (s, 3H) 4.22-4.27 (m, 1H) 4.40-4.50 (m, 1H) 4.54-4.62 (m, 1H) 7.09 (s, 1H) 7.48 (t, J=7.73 Hz, 1H) 7.66 (d, J=7.54 Hz, 1H) 8.47 (d, J=7.93 Hz, 1H) 8.57 (s, 1H); MS (DCI/NH$_3$) m/z 367 (M+H)$^+$.

Example 131 ethyl 3-[2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl]propanoate The title compound was prepared as described in Example 111, substituting (3-ethoxy-3-oxopropyl)zinc(II) bromide for (2-tert-butoxy-2-oxoethyl)zinc(II) bromide. $^1$H NMR (300 MHz, CDCl$_3$) δ ppm 1.17-1.29 (m, 3H) 1.44 (s, 9H) 1.82-1.90 (m, 3H) 2.00-2.09 (m, 1H) 2.74 (t, J=7.97 Hz, 2H) 3.37-3.48 (m, 2H) 3.68-3.80 (m, 2H) 3.88 (s, 3H) 4.10 (q, J=7.12 Hz, 2H) 4.16-4.31 (m, 2H) 4.52-4.60 (m, 1H) 7.01 (s, 1H) 7.31 (d, J=8.14 Hz, 1H) 7.46 (dd, J=7.97, 1.53 Hz, 1H) 8.16 (s, 1H); MS (DCI/NH$_3$) m/z 510 (M+H)$^+$.

Example 132

5-bromo-N-{(3E)-5-tert-butyl-1-methyl-2-[(2R)-tetrahydrofuran-2-ylmethyl]-1,2-dihydro-3H-pyrazol-3-ylidene}-2-fluorobenzamide The title compound was prepared as described in Example 115, substituting 5-bromo-2-fluorobenzoic acid for 3-(methoxycarbonyl)benzoic acid. $^1$H NMR (300 MHz, CDCl$_3$) δ ppm 1.42 (s, 9H) 1.72-1.90 (m, 3H) 1.98-2.10 (m, 1H) 3.68-3.81 (m, 2H) 3.88 (s, 3H) 4.18-4.26 (m, 1H) 4.30-4.39 (m, 1H) 4.51-4.58 (m, 1H) 6.92 (dd, J=10.17, 8.82 Hz, 1 H) 7.06 (s, 1H) 7.38 (ddd, J=8.65, 4.24, 2.71 Hz, 1H) 8.12 (dd, J=6.44, 2.71 Hz, 1H); MS (DCI/NH$_3$) m/z 438 (M+H)$^+$.

Example 133

N-{(3E)-5-tert-butyl-1-methyl-2-[(2R)-tetrahydrofuran-2-ylmethyl]-1,2-dihydro-3H-pyrazol-3-ylidene}-2-phenoxy-5-(trifluoromethyl)benzamide To a 20-mL vial were added Example 16B (325 mg, 0.600 mmol), solid potassium t-butodixide (Aldrich, 86 mg, 0.90 mmol), and anhydrous tyetrahydrofuran (6 mL). Phenol (Aldrich, 113 mg, 1.20 mmol) was added. The reaction mixture was heated at 60° C. overnight. After cooling, water (10 mL) was added and the mixture was extracted with dichloromethane (3×10 mL). The combined organic extracts were dried over sodium sulfate, filtered, and concentrated by rotary evaporator. Flash chromatography (silica gel, 5-35% methanol in dichloromethane) afforded 74 mg (25%) of the title compound. $^1$H NMR (300 MHz, DMSO-d$_6$) δ 1.35 (s, 9H), 1.49-1.73 (m, 4H), 3.51-3.58 (m, 1H), 3.64-3.71 (m, 1H), 3.84 (s, 3H), 3.91-4.04 (m, 1H), 4.09-4.23 (m, 2H), 6.77 (s, 1H), 6.95-7.03 (m, 3H), 7.09-7.14 (m, 1H), 7.35-7.40 (m, 2H), 7.64 (dd, J=8.5, 2.6 Hz, 1H), 7.98 (d, J=2.4 Hz, 1H). MS (ESI+) m/z 502 (M+H)$^+$ It is understood that the foregoing detailed description and accompanying examples are merely illustrative and are not to be taken as limitations upon the scope of the invention, which is defined solely by the appended claims and their equivalents. Various changes and modifications to the disclosed embodiments can be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

What is claimed is:
1. A compound according to formula (I),

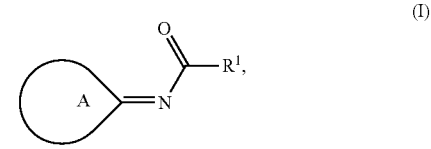

or a pharmaceutically acceptable salt thereof, wherein
R$^1$ is alkyl, haloalkyl, G$^1$, —(CR$^x$R$^y$)$_m$-G$^1$, or —N(R$^{1a}$)(R$^z$);
R$^z$ is alkyl, haloalkyl, G$^2$, —(CR$^x$R$^y$)$_m$—G$^2$, —(CR$^x$R$^y$)$_n$—OR$^{za}$, —(CR$^x$R$^y$)$_n$—N(R$^{za}$)(R$^{zb}$)—(CR$^x$R$^y$)$_m$—C(O)O(R$^{za}$), —(CR$^x$R$^y$)$_m$—C(O)R$^{za}$, —(CR$^x$R$^y$)$_m$—C(O)N(R$^{za}$)(R$^{zb}$), —(CR$^x$R$^y$)$_m$—S(O)$_2$O(R$^{za}$), —(CR$^x$R$^y$)$_m$—S(O)$_2$R$^{za}$, —(CR$^x$R$^y$)$_m$—S(O)$_2$N(R$^{za}$)(R$^{zb}$), or —(CR$^x$R$^y$)$_m$—CN;
G$^1$ and G$^2$, at each occurrence, are each independently aryl, heteroaryl, heterocycle, cycloalkyl, or cycloalkenyl; wherein each ring is independently unsubstituted or substituted with 1, 2, 3, 4, 5, or 6 substituents independently selected from the group consisting of alkyl, alkenyl, alkynyl, —NO$_2$, —CN, halogen, oxo, —OR$^e$, —O—(CR$^j$R$^k$)$_n$—N(R$^w$)$_2$, —OC(O)R$^e$, —SR$^e$, —SF$_5$, —S(O)R$^f$, —S(O)$_2$R$^f$, —S(O)$_2$N(R$^e$)(R$^g$), —N(R$^e$)(R$^g$), —N(R$^g$)C(O)R$^e$, —N(R$^g$)C(O)O(R$^f$), —N(R$^g$)S(O)$_2$R$^f$, —N(R$^g$)C(O)N(R$^e$)(R$^g$), —N(R$^g$)S(O)$_2$N(R$^e$)(R$^g$), —C(O)R$^e$, —C(O)O(R$^e$), —C(O)N(R$^e$)(R$^g$), alkoxyalkenyl, hydroxyalkenyl, haloalkyl, —(CR$^j$R$^k$)$_q$—CN, —(CR$^j$R$^k$)$_q$—OR$^e$, —(CR$^j$R$^k$)$_q$—OC(O)R$^e$, —(CR$^j$R$^k$)$_q$—SR$^e$, —(CR$^j$R$^k$)$_q$—S(O)R$^f$, —(CR$^j$R$^k$)$_q$—S(O)$_2$R$^f$, —(CR$^j$R$^k$)$_q$—N(R$^e$)(R$^g$), —(CR$^j$R$^k$)$_q$—N(R$^g$)C(O)R$^e$, —(CR$^j$R$^k$)$_q$—N(R$^g$)S(O)$_2$R$^f$, —(CR$^j$R$^k$)$_q$—N(R$^g$)C(O)N(R$^e$)(R$^g$), —(CR$^j$R$^k$)$_q$—N(R$^g$)S(O)$_2$N(R$^e$)(R$^g$), —(CR$^j$R$^k$)$_q$—C(O)R$^e$, —(CR$^j$R$^k$)$_q$—C(O)O(R$^e$), —(CR$^j$R$^k$)$_q$—C(O)N(R$^e$)(R$^g$), —C(R$^w$)=N—OR$^w$, and morpholinyl;
Ring A represents formula (a), (b), or (d)

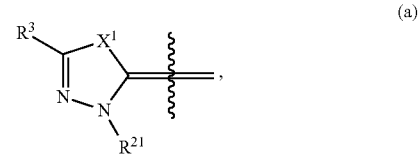

-continued

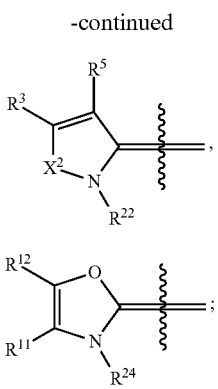

$R^{21}$, $R^{22}$, $R^{23}$, and $R^{24}$ are -alkylene-$G^3$ wherein $G^3$, at each occurrence, is independently furanyl, oxazolyl, isoxazolyl, oxadiazolyl, or a 4-, 5-, 6-, 7-, 8-, or 9-membered monocyclic heterocycle containing zero or one double bond, one or two oxygen, and zero or one nitrogen as ring atoms, wherein two non-adjacent atoms of said monocyclic heterocycle is optionally linked by an alkenylene bridge of 2, 3, or 4 carbon atoms, or optionally linked by an alkylene bridge of 1, 2, 3, or 4 carbon atoms; each $G^3$ ring is optionally fused with a monocyclic ring selected from the group consisting of benzo, cycloalkyl, cycloalkenyl, heterocycle, and heteroaryl; and each $G^3$ is independently unsubstituted or substituted with 1, 2, 3, 4, 5, or 6 substituents independently selected from the group consisting of oxo, alkyl, halogen, —OH, —O(alkyl), —O(haloalkyl), and haloalkyl;

$R^w$, at each occurrence, is independently hydrogen or alkyl;

$R^3$, $R^6$, $R^7$, $R^8$, $R^9$, $R^{11}$, and $R^{12}$ are each independently hydrogen, alkyl, alkenyl, alkynyl, —$NO_2$, —CN, halogen, —$OR^a$, —$N(R^a)(R^b)$, —$C(O)R^a$, —$C(O)O(R^a)$, haloalkyl, —$(CR^cR^d)_p$—$OR^a$, —$(CR^cR^d)_p$—$N(R^a)(R^b)$, —$(CR^cR^d)_p$—$C(O)R^a$, —$(CR^cR^d)_p$—$C(O)O(R^a)$, cycloalkyl, cycloalkenyl, or heterocycle;

$R^4$ and $R^5$, are each independently hydrogen, alkyl, alkenyl, alkynyl, —$NO_2$, —CN, halogen, —$OR^a$, —$N(R^a)(R^b)$, —$C(O)R^a$, —$C(O)O(R^a)$, haloalkyl, —$(CR^cR^d)_p$—$OR^a$, —$(CR^cR^d)_p$—$N(R^a)(R^b)$, —$(CR^cR^d)_p$—$C(O)R^a$, —$(CR^cR^d)_p$—$C(O)O(R^a)$, cycloalkyl, cycloalkenyl, or heterocycle; or $R^4$ and $R^5$, together with the carbon atoms to which they are attached, form a monocyclic cycloalkyl ring which is optionally further substituted with 1, 2, 3, or 4 substituents selected from the group consisting of halogen, alkyl, haloalkyl, and oxo;

$R^a$, $R^b$, $R^{1a}$, $R^{za}$, and $R^{zb}$, at each occurrence, are each independently hydrogen, alkyl, or haloalkyl;

$R^x$, at each occurrence, is independently hydrogen, halogen, alkyl, haloalkyl, or benzyl;

$R^y$, $R^c$, and $R^d$, at each occurrence, are each independently hydrogen, halogen, alkyl, or haloalkyl;

$X^1$ and $X^2$ are independently O, S, or $N(R^{10})$ wherein $R^{10}$ is alkyl, alkoxyalkyl, haloalkoxyalkyl, or haloalkyl;

the cycloalkyl, cycloalkenyl, and heterocycle, as represented by $R^3$, $R^4$, $R^5$, $R^6$, $R^7$, $R^8$, $R^9$, $R^{11}$, and $R^{12}$ are each independently unsubstituted or substituted with 1, 2, 3, 4, 5, or 6 substituents independently selected from the group consisting of alkyl, alkenyl, alkynyl, —$NO_2$, —CN, halogen, oxo, —$OR^e$, —$OC(O)R^e$, —$SR^e$, —$S(O)R^f$, —$S(O)_2R^f$, —$S(O)_2N(R^e)(R^g)$, —$N(R^e)(R^g)$, —$N(R^g)C(O)R^e$, —$N(R^g)S(O)_2R^f$, —$N(R^g)C(O)N(R^e)(R^g)$, —$N(R^g)S(O)_2N(R^e)(R^g)$, —$C(O)R^e$, —$C(O)O(R^e)$, —$C(O)N(R^e)(R^g)$, haloalkyl, —$(CR^jR^k)_q$—CN, —$(CR^jR^k)_q$—$OR^e$, —$(CR^jR^k)_q$—$OC(O)R^e$, —$(CR^jR^k)_q$—$SR^e$, —$(CR^jR^k)_q$—$S(O)R^f$, —$(CR^jR^k)_q$—$S(O)_2R^f$, —$(CR^jR^k)_q$—$N(R^e)(R^g)$, —$(CR^jR^k)_q$—$N(R^g)C(O)R^e$, —$(CR^jR^k)_q$—$N(R^g)S(O)_2R^f$, —$(CR^jR^k)_q$—$N(R^g)C(O)N(R^e)(R^g)$, —$(CR^jR^k)_q$—$N(R^g)S(O)_2N(R^e)(R^g)$, —$(CR^jR^k)_q$—$C(O)R^e$, —$(CR^jR^k)_q$—$C(O)O(R^e)$, and —$(CR^jR^k)_q$—$C(O)N(R^e)(R^g)$;

$R^e$ and $R^g$, at each occurrence, are each independently hydrogen, alkyl, alkenyl, alkynyl, alkoxyalkyl, cycloalkyl, cycloalkylalkyl, heterocycle, aryl, heteroaryl, haloalkoxyalkyl, or haloalkyl; wherein the aryl, the heteroaryl, the cycloalkyl, and the heterocycle moieties, by itself or as part of the substituents of $R^e$ and $R^g$, are each independently unsubstituted or substituted with 1, 2, 3, 4, 5 or 6 substituents selected from the group consisting of alkyl, halogen, haloalkyl, hydroxy, oxo, =N—O(H), =N—O(alkyl), and alkoxy;

$R^f$, at each occurrence, is independently alkyl or haloalkyl;

$R^j$ and $R^k$, at each occurrence, are each independently hydrogen, halogen, alkyl, or haloalkyl;

m, p, and q, at each occurrence, are each independently 1, 2, 3, or 4; and n is 2, 3 or 4.

2. The compound of claim 1 having formula (I), or a pharmaceutically acceptable salt thereof, wherein $R^{21}$, $R^{22}$, $R^{23}$, and $R^{24}$ are -alkylene-$G^3$, $G^3$, at each occurrence, is independently a 4-, 5-, or 6-membered monocyclic heterocycle containing zero or one double bond, one or two oxygen, and zero or one nitrogen as ring atoms, and each $G^3$ is independently unsubstituted or substituted with 1, 2, 3, 4, 5, or 6 substituents independently selected from the group consisting of oxo, alkyl, halogen, —OH, —O (alkyl), —O (haloalkyl), and haloalkyl.

3. The compound of claim 2 having formula (I), or a pharmaceutically acceptable salt thereof, wherein $G^3$, at each occurrence, is independently oxetanyl, oxazolidinyl, tetrahydrofuranyl, tetrahydropyranyl, 1,3-dioxalanyl, or 1,4-dioxanyl, each of which is independently unsubstituted or substituted.

4. The compound of claim 2 having formula (I), or a pharmaceutically acceptable salt thereof, wherein $R^1$ is $G^1$ or $N(R^{1a})(R^z)$.

5. The compound of claim 2 having formula (I), or a pharmaceutically acceptable salt thereof, wherein ring A is formula (a).

6. The compound of claim 5 having formula (I), or a pharmaceutically acceptable salt thereof, wherein $X^1$ is S.

7. The compound of claim 6 having formula (I), or a pharmaceutically acceptable salt thereof, wherein $R^1$ is $G^1$, and $G^1$ is phenyl or naphthyl, each of which is optionally substituted.

8. The compound of claim 6 having formula (I), or a pharmaceutically acceptable salt thereof, wherein $R^1$ is —$N(R^{1a})(R^z)$.

9. The compound of claim 2 having formula (I), or a pharmaceutically acceptable salt thereof, wherein ring A is formula (b).

10. The compound of claim 9 having formula (I), or a pharmaceutically acceptable salt thereof, wherein $X^2$ is O.

11. The compound of claim 9 having formula (I), or a pharmaceutically acceptable salt thereof, wherein $X^2$ is $N(R^{10})$ and $R^{10}$ is $C_1$-$C_4$ alkyl.

12. The compound of claim 9 having formula (I), or a pharmaceutically acceptable salt thereof, wherein $R^1$ is $G^1$, and $G^1$ is phenyl or naphthyl, each of which is optionally substituted.

13. The compound of claim 9 having formula (I), or a pharmaceutically acceptable salt thereof, wherein $R^1$ is $G^1$, and $G^1$ is optionally substituted cycloalkyl.

14. The compound of claim 2 having formula (I), or a pharmaceutically acceptable salt thereof, wherein ring A is formula (d).

15. The compound according to claim 1 or a pharmaceutically acceptable salt thereof, selected from the group consisting of 5-chloro-2-methoxy-N-[(2Z)-3-[(2R)-tetrahydrofuran-2-ylmethyl]-5-[1-(trifluoromethyl)cyclopropyl]-1,3,4-thiadiazol-2(3H)-ylidene]benzamide;

5-chloro-N-[(2Z)-5-cyclopropyl-3-(tetrahydrofuran-2-ylmethyl)-1,3,4-thiadiazol-2(3H)-ylidene]-2-methoxybenzamide;

N-[(2Z)-5-cyclopropyl-3-(tetrahydrofuran-2-ylmethyl)-1,3,4-thiadiazol-2(3H)-ylidene]-2-ethoxybenzamide;

N-[(2Z)-5-tert-butyl-3-[(2R)-tetrahydrofuran-2-ylmethyl]-1,3,4-thiadiazol-2(3H)-ylidene]-5-chloro-2-methoxybenzamide;

5-chloro-2-methoxy-N-[(2Z)-5-(1-methylcyclopropyl)-3-[(2R)-tetrahydrofuran-2-ylmethyl]-1,3,4-thiadiazol-2(3H)-ylidene]benzamide;

5-chloro-N-[(2Z)-5-(1,1-dimethylprop-2-ynyl)-3-[(2R)-tetrahydrofuran-2-ylmethyl]-1,3,4-thiadiazol-2(3H)-ylidene]-2-methoxybenzamide;

5-chloro-2-methoxy-N-[(2Z)-5-(2,2,3,3-tetrafluoro-1-methylcyclobutyl)-3-[(2R)-tetrahydrofuran-2-ylmethyl]-1,3,4-thiadiazol-2(3H)-ylidene]benzamide;

5-chloro-2-methoxy-N-[(2Z)-3-[(2R)-tetrahydrofuran-2-ylmethyl]-5-[1-(trifluoromethyl)cyclobutyl]-1,3,4-thiadiazol-2(3H)-ylidene]benzamide;

5-chloro-2-methoxy-N-[(2Z)-3-[(2R)-tetrahydrofuran-2-ylmethyl]-5-(2,2,2-trifluoro-1,1-dimethylethyl)-1,3,4-thiadiazol-2(3H)-ylidene]benzamide;

N-[(3E)-5-tert-butyl-2-[(2R)-tetrahydrofuran-2-ylmethyl]isoxazol-3(2H)-ylidene]-5-chloro-2-methoxybenzamide;

N-{(3E)-5-tert-butyl-1-methyl-2-[(2S)-tetrahydrofuran-2-ylmethyl]-1,2-dihydro-3H-pyrazol-3-ylidene}-5-chloro-2-methoxybenzamide;

N-[(2Z)-5-tert-butyl-3-[(2R)-tetrahydrofuran-2-ylmethyl]-1,3-oxazol-2(3H)-ylidene]-5-chloro-2-methoxybenzamide;

N-{(3E)-5-tert-butyl-1-methyl-2-[(2R)-tetrahydrofuran-2-ylmethyl]-1,2-dihydro-3H-pyrazol-3-ylidene}-2-ethoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-(pentafluoro-lambda-6-sulfanyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(cis-3-hydroxycyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3-oxocyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(cis-3-methoxycyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3,3-difluorocyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-methoxy-3-methylbutoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2,2,2-trifluoroethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-hydroxy-5-(trifluoromethyl)benzamide;

2-tert-butoxy-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[2-(dimethylamino)ethoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(dimethylamino)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-{[(2S)-2-methoxypropyl]oxy}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-ethoxypropoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-methoxypropoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2-ethoxyethoxy)-5-(trifluoromethyl)benzamide;

2-methoxy-N-[(3E)-1-methyl-2-[(2R)-tetrahydrofuran-2-ylmethyl]-1,4,5,6-tetrahydrocyclopenta[c]pyrazol-3(2H)-ylidene]-5-(trifluoromethyl)benzamide;

2-methoxy-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(2-methoxyethyl)amino]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2,2-difluoroethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3R)-tetrahydrofuran-3-yloxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3S)-tetrahydrofuran-3-yloxy]-5-(trifluoromethyl)benzamide;

(E)-N-(5-tert-butyl-2-(((2R,3R)-3-fluorotetrahydrofuran-2-yl)methyl)-1-methyl-1H-pyrazol-3(2H)-ylidene)-2-methoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(2-fluoroethyl)amino]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2-fluoropropoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-{[(2R)-2-fluoropropyl]oxy}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2-fluoro-1-methylethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-fluoro-3-methylbutoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(1-hydroxycyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-5-chloro-2-methoxybenzamide;

N-{(3E)-5-tert-butyl-1-methyl-2-[(2R)-tetrahydrofuran-2-ylmethyl]-1,2-dihydro-3H-pyrazol-3-ylidene}-2-fluoro-3-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-methoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-5-cyano-2-methoxybenzamide;

5-bromo-N-{(3E)-5-tert-butyl-1-methyl-2-[(2R)-tetrahydrofuran-2-ylmethyl]-1,2-dihydro-3H-pyrazol-3-ylidene}-2-methoxybenzamide;

N-{(3E)-5-tert-butyl-1-methyl-2-[(2R)-tetrahydrofuran-2-ylmethyl]-1,2-dihydro-3H-pyrazol-3-ylidene}-2-chloro-5-fluorobenzamide;

N-{(3E)-5-tert-butyl-1-methyl-2-[(2R)-tetrahydrofuran-2-ylmethyl]-1,2-dihydro-3H-pyrazol-3-ylidene}-2,3,5-trifluorobenzamide;

N-{(3E)-5-tert-butyl-1-methyl-2-[(2R)-tetrahydrofuran-2-ylmethyl]-1,2-dihydro-3H-pyrazol-3-ylidene}-3-chloro-2-fluoro-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-chloro-2-methoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-chloro-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3,5-difluoro-2-methoxybenzamide;

N-{(3E)-5-tert-butyl-1-methyl-2-[(2R)-tetrahydrofuran-2-ylmethyl]-1,2-dihydro-3H-pyrazol-3-ylidene}-3-chloro-2-(2-methoxyethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-chloro-2-(2-fluoroethoxy)-5-(trifluoromethyl)benzamide;

5-bromo-N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)benzamide;

5-bromo-N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)benzamide;

5-bromo-N-{(3E)-5-tert-butyl-1-methyl-2-[(2R)-tetrahydrofuran-2-ylmethyl]-1,2-dihydro-3H-pyrazol-3-ylidene}-2,3-dihydro-1-benzofuran-7-carboxamide;

N-[(3E)-5-tert-butyl-1-methyl-2-(tetrahydro-2H-pyran-2-ylmethyl)-1,2-dihydro-3H-pyrazol-3-ylidene]-2-methoxy-5-(trifluoromethyl)benzamide;

N-((3E)-5-tert-butyl-1-methyl-2-{[(5R)-5-methyltetrahydrofuran-2-yl]methyl}-1,2-dihydro-3H-pyrazol-3-ylidene)-2-methoxy-5-(trifluoromethyl)benzamide;

N-((3E)-5-tert-butyl-1-methyl-2-{[(5S)-5-methyltetrahydrofuran-2-yl]methyl}-1,2-dihydro-3H-pyrazol-3-ylidene)-2-methoxy-5-(trifluoromethyl)benzamide;

N-[(2Z)-5-tert-butyl-3-[(2R)-tetrahydrofuran-2-ylmethyl]-1,3-oxazol-2(3H)-ylidene]-2-methoxy-5-(trifluoromethyl)benzamide;

N-[(2Z)-5-tert-butyl-3-[(2R)-tetrahydrofuran-2-ylmethyl]-1,3,4-thiadiazol-2(3H)-ylidene]-N'-(4-methylcyclohexyl)urea;

N-(1-adamantylmethyl)-N'-[(2Z)-5-tert-butyl-3-[(2R)-tetrahydrofuran-2-ylmethyl]-1,3,4-thiadiazol-2(3H)-ylidene]urea;

N-[(2Z)-5-tert-butyl-3-[(2R)-tetrahydrofuran-2-ylmethyl]-1,3,4-thiadiazol-2(3H)-ylidene]-N'-{[(1S,2R,5S)-6,6-dimethylbicyclo[3.1.1]hept-2-yl]methyl}urea;

N-[(2Z)-5-tert-butyl-3-[(2R)-tetrahydrofuran-2-ylmethyl]-1,3,4-thiadiazol-2(3H)-ylidene]-N'-[1-(hydroxymethyl)-3-methylbutyl]urea;

N-[(2Z)-5-tert-butyl-3-[(2R)-tetrahydrofuran-2-ylmethyl]-1,3,4-thiadiazol-2(3H)-ylidene]-N'-(1,2-dimethylpropyl)urea;

N-[(2Z)-5-tert-butyl-3-[(2R)-tetrahydrofuran-2-ylmethyl]-1,3,4-thiadiazol-2(3H)-ylidene]-N'-(1-ethylpropyl)urea;

N-[(2Z)-5-tert-butyl-3-[(2R)-tetrahydrofuran-2-ylmethyl]-1,3,4-thiadiazol-2(3H)-ylidene]-N'-1,2,3,4-tetrahydronaphthalen-1-ylurea;

N-[(2Z)-5-tert-butyl-3-[(2R)-tetrahydrofuran-2-ylmethyl]-1,3,4-thiadiazol-2(3H)-ylidene]-N'-[(1S)-1-cyclohexylethyl]urea;

N-(tert-butyl)-N'-[(2Z)-5-tert-butyl-3-[(2R)-tetrahydrofuran-2-ylmethyl]-1,3,4-thiadiazol-2(3H)-ylidene]urea;

N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2,2-dimethylpropyl]urea;

N-[(2Z)-5-tert-butyl-3-[(2R)-tetrahydrofuran-2-ylmethyl]-1,3,4-thiadiazol-2(3H)-ylidene]-N'-cycloheptylurea;

N-[(2Z)-5-tert-butyl-3-[(2R)-tetrahydrofuran-2-ylmethyl]-1,3,4-thiadiazol-2(3H)-ylidene]-N'-(2-ethylhexyl)urea;

N-[(2Z)-5-tert-butyl-3-[(2R)-tetrahydrofuran-2-ylmethyl]-1,3,4-thiadiazol-2(3H)-ylidene]-N'-(1-methyl-3-phenylpropyl)urea;

N-({[(2Z)-5-tert-butyl-3-[(2R)-tetrahydrofuran-2-ylmethyl]-1,3,4-thiadiazol-2(3H)-ylidene]amino}carbonyl)-L-phenylalaninamide;

$N^2$-({[(2Z)-5-tert-butyl-3-[(2R)-tetrahydrofuran-2-ylmethyl]-1,3,4-thiadiazol-2(3H)-ylidene]amino}carbonyl)-L-isoleucinamide;

$N^2$-({[(2Z)-5-tert-butyl-3-[(2R)-tetrahydrofuran-2-ylmethyl]-1,3,4-thiadiazol-2(3H)-ylidene]amino}carbonyl)-$N^{1,3}$-dimethyl-L-valinamide;

N-[(2Z)-5-tert-butyl-3-[(2R)-tetrahydrofuran-2-ylmethyl]-1,3,4-thiadiazol-2(3H)-ylidene]-N'-neopentylurea;

N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2-methylpropyl]urea;

N-[(3E)-5-tert-butyl-1-methyl-2-(tetrahydrofuran-3-ylmethyl)-1,2-dihydro-3H-pyrazol-3-ylidene]-2-methoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide;

N-{(3E)-4-bromo-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide;

2-bromo-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(1E)-3-methoxyprop-1-enyl]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-methoxypropyl)-5-(trifluoromethyl)benzamide;

N-[(2Z)-5-tert-butyl-3-{[(4S)-2-oxo-1,3-oxazolidin-4-yl]methyl}-1,3,4-thiadiazol-2(3H)-ylidene]-5-chloro-2-methoxybenzamide;

2-(2-amino-2-methylpropoxy)-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3-methylbut-2-enyl)oxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[2-(1-hydroxycyclopentyl)ethoxy]-5-(trifluoromethyl)benzamide;

2-(azetidin-3-yloxy)-N-[(2Z)-5-tert-butyl-3-[(2R)-tetrahydrofuran-2-ylmethyl]-1,3-oxazol-2(3H)-ylidene]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-fluoro-5-(trifluoromethyl)benzamide;

N-[(2Z)-5-tert-butyl-3-[(2R)-tetrahydrofuran-2-ylmethyl]-1,3,4-thiadiazol-2(3H)-ylidene]-2-{[(3S)-1-methylpyrrolidin-3-yl]oxy}-5-(trifluoromethyl)benzamide;

N-[(2Z)-5-tert-butyl-3-[(2R)-tetrahydrofuran-2-ylmethyl]-1,3-oxazol-2(3H)-ylidene]-2-{[(3S)-1-methylpyrrolidin-3-yl]oxy}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(1E)-prop-1-enyl]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(1E)-3-hydroxy-3-methylbut-1-enyl]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-hydroxy-3-methylbutyl)-5-(trifluoromethyl)benzamide;

2-[(1-hydroxycyclobutyl)methoxy]-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-hydroxy-5-(trifluoromethyl)benzamide;

3-bromo-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-(2-fluoro ethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-nitro-5-(trifluoromethyl)benzamide;

3-amino-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-[(2Z)-5-tert-butyl-3-[(2R)-tetrahydrofuran-2-ylmethyl]-1,3-oxazol-2(3H)-ylidene]-2-[2-(dimethylamino)ethoxy]-5-(trifluoromethyl)benzamide;

2-[(Z)-(tert-butoxyimino)methyl]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(methoxymethyl)-5-(trifluoromethyl)benzamide;

tert-butyl [2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl]acetate;

2-amino-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(methylsulfonyl)amino]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-5-cyano-2-fluorobenzamide;

methyl 3-[({(3E)-5-tert-butyl-1-methyl-2-[(2R)-tetrahydrofuran-2-ylmethyl]-1,2-dihydro-3H-pyrazol-3-ylidene}amino)carbonyl]benzoate;

N-{(3E)-5-tert-butyl-1-methyl-2-[(2R)-tetrahydrofuran-2-ylmethyl]-1,2-dihydro-3H-pyrazol-3-ylidene}-5-chloro-2-fluorobenzamide;

methyl 4-[({(3E)-5-tert-butyl-1-methyl-2-[(2R)-tetrahydrofuran-2-ylmethyl]-1,2-dihydro-3H-pyrazol-3-ylidene}amino)carbonyl]bicyclo [2.2.1]heptane-1-carboxylate;

methyl 3-({[(3E)-5-tert-butyl-1-methyl-2-[(2R)-tetrahydrofuran-2-ylmethyl]-1,2-dihydro-3H-pyrazol-3-ylidene]amino}carbonyl)adamantane-1-carboxylate;

N-{(3E)-5-tert-butyl-1-methyl-2-[(2R)-tetrahydrofuran-2-ylmethyl]-1,2-dihydro-3H-pyrazol-3-ylidene}-2-{[3-(hydroxyimino)cyclobutyl]methoxy}-5-(trifluoromethyl)benzamide;

tert-butyl 2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenylcarbamate;

N-{(3E)-5-tert-butyl-1-methyl-2-[(2R)-tetrahydrofuran-2-ylmethyl]-1,2-dihydro-3H-pyrazol-3-ylidene}-2-{[(dimethylamino)sulfonyl]amino}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-5-(trifluoromethyl)-2-vinylbenzamide;

N-{(3E)-5-tert-butyl-1-methyl-2-[(2R)-tetrahydrofuran-2-ylmethyl]-1,2-dihydro-3H-pyrazol-3-ylidene}-2-morpholin-4-yl-5-(trifluoromethyl)benzamide;

2-[bis(2-ethoxyethyl)amino]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(isobutylsulfonyl)amino]-5-(trifluoromethyl)benzamide;

3-acetyl-N-{(3E)-5-tert-butyl-1-methyl-2-[(2R)-tetrahydrofuran-2-ylmethyl]-1,2-dihydro-3H-pyrazol-3-ylidene}benzamide;

N-{(3E)-5-tert-butyl-1-methyl-2-[(2R)-tetrahydrofuran-2-ylmethyl]-1,2-dihydro-3H-pyrazol-3-ylidene}-3-(methylsulfonyl)benzamide;

methyl [2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl]acetate;

N-{(3E)-5-tert-butyl-1-methyl-2-[(2R)-tetrahydrofuran-2-ylmethyl]-1,2-dihydro-3H-pyrazol-3-ylidene}-2-fluoro-5-nitrobenzamide;

N-{(3E)-5-tert-butyl-1-methyl-2-[(2R)-tetrahydrofuran-2-ylmethyl]-1,2-dihydro-3H-pyrazol-3-ylidene}-3-cyanobenzamide;

ethyl 3-[2-[({(3E)-5-tert-butyl-1-methyl-2-[(2R)-tetrahydrofuran-2-ylmethyl]-1,2-dihydro-3H-pyrazol-3-ylidene}amino)carbonyl]-4-(trifluoromethyl)phenyl]propanoate; 5-bromo-N-{(3E)-5-tert-butyl-1-methyl-2-[(2R)-tetrahydrofuran-2-ylmethyl]-1,2-dihydro-3H-pyrazol-3-ylidene}-2-fluorobenzamide; and N-{(3E)-5-tert-butyl-1-methyl-2-[(2R)-tetrahydrofuran-2-ylmethyl]-1,2-dihydro-3H-pyrazol-3-ylidene}-1-2-phenoxy-5-(trifluoromethyl)benzamide.

16. A pharmaceutical composition comprising a therapeutically effective amount of a compound of formula (I) according to claim 1, or a pharmaceutically acceptable salt thereof, in combination with one or more pharmaceutically acceptable carriers.

17. A method for treating pain in a mammal in need of such treatment comprising administering to the mammal having pain a therapeutically effective amount of a compound of formula (I) according to claim 1, or a pharmaceutically acceptable salt thereof.

* * * * *